US011632921B2

(12) United States Patent
Cannon et al.

(10) Patent No.: US 11,632,921 B2
(45) Date of Patent: Apr. 25, 2023

(54) METHODS FOR HYBRID CORN SEED PRODUCTION

(71) Applicant: Monsanto Technology LLC, St. Louis, MO (US)

(72) Inventors: Paul Cannon, Chesterfield, MO (US); Edward J. Cargill, Chesterfield, MO (US); Charles T. Foresman, St. Louis, MO (US); Michael A. Hall, Wildwood, MO (US); Scott C. Johnson, Wildwood, MO (US); John A. Miklos, Des Peres, MO (US)

(73) Assignee: Monsanto Technology LLC, St. Louis, MO (US)

( * ) Notice: Subject to any disclaimer, the term of this patent is extended or adjusted under 35 U.S.C. 154(b) by 193 days.

(21) Appl. No.: 17/101,202

(22) Filed: Nov. 23, 2020

(65) Prior Publication Data

US 2021/0076582 A1 Mar. 18, 2021

Related U.S. Application Data

(63) Continuation of application No. 16/276,615, filed on Feb. 15, 2019, now Pat. No. 10,881,057.

(60) Provisional application No. 62/631,199, filed on Feb. 15, 2018, provisional application No. 62/775,343, filed on Dec. 4, 2018.

(51) Int. Cl.
*A01H 1/02* (2006.01)
*C12N 15/82* (2006.01)

(52) U.S. Cl.
CPC .......... *A01H 1/02* (2013.01); *C12N 15/8218* (2013.01); *C12N 15/8297* (2013.01)

(58) Field of Classification Search
None
See application file for complete search history.

(56) References Cited

U.S. PATENT DOCUMENTS

| | | | |
|---|---|---|---|
| 4,368,592 | A | 1/1983 | Welch |
| 5,939,539 | A | 8/1999 | Lange et al. |
| 6,198,021 | B1 | 3/2001 | Lange et al. |
| 6,380,467 | B1 | 4/2002 | Duclos |
| 6,765,133 | B2 | 7/2004 | Koehring |
| 7,041,874 | B2 * | 5/2006 | Johal et al. |
| 10,881,057 | B2 * | 1/2021 | Cannon .............. C12N 15/8218 |
| 2002/0162142 | A1 | 10/2002 | Johal et al. |
| 2003/0172409 | A1 | 9/2003 | Horn |
| 2009/0070898 | A1 | 3/2009 | Allen et al. |
| 2011/0035839 | A1 | 2/2011 | Lutfitta et al. |
| 2011/0126310 | A1 | 5/2011 | Feng et al. |
| 2011/0296555 | A1 | 12/2011 | Ivashuta et al. |
| 2013/0121101 | A1 | 5/2013 | Ochampaugh et al. |
| 2013/0345937 | A1 | 12/2013 | Strelioff et al. |
| 2014/0013464 | A1 | 1/2014 | Davie |
| 2015/0201619 | A1 | 7/2015 | Annigeri et al. |
| 2016/0050865 | A1 | 2/2016 | Morse et al. |
| 2016/0319375 | A1 | 11/2016 | Barten et al. |
| 2017/0079224 | A1 | 3/2017 | Jolliffe et al. |
| 2018/0051295 | A1 | 2/2018 | Allen et al. |
| 2019/0014730 | A1 | 1/2019 | Dong et al. |
| 2019/0014731 | A1 | 1/2019 | Ovadya et al. |
| 2019/0241903 | A1 | 8/2019 | Ellis et al. |
| 2019/0246619 | A1 | 8/2019 | Barten et al. |
| 2022/0039320 | A1 | 2/2022 | Barten et al. |

FOREIGN PATENT DOCUMENTS

| | | |
|---|---|---|
| WO | WO 2016/176286 A1 | 11/2016 |
| WO | WO 2017/011791 A1 | 1/2017 |
| WO | WO 2018/035354 A1 | 2/2018 |
| WO | WO 2018/119225 A1 | 6/2018 |
| WO | WO 2018/129302 A1 | 7/2018 |
| WO | WO 2019/161143 A1 | 8/2019 |
| WO | WO 2019/161145 A2 | 8/2019 |
| WO | WO 2019/161149 A1 | 8/2019 |

OTHER PUBLICATIONS

Crommelinck et al., "*Simulating* an Autonomously Operating Low-Cost Static Terrestrial LiDAR for Multitemporal Maize Crop Height Measurements," *Remote Sensing*, 8(3):205, pp. 1-17 (2016).
D'Andrea et al., "Genotypic Variability in Morphological and Physiological Traits among Maize Inbred Lines-Nitrogen Responses," *Crop Sci.*, 46:1266-1276 (2006).
GenBank Accession No. AY366085, "*Zea mays* cultivar B73 PGP1 (pgpl) gene, complete cds" (2003).
International Search Report and Written Opinion dated Aug. 8, 2019, in International Application No. PCT/US2019/018129.
International Search Report and Written Opinion dated May 10, 2019, in International Application No. PCT/US2019/018127.
Kempton, "Heritable Characters of Maize, III. Brachytic Culms," *Jour. Hexed.*, 11(1):111-115 (1920).
Mourtzinis et al., "Corn Grain and Stover Yield Prediction at RI Growth Stage," *Agronomy Journal*, 105(4):1045-1050 (2013).
Multani et al., "Loss of an MDR Transporter in Compact Stalks of Maize br2 and Sorghum dw3 Mutants," *Science*, 302:81-84 (2003).
Pilu et al., "Isolation and characterization of a new mutant allele of brachytic 2 maize gene," *Molecular Breeding*, 20:83-91 (2007).
Weng et al., "Genome-Wide Association Study Identifies Candidate Genes That Affect Plant Height in Chinese Elite Maize (*Zea mays* L.) Inbred Lines," PloS ONE, vol. 6, pp. 1-8 (2011).
Zaidi et al., "Phenotyping for Abiotic Stress Tolerance in Maize Heat Stress," *CIMMYT*, pp. 1-40 (2016).
Butzen, "Timing Corn Harvest," *Crop Insights*, (Sep. 2018).

(Continued)

*Primary Examiner* — Medina A Ibrahim
(74) *Attorney, Agent, or Firm* — Dentons US LLP; David Lanzotti, Esq.

(57) ABSTRACT

Methods for improving the efficiency and productivity of hybrid corn seed production are provided herein. Various methods to improve the transfer of pollen from male corn plants to female corn plants, and thus increase yield, are provided herein. Without being limiting, these methods include varying the height of male and female corn plants in a field, as well as varying the number, arrangement, and ratio of male-to-female rows in a field.

37 Claims, 12 Drawing Sheets

Specification includes a Sequence Listing.

(56) References Cited

OTHER PUBLICATIONS

Chen et al., "Identification and genetic mapping for rht-DM, a dominant dwarfing gene in mutant semi-dwarf maize using QTL-seq approach," *Genes & Genomics* 40, pp. 1091-1099 (Jun. 2018) (electronic publication).
Elmore et al., "In-Field Drydown Rates and Harvest," Iowa State University Extension and Outreach, https://crops.extension.iastate.edu/cropnews/2010/09/field-drydown-rates-and-harvest (Sep. 28, 2010).
Spelhaug, "Predicting Your Corn Harvest Date," *Peterson Farms Seed* (2013).
Supplementary European Search Report dated Oct. 11, 2022 in EP 19 89 2688.
Thomison et al., "Corn Response to Harvest Date a Affected by Plant Population and Hybrid," *Agron J.* 103, pp. 1765-1772 (Sep. 2011) (electronic publication).
"4 Series Sprayers," Published in May 2016, obtained from https://www[dot]deere[dot]com/en_CAF/docs/product/equipment/4_Series_Sprayers[dot]pdf (2016).
Amanullah et al., "Phenology, Growth, and Grain Yield of Maize as Influenced by Foliar Applied Urea at Different Growth Stages," *Journal of Plant Nutrition* 33:71-79 (2010).
"Corn Herbicide Application Timings," published by online by PennState Extension; obtained from https://extension[dot]psu[dot]edu/corn-herbicide-application-timings (2015).
International Search Report and Written Opinion dated Apr. 22, 2020, in International Application No. PCT/US2019/064270, pp. 1-14.
Lu, "Chapter 3 Research on Production Increase Technology in Late Harvesting of Maize in Optimum Period," *Theory and Technology of Maize High Yield* (2015).
Qiao et al., "The influence of RNAi targeting of OsGA20oX2 gene on plant height in rice," *Plant Molecular Biology Reporting* 29.4:952-960 (2011)
Wang et al., "Analysis of hormone sensitivity of a dwarf mutant of maize," *Journal of Northwest A&F University* (*Nat. Sci. Ed.*) 45(8) (2017).

\* cited by examiner

METHODS FOR HYBRID CORN SEED PRODUCTION

CROSS REFERENCE TO RELATED APPLICATIONS

This application is a continuation of U.S. patent application Ser. No. 16/276,615, filed Feb. 15, 2019, claims the benefit of U.S. Provisional Application No. 62/631,199, filed Feb. 15, 2018, and U.S. Provisional Application No. 62/775,343, filed Dec. 4, 2018, all of which are incorporated herein by reference in their entireties.

FIELD OF THE INVENTION

The present disclosure relates to methods of improving hybrid corn seed production.

INCORPORATION OF SEQUENCE LISTING

A sequence listing contained in the filed named P34580US03_SEQ.txt, which is 171,962 bytes (measured in MS-Windows®) and created on Nov. 23, 2020, comprises 131 sequences, and is filed electronically herewith and incorporated by reference in its entirety.

BACKGROUND

Hybrid corn seeds are produced by crossing two different parental inbred corn lines. Increasing the profitability of commercial corn seed production largely relies on the ability to improve female inbred plant yield. A need continues to exist in the art for further improvements in the efficiency and productivity of corn seed production, especially if agricultural demand and costs of production continue to rise.

SUMMARY

In an aspect, this disclosure provides a method comprising: (a) fertilizing a plurality of female inbred corn plants with pollen from at least one male inbred corn plant to produce hybrid corn seeds, where the female inbred corn plants have an average height that is at least 2.5% lower than the average height of the least one male inbred corn plant; and (b) harvesting the hybrid corn seeds from one or more of the female inbred corn plants.

In an aspect, this disclosure provides a method comprising: (a) crossing at least one male inbred corn plant with a plurality of female inbred corn plants to produce hybrid corn seeds, where the female inbred corn plants have an average height that is at least 2.5% lower than the height of the at least one male inbred corn plant; and (b) harvesting the hybrid corn seeds from one or more of the female inbred corn plants.

In an aspect, this disclosure provides a method comprising: (a) planting at least one male inbred corn plant in proximity to a plurality of female inbred corn plants to produce hybrid corn seeds, where the female inbred corn plants have an average height that is at least 2.5% lower than the height or average height of the at least one male inbred corn plant; and (b) harvesting said hybrid corn seeds from one or more of the female inbred corn plants.

DETAILED DESCRIPTION

Figure 1:
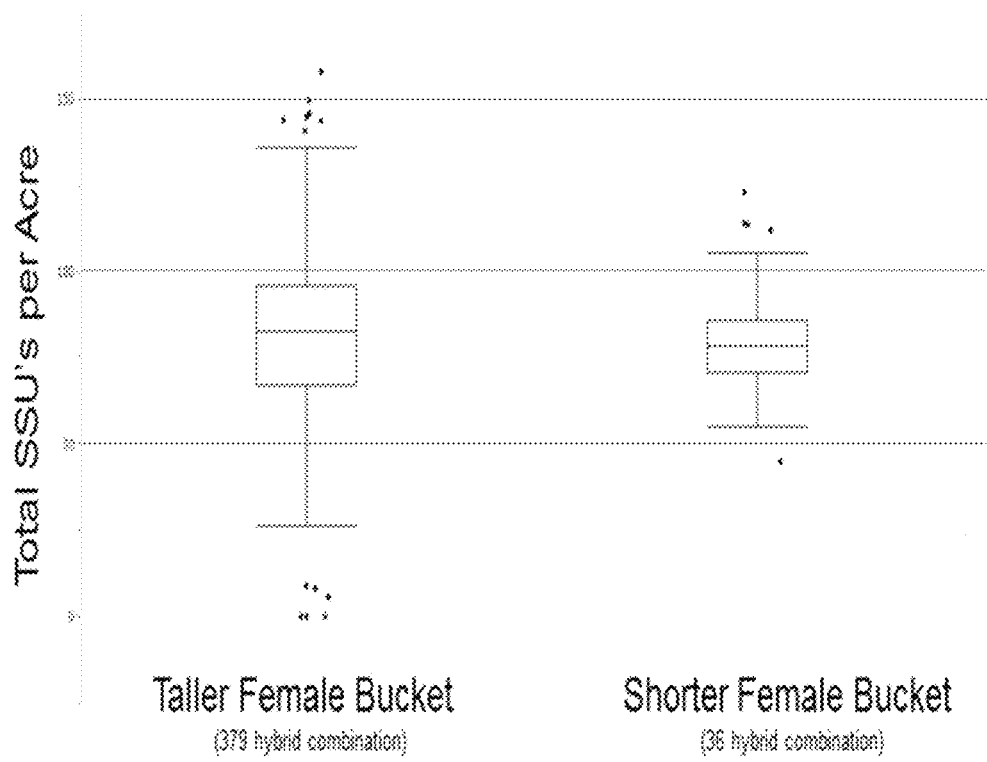
FIG. 1 is a chart illustrating the variability in hybrid corn seed yield produced for a set of 415 different hybrid corn combinations separated into two groupings based upon the average female to male parent plant height ratio for each combination.

Unless defined otherwise, all technical and scientific terms used have the same meaning as commonly understood by one of ordinary skill in the art to which this disclosure belongs. Where a term is provided in the singular, the inventors also contemplate aspects of the disclosure being described by the plural of that term. Where there are discrepancies in terms and definitions used in references that are incorporated by reference, the terms used in this application shall apply. Other technical terms that are used herein have their ordinary meaning in the art in which they are used, as can be exemplified or defined by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives are specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

As used herein, terms in the singular, and the singular forms "a," "an," and "the," for example, include plural referents unless the content clearly dictates otherwise.

As is well understood in the art, metric measurement values provided herein can be easily converted to standard (S.I.) units and vice versa.

As used herein, "plant" includes an explant, plant part, seedling, plantlet or whole plant at any stage of regeneration or development. As commonly understood, a "corn plant" or "maize plant" refers to any plant of species *Zea mays* and includes all plant varieties that can be bred with corn, including wild maize species. In an aspect, corn plants disclosed herein are selected from the subspecies *Zea mays* L. ssp. *mays*. In an additional aspect, corn plants disclosed herein are selected from the group *Zea mays* L. subsp. *mays Indentata*, otherwise known as dent corn. In another aspect, corn plants disclosed herein are selected from the group *Zea mays* L. subsp. *mays Indurata*, otherwise known as flint corn. In an aspect, corn plants disclosed herein are selected from the group *Zea mays* L. subsp. *mays Saccharata*, otherwise known as sweet corn. In another aspect, corn plants disclosed herein are selected from the group *Zea mays* L. subsp. *mays Amylacea*, otherwise known as flour corn. In a further aspect, corn plants disclosed herein are selected from the group *Zea mays* L. subsp. *mays Everta*, otherwise known as popcorn. Plants disclosed herein also include hybrids, inbreds, partial inbreds, or members of defined or undefined populations.

As used herein, the term "inbred" refers to a plant line that has been bred for genetic homogeneity. In an aspect, a corn plant provided herein can be an inbred corn plant.

As used herein, the term "parent" refers to a member of a parental line which, when crossed with another parent, produces seed that can be used to generate a set of offspring plants, which can be referred to as the first filial (F1) generation. A "parent" can be a male or female parent used to produce the seed or offspring.

As used herein, the term "hybrid" means a progeny of mating between at least two genetically dissimilar parents or inbreds. Without limitation, examples of mating schemes include single crosses (A×B), modified single cross ((A×A')×B), double modified single cross ((A×A')×(B×B')), three-way cross ((A×B)×C), modified three-way cross ((A×B)×(C×C')), and double cross ((A×B)×(C×D)) where at least one parent in a modified cross is the progeny of a cross between sister lines. In an aspect, a corn plant provided herein is a hybrid corn plant. In another aspect, a corn seed provided herein is a hybrid corn seed. In an aspect, a hybrid corn seed can be produced by crossing two different inbred corn plants or populations.

As used herein, a "female" corn plant refers to a corn plant that comprises one or more female reproductive structures that are capable of producing corn ear(s) and kernels (seed). In an aspect, a corn plant provided herein is a female corn plant. In an aspect, a female corn plant is male sterile. In another aspect, a female corn plant is detasseled. In an aspect, the male reproductive organs or flowers (e.g., tassels) of a female corn plant are chemically sterilized (e.g., by application of an herbicide to plants lacking tolerance to the herbicide in those male reproductive organs, flowers or tassels), such as with a Roundup® Hybridization System (RHS). In another aspect, the male reproductive organs or flowers (e.g., tassels) of a female corn plant are sterilized due to cytoplasmic male sterility (or CMS). It is appreciated in the art that a corn plant is monoecious and can be considered both a male corn plant and a female corn plant. In an aspect, a female corn plant is capable of producing pollen. For purposes of the present disclosure, a corn plant having one or more male reproductive organ or structure, such as tassels, and/or capable of producing pollen, is considered a "female" plant if used to generate a corn ear(s) and/or corn seed (i.e., kernels) for production and harvest. A corn plant lacking a male reproductive organ or structure, such as tassels, having a sterilized male reproductive organ or structure, and/or incapable of producing pollen, is also considered a "female" plant if used to generate a corn ear(s) and/or seed (i.e., kernels) for production and harvest. A "female" corn plant may include any pollen-receiving corn plant that produces an ear or female reproductive organ, which can receive pollen from a pollen-bearing corn plant.

As used herein, a "male" corn plant refers to a corn plant that is capable of producing pollen (e.g., form one or more tassels) and is used to pollinate and/or fertilize one or more female corn plant(s) for seed production and harvest, even if the male plant further has a female reproductive structure(s) that is/are capable of producing a corn ear and kernels (seed), which may or may not be harvested. A "male" corn plant may include any pollen-bearing (or pollen-producing) corn plant, which can provide its pollen to a pollen-receiving corn plant.

As used herein, the term "plurality" in reference to an item means two or more of such items. For example, a "plurality of plants" means two or more plants.

As used herein, the phrase "at least one" in reference to something (e.g., any object, method step, etc.) means one or more of that something. For example, "at least one plant" or "at least one plants" each means one or more plants. Accordingly, "at least one" can include one or a plurality. Thus, where the present disclosure provides "one or more" of something or "at least one" of something, then the description further supports a plurality of that something.

As used herein, a "control plant" refers to a wild-type plant that does not have or exhibit a trait or phenotype to be analyzed, such as reduced plant height or stature.

In an aspect, the corn plants provided herein are dwarf corn plants. In another aspect, the female inbred corn plants provided herein are dwarf inbred corn plants. As used herein, a "dwarf" plant refers to an atypically small plant. Generally, such a "dwarf plant" has a stature or height that is reduced relative to a control plant (e.g., a wild-type sibling plant comprising all other traits except the dwarf trait) by about 30%, 35%, 40%, 45%, 50%, 55%, 60% or greater. In an aspect, corn plants provided herein are semi-dwarf inbred corn plants.

In another aspect, the female inbred corn plants provided herein are semi-dwarf inbred corn plants. As used herein, a "semi-dwarf plant" refers to a plant having a stature or height that is reduced relative to a control plant (e.g., a wild-type sibling plant comprising all other traits except the semi-dwarf trait) by about 5%, 10%, 15%, 20%, 25%, 30%, 35%, 40%, 45% or less. Such a semi-dwarf plant can be characterized by a reduced stem, stalk, or trunk length when compared to a control wild-type plant under comparable growth conditions, which can result from fewer internodes or shorter average internode length.

As used herein, the term "polynucleotide" refers to a nucleic acid molecule containing multiple nucleotides and generally comprises at least 2, at least 5, at least 10, at least 20, at least 30, at least 40, at least 50, at least 100, at least 250, at least 500, at least 1,000, at least 1,500, at least 2,000, at least 2,500, at least 3,000, at least 5,000, or at least 10,000 nucleotide bases. As an example, a polynucleotide provided herein can be a plasmid. The use of the terms "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. In an aspect, a polynucleotide provided herein is single-stranded. In another aspect, a polynucleotide provided herein is double-stranded.

As used herein, a "gene" refers to a polynucleotide that can produce a functional unit (without being limiting, for example, a mRNA and/or protein or a non-coding RNA molecule). A polynucleotide sequence encoding a non-coding RNA molecule can also be described as a transcribable DNA sequence. A non-coding RNA molecule can act as a suppression element that targets one or more gene(s) in a plant cell, such as one or more endogenous GA20 or GA3 oxidase gene(s), or as a RNA molecule, such as a guide RNA, etc., that guides a sequence-specific nuclease to cut and trigger a genome editing event at a target site in the genome. Non-limiting examples of non-coding RNA molecules include a microRNA (miRNA), a miRNA precursor (pre-miRNA), a small interfering RNA (siRNA), a small RNA (18-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA). In an aspect, a non-coding RNA provided herein is selected from the group consisting of a microRNA, a small interfering RNA, a secondary small interfering RNA, a transfer RNA, a ribosomal RNA, a trans-acting small interfering RNA, a naturally occurring antisense small interfering RNA, a heterochromatic small interfering RNA, and precursors thereof. In another aspect, a non-coding RNA provided herein is selected from the group consisting of a miRNA, a pre-miRNA, a siRNA, a hc-siRNA, a piRNA, a hairpin dsRNA, a ta-siRNA, a nat-siRNA, a crRNA, a tracrRNA, a gRNA, and a sgRNA. In another aspect, a non-coding RNA provided herein is a miRNA. In another aspect, a non-coding RNA provided herein is a siRNA.

As used herein, the term "genome" refers to the genetic material of an organism, consisting of DNA. The genome includes both coding and noncoding regions of DNA molecules. A genome can be a nuclear genome, a plastid genome, or a mitochondrial genome.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "transgene" refers to a recombinant DNA molecule, construct, or sequence comprising a gene and/or transcribable DNA sequence and integrated or inserted into a plant genome.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

As used herein, the term "heterologous" can refer broadly to a combination of two or more DNA molecules or sequences, such as a promoter and an associated transcribable DNA sequence, coding sequence, or gene, when such a combination is man-made and not normally found in nature. The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence. For example, a transcribable DNA sequence encoding a non-coding RNA molecule that targets one or more GA oxidase gene(s) for suppression can be operably linked to a heterologous plant-expressible promoter.

As used herein, the term "expression" refers to the process for converting the genetic information of a gene into a functional unit (without being limiting, for example, a mRNA and/or protein or a non-coding RNA molecule).

As used herein, the term "suppression" refers to a lowering, reduction or elimination of the expression level of a mRNA and/or protein encoded by a gene in a plant, plant cell, or plant tissue at one or more stage(s) of plant development, as compared to the expression level of such mRNA and/or protein in a wild-type or control plant, cell, or tissue at the same stage(s) of plant development. In an aspect, a polynucleotide provided herein can suppress the expression of a complementary target gene. In another aspect, a non-coding RNA molecule can suppress the expression of a complementary target gene.

As used herein, a "mutation" refers to an insertion, deletion, substitution, duplication, or inversion of one or more nucleotides and/or encoded amino acids as compared to a reference or wild-type nucleotide and/or amino acid sequence, which can be introduced by any suitable mutagenesis or gene editing technique.

Without being limited by any theory, it is presently proposed that the productivity and yield of commercial corn seed production can be increased by using certain combinations of male and female plants. Typically for commercial corn seed production, one inbred line is used as a male corn plant and another inbred line is used as a female corn plant. By placing or juxtaposing one or more (e.g., a population or row(s)) of male inbred plants next to or near one or more (e.g., a population or row(s)) of female inbred plants in an environment (e.g., the field), the male plants can contribute their genetic material (pollen) to the silk of the ears of the female plants to pollinate and fertilize the ears to produce seed (kernels). Since corn plants have both male and female reproductive structures or flowers, plants can be made "female" by removing, detasseling and/or sterilizing the male reproductive structures, flowers or tassels, such that the genetic contribution of pollen from the female plant is minimized or eliminated and the genetic contribution from pollen can be exclusively or nearly exclusively from the "male" plants. By selectively fertilizing the female ears with pollen from the male plants, hybrid corn seed can be produced if the male and female corn plants are different inbred lines. As well known in the art, corn plants grown from hybrid corn seed have increased yield for growers due to heterosis, or hybrid vigor. To improve agronomic practices with corn seed production, the male and female plants can each be planted in groups or rows. The rows of corn plants can be arranged in a regular or irregular pattern. Furthermore, more female corn plants than male corn plants can be planted to increase yield since corn ears and seeds are harvested from the female corn plants.

One limitation on increasing the number of female corn plants to increase seed production, such as by increasing the number of rows of female corn plants and thus the number of harvested ears, is that there needs to be a sufficient number of male plants to fully pollinate the female corn ears. There is a limit to how far pollen can flow or be distributed by wind, etc., with a decreasing amount or concentration of pollen at increasing distances from the male pollen donor. Thus, corn seed production can be effectively achieved with 4:1, 5:2 or 6:2 row arrangements of female and male plants, respectively (e.g., four female rows, followed by one male row, followed by four female rows, etc., or six female rows, followed by two male rows, followed by six female rows, etc.). Without being limited by any theory, greater numbers of female rows may lead to reduced pollination, fertilization, and/or yield, especially for females in the more interior or distant rows relative to the male plants. Other factors can interfere with pollen flow to female corn plants, such as obstruction by neighboring plants. If the female plants have the same or similar height as the male plant, then the neighboring plants themselves can obstruct air and pollen flow to more interior or distant female rows, even after detasseling of the female plants.

Without being limited by any theory, it is presently proposed, however, that pollen flow could be improved and increased to more interior or distant females or female rows if the female corn plants or rows could be made shorter in height relative to the male plants or rows to not obstruct, or lessen the obstruction of, the flow of pollen to the more interior or distant female corn plants. Indeed, it has been observed that the middle two rows of females in a 4:1 configuration in the field of females to males can have a small yield reduction relative to the other two rows of females. Without being limited by any theory, if pollen flow and/or pollen load could be improved or increased, not only could ear pollination and fertilization rates be increased, leading to larger ears and/or reduced ear tip void, but the number of female corn plants and/or rows, relative to the number of male plants, could be increased to increase the number of ears/seeds harvested due to the ability to pollinate and/or fertilize the more interior or distant female corn plants. Thus, alternative row arrangements of female and male plants, such as 5:1 or 6:1, and potentially 7:1, 8:1, 7:2, 8:2, etc., female to male rows, respectively, can be made more effective and productive with improved pollination and/or fertilization of the more interior or distant female corn plants. If the male and female plants are planted in a regular pattern of rows, the male plants may be planted in rows with equal or similar spacing to the other (female) rows, or male plants may alternatively be inter-planted between female rows.

Even though detasseling can reduce the effective plant height of females (to some extent) at the time of pollination, females having a shorter plant height prior to detasseling should allow for improved pollen flow relative female plants having a more normal height due to the greater height differences between the male and female plants and lower obstruction of pollen flow with the shorter females. This benefit can be additionally useful for female plants having male reproductive structures or tassels that are sterilized by chemical treatment without a reduction in plant height due to detasseling. As a result of the improved pollen flow and/or pollen load, the process of seed production could be made more environmentally sustainable due to the ability to produce as much or more seed on a smaller footprint of fewer acres.

Without being limited by any theory, it is further proposed that shorter plant heights of females may decrease light shading of neighboring male plants, and with reduced shading the male plants may have a reduced or eliminated tassel skeletonization (TSK) in comparison to male plants next to female plants having the same or similar plant height. With reduced tassel skeletonization, pollen production or load by or from the male corn plants can be increased. In some prior cases, row arrangements, such as 4:3, 3:2, and 2:2 females to males, have been used to increased pollen load. However, the present system and method can help overcome these hurdles by reducing tassel skeletonization and permitting fewer numbers of male plants or rows of male plants used for seed production due to the higher pollen load produced per male plant. Therefore, without being limited by theory, it is proposed that corn seed production can be increased with shorter females not only by improving pollen flow, but also by increasing pollen load due to reduced tassel skeletonization of the male plants.

According to another aspect of the present disclosure, it is proposed that corn seed production can be increased with shorter females because shorter female plants can exhibit less root and stalk lodging and/or increased standability at or after the normal time of harvest, which may allow for more flexibility in how long corn is left in the field after drying down and/or allow for direct harvesting of hybrid seeds in a production field. These benefits may further enhance the yield and/or efficiency of corn seed production fields in addition to improved pollen flow, reduced skeletonization and higher number of females in the field. In an aspect, hybrid seeds produced here are collected via direct harvesting. In another aspect, shorter female corn plants are left in a corn field post maturity and can afford a much longer time period for harvesting seeds without jeopardizing the eventual seed yield. As used herein, "direct harvesting" refers to the harvesting of crop seeds from plants with a combine harvester in the field with little or no further drying or other processing or desiccation steps prior to seed storage. As used herein, "standability" refers to the ability of a plant to stand upright in a position that enables it to be harvested by standard farm equipment (e.g., a combine harvester). Corn plants with better standability, such as dwarf corn plants, semi-dwarf corn plants, and brachytic corn plants, are resistant to lodging. As used herein, "lodging" can refer to either "stalk lodging" or "root lodging." Stalk lodging occurs when the corn plant stalk is severely bent or broken below the ear. Root lodging occurs when the corn plant is leaning at an angle (e.g., greater than or equal to 45° relative to perpendicular from the ground, or at an angle less than 45° relative to the ground).

According to some embodiments, it is proposed that pollen flow could be further improved or increased by optionally using a fan, blower or other device that increases or directs air flow (collectively, "air flow device"). Such an air flow device(s) could be placed at one or more predetermined distance(s) from a male corn plant(s), such as a row(s) of male corn plants, on one side of such male corn plant(s) and/or row or rows of male corn plants, wherein the female corn plant(s), such as a row(s) of female corn plants, are on the other (or opposite) side of such male corn plant(s) and/or row or rows of male corn plants relative to the air flow device(s). Such an air flow device could be fixed (i.e., stationary) or mobile. For example, a mobile or moveable air flow device may move along or parallel to a row of male plants. According to another embodiment, a pollinating device or vehicle may be used to promote or enhance the efficient release, distribution or spreading of pollen from male plants to female plants. See, e.g., PCT Application Publication No. WO 2018/129302, the entire contents and disclosure of which are incorporated herein by reference.

There are various ways in which a corn plant can be made to have a shorter semi-dwarf plant height. According to many aspects, a corn plant can be made shorter or semi-dwarf relative to a control plant by lowering the level(s) of active GAs in one or more tissue(s) of the plant, such as by suppressing, mutating or editing one or more GA oxidase gene(s) in the corn plant. According to other aspects, a corn plant or plurality of corn plants provided herein can have a mutation or edit in an auxin, brassinosteroid, jasmonic acid, cell cycle regulation, and/or other pathway gene(s) that are known to affect plant height. According to yet other aspects, a female corn plant or plurality of female corn plants provided herein can be made shorter by application of one or more chemistries, such as GA inhibitors, known to affect plant height. Additional information regarding chemistries, such as GA inhibitors, can be found in WO 2017/011791 and U.S. Patent Application Publication Nos. 2019/0014730 and 2019/0014731, which are incorporated herein by reference in their entireties. According to another aspect, a corn plant or plurality of corn plants provided herein can comprise a mutation or mutant allele in one or more loci or genes that have been associated with a short stature phenotype in corn, such as one or more of the following: anther ear 1 (An1), brachytic 1 (Br1), *brevis* plant 1 (Bv1) or brachytic 3 (br3), crinkly 4 (Cr4), compact plant 2 (Ct2), dwarf plant 1 (d1), dwarf plant 8 (d8), dwarf plant 9 (d9), *nana* plant 1 (Na1), *nana* plant 2 (Na2), non-chromosomal stripe 3 (Nsc3), narrow leaf dwarf 1 (N1d1), reduced plant 1 (Rd1), semi-dwarf/(Sdw1), semi-dwarf 2 (Sdw2), tangled 1 (Tan1), terminal ear 1 (Te1), and vanishing tassel 2 (Vt2).

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the $20^{th}$ century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro bacilliform virus (RTBV) promoter, which drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), may be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this can be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

In an aspect, a corn plant or plurality of corn plants provided herein can each comprise a recombinant DNA construct or polynucleotide sequence, where the recombinant DNA construct or polynucleotide sequence comprises a transcribable DNA sequence encoding a non-coding RNA molecule that targets at least one endogenous GA20 or GA3 oxidase gene for suppression. In another aspect, a corn plant provided herein can comprise suppressed GA3 oxidase gene expression in one or more tissues as compared to a wild-type control plant. In another aspect, a corn plant provided herein can comprise suppressed GA20 oxidase gene expression in one or more tissues as compared to a wild-type control plant. In another aspect, a corn plant provided herein can comprise a mutation at or near an endogenous GA oxidase gene, where the expression level of the endogenous GA oxidase gene is reduced or eliminated in the corn plant, and where the corn plant has a shorter plant height as compared to a wild-type control plant. In an aspect, a corn plant provided herein can comprise a recombinant polynucleotide capable of suppressing expression of one or more GA20 oxidase and/or GA3 oxidase gene(s) and/or mRNA(s) transcribed therefrom. Alternatively, a corn plant provided herein can comprise one or more mutation(s) or edit(s) in one or more GA20 oxidase and/or GA3 oxidase gene(s). In an aspect, a female corn plant provided herein can comprise a mutation in a GA20 oxidase locus or gene as compared to a wildtype GA20 oxidase locus or gene. In an aspect, a corn plant provided herein is homozygous (or biallelic) for a mutation or an edit in one or more GA20 oxidase loci or genes as compared to a wildtype GA20 oxidase locus or gene. In another aspect, a corn plant provided herein is heterozygous for a mutation or an edit in one or more GA20 oxidase loci or genes as compared to a wildtype GA20 oxidase locus or gene. In another aspect, a corn plant provided herein can comprise a mutation in a GA3 oxidase locus or gene as compared to a wildtype GA3 oxidase locus or gene. In an aspect, a corn plant provided herein is homozygous (or biallelic) for a mutation or an edit in one or more GA3 oxidase loci or genes as compared to a wildtype GA3 oxidase locus or gene. In another aspect, a corn plant provided herein is heterozygous for a mutation or an edit in a one or more GA3 oxidase loci or genes as compared to a wildtype GA3 oxidase locus or gene. In another aspect, a corn plant provided herein can comprise a heterologous polynucleotide capable of suppressing expression of a GA20 oxidase gene or an mRNA transcribed therefrom.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

As introduced above, instead of suppressing one or more GA oxidase gene(s), active GA levels can also be reduced in a corn plant by mutation or editing of one or more GA20 and/or GA3 oxidase gene(s).

Corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

In an aspect, a corn plant provided herein is homozygous (or biallelic) for a mutation or an edit in a GA20 oxidase_5 locus or gene as compared to a wildtype GA20 oxidase_5 locus or gene and homozygous (or biallelic) for a mutation or an edit in a GA20 oxidase_3 locus or gene as compared to a wildtype GA20 oxidase_3 locus or gene. In an aspect, a corn plant provided herein is homozygous (or biallelic) for a mutation or an edit in a GA20 oxidase_5 locus or gene as compared to a wildtype GA20 oxidase_5 locus or gene and heterozygous for a mutation or an edit in a GA20 oxidase_3 locus or gene as compared to a wildtype GA20 oxidase_3 locus or gene. In an aspect, a corn plant provided herein is heterozygous for a mutation or an edit in a GA20 oxidase_5 locus or gene as compared to a wildtype GA20 oxidase_5 locus or gene and homozygous (or biallelic) for a mutation or an edit in a GA20 oxidase_3 locus or gene as compared to a wildtype GA20 oxidase_3 locus or gene. See, e.g., U.S. Provisional Patent Application Nos. 62/631,412; 62/631, 416; and 62/710,302; the contents and disclosures of which are incorporated herein by reference in their entireties.

TABLE 1

DNA and protein sequences by sequence identifier for GA20 oxidase genes in corn.

| GA20 oxidase Gene | cDNA | Coding Sequence (CDS) | Protein |
| --- | --- | --- | --- |
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
| --- | --- | --- | --- |
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon;

nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

In addition to phenotypic observations with targeting the GA20 oxidase_3 and/or GA20 oxidase_5 gene(s), or the GA3 oxidase_1 and/or GA3 oxidase_2 gene(s), for suppression, a semi-dwarf phenotype is also observed with suppression of the GA20 oxidase_4 gene. The genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

In an aspect, the present disclosure provides a corn plant or plurality of corn plants each comprising a recombinant DNA construct or polynucleotide sequence comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or corn cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, and/or 33, and wherein the transcribable DNA sequence is operably linked to a plant-expressible promoter, which can be heterologous with respect to the transcribable DNA sequence and/or the corn plant.

Recombinant DNA constructs and transgenic corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues.

As used herein, a "plant-expressible promoter" refers to a promoter that drives, causes, or initiates expression of a transcribable DNA sequence or transgene operably linked to such promoter in one or more plant cells or tissues, such as one or more cells or tissues of a corn plant. In an aspect, a plant-expressible promoter is a constitutive promoter. In another aspect, a plant-expressible promoter is a vascular promoter. As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters. In another aspect, a plant-expressible promoter is a leaf promoter. As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

Promoters that drive enhanced expression in certain tissues of the plant relative to other plant tissues are referred to as "tissue-enhanced" or "tissue-preferred" promoters. Thus, a "tissue-preferred" promoter causes relatively higher or preferential or predominant expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters.

A non-limiting exemplary plant-expressible promoter is the RTBV promoter. In an aspect, a plant-expressible promoter is an RTBV promoter. In another aspect, a plant expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 39, SEQ ID NO: 40, or a functional portion thereof.

Non-limiting exemplary vascular promoters include a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, and a rice yellow stripe 2 (OsYSL2) promoter. In an aspect, a vascular promoter is selected from the group consisting of a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat protein (CP) promoter, a rice yellow stripe 1 (YS1)-like promoter, a rice yellow stripe 2 (OsYSL2) promoter, and functional portions thereof. In an aspect, a vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 41, SEQ ID NO: 42, SEQ ID NO: 43, SEQ ID NO: 44, SEQ ID NO: 45, or a functional portion thereof.

Non-limiting exemplary leaf promoters include a RuBisCO promoter, a PPDK promoter, a FDA promoter, a Nadh-Gogat promoter, a chlorophyll a/b binding protein gene promoter, a phosphoenolpyruvate carboxylase (PEPC) promoter, and a Myb gene promoter. In an aspect, a leaf promoter is selected from the group consisting of a RuBisCO promoter, a PPDK promoter, a FDA promoter, a Nadh-Gogat promoter, a chlorophyll a/b binding protein gene promoter, a phosphoenolpyruvate carboxylase (PEPC) promoter, a Myb gene promoter, and functional portions thereof. In an aspect, a leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 46, SEQ ID NO: 47, SEQ ID NO: 48, or a functional portion thereof.

Non-limiting exemplary constitutive promoters include an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, and a maize alcohol dehydrogenase. In an aspect, a constitutive promoter is selected from the group consisting of an actin promoter, a CaMV 35S or 19S promoter, a plant ubiquitin promoter, plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, a maize alcohol dehydrogenase, or functional portions thereof. In an aspect, a constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, or a functional portion thereof.

In another aspect, the present disclosure provides a corn plant or plurality of corn plants each comprising a recombinant DNA construct or polynucleotide sequence comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase gene having at least 80%, at least 85%, at least 90%, at least 95%, at least 96%, at least 97%, at least 98%, at least 99%, at least 99.5%, or 100% identical to SEQ ID NO: 9, 12, 15, 30, and/or 33, and wherein the transcribable DNA sequence is operably linked to a plant-expressible promoter, which can be heterologous with respect to the transcribable DNA sequence and/or the corn plant.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to some embodiments, the first expression cassette comprises a first transcribable DNA sequence encoding a non-coding RNA targeting a GA20 oxidase_3 gene for suppression. According to other embodiments, the first expression cassette comprises a first transcribable DNA sequence encoding a non-coding RNA targeting a GA20 oxidase_5 gene for suppression. According to yet further embodiments, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

For suppression of a GA20 oxidase_3 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 7, SEQ ID NO: 8, and SEQ ID NO: 34.

For suppression of a GA20 oxidase_4 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 10, SEQ ID NO: 11, and SEQ ID NO: 38.

For suppression of a GA20 oxidase_5 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 13, SEQ ID NO: 14, and SEQ ID NO: 35.

For suppression of a GA20 oxidase_3 gene and a GA20 oxidase_5 gene, a transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 7, SEQ ID NO: 8, and SEQ ID NO: 34; and the transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 13, SEQ ID NO: 14, and SEQ ID NO: 35.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

For suppression of a GA3 oxidase_1 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 28, SEQ ID NO: 29, and SEQ ID NO: 36.

For suppression of a GA3 oxidase_2 gene, a first transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 31, SEQ ID NO: 32, and SEQ ID NO: 37.

For suppression of a GA3 oxidase_1 gene and a GA3 oxidase_2 gene, a transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 28, SEQ ID NO: 29, and SEQ ID NO: 36; and the transcribable DNA sequence comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence selected from the group consisting of SEQ ID NO: 31, SEQ ID NO: 32 and SEQ ID NO: 37.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA interference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the corn plant, thereby suppressing the endogenous GA20 oxidase and/or GA3 oxidase gene(s).

According to an aspect, a corn plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control corn plant.

According to an aspect, a corn plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control corn plant.

According to an aspect, a corn plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control corn plant.

According to an aspect, a corn plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control corn plant.

According to an aspect, the at least one tissue of a corn plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

Certain mutations of brachytic genes have been shown to result in a short stature, semi-dwarf phenotype. In an aspect of the present disclosure, a female corn plant is provided having a non-silent mutation or edit in a brachytic gene. See, e.g., PCT Application No. PCT/US2016/029492 and PCT/US2017/067888, the entire contents and disclosures of which are incorporated herein by reference. Thus, a shorter female corn plant can comprise a mutation (or edit) in a brachytic gene, and can be homozygous (or biallelic) for a mutation (or edit) in a brachytic gene. As used herein, a "brachytic mutant plant" refers to a plant having a short semi-dwarf height and stature relative to a control plant (e.g., a wild-type sibling plant comprising all other traits except the brachytic trait) due to a shortening of the average internode length. Such a brachytic mutant plant can have a short semi-dwarf height and stature due to a shortening of the average internode length. As used herein, a "brachytic gene", "BR gene" or "br gene", or "Br gene" refers to any brachytic gene in a corn plant that when mutated or edited to reduce its expression or function can result in a shorter, semi-dwarf corn plant and phenotype. In an aspect, a female inbred corn plant or plurality of female inbred corn plants provided herein each has a non-silent mutation or edit in a brachytic gene. In an aspect, the brachytic gene is a br1 mutant gene. In another aspect, the brachytic gene is a br2 mutant gene. In yet another aspect, the brachytic gene is a br3 mutant gene.

In maize, brachytic mutants have a short stature due to a shortening of the internode length without a corresponding reduction in the number of internodes or the number and size of other organs, including the leaves, ear and tassel. See Kempton *J. Hered.* 11:111-115(1920); Pilu et al., *Molecular Breeding,* 20:83-91(2007). Three brachytic mutants have been isolated in maize to date: brachytic1 (br1), brachytic2 (br2) and brachytic3 (br3). Both br1 and br3 mutations cause a reduction in corn plant height, which has been thought too severe for commercial exploitation due to potential impacts on yield. In contrast, the br2 mutant has particular agronomic potential because of shortening of the internodes of the lower stalk without an obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with gibberellins, auxins, brassinosteroids and cytokinins, suggesting that the biosynthesis of these hormones is not modified by the br2 mutation. Multani et al. identified the genomic sequence of the br2 gene (SEQ ID NO: 58) and deposited it under GenBank Accession No. AY366085. See Multani et al., Science, 302(5642)81-84 (2003). br2 was annotated to encode a putative protein similar to adenosine triphosphate (ATP)-binding cassette transporters of the multidrug resistant (MDR) class of P-glycoproteins (PGPs). Pilu et al. reported a br2-23 allele having an 8-bp deletion in the 3' end of the br2 gene and claimed a direct relationship between this deletion and the brachytic phenotype in their br2-23 plants. See Pilu et al., *Molecular Breeding,* 20:83-91(2007). Nevertheless, the use of brachytic mutations in corn has not been exploited commercially partly because of the severity of the available brachytic mutant alleles.

As used herein, a "brachytic allele" is an allele at a particular genomic locus that confers, or contributes to, a brachytic or semi-dwarf phenotype, such as an allele of a brachytic gene that causes a brachytic or semi-dwarf phenotype, or alternatively, is an allele that allows for the identification of plants that comprise a brachytic phenotype or plants that can give rise to progenies with a brachytic phenotype. For example, a brachytic allele of a marker can be a marker allele that segregates with a brachytic phenotype.

In some aspects, a brachytic, dwarf, or semi-dwarf corn plant comprises a reduced level of br2 mRNA and/or protein, as compared to a control corn plant not having the brachytic allele. In other aspects, the corn plants or seeds comprise reduced br2 protein activity compared to a control plant not having the brachytic allele. In some aspects, the height of a brachytic, dwarf, or semi-dwarf plant comprising a brachytic allele at maturity is reduced by at least 10%, at least 20%, at least 30%, at least 40%, at least 50%, at least 60%, or at least 70% compared to a control plant not having a brachytic allele. In another aspect, the yield of a brachytic, dwarf, or semi-dwarf corn plant comprising a brachytic allele is equal to or more than the yield of a control plant not having the brachytic allele. In an aspect, a brachytic, dwarf, or semi-dwarf corn plant comprising a brachytic allele requires about 5%, 10%, 15%, 20%, or 25% fewer heat units than a control plant not having the brachytic allele to reach anthesis. In an aspect, a brachytic, dwarf, or semi-dwarf corn plant is homozygous for a brachytic allele. In another aspect, a brachytic, dwarf, or semi-dwarf corn plant is heterozygous for a brachytic allele. In another aspect, a brachytic, dwarf, or semi-dwarf corn plant is a hybrid. In another aspect, a brachytic, dwarf, or semi-dwarf corn plant is an inbred, such as a female inbred.

In an aspect, this disclosure provides brachytic, dwarf, or semi-dwarf corn plants comprising a brachytic allele comprising one or more sequences selected from the group consisting of SEQ ID Nos: 59-85. In another aspect, a brachytic, dwarf, or semi-dwarf corn plant comprises a single gene conversion of the br2 genomic region.

In an aspect, a brachytic, dwarf, or semi-dwarf corn plant comprises a brachytic allele at a polymorphic locus, wherein the polymorphic locus is associated with, or linked to, a marker selected from the group consisting of SEQ ID NOs: 86-131. In another aspect, a brachytic allele at a polymorphic locus is within 20 cM (centimorgans), within 10 cM, within 5 cM, within 1 cM, or within 0.5 cM of a marker selected from the group consisting of SEQ ID NOs: 86-131. In another aspect, a brachytic allele is at a polymorphic locus within 20 cM, within 10 cM, within 5 cM, within 1 cM, or within 0.5 cM of a marker selected from the group consisting of SEQ ID NOs: 90-117. In another aspect, a brachytic allele is at a polymorphic locus within 20 cM, within 10 cM, within 5 cM, within 1 cM, or within 0.5 cM of a marker selected from the group consisting of SEQ ID NOs: 92 and 117.

In an aspect, a corn plant or plurality of corn plants provided herein, such as a female corn plant or inbred or a plurality or population of female corn plants, can comprise at least one non-natural brachytic mutation, where the corn plant exhibits a semi-dwarf phenotype compared to a control corn plant not comprising the at least one non-natural brachytic mutation when grown under comparable conditions. In another aspect, a corn plant provided herein can comprise at least one non-natural brachytic mutation. In another aspect, a corn plant provided herein can comprise at least one non-natural brachytic mutant allele. In another aspect, a corn plant provided herein can comprise at least one non-natural brachytic mutation and exhibits a semi-dwarf phenotype. In another aspect, a corn plant provided herein can comprise at least one non-natural brachytic mutant allele and exhibit a semi-dwarf phenotype. In another aspect, a corn plant provided herein can comprise a non-naturally occurring mutation in a br gene reducing the activity of the br gene, where the mutation is not introduced via a transposon. In another aspect, a corn plant provided herein can comprise a mutation in a br2 locus or gene as compared to a wildtype br2 locus or gene. In an aspect, a corn plant provided herein is homozygous (or biallelic) for a mutation in a br2 locus or gene as compared to a wildtype br2 locus or gene. In another aspect, a corn plant provided herein is heterozygous for a mutation in a br2 locus or gene as compared to a wildtype br2 locus or gene. In another aspect, a corn plant provided herein can comprise a modified br2 gene with reduced activity, where the corn plant does not comprise a br2-23 brachytic allele or SNP5259. In another aspect, a corn plant provided herein can comprise a synthetic mutation in a br gene, reducing the activity of the br gene.

In an aspect, a corn plant or plurality of corn plants provided herein, such as a female corn plant or inbred or a plurality or population of female corn plants, can each comprise a non-transgene or non-transposon mediated mutation in a br gene reducing the activity of the br gene. In another aspect, a corn plant provided herein can comprise a recessive, non-transgenic br mutant allele. In another aspect, a corn plant provided herein can comprise a heterologous polynucleotide capable of suppressing expression of a br gene or an mRNA transcribed therefrom. In another aspect, a corn plant provided herein can comprise a heterologous polynucleotide capable of suppressing expression of a br1 gene or an mRNA transcribed therefrom. In another aspect, a corn plant provided herein can comprise a heterologous polynucleotide capable of suppressing expression of a br2 gene or an mRNA transcribed therefrom. In another aspect, a corn plant provided herein can comprise a heterologous polynucleotide capable of suppressing expression of a br3 gene or an mRNA transcribed therefrom. Additional details about altering the expression of br genes can be found in PCT Application No. PCT/US2016/029492 and PCT/US2017/067888, the entire contents and disclosure of which are incorporated herein by reference.

Corn leaves consist of four main anatomical parts: a proximal sheath, a ligule, an auricle, and a distal blade. The sheath wraps around the stem and younger leaves, while the blade is flattened in the mediolateral axis (midrib to margin). The ligule and auricle are found at the blade/sheath boundary; the ligule is an adaxial (upper) membranous structure that acts as a collar around the stem, and the auricle is a projection on the lower surface of the blade base that connects the blade to the sheath. Stages of corn plant growth are divided into vegetative (V) stages and reproductive (R) stages. Upon germination, a corn plant is in the VE stage (emergence). Once the first leaf collar (e.g., the ligule) is visible, the corn plant is in the V1 stage. The emergence of the second leaf collar signifies V2 stage; the emergence of the third leaf collar signifies the V3 stage; and so on until the tassel emerges. For example, if twelve leaf collars are visible, the plant is a V12 stage plant. Once the bottom-most branch of the tassel emerges the plant is in VT stage, which is the final vegetative stage. The reproductive stage of growth occurs after the vegetative stage. The number of vegetative stages prior to VT stage can vary by environment and corn line. The first reproductive stage (R1; silking stage) occurs when silk is visible outside the husk leaves surrounding an ear of corn. R2 (blistering stage) occurs when corn kernels are white on the outside and are filled with a clear liquid inside. R3 (milk stage) occurs when the kernels are yellow on the outside and are filled with a milky white fluid inside. R4 (dough stage) occurs when the kernels are filled with a thick, or pasty, fluid. In some corn lines the cob will also turn pink or red at this stage. R5 (dent stage) occurs when a majority of the kernels are at least partially dented. The final reproductive stage, R6 (physiological maturity), occurs when the kernels have attained their maximum dry weight.

The height of a corn plant can be measured using a variety of methods known in the art. The height of a corn plant can also be determined based on a variety of anatomical locations on a corn plant. In an aspect, the height of a corn plant is measured as the distance between the soil or ground and the ligule of the uppermost fully-expanded leaf of the corn plant. As used herein, a "fully-expanded leaf" is a leaf where the leaf blade is exposed and both the ligule and auricle are visible at the blade/sheath boundary. In another aspect, the height of a corn plant is measured as the distance between the soil or ground and the upper leaf surface of the leaf farthest from the soil. In another aspect, the height of a corn plant is measured as the distance between the soil or ground and the arch of the highest corn leaf that is at least 50% developed. As used herein, an "arch of the highest corn leaf" is the highest point of the arch of the uppermost leaf of the corn plant that is curving downward. In another aspect, the height of a corn plant is measured at the first reproductive (R1) stage. Exemplary, non-limiting methods of measuring plant height include comparing photographs of corn plants to a height reference, or physically measuring individual corn plants with a suitable ruler.

As used herein, the term "ground" or "ground level" used in relation to a corn plant, such as to measure plant height, refers to the top or uppermost surface of the growth medium or soil (e.g., earth) from which the corn plant grows.

Corn plant height varies depending on the line or variety grown, whether the plant is a hybrid or inbred, and environmental conditions. Although hybrid corn plants can reach a height of over 3.6 meters tall by maturity, a height of around 2.0-2.5 meters by maturity for hybrid plants is more common. Inbred corn lines tend to be shorter than hybrids and can commonly have an average plant height ranging from about 1.75 meters to about 2.25 meters, or from about 1.85 meters to about 2.25 meters, or from about 1.95 meters to about 2.25 meters, or from about 2.05 meters to about 2.25 meters, or from about 1.85 to about 2.35 meters, or from about 1.95 meters to about 2.35 meters, or from about 2.05 meters to about 2.35 meters, or from about 2.15 meters to about 2.35 meters, or from about 1.8 meters to about 2.0 meters, or from about 1.8 meters to about 2.1 meters, or from about 1.8 meters to about 2.2 meters, or from about 1.8 meters to about 2.3 meters, or from about 1.9 meters to about 2.1 meters, or from about 1.9 meters to about 2.2 meters, or from about 1.9 meters to about 2.3 meters, or from about 2.0 meters to 2.2 meters, or from about 2.0 meters to 2.3 meters, or from about 1.75 meters to about 2.35 meters. According to some embodiments, a corn line or variety, or transgenic, mutated or edited corn plant, or a plurality or population of such a line, variety, transgenic, mutated, or edited corn plant, is provided having a reduced average plant height at maturity relative to a control plant of about 2.3 meters or less, about 2.2 meters or less, about 2.1 meters or less, about 2.0 meters or less, about 1.9 meters or less, about 1.8 meters or less, about 1.7 meters or less, about 1.6 meters or less, or about 1.5 meters or less.

The "average height" of a group of corn plants is the height obtained by dividing the sum of the heights of all plants within the group by the total number of plants within the group. For clarity, an "average height" for one plant is simply the height of that plant (i.e., its height divided by "1" equals its height).

In an aspect, the average height of the female inbred corn plants provided herein is at least 2% less or lower than the height (or average height) of at least one male inbred corn plant(s) (or the average plant height of male inbred corn plants) provided herein. In an aspect, the average height of the female inbred corn plants provided herein is at least 2.5% less or lower than the height (or average height) of at least one male inbred corn plant(s) (or the average plant height of male inbred corn plants) provided herein. In an aspect, the average height of the female inbred corn plants provided herein is at least 3% less or lower than the height (or average height) of at least one male inbred corn plant(s) (or the average plant height of male inbred corn plants) provided herein. In an aspect, the average height of the female inbred corn plants provided herein is at least 4% less or lower than the height (or average height) of at least one male inbred corn plant(s) (or the average plant height of male inbred corn plants) provided herein. In an aspect, the average height of the female inbred corn plants provided herein is at least 5% less or lower than the height (or average height) of at least one male inbred corn plant(s) provided herein. In an aspect, the average height of the female inbred corn plants provided herein is at least 10% less or lower than the height (or average height) of at least one male inbred corn plant(s) provided herein. In another aspect, the average height of the female inbred corn plants provided herein is at least 15% less or lower than the height (or average height) of at least one male inbred corn plant(s) provided herein. In another aspect, the average height of the female inbred corn plants provided herein is at least 20% less or lower than the height (or average height) of at least one male inbred corn plant(s) provided herein. In another aspect, the average height of the female inbred corn plants provided herein is at least 25% less or lower than the height (or average height) of at least one male inbred corn plant provided herein. In another aspect, the average height of the female inbred corn plants provided herein is at least 30% less or lower than the height (or average height) of at least one male inbred corn plant(s) provided herein. In another aspect, the average height of the female inbred corn plants provided herein is at least 35% less or lower than the height (or average height) of at least one male inbred corn plant(s) provided herein. In another aspect, the average height of the female inbred corn plants provided herein is at least 40% less or lower than the height (or average height) of at least one male inbred corn plant(s) provided herein. In another aspect, the average height of the female inbred corn plants provided herein is at least 45% less or lower than the height (or average height) of at least one male inbred corn plant(s) provided herein. In another aspect, the average height of the female inbred corn plants provided herein is at least 50% less or lower than the height (or average height) of at least one male inbred corn plant(s) provided herein. In another aspect, the average height of the female inbred corn plants provided herein is at least 55% less or lower than the height (or average height) of at least one male inbred corn plant(s) provided herein. In another aspect, the average height of the female inbred corn plants provided herein is at least 60% less or lower than the height (or average height) of at least one male inbred corn plant(s) provided herein. In another aspect, the average height of the female inbred corn plants provided herein is at least 65% less or lower than the height (or average height) of at least one male inbred corn plant(s) provided herein. In another aspect, the average height of the female inbred corn plants provided herein is at least 70% less or lower than the height (or average height) of at least one male inbred corn plant(s) provided herein. In another aspect, the average height of the female inbred corn plants provided herein is at least 75% less or lower than the height (or average height) of at least one male inbred corn plant(s) provided herein.

Corn plant height can be measured according to two different methods. According to one method, corn plant height is measured from the ground or soil to the ligule (or collar) of the uppermost fully expanded leaf—i.e., from the ground or soil to the base of the uppermost collared leaf. According to another method, corn plant height is measured from the ground or soil to the uppermost leaf surface of the leaf farthest from the soil. This latter method will typically give a higher plant height than the former method due to measuring a feature of the plant that is further from the ground. According to another method for measuring the height of a corn plant during and after VT stage, plant height can be measured from the ground or soil to the tops of the tassel. Relative plant heights and percentage differences in plant height as provided herein may be applied to each of these methods. For purposes of clarity, however, if the method for measuring plant height is not expressly stated herein, then the plant height is measured as the distance between the ground or soil and the ligule (or collar) of the uppermost fully expanded leaf—i.e., from the ground or soil to the base of the uppermost collared leaf.

According to embodiments of the present disclosure, corn plant heights, average corn plant heights, male-to-female or female-to-male corn plant height differences, male-to-female or female-to-male average corn plant height differences, male-to-female average plant height ratios, female-to-male average plant height ratios, male-to-female plant height ratios, and female-to-male plant height ratios as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the corn plant height(s), average corn plant height(s), male-to-female or female-to-male corn plant height difference(s), male-to-female plant height ratio(s), and/or female-to-male plant height ratio(s) as described herein is at R1 stage. According to present embodiments, corn developmental stages are defined according to the Iowa State University (ISU) method. See, e.g., Ritchie, S. W. et al., How a corn plant develops. Special Report No. 48, Iowa State University, CES, Ames, Iowa, reprinted 1996, the entire contents and disclosure of which are incorporated herein by reference.

In an aspect, the female inbred corn plants provided herein comprise an average height that is between 2% and 30% less or lower than the height (or average height) of at least one male inbred corn plant(s) (or the average plant height of male inbred corn plants) provided herein. In an aspect, the female inbred corn plants provided herein comprise an average height that is between 2% and 25% less or lower than the height (or average height) of at least one male inbred corn plant(s) (or the average plant height of male inbred corn plants) provided herein. In an aspect, the female inbred corn plants provided herein comprise an average height that is between 2% and 20% less or lower than the height (or average height) of at least one male inbred corn plant(s) (or the average plant height of male inbred corn plants) provided herein. In an aspect, the female inbred corn plants provided herein comprise an average height that is between 2% and 15% less or lower than the height (or average height) of at least one male inbred corn plant(s) (or the average plant height of male inbred corn plants) provided herein. In an aspect, the female inbred corn plants provided herein comprise an average height that is between 2% and 10% less or lower than the height (or average height) of at least one male inbred corn plant(s) (or the average plant height of male inbred corn plants) provided herein. In an aspect, the female inbred corn plants provided herein comprise an average height that is between 2% and 5% less or lower than the height (or average height) of at least one male inbred corn plant(s) (or the average plant height of male inbred corn plants) provided herein. In an aspect, the female inbred corn plants provided herein comprise an average height that is between 2.5% and 30% less or lower than the height (or average height) of at least one male inbred corn plant(s) (or the average plant height of male inbred corn plants) provided herein. In an aspect, the female inbred corn plants provided herein comprise an average height that is between 2.5% and 25% less or lower than the height of at least one male inbred corn plant(s) (or the average plant height of male inbred corn plants) provided herein. In an aspect, the female inbred corn plants provided herein comprise an average height that is between 2.5% and 20% less or lower than the height of at least one male inbred corn plant(s) (or the average plant height of male inbred corn plants) provided herein. In an aspect, the female inbred corn plants provided herein comprise an average height that is between 2.5% and 15% less or lower than the height of at least one male inbred corn plant(s) (or the average plant height of male inbred corn plants) provided herein. In an aspect, the female inbred corn plants provided herein comprise an average height that is between 2.5% and 10% less or lower than the height (or average height) of at least one male inbred corn plant(s) (or the average plant height of male inbred corn plants) provided herein. In an aspect, the female inbred corn plants provided herein comprise an average height that is between 2.5% and 5% less or lower than the height (or average height) of at least one male inbred corn plant(s) (or the average plant height of male inbred corn plants) provided herein.

In an aspect, the female inbred corn plants provided herein comprise an average height that is between 5% and 50% less or lower than the height (or average height) of at least one male inbred corn plant(s) (or the average plant height of male inbred corn plants) provided herein. In an aspect, the female inbred corn plants provided herein comprise an average height that is between 5% and 40% less or lower than the height (or average height) of at least one male inbred corn plant(s) (or the average plant height of male inbred corn plants) provided herein. In an aspect, the female inbred corn plants provided herein comprise an average height that is between 5% and 30% less or lower than the height (or average height) of at least one male inbred corn plant(s) (or the average plant height of male inbred corn plants) provided herein. In an aspect, the female inbred corn plants provided herein comprise an average height that is between 5% and 25% less or lower than the height (or average height) of at least one male inbred corn plant(s) (or the average plant height of male inbred corn plants) provided herein. In an aspect, the female inbred corn plants provided herein comprise an average height that is between 5% and 20% less or lower than the height of at least one male inbred corn plant(s) (or the average plant height of male inbred corn plants) provided herein. In an aspect, the female inbred corn plants provided herein comprise an average height that is between 5% and 15% less or lower than the height of at least one male inbred corn plant(s) (or the average plant height of male inbred corn plants) provided herein. In an aspect, the female inbred corn plants provided herein comprise an average height that is between 5% and 10% less or lower than the height of at least one male inbred corn plant(s) (or the average plant height of male inbred corn plants) provided herein.

In an aspect, the female inbred corn plants provided herein comprise an average height that is between 10% and 50% less or lower than the height (or average height) of at least one male inbred corn plant(s) (or the average plant height of male inbred corn plants) provided herein. In an aspect, the female inbred corn plants provided herein comprise an average height that is between 10% and 40% less or lower than the height (or average height) of at least one male inbred corn plant(s) (or the average plant height of male inbred corn plants) provided herein. In an aspect, the female inbred corn plants provided herein comprise an average height that is between 10% and 30% less or lower than the height (or average height) of at least one male inbred corn plant(s) (or the average plant height of male inbred corn plants) provided herein. In an aspect, the female inbred corn plants provided herein comprise an average height that is between 10% and 25% less or lower than the height (or average height) of at least one male inbred corn plant(s) (or the average plant height of male inbred corn plants) provided herein. In an aspect, the female inbred corn plants provided herein comprise an average height that is between 10% and 20% less or lower than the height (or average height) of at least one male inbred corn plant(s) (or the average plant height of male inbred corn plants) provided herein. In an aspect, the female inbred corn plants provided herein comprise an average height that is between 10% and 15% less or lower than the height (or average height) of at least one male inbred corn plant(s) (or the average plant height of male inbred corn plants) provided herein.

In another aspect, the female inbred corn plants provided herein comprise an average height that is between 15% and 60% less or lower than the height (or average height) of at least one male inbred corn plant(s) (or the average plant height of male inbred corn plants) provided herein. In another aspect, the female inbred corn plants provided herein comprise an average height that is between 15% and 50% less or lower than the height (or average height) of at least one male inbred corn plant(s) (or the average plant height of male inbred corn plants) provided herein. In another aspect, the female inbred corn plants provided herein comprise an average height that is between 15% and 40% less or lower than the height (or average height) of at least one male inbred corn plant(s) (or the average plant height of male inbred corn plants) provided herein. In another aspect, the female inbred corn plants provided herein comprise an average height that is between 15% and 30% less or lower than the height (or average height) of at least one male inbred corn plant(s) (or the average plant height of male inbred corn plants) provided herein. In another aspect, the female inbred corn plants provided herein comprise an average height that is between 15% and 25% less or lower than the height (or average height) of at least one male inbred corn plant(s) (or the average plant height of male inbred corn plants) provided herein. In another aspect, the female inbred corn plants provided herein comprise an average height that is between 15% and 20% less or lower than the height (or average height) of at least one male inbred corn plant(s) (or the average plant height of male inbred corn plants) provided herein.

In another aspect, the female inbred corn plants provided herein comprise an average height that is between 20% and 70% less or lower than the height (or average height) of at least one male inbred corn plant(s) (or the average plant height of male inbred corn plants) provided herein. In another aspect, the female inbred corn plants provided herein comprise an average height that is between 20% and 60% less or lower than the height (or average height) of at least one male inbred corn plant(s) (or the average plant height of male inbred corn plants) provided herein. In another aspect, the female inbred corn plants provided herein comprise an average height that is between 20% and 50% less or lower than the height (or average height) of at least one male inbred corn plant(s) (or the average plant height of male inbred corn plants) provided herein. In another aspect, the female inbred corn plants provided herein comprise an average height that is between 20% and 40% less or lower than the height (or average height) of at least one male inbred corn plant(s) (or the average plant height of male inbred corn plants) provided herein. In another aspect, the female inbred corn plants provided herein comprise an average height that is between 20% and 30% less or lower than the height (or average height) of at least one male inbred corn plant(s) (or the average plant height of male inbred corn plants) provided herein.

In an aspect, the average height of the female inbred corn plants provided herein is at least 0.05 meters less or lower than the height (or average height) of at least one male inbred corn plant(s) (or the average plant height of male inbred corn plants) provided herein. In an aspect, the average height of the female inbred corn plants provided herein is at least 0.06 meters less or lower than the height (or average height) of at least one male inbred corn plant(s) (or the average plant height of male inbred corn plants) provided herein. In an aspect, the average height of the female inbred corn plants provided herein is at least 0.07 meters less or lower than the height (or average height) of at least one male inbred corn plant(s) (or the average plant height of male inbred corn plants) provided herein. In an aspect, the average height of the female inbred corn plants provided herein is at least 0.08 meters less or lower than the height (or average height) of at least one male inbred corn plant(s) (or the average plant height of male inbred corn plants) provided herein. In an aspect, the average height of the female inbred corn plants provided herein is at least 0.09 meters less or lower than the height (or average height) of at least one male inbred corn plant(s) (or the average plant height of male inbred corn plants) provided herein. In an aspect, the average height of the female inbred corn plants provided herein is at least 0.1 meters less or lower than the height (or average height) of at least one male inbred corn plant(s) (or the average plant height of male inbred corn plants) provided herein. In another aspect, the average height of the female inbred corn plants provided herein is at least 0.2 meters less or lower than the height (or average height) of at least one male inbred corn plant(s) (or the average plant height of male inbred corn plants) provided herein. In another aspect, the average height of the female inbred corn plants provided herein is at least 0.3 meters less or lower than the height (or average height) of at least one male inbred corn plant(s) (or the average plant height of male inbred corn plants) provided herein. In another aspect, the average height of the female inbred corn plants provided herein is at least 0.4 meters less or lower than the height (or average height) of at least one male inbred corn plant(s) (or the average plant height of male inbred corn plants) provided herein. In another aspect, the average height of the female inbred corn plants provided herein is at least 0.5 meters less or lower than the height (or average height) of at least one male inbred corn plant(s) (or the average plant height of male inbred corn plants) provided herein. In another aspect, the average height of the female inbred corn plants provided herein is at least 0.6 meters less or lower than the height (or average height) of at least one male inbred corn plant(s) (or the average plant height of male inbred corn plants) provided herein. In another aspect, the average height of the female inbred corn plants provided herein is at least 0.7 meters less or lower than the height (or average height) of at least one male inbred corn plant(s) (or the average plant height of male inbred corn plants) provided herein. In another aspect, the average height of the female inbred corn plants provided herein is at least 0.8 meters less or lower than the height (or average height) of at least one male inbred corn plant(s) (or the average plant height of male inbred corn plants) provided herein. In another aspect, the average height of the female inbred corn plants provided herein is at least 0.9 meters less or lower than the height (or average height) of at least one male inbred corn plant(s) (or the average plant height of male inbred corn plants) provided herein. In another aspect, the average height of the female inbred corn plants provided herein is at least 1.0 meters less or lower than the height (or average height) of at least one male inbred corn plant(s) (or the average plant height of male inbred corn plants) provided herein. In another aspect, the average height of the female inbred corn plants provided herein is at least 1.2 meters less or lower than the height (or average height) of at least one male inbred corn plant(s) (or the average plant height of male inbred corn plants) provided herein. In another aspect, the average height of the female inbred corn plants provided herein is at least 1.4 meters less or lower than the height (or average height) of at least one male inbred corn plant(s) (or the average plant height of male inbred corn plants) provided herein. In another aspect, the average height of the female inbred corn plants provided herein is at least 1.6 meters less or lower than the height (or average height) of at least one male inbred corn plant(s) (or the average plant height of male inbred corn plants) provided herein. In another aspect, the average height of the female inbred corn plants provided herein is at least 1.8 meters less or lower than the height (or average height) of at least one male inbred corn plant(s) (or the average plant height of male inbred corn plants) provided herein. In another aspect, the average height of the female inbred corn plants provided herein is at least 2.0 meters less or lower than the height (or average height) of at least one male inbred corn plant(s) (or the average plant height of male inbred corn plants) provided herein. In another aspect, the average height of the female inbred corn plants provided herein is at least 2.2 meters less or lower than the height (or average height) of at least one male inbred corn plant(s) (or the average plant height of male inbred corn plants) provided herein.

In an aspect, the female inbred corn plants provided herein comprise an average height that is between 0.05 and 1.0 meters less or lower than the height (or average height) of at least one male inbred corn plant(s) (or the average plant height of male inbred corn plants) provided herein. In an aspect, the female inbred corn plants provided herein comprise an average height that is between 0.05 and 0.9 meters less or lower than the height (or average height) of at least one male inbred corn plant(s) (or the average plant height of male inbred corn plants) provided herein. In an aspect, the female inbred corn plants provided herein comprise an average height that is between 0.05 and 0.8 meters less or lower than the height (or average height) of at least one male inbred corn plant(s) (or the average plant height of male inbred corn plants) provided herein. In an aspect, the female inbred corn plants provided herein comprise an average height that is between 0.05 and 0.7 meters less or lower than the height (or average height) of at least one male inbred corn plant(s) (or the average plant height of male inbred corn plants) provided herein. In an aspect, the female inbred corn plants provided herein comprise an average height that is between 0.05 and 0.6 meters less or lower than the height (or average height) of at least one male inbred corn plant(s) (or the average plant height of male inbred corn plants) provided herein. In an aspect, the female inbred corn plants provided herein comprise an average height that is between 0.05 and 0.5 meters less or lower than the height (or average height) of at least one male inbred corn plant(s) (or the average plant height of male inbred corn plants) provided herein. In an aspect, the female inbred corn plants provided herein comprise an average height that is between 0.05 and 0.4 meters less or lower than the height (or average height) of at least one male inbred corn plant(s) (or the average plant height of male inbred corn plants) provided herein. In an aspect, the female inbred corn plants provided herein comprise an average height that is between 0.05 and 0.3 meters less or lower than the height (or average height) of at least one male inbred corn plant(s) (or the average plant height of male inbred corn plants) provided herein. In an aspect, the female inbred corn plants provided herein comprise an average height that is between 0.05 and 0.2 meters less or lower than the height (or average height) of at least one male inbred corn plant(s) (or the average plant height of male inbred corn plants) provided herein. In an aspect, the female inbred corn plants provided herein comprise an average height that is between 0.05 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.06 and 1.0 meters less or lower than the height (or average height) of at least one male inbred corn plant(s) (or the average plant height of male inbred corn plants) provided herein. In an aspect, the female inbred corn plants provided herein comprise an average height that is between 0.06 and 0.9 meters less or lower than the height (or average height) of at least one male inbred corn plant(s) (or the average plant height of male inbred corn plants) provided herein. In an aspect, the female inbred corn plants provided herein comprise an average height that is between 0.06 and 0.8 meters less or lower than the height (or average height) of at least one male inbred corn plant(s) (or the average plant height of male inbred corn plants) provided herein. In an aspect, the female inbred corn plants provided herein comprise an average height that is between 0.06 and 0.7 meters less or lower than the height (or average height) of at least one male inbred corn plant(s) (or the average plant height of male inbred corn plants) provided herein. In an aspect, the female inbred corn plants provided herein comprise an average height that is between 0.06 and 0.6 meters less or lower than the height (or average height) of at least one male inbred corn plant(s) (or the average plant height of male inbred corn plants) provided herein. In an aspect, the female inbred corn plants provided herein comprise an average height that is between 0.06 and 0.5 meters less or lower than the height (or average height) of at least one male inbred corn plant(s) (or the average plant height of male inbred corn plants) provided herein. In an aspect, the female inbred corn plants provided herein comprise an average height that is between 0.06 and 0.4 meters less or lower than the height (or average height) of at least one male inbred corn plant(s) (or the average plant height of male inbred corn plants) provided herein. In an aspect, the female inbred corn plants provided herein comprise an average height that is between 0.06 and 0.3 meters less or lower than the height (or average height) of at least one male inbred corn plant(s) (or the average plant height of male inbred corn plants) provided herein. In an aspect, the female inbred corn plants provided herein comprise an average height that is between 0.06 and 0.2 meters less or lower than the height (or average height) of at least one male inbred corn plant(s) (or the average plant height of male inbred corn plants) provided herein. In an aspect, the female inbred corn plants provided herein comprise an average height that is between 0.06 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.07 and 1.0 meters less or lower than the height (or average height) of at least one male inbred corn plant(s) (or the average plant height of male inbred corn plants) provided herein. In an aspect, the female inbred corn plants provided herein comprise an average height that is between 0.07 and 0.9 meters less or lower than the height (or average height) of at least one male inbred corn plant(s) (or the average plant height of male inbred corn plants) provided herein. In an aspect, the female inbred corn plants provided herein comprise an average height that is between 0.07 and 0.8 meters less or lower than the height (or average height) of at least one male inbred corn plant(s) (or the average plant height of male inbred corn plants) provided herein. In an aspect, the female inbred corn plants provided herein comprise an average height that is between 0.07 and 0.7 meters less or lower than the height (or average height) of at least one male inbred corn plant(s) (or the average plant height of male inbred corn plants) provided herein. In an aspect, the female inbred corn plants provided herein comprise an average height that is between 0.07 and 0.6 meters less or lower than the height (or average height) of at least one male inbred corn plant(s) (or the average plant height of male inbred corn plants) provided herein. In an aspect, the female inbred corn plants provided herein comprise an average height that is between 0.07 and 0.5 meters less or lower than the height (or average height) of at least one male inbred corn plant(s) (or the average plant height of male inbred corn plants) provided herein. In an aspect, the female inbred corn plants provided herein comprise an average height that is between 0.07 and 0.4 meters less or lower than the height (or average height) of at least one male inbred corn plant(s) (or the average plant height of male inbred corn plants) provided herein. In an aspect, the female inbred corn plants provided herein comprise an average height that is between 0.07 and 0.3 meters less or lower than the height (or average height) of at least one male inbred corn plant(s) (or the average plant height of male inbred corn plants) provided herein. In an aspect, the female inbred corn plants provided herein comprise an average height that is between 0.07 and 0.2 meters less or lower than the height (or average height) of at least one male inbred corn plant(s) (or the average plant height of male inbred corn plants) provided herein. In an aspect, the female inbred corn plants provided herein comprise an average height that is between 0.07 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.08 and 1.0 meters less or lower than the height (or average height) of at least one male inbred corn plant(s) (or the average plant height of male inbred corn plants) provided herein. In an aspect, the female inbred corn plants provided herein comprise an average height that is between 0.08 and 0.9 meters less or lower than the height (or average height) of at least one male inbred corn plant(s) (or the average plant height of male inbred corn plants) provided herein. In an aspect, the female inbred corn plants provided herein comprise an average height that is between 0.08 and 0.8 meters less or lower than the height (or average height) of at least one male inbred corn plant(s) (or the average plant height of male inbred corn plants) provided herein. In an aspect, the female inbred corn plants provided herein comprise an average height that is between 0.08 and 0.7 meters less or lower than the height (or average height) of at least one male inbred corn plant(s) (or the average plant height of male inbred corn plants) provided herein. In an aspect, the female inbred corn plants provided herein comprise an average height that is between 0.08 and 0.6 meters less or lower than the height (or average height) of at least one male inbred corn plant(s) (or the average plant height of male inbred corn plants) provided herein. In an aspect, the female inbred corn plants provided herein comprise an average height that is between 0.08 and 0.5 meters less or lower than the height (or average height) of at least one male inbred corn plant(s) (or the average plant height of male inbred corn plants) provided herein. In an aspect, the female inbred corn plants provided herein comprise an average height that is between 0.08 and 0.4 meters less or lower than the height (or average height) of at least one male inbred corn plant(s) (or the average plant height of male inbred corn plants) provided herein. In an aspect, the female inbred corn plants provided herein comprise an average height that is between 0.08 and 0.3 meters less or lower than the height (or average height) of at least one male inbred corn plant(s) (or the average plant height of male inbred corn plants) provided herein. In an aspect, the female inbred corn plants provided herein comprise an average height that is between 0.08 and 0.2 meters less or lower than the height (or average height) of at least one male inbred corn plant(s) (or the average plant height of male inbred corn plants) provided herein. In an aspect, the female inbred corn plants provided herein comprise an average height that is between 0.08 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.09 and 1.0 meters less or lower than the height (or average height) of at least one male inbred corn plant(s) (or the average plant height of male inbred corn plants) provided herein. In an aspect, the female inbred corn plants provided herein comprise an average height that is between 0.09 and 0.9 meters less or lower than the height (or average height) of at least one male inbred corn plant(s) (or the average plant height of male inbred corn plants) provided herein. In an aspect, the female inbred corn plants provided herein comprise an average height that is between 0.09 and 0.8 meters less or lower than the height (or average height) of at least one male inbred corn plant(s) (or the average plant height of male inbred corn plants) provided herein. In an aspect, the female inbred corn plants provided herein comprise an average height that is between 0.09 and 0.7 meters less or lower than the height (or average height) of at least one male inbred corn plant(s) (or the average plant height of male inbred corn plants) provided herein. In an aspect, the female inbred corn plants provided herein comprise an average height that is between 0.09 and 0.6 meters less or lower than the height (or average height) of at least one male inbred corn plant(s) (or the average plant height of male inbred corn plants) provided herein. In an aspect, the female inbred corn plants provided herein comprise an average height that is between 0.09 and 0.5 meters less or lower than the height (or average height) of at least one male inbred corn plant(s) (or the average plant height of male inbred corn plants) provided herein. In an aspect, the female inbred corn plants provided herein comprise an average height that is between 0.09 and 0.4 meters less or lower than the height (or average height) of at least one male inbred corn plant(s) (or the average plant height of male inbred corn plants) provided herein. In an aspect, the female inbred corn plants provided herein comprise an average height that is between 0.09 and 0.3 meters less or lower than the height (or average height) of at least one male inbred corn plant(s) (or the average plant height of male inbred corn plants) provided herein. In an aspect, the female inbred corn plants provided herein comprise an average height that is between 0.09 and 0.2 meters less or lower than the height (or average height) of at least one male inbred corn plant(s) (or the average plant height of male inbred corn plants) provided herein. In an aspect, the female inbred corn plants provided herein comprise an average height that is between 0.09 and 0.1 meters less or lower than the height (or average height) of at least one male inbred corn plant(s) (or the average plant height of male inbred corn plants) provided herein.

In an aspect, the female inbred corn plants provided herein comprise an average height that is between 0.1 and 1.5 meters less or lower than the height (or average height) of at least one male inbred corn plant(s) (or the average plant height of male inbred corn plants) provided herein. In an aspect, the female inbred corn plants provided herein comprise an average height that is between 0.1 and 1.4 meters less or lower than the height (or average height) of at least one male inbred corn plant(s) (or the average plant height of male inbred corn plants) provided herein. In an aspect, the female inbred corn plants provided herein comprise an average height that is between 0.1 and 1.3 meters less or lower than the height (or average height) of at least one male inbred corn plant(s) (or the average plant height of male inbred corn plants) provided herein. In an aspect, the female inbred corn plants provided herein comprise an average height that is between 0.1 and 1.2 meters less or lower than the height (or average height) of at least one male inbred corn plant(s) (or the average plant height of male inbred corn plants) provided herein. In an aspect, the female inbred corn plants provided herein comprise an average height that is between 0.1 and 1.1 meters less or lower than the height (or average height) of at least one male inbred corn plant(s) (or the average plant height of male inbred corn plants) provided herein. In an aspect, the female inbred corn plants provided herein comprise an average height that is between 0.1 and 1.0 meters less or lower than the height (or average height) of at least one male inbred corn plant(s) (or the average plant height of male inbred corn plants) provided herein. In an aspect, the female inbred corn plants provided herein comprise an average height that is between 0.1 and 0.9 meters less or lower than the height (or average height) of at least one male inbred corn plant(s) (or the average plant height of male inbred corn plants) provided herein. In an aspect, the female inbred corn plants provided herein comprise an average height that is between 0.1 and 0.8 meters less or lower than the height (or average height) of at least one male inbred corn plant(s) (or the average plant height of male inbred corn plants) provided herein. In an aspect, the female inbred corn plants provided herein comprise an average height that is between 0.1 and 0.7 meters less or lower than the height (or average height) of at least one male inbred corn plant(s) (or the average plant height of male inbred corn plants) provided herein. In an aspect, the female inbred corn plants provided herein comprise an average height that is between 0.1 and 0.6 meters less or lower than the height (or average height) of at least one male inbred corn plant(s) (or the average plant height of male inbred corn plants) provided herein. In an aspect, the female inbred corn plants provided herein comprise an average height that is between 0.1 and 0.5 meters less or lower than the height (or average height) of at least one male inbred corn plant(s) (or the average plant height of male inbred corn plants) provided herein. In an aspect, the female inbred corn plants provided herein comprise an average height that is between 0.1 and 0.4 meters less or lower than the height (or average height) of at least one male inbred corn plant(s) (or the average plant height of male inbred corn plants) provided herein. In an aspect, the female inbred corn plants provided herein comprise an average height that is between 0.1 and 0.3 meters less or lower than the height (or average height) of at least one male inbred corn plant(s) (or the average plant height of male inbred corn plants) provided herein. In an aspect, the female inbred corn plants provided herein comprise an average height that is between 0.1 and 0.2 meters less or lower than the height (or average height) of at least one male inbred corn plant(s) (or the average plant height of male inbred corn plants) provided herein.

In another aspect, the female inbred corn plants provided herein comprise an average height that is between 0.2 and 1.5 meters less or lower than the height (or average height) of at least one male inbred corn plant(s) (or the average plant height of male inbred corn plants) provided herein. In another aspect, the female inbred corn plants provided herein comprise an average height that is between 0.2 and 1.4 meters less or lower than the height (or average height) of at least one male inbred corn plant(s) (or the average plant height of male inbred corn plants) provided herein. In another aspect, the female inbred corn plants provided herein comprise an average height that is between 0.2 and 1.3 meters less or lower than the height (or average height) of at least one male inbred corn plant(s) (or the average plant height of male inbred corn plants) provided herein. In another aspect, the female inbred corn plants provided herein comprise an average height that is between 0.2 and 1.2 meters less or lower than the height (or average height) of at least one male inbred corn plant(s) (or the average plant height of male inbred corn plants) provided herein. In another aspect, the female inbred corn plants provided herein comprise an average height that is between 0.2 and 1.1 meters less or lower than the height (or average height) of at least one male inbred corn plant(s) (or the average plant height of male inbred corn plants) provided herein. In another aspect, the female inbred corn plants provided herein comprise an average height that is between 0.2 and 1.0 meters less or lower than the height (or average height) of at least one male inbred corn plant(s) (or the average plant height of male inbred corn plants) provided herein. In another aspect, the female inbred corn plants provided herein comprise an average height that is between 0.2 and 0.9 meters less or lower than the height (or average height) of at least one male inbred corn plant(s) (or the average plant height of male inbred corn plants) provided herein. In another aspect, the female inbred corn plants provided herein comprise an average height that is between 0.2 and 0.8 meters less or lower than the height (or average height) of at least one male inbred corn plant(s) (or the average plant height of male inbred corn plants) provided herein. In another aspect, the female inbred corn plants provided herein comprise an average height that is between 0.2 and 0.7 meters less or lower than the height (or average height) of at least one male inbred corn plant(s) (or the average plant height of male inbred corn plants) provided herein. In another aspect, the female inbred corn plants provided herein comprise an average height that is between 0.2 and 0.6 meters less or lower than the height (or average height) of at least one male inbred corn plant(s) (or the average plant height of male inbred corn plants) provided herein. In another aspect, the female inbred corn plants provided herein comprise an average height that is between 0.2 and 0.5 meters less or lower than the height (or average height) of at least one male inbred corn plant(s) (or the average plant height of male inbred corn plants) provided herein. In another aspect, the female inbred corn plants provided herein comprise an average height that is between 0.2 and 0.4 meters less or lower than the height (or average height) of at least one male inbred corn plant(s) (or the average plant height of male inbred corn plants) provided herein. In another aspect, the female inbred corn plants provided herein comprise an average height that is between 0.2 and 0.3 meters less or lower than the height (or average height) of at least one male inbred corn plant(s) (or the average plant height of male inbred corn plants) provided herein.

In another aspect, the female inbred corn plants provided herein comprise an average height that is between 0.3 and 1.5 meters less or lower than the height (or average height) of at least one male inbred corn plant(s) (or the average plant height of male inbred corn plants) provided herein. In another aspect, the female inbred corn plants provided herein comprise an average height that is between 0.3 and 1.4 meters less or lower than the height (or average height) of at least one male inbred corn plant(s) (or the average plant height of male inbred corn plants) provided herein. In another aspect, the female inbred corn plants provided herein comprise an average height that is between 0.3 and 1.3 meters less or lower than the height (or average height) of at least one male inbred corn plant(s) (or the average plant height of male inbred corn plants) provided herein. In another aspect, the female inbred corn plants provided herein comprise an average height that is between 0.3 and 1.2 meters less or lower than the height (or average height) of at least one male inbred corn plant(s) (or the average plant height of male inbred corn plants) provided herein. In another aspect, the female inbred corn plants provided herein comprise an average height that is between 0.3 and 1.1 meters less or lower than the height (or average height) of at least one male inbred corn plant(s) (or the average plant height of male inbred corn plants) provided herein. In another aspect, the female inbred corn plants provided herein comprise an average height that is between 0.3 and 1.0 meters less or lower than the height (or average height) of at least one male inbred corn plant(s) (or the average plant height of male inbred corn plants) provided herein. In another aspect, the female inbred corn plants provided herein comprise an average height that is between 0.3 and 0.9 meters less or lower than the height (or average height) of at least one male inbred corn plant(s) (or the average plant height of male inbred corn plants) provided herein. In another aspect, the female inbred corn plants provided herein comprise an average height that is between 0.3 and 0.8 meters less or lower than the height (or average height) of at least one male inbred corn plant(s) (or the average plant height of male inbred corn plants) provided herein. In another aspect, the female inbred corn plants provided herein comprise an average height that is between 0.3 and 0.7 meters less or lower than the height (or average height) of at least one male inbred corn plant(s) (or the average plant height of male inbred corn plants) provided herein. In another aspect, the female inbred corn plants provided herein comprise an average height that is between 0.3 and 0.6 meters less or lower than the height (or average height) of at least one male inbred corn plant(s) (or the average plant height of male inbred corn plants) provided herein. In another aspect, the female inbred corn plants provided herein comprise an average height that is between 0.3 and 0.5 meters less or lower than the height (or average height) of at least one male inbred corn plant(s) (or the average plant height of male inbred corn plants) provided herein. In another aspect, the female inbred corn plants provided herein comprise an average height that is between 0.3 and 0.4 meters less or lower than the height (or average height) of at least one male inbred corn plant(s) (or the average plant height of male inbred corn plants) provided herein.

In another aspect, the female inbred corn plants provided herein comprise an average height that is between 0.4 and 2.0 meters less or lower than the height (or average height) of at least one male inbred corn plant(s) (or the average plant height of male inbred corn plants) provided herein. In another aspect, the female inbred corn plants provided herein comprise an average height that is between 0.4 and 1.9 meters less or lower than the height (or average height) of at least one male inbred corn plant(s) (or the average plant height of male inbred corn plants) provided herein. In another aspect, the female inbred corn plants provided herein comprise an average height that is between 0.4 and 1.8 meters less or lower than the height (or average height) of at least one male inbred corn plant(s) (or the average plant height of male inbred corn plants) provided herein. In another aspect, the female inbred corn plants provided herein comprise an average height that is between 0.4 and 1.7 meters less or lower than the height (or average height) of at least one male inbred corn plant(s) (or the average plant height of male inbred corn plants) provided herein. In another aspect, the female inbred corn plants provided herein comprise an average height that is between 0.4 and 1.6 meters less or lower than the height (or average height) of at least one male inbred corn plant(s) (or the average plant height of male inbred corn plants) provided herein. In another aspect, the female inbred corn plants provided herein comprise an average height that is between 0.4 and 1.5 meters less or lower than the height (or average height) of at least one male inbred corn plant(s) (or the average plant height of male inbred corn plants) provided herein. In another aspect, the female inbred corn plants provided herein comprise an average height that is between 0.4 and 1.4 meters less or lower than the height (or average height) of at least one male inbred corn plant(s) (or the average plant height of male inbred corn plants) provided herein. In another aspect, the female inbred corn plants provided herein comprise an average height that is between 0.4 and 1.3 meters less or lower than the height (or average height) of at least one male inbred corn plant(s) (or the average plant height of male inbred corn plants) provided herein. In another aspect, the female inbred corn plants provided herein comprise an average height that is between 0.4 and 1.2 meters less or lower than the height (or average height) of at least one male inbred corn plant(s) (or the average plant height of male inbred corn plants) provided herein. In another aspect, the female inbred corn plants provided herein comprise an average height that is between 0.4 and 1.1 meters less or lower than the height (or average height) of at least one male inbred corn plant(s) (or the average plant height of male inbred corn plants) provided herein. In another aspect, the female inbred corn plants provided herein comprise an average height that is between 0.4 and 1.0 meters less or lower than the height (or average height) of at least one male inbred corn plant(s) (or the average plant height of male inbred corn plants) provided herein. In another aspect, the female inbred corn plants provided herein comprise an average height that is between 0.4 and 0.9 meters less or lower than the height (or average height) of at least one male inbred corn plant(s) (or the average plant height of male inbred corn plants) provided herein. In another aspect, the female inbred corn plants provided herein comprise an average height that is between 0.4 and 0.8 meters less or lower than the height (or average height) of at least one male inbred corn plant(s) (or the average plant height of male inbred corn plants) provided herein. In another aspect, the female inbred corn plants provided herein comprise an average height that is between 0.4 and 0.7 meters less or lower than the height (or average height) of at least one male inbred corn plant(s) (or the average plant height of male inbred corn plants) provided herein. In another aspect, the female inbred corn plants provided herein comprise an average height that is between 0.4 and 0.6 meters less or lower than the height (or average height) of at least one male inbred corn plant(s) (or the average plant height of male inbred corn plants) provided herein. In another aspect, the female inbred corn plants provided herein comprise an average height that is between 0.4 and 0.5 meters less or lower than the height (or average height) of at least one male inbred corn plant(s) (or the average plant height of male inbred corn plants) provided herein.

In another aspect, the female inbred corn plants provided herein comprise an average height that is between 0.5 and 2.0 meters less or lower than the height (or average height) of at least one male inbred corn plant(s) (or the average plant height of male inbred corn plants) provided herein. In another aspect, the female inbred corn plants provided herein comprise an average height that is between 0.5 and 1.9 meters less or lower than the height (or average height) of at least one male inbred corn plant(s) (or the average plant height of male inbred corn plants) provided herein. In another aspect, the female inbred corn plants provided herein comprise an average height that is between 0.5 and 1.8 meters less or lower than the height (or average height) of at least one male inbred corn plant(s) (or the average plant height of male inbred corn plants) provided herein. In another aspect, the female inbred corn plants provided herein comprise an average height that is between 0.5 and 1.7 meters less or lower than the height (or average height) of at least one male inbred corn plant(s) (or the average plant height of male inbred corn plants) provided herein. In another aspect, the female inbred corn plants provided herein comprise an average height that is between 0.5 and 1.6 meters less or lower than the height (or average height) of at least one male inbred corn plant(s) (or the average plant height of male inbred corn plants) provided herein. In another aspect, the female inbred corn plants provided herein comprise an average height that is between 0.5 and 1.5 meters less or lower than the height (or average height) of at least one male inbred corn plant(s) (or the average plant height of male inbred corn plants) provided herein. In another aspect, the female inbred corn plants provided herein comprise an average height that is between 0.5 and 1.4 meters less or lower than the height (or average height) of at least one male inbred corn plant(s) (or the average plant height of male inbred corn plants) provided herein. In another aspect, the female inbred corn plants provided herein comprise an average height that is between 0.5 and 1.3 meters less or lower than the height (or average height) of at least one male inbred corn plant(s) (or the average plant height of male inbred corn plants) provided herein. In another aspect, the female inbred corn plants provided herein comprise an average height that is between 0.5 and 1.2 meters less or lower than the height (or average height) of at least one male inbred corn plant(s) (or the average plant height of male inbred corn plants) provided herein. In another aspect, the female inbred corn plants provided herein comprise an average height that is between 0.5 and 1.1 meters less or lower than the height (or average height) of at least one male inbred corn plant(s) (or the average plant height of male inbred corn plants) provided herein. In another aspect, the female inbred corn plants provided herein comprise an average height that is between 0.5 and 1.0 meters less or lower than the height (or average height) of at least one male inbred corn plant(s) (or the average plant height of male inbred corn plants) provided herein. In another aspect, the female inbred corn plants provided herein comprise an average height that is between 0.5 and 0.9 meters less or lower than the height (or average height) of at least one male inbred corn plant(s) (or the average plant height of male inbred corn plants) provided herein. In another aspect, the female inbred corn plants provided herein comprise an average height that is between 0.5 and 0.8 meters less or lower than the height (or average height) of at least one male inbred corn plant(s) (or the average plant height of male inbred corn plants) provided herein. In another aspect, the female inbred corn plants provided herein comprise an average height that is between 0.5 and 0.7 meters less or lower than the height (or average height) of at least one male inbred corn plant(s) (or the average plant height of male inbred corn plants) provided herein. In another aspect, the female inbred corn plants provided herein comprise an average height that is between 0.5 and 0.6 meters less or lower than the height (or average height) of at least one male inbred corn plant(s) (or the average plant height of male inbred corn plants) provided herein.

In another aspect, the female inbred corn plants provided herein comprise an average height that is between 0.6 and 2.2 meters less or lower than the height (or average height) of at least one male inbred corn plant(s) (or the average plant height of male inbred corn plants) provided herein. In another aspect, the female inbred corn plants provided herein comprise an average height that is between 0.6 and 2.1 meters less or lower than the height (or average height) of at least one male inbred corn plant(s) (or the average plant height of male inbred corn plants) provided herein. In another aspect, the female inbred corn plants provided herein comprise an average height that is between 0.6 and 2.0 meters less or lower than the height (or average height) of at least one male inbred corn plant(s) (or the average plant height of male inbred corn plants) provided herein. In another aspect, the female inbred corn plants provided herein comprise an average height that is between 0.6 and 1.9 meters less or lower than the height (or average height) of at least one male inbred corn plant(s) (or the average plant height of male inbred corn plants) provided herein. In another aspect, the female inbred corn plants provided herein comprise an average height that is between 0.6 and 1.8 meters less or lower than the height (or average height) of at least one male inbred corn plant(s) (or the average plant height of male inbred corn plants) provided herein. In another aspect, the female inbred corn plants provided herein comprise an average height that is between 0.6 and 1.7 meters less or lower than the height (or average height) of at least one male inbred corn plant(s) (or the average plant height of male inbred corn plants) provided herein. In another aspect, the female inbred corn plants provided herein comprise an average height that is between 0.6 and 1.6 meters less or lower than the height (or average height) of at least one male inbred corn plant(s) (or the average plant height of male inbred corn plants) provided herein. In another aspect, the female inbred corn plants provided herein comprise an average height that is between 0.6 and 1.5 meters less or lower than the height (or average height) of at least one male inbred corn plant(s) (or the average plant height of male inbred corn plants) provided herein. In another aspect, the female inbred corn plants provided herein comprise an average height that is between 0.6 and 1.4 meters less or lower than the height (or average height) of at least one male inbred corn plant(s) (or the average plant height of male inbred corn plants) provided herein. In another aspect, the female inbred corn plants provided herein comprise an average height that is between 0.6 and 1.3 meters less or lower than the height (or average height) of at least one male inbred corn plant(s) (or the average plant height of male inbred corn plants) provided herein. In another aspect, the female inbred corn plants provided herein comprise an average height that is between 0.6 and 1.2 meters less or lower than the height (or average height) of at least one male inbred corn plant(s) (or the average plant height of male inbred corn plants) provided herein. In another aspect, the female inbred corn plants provided herein comprise an average height that is between 0.6 and 1.1 meters less or lower than the height (or average height) of at least one male inbred corn plant(s) (or the average plant height of male inbred corn plants) provided herein. In another aspect, the female inbred corn plants provided herein comprise an average height that is between 0.6 and 1.0 meters less or lower than the height (or average height) of at least one male inbred corn plant(s) (or the average plant height of male inbred corn plants) provided herein. In another aspect, the female inbred corn plants provided herein comprise an average height that is between 0.6 and 0.9 meters less or lower than the height (or average height) of at least one male inbred corn plant(s) (or the average plant height of male inbred corn plants) provided herein. In another aspect, the female inbred corn plants provided herein comprise an average height that is between 0.6 and 0.8 meters less or lower than the height (or average height) of at least one male inbred corn plant(s) (or the average plant height of male inbred corn plants) provided herein. In another aspect, the female inbred corn plants provided herein comprise an average height that is between 0.6 and 0.7 meters less or lower than the height (or average height) of at least one male inbred corn plant(s) (or the average plant height of male inbred corn plants) provided herein.

In another aspect, the female inbred corn plants provided herein comprise an average height that is between 0.7 and 2.2 meters less or lower than the height (or average height) of at least one male inbred corn plant(s) (or the average plant height of male inbred corn plants) provided herein. In another aspect, the female inbred corn plants provided herein comprise an average height that is between 0.7 and 2.1 meters less or lower than the height (or average height) of at least one male inbred corn plant(s) (or the average plant height of male inbred corn plants) provided herein. In another aspect, the female inbred corn plants provided herein comprise an average height that is between 0.7 and 2.0 meters less or lower than the height (or average height) of at least one male inbred corn plant(s) (or the average plant height of male inbred corn plants) provided herein. In another aspect, the female inbred corn plants provided herein comprise an average height that is between 0.7 and 1.9 meters less or lower than the height (or average height) of at least one male inbred corn plant(s) (or the average plant height of male inbred corn plants) provided herein. In another aspect, the female inbred corn plants provided herein comprise an average height that is between 0.7 and 1.8 meters less or lower than the height (or average height) of at least one male inbred corn plant(s) (or the average plant height of male inbred corn plants) provided herein. In another aspect, the female inbred corn plants provided herein comprise an average height that is between 0.7 and 1.7 meters less or lower than the height (or average height) of at least one male inbred corn plant(s) (or the average plant height of male inbred corn plants) provided herein. In another aspect, the female inbred corn plants provided herein comprise an average height that is between 0.7 and 1.6 meters less or lower than the height (or average height) of at least one male inbred corn plant(s) (or the average plant height of male inbred corn plants) provided herein. In another aspect, the female inbred corn plants provided herein comprise an average height that is between 0.7 and 1.5 meters less or lower than the height (or average height) of at least one male inbred corn plant(s) (or the average plant height of male inbred corn plants) provided herein. In another aspect, the female inbred corn plants provided herein comprise an average height that is between 0.7 and 1.4 meters less or lower than the height (or average height) of at least one male inbred corn plant(s) (or the average plant height of male inbred corn plants) provided herein. In another aspect, the female inbred corn plants provided herein comprise an average height that is between 0.7 and 1.3 meters less or lower than the height (or average height) of at least one male inbred corn plant(s) (or the average plant height of male inbred corn plants) provided herein. In another aspect, the female inbred corn plants provided herein comprise an average height that is between 0.7 and 1.2 meters less or lower than the height (or average height) of at least one male inbred corn plant(s) (or the average plant height of male inbred corn plants) provided herein. In another aspect, the female inbred corn plants provided herein comprise an average height that is between 0.7 and 1.1 meters less or lower than the height (or average height) of at least one male inbred corn plant(s) (or the average plant height of male inbred corn plants) provided herein. In another aspect, the female inbred corn plants provided herein comprise an average height that is between 0.7 and 1.0 meters less or lower than the height (or average height) of at least one male inbred corn plant(s) (or the average plant height of male inbred corn plants) provided herein. In another aspect, the female inbred corn plants provided herein comprise an average height that is between 0.7 and 0.9 meters less or lower than the height (or average height) of at least one male inbred corn plant(s) (or the average plant height of male inbred corn plants) provided herein. In another aspect, the female inbred corn plants provided herein comprise an average height that is between 0.7 and 0.8 meters less or lower than the height (or average height) of at least one male inbred corn plant(s) (or the average plant height of male inbred corn plants) provided herein.

In another aspect, the female inbred corn plants provided herein comprise an average height that is between 0.8 and 2.4 meters less or lower than the height (or average height) of at least one male inbred corn plant(s) (or the average plant height of male inbred corn plants) provided herein. In another aspect, the female inbred corn plants provided herein comprise an average height that is between 0.8 and 2.3 meters less or lower than the height (or average height) of at least one male inbred corn plant(s) (or the average plant height of male inbred corn plants) provided herein. In another aspect, the female inbred corn plants provided herein comprise an average height that is between 0.8 and 2.2 meters less or lower than the height (or average height) of at least one male inbred corn plant(s) (or the average plant height of male inbred corn plants) provided herein. In another aspect, the female inbred corn plants provided herein comprise an average height that is between 0.8 and 2.1 meters less or lower than the height (or average height) of at least one male inbred corn plant(s) (or the average plant height of male inbred corn plants) provided herein. In another aspect, the female inbred corn plants provided herein comprise an average height that is between 0.8 and 2.0 meters less or lower than the height (or average height) of at least one male inbred corn plant(s) (or the average plant height of male inbred corn plants) provided herein. In another aspect, the female inbred corn plants provided herein comprise an average height that is between 0.8 and 1.9 meters less or lower than the height (or average height) of at least one male inbred corn plant(s) (or the average plant height of male inbred corn plants) provided herein. In another aspect, the female inbred corn plants provided herein comprise an average height that is between 0.8 and 1.8 meters less or lower than the height (or average height) of at least one male inbred corn plant(s) (or the average plant height of male inbred corn plants) provided herein. In another aspect, the female inbred corn plants provided herein comprise an average height that is between 0.8 and 1.7 meters less or lower than the height (or average height) of at least one male inbred corn plant(s) (or the average plant height of male inbred corn plants) provided herein. In another aspect, the female inbred corn plants provided herein comprise an average height that is between 0.8 and 1.6 meters less or lower than the height (or average height) of at least one male inbred corn plant(s) (or the average plant height of male inbred corn plants) provided herein. In another aspect, the female inbred corn plants provided herein comprise an average height that is between 0.8 and 1.5 meters less or lower than the height (or average height) of at least one male inbred corn plant(s) (or the average plant height of male inbred corn plants) provided herein. In another aspect, the female inbred corn plants provided herein comprise an average height that is between 0.8 and 1.4 meters less or lower than the height (or average height) of at least one male inbred corn plant(s) (or the average plant height of male inbred corn plants) provided herein. In another aspect, the female inbred corn plants provided herein comprise an average height that is between 0.8 and 1.3 meters less or lower than the height (or average height) of at least one male inbred corn plant(s) (or the average plant height of male inbred corn plants) provided herein. In another aspect, the female inbred corn plants provided herein comprise an average height that is between 0.8 and 1.2 meters less or lower than the height (or average height) of at least one male inbred corn plant(s) (or the average plant height of male inbred corn plants) provided herein. In another aspect, the female inbred corn plants provided herein comprise an average height that is between 0.8 and 1.1 meters less or lower than the height (or average height) of at least one male inbred corn plant(s) (or the average plant height of male inbred corn plants) provided herein. In another aspect, the female inbred corn plants provided herein comprise an average height that is between 0.8 and 1.0 meters less or lower than the height (or average height) of at least one male inbred corn plant(s) (or the average plant height of male inbred corn plants) provided herein. In another aspect, the female inbred corn plants provided herein comprise an average height that is between 0.8 and 0.9 meters less or lower than the height of at least one male inbred corn plant (or the average plant height of male inbred corn plants) provided herein.

In another aspect, the female inbred corn plants provided herein comprise an average height that is between 0.9 and 2.4 meters less or lower than the height (or average height) of at least one male inbred corn plant(s) (or the average plant height of male inbred corn plants) provided herein. In another aspect, the female inbred corn plants provided herein comprise an average height that is between 0.9 and 2.3 meters less or lower than the height (or average height) of at least one male inbred corn plant(s) (or the average plant height of male inbred corn plants) provided herein. In another aspect, the female inbred corn plants provided herein comprise an average height that is between 0.9 and 2.2 meters less or lower than the height (or average height) of at least one male inbred corn plant(s) (or the average plant height of male inbred corn plants) provided herein. In another aspect, the female inbred corn plants provided herein comprise an average height that is between 0.9 and 2.1 meters less or lower than the height (or average height) of at least one male inbred corn plant(s) (or the average plant height of male inbred corn plants) provided herein. In another aspect, the female inbred corn plants provided herein comprise an average height that is between 0.9 and 2.0 meters less or lower than the height (or average height) of at least one male inbred corn plant(s) (or the average plant height of male inbred corn plants) provided herein. In another aspect, the female inbred corn plants provided herein comprise an average height that is between 0.9 and 1.9 meters less or lower than the height (or average height) of at least one male inbred corn plant(s) (or the average plant height of male inbred corn plants) provided herein. In another aspect, the female inbred corn plants provided herein comprise an average height that is between 0.9 and 1.8 meters less or lower than the height (or average height) of at least one male inbred corn plant(s) (or the average plant height of male inbred corn plants) provided herein. In another aspect, the female inbred corn plants provided herein comprise an average height that is between 0.9 and 1.7 meters less or lower than the height (or average height) of at least one male inbred corn plant(s) (or the average plant height of male inbred corn plants) provided herein. In another aspect, the female inbred corn plants provided herein comprise an average height that is between 0.9 and 1.6 meters less or lower than the height (or average height) of at least one male inbred corn plant(s) (or the average plant height of male inbred corn plants) provided herein. In another aspect, the female inbred corn plants provided herein comprise an average height that is between 0.9 and 1.5 meters less or lower than the height (or average height) of at least one male inbred corn plant(s) (or the average plant height of male inbred corn plants) provided herein. In another aspect, the female inbred corn plants provided herein comprise an average height that is between 0.9 and 1.4 meters less or lower than the height (or average height) of at least one male inbred corn plant(s) (or the average plant height of male inbred corn plants) provided herein. In another aspect, the female inbred corn plants provided herein comprise an average height that is between 0.9 and 1.3 meters less or lower than the height (or average height)

of at least one male inbred corn plant(s) (or the average plant height of male inbred corn plants) provided herein. In another aspect, the female inbred corn plants provided herein comprise an average height that is between 0.9 and 1.2 meters less or lower than the height (or average height) of at least one male inbred corn plant(s) (or the average plant height of male inbred corn plants) provided herein. In another aspect, the female inbred corn plants provided herein comprise an average height that is between 0.9 and 1.1 meters less or lower than the height (or average height) of at least one male inbred corn plant(s) (or the average plant height of male inbred corn plants) provided herein. In another aspect, the female inbred corn plants provided herein comprise an average height that is between 0.9 and 1.0 meters less or lower than the height of at least one male inbred corn plant (or the average plant height of male inbred corn plants) provided herein.

In another aspect, the female inbred corn plants provided herein comprise an average height that is between 1.0 and 2.5 meters less or lower than the height (or average height) of at least one male inbred corn plant(s) (or the average plant height of male inbred corn plants) provided herein. In another aspect, the female inbred corn plants provided herein comprise an average height that is between 1.0 and 2.4 meters less or lower than the height (or average height) of at least one male inbred corn plant(s) (or the average plant height of male inbred corn plants) provided herein. In another aspect, the female inbred corn plants provided herein comprise an average height that is between 1.0 and 2.3 meters less or lower than the height (or average height) of at least one male inbred corn plant(s) (or the average plant height of male inbred corn plants) provided herein. In another aspect, the female inbred corn plants provided herein comprise an average height that is between 1.0 and 2.2 meters less or lower than the height (or average height) of at least one male inbred corn plant(s) (or the average plant height of male inbred corn plants) provided herein. In another aspect, the female inbred corn plants provided herein comprise an average height that is between 1.0 and 2.1 meters less or lower than the height (or average height) of at least one male inbred corn plant(s) (or the average plant height of male inbred corn plants) provided herein. In another aspect, the female inbred corn plants provided herein comprise an average height that is between 1.0 and 2.0 meters less or lower than the height (or average height) of at least one male inbred corn plant(s) (or the average plant height of male inbred corn plants) provided herein. In another aspect, the female inbred corn plants provided herein comprise an average height that is between 1.0 and 1.9 meters less or lower than the height (or average height) of at least one male inbred corn plant(s) (or the average plant height of male inbred corn plants) provided herein. In another aspect, the female inbred corn plants provided herein comprise an average height that is between 1.0 and 1.8 meters less or lower than the height (or average height) of at least one male inbred corn plant(s) (or the average plant height of male inbred corn plants) provided herein. In another aspect, the female inbred corn plants provided herein comprise an average height that is between 1.0 and 1.7 meters less or lower than the height (or average height) of at least one male inbred corn plant(s) (or the average plant height of male inbred corn plants) provided herein. In another aspect, the female inbred corn plants provided herein comprise an average height that is between 1.0 and 1.6 meters less or lower than the height (or average height) of at least one male inbred corn plant(s) (or the average plant height of male inbred corn plants) provided herein. In another aspect, the female inbred corn plants provided herein comprise an average height that is between 1.0 and 1.5 meters less or lower than the height (or average height) of at least one male inbred corn plant(s) (or the average plant height of male inbred corn plants) provided herein. In another aspect, the female inbred corn plants provided herein comprise an average height that is between 1.0 and 1.4 meters less or lower than the height (or average height) of at least one male inbred corn plant(s) (or the average plant height of male inbred corn plants) provided herein. In another aspect, the female inbred corn plants provided herein comprise an average height that is between 1.0 and 1.3 meters less or lower than the height (or average height) of at least one male inbred corn plant(s) (or the average plant height of male inbred corn plants) provided herein. In another aspect, the female inbred corn plants provided herein comprise an average height that is between 1.0 and 1.2 meters less or lower than the height (or average height) of at least one male inbred corn plant(s) (or the average plant height of male inbred corn plants) provided herein. In another aspect, the female inbred corn plants provided herein comprise an average height that is between 1.0 and 1.1 meters less or lower than the height (or average height) of at least one male inbred corn plant(s) (or the average plant height of male inbred corn plants) provided herein.

In another aspect, the female inbred corn plants provided herein comprise an average height that is between 1.2 and 2.5 meters less or lower than the height (or average height) of at least one male inbred corn plant(s) (or the average plant height of male inbred corn plants) provided herein. In another aspect, the female inbred corn plants provided herein comprise an average height that is between 1.2 and 2.4 meters less or lower than the height (or average height) of at least one male inbred corn plant(s) (or the average plant height of male inbred corn plants) provided herein. In another aspect, the female inbred corn plants provided herein comprise an average height that is between 1.2 and 2.3 meters less or lower than the height (or average height) of at least one male inbred corn plant(s) (or the average plant height of male inbred corn plants) provided herein. In another aspect, the female inbred corn plants provided herein comprise an average height that is between 1.2 and 2.2 meters less or lower than the height (or average height) of at least one male inbred corn plant(s) (or the average plant height of male inbred corn plants) provided herein. In another aspect, the female inbred corn plants provided herein comprise an average height that is between 1.2 and 2.1 meters less or lower than the height (or average height) of at least one male inbred corn plant(s) (or the average plant height of male inbred corn plants) provided herein. In another aspect, the female inbred corn plants provided herein comprise an average height that is between 1.2 and 2.0 meters less or lower than the height (or average height) of at least one male inbred corn plant(s) (or the average plant height of male inbred corn plants) provided herein. In another aspect, the female inbred corn plants provided herein comprise an average height that is between 1.2 and 1.9 meters less or lower than the height (or average height) of at least one male inbred corn plant(s) (or the average plant height of male inbred corn plants) provided herein. In another aspect, the female inbred corn plants provided herein comprise an average height that is between 1.2 and 1.8 meters less or lower than the height (or average height) of at least one male inbred corn plant(s) (or the average plant height of male inbred corn plants) provided herein. In another aspect, the female inbred corn plants provided herein comprise an average height that is between 1.2 and 1.7 meters less or lower than the height (or average height) of at least one male inbred corn plant(s) (or the average plant height of male inbred corn plants) provided herein. In another aspect, the female inbred corn plants provided herein comprise an average height that is between 1.2 and 1.6 meters less or lower than the height (or average height) of at least one male inbred corn plant(s) (or the average plant height of male inbred corn plants) provided herein. In another aspect, the female inbred corn plants provided herein comprise an average height that is between 1.2 and 1.5 meters less or lower than the height (or average height) of at least one male inbred corn plant(s) (or the average plant height of male inbred corn plants) provided herein. In another aspect, the female inbred corn plants provided herein comprise an average height that is between 1.2 and 1.4 meters less or lower than the height (or average height) of at least one male inbred corn plant(s) (or the average plant height of male inbred corn plants) provided herein. In another aspect, the female inbred corn plants provided herein comprise an average height that is between 1.2 and 1.3 meters less or lower than the height (or average height) of at least one male inbred corn plant(s) (or the average plant height of male inbred corn plants) provided herein.

In another aspect, the female inbred corn plants provided herein comprise an average height that is between 1.4 and 2.5 meters less or lower than the height (or average height) of at least one male inbred corn plant(s) (or the average plant height of male inbred corn plants) provided herein. In another aspect, the female inbred corn plants provided herein comprise an average height that is between 1.4 and 2.4 meters less or lower than the height (or average height) of at least one male inbred corn plant(s) (or the average plant height of male inbred corn plants) provided herein. In another aspect, the female inbred corn plants provided herein comprise an average height that is between 1.4 and 2.3 meters less or lower than the height (or average height) of at least one male inbred corn plant(s) (or the average plant height of male inbred corn plants) provided herein. In another aspect, the female inbred corn plants provided herein comprise an average height that is between 1.4 and 2.2 meters less or lower than the height (or average height) of at least one male inbred corn plant(s) (or the average plant height of male inbred corn plants) provided herein. In another aspect, the female inbred corn plants provided herein comprise an average height that is between 1.4 and 2.1 meters less or lower than the height (or average height) of at least one male inbred corn plant(s) (or the average plant height of male inbred corn plants) provided herein. In another aspect, the female inbred corn plants provided herein comprise an average height that is between 1.4 and 2.0 meters less or lower than the height (or average height) of at least one male inbred corn plant(s) (or the average plant height of male inbred corn plants) provided herein. In another aspect, the female inbred corn plants provided herein comprise an average height that is between 1.4 and 1.9 meters less or lower than the height (or average height) of at least one male inbred corn plant(s) (or the average plant height of male inbred corn plants) provided herein. In another aspect, the female inbred corn plants provided herein comprise an average height that is between 1.4 and 1.8 meters less or lower than the height (or average height) of at least one male inbred corn plant(s) (or the average plant height of male inbred corn plants) provided herein. In another aspect, the female inbred corn plants provided herein comprise an average height that is between 1.4 and 1.7 meters less or lower than the height (or average height) of at least one male inbred corn plant(s) (or the average plant height of male inbred corn plants) provided herein. In another aspect, the female inbred corn plants provided herein comprise an average height that is between 1.4 and 1.6 meters less or lower than the height (or average height) of at least one male inbred corn plant(s) (or the average plant height of male inbred corn plants) provided herein. In another aspect, the female inbred corn plants provided herein comprise an average height that is between 1.4 and 1.5 meters less or lower than the height (or average height) of at least one male inbred corn plant(s) (or the average plant height of male inbred corn plants) provided herein.

In another aspect, the female inbred corn plants provided herein comprise an average height that is between 1.6 and 2.5 meters less or lower than the height (or average height) of at least one male inbred corn plant(s) (or the average plant height of male inbred corn plants) provided herein. In another aspect, the female inbred corn plants provided herein comprise an average height that is between 1.6 and 2.4 meters less or lower than the height (or average height) of at least one male inbred corn plant(s) (or the average plant height of male inbred corn plants) provided herein. In another aspect, the female inbred corn plants provided herein comprise an average height that is between 1.6 and 2.3 meters less or lower than the height (or average height) of at least one male inbred corn plant(s) (or the average plant height of male inbred corn plants) provided herein. In another aspect, the female inbred corn plants provided herein comprise an average height that is between 1.6 and 2.2 meters less or lower than the height (or average height) of at least one male inbred corn plant(s) (or the average plant height of male inbred corn plants) provided herein. In another aspect, the female inbred corn plants provided herein comprise an average height that is between 1.6 and 2.1 meters less or lower than the height (or average height) of at least one male inbred corn plant(s) (or the average plant height of male inbred corn plants) provided herein. In another aspect, the female inbred corn plants provided herein comprise an average height that is between 1.6 and 2.0 meters less or lower than the height (or average height) of at least one male inbred corn plant(s) (or the average plant height of male inbred corn plants) provided herein. In another aspect, the female inbred corn plants provided herein comprise an average height that is between 1.6 and 1.9 meters less or lower than the height (or average height) of at least one male inbred corn plant(s) (or the average plant height of male inbred corn plants) provided herein. In another aspect, the female inbred corn plants provided herein comprise an average height that is between 1.6 and 1.8 meters less or lower than the height of at least one male inbred corn plant (or the average plant height of male inbred corn plants) provided herein.

In another aspect, the female inbred corn plants provided herein comprise an average height that is between 1.8 and 2.5 meters less or lower than the height (or average height) of at least one male inbred corn plant(s) (or the average plant height of male inbred corn plants) provided herein. In another aspect, the female inbred corn plants provided herein comprise an average height that is between 1.8 and 2.4 meters less or lower than the height (or average height) of at least one male inbred corn plant(s) (or the average plant height of male inbred corn plants) provided herein. In another aspect, the female inbred corn plants provided herein comprise an average height that is between 1.8 and 2.3 meters less or lower than the height (or average height) of at least one male inbred corn plant(s) (or the average plant height of male inbred corn plants) provided herein. In another aspect, the female inbred corn plants provided herein comprise an average height that is between 1.8 and 2.2 meters less or lower than the height (or average height) of at least one male inbred corn plant(s) (or the average plant height of male inbred corn plants) provided herein. In another aspect, the female inbred corn plants provided herein comprise an average height that is between 1.8 and 2.1 meters less or lower than the height (or average height) of at least one male inbred corn plant(s) (or the average plant height of male inbred corn plants) provided herein. In another aspect, the female inbred corn plants provided herein comprise an average height that is between 1.8 and 2.0 meters less or lower than the height of at least one male inbred corn plant (or the average plant height of male inbred corn plants) provided herein.

In an aspect, a female corn plant provided herein comprises one or more ears at least 14 inches above ground level. In another aspect, a female corn plant provided herein comprises one or more ears at least 15 inches above ground level. In another aspect, a female corn plant provided herein comprises one or more ears at least 16 inches above ground level. In another aspect, a female corn plant provided herein comprises one or more ears at least 17 inches above ground level. In another aspect, a female corn plant provided herein comprises one or more ears at least 18 inches above ground level. In another aspect, a female corn plant provided herein comprises one or more ears at least 19 inches above ground level. In another aspect, a female corn plant provided herein comprises one or more ears at least 20 inches above ground level. In another aspect, a female corn plant provided herein comprises one or more ears at least 21 inches above ground level. In another aspect, a female corn plant provided herein comprises one or more ears at least 22 inches above ground level. In another aspect, a female corn plant provided herein comprises one or more ears at least 23 inches above ground level. In another aspect, a female corn plant provided herein comprises one or more ears at least 24 inches above ground level. In another aspect, a female corn plant provided herein comprises one or more ears at least 25 inches above ground level. In another aspect, a female corn plant provided herein comprises one or more ears at least 26 inches above ground level. In another aspect, a female corn plant provided herein comprises one or more ears at least 27 inches above ground level. In another aspect, a female corn plant provided herein comprises one or more ears at least 28 inches above ground level. In another aspect, a female corn plant provided herein comprises one or more ears at least 29 inches above ground level. In another aspect, a female corn plant provided herein comprises one or more ears at least 30 inches above ground level.

According to embodiments of the present disclosure, corn ear heights or average corn ear height of (or on) female corn plants as described herein (e.g., in a corn production field) may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the corn ear height(s) and/or average corn ear height(s) of (or on) female corn plants as described herein is at R1 stage.

In an aspect, at least one female corn plant provided herein comprises at least one ear or an average ear height that is at least 14 inches above ground level. In another aspect, at least one female corn plant provided herein comprises at least one ear or an average ear height that is at least 15 inches above ground level. In another aspect, at least one female corn plant provided herein comprises at least one ear that is at least 16 inches above ground level. In another aspect, at least one female corn plant provided herein comprises at least one ear or an average ear height that is at least 17 inches above ground level. In another aspect, at least one female corn plant provided herein comprises at least one ear that is at least 18 inches above ground level. In another aspect, at least one female corn plant provided herein comprises at least one ear or an average ear height that is at least 19 inches above ground level. In another aspect, at least one female corn plant provided herein comprises at least one ear that is at least 20 inches above ground level. In another aspect, at least one female corn plant provided herein comprises at least one ear or an average ear height that is at least 21 inches above ground level. In another aspect, at least one female corn plant provided herein comprises at least one ear or an average ear height that is at least 22 inches above ground level. In another aspect, at least one female corn plant provided herein comprises at least one ear that is at least 23 inches above ground level. In another aspect, at least one female corn plant provided herein comprises at least one ear or an average ear height that is at least 24 inches above ground level. In another aspect, at least one female corn plant provided herein comprises at least one ear or an average ear height that is at least 25 inches above ground level. In another aspect, at least one female corn plant provided herein comprises at least one ear or an average ear height that is at least 26 inches above ground level. In another aspect, at least one female corn plant provided herein comprises at least one ear or an average ear height that is at least 27 inches above ground level. In another aspect, at least one female corn plant provided herein comprises at least one ear or an average ear height that is at least 28 inches above ground level. In another aspect, at least one female corn plant provided herein comprises at least one ear or an average ear height that is at least 29 inches above ground level. In another aspect, at least one female corn plant provided herein comprises at least one ear or an average ear height that is at least 30 inches above ground level.

In an aspect, at least one female corn plant provided herein comprises at least one ear or an average ear height between 14 and 40 inches above ground level. In an aspect, at least one female corn plant provided herein comprises at least one ear or an average ear height between 14 and 35 inches above ground level. In an aspect, at least one female corn plant provided herein comprises at least one ear or an average ear height between 14 and 30 inches above ground level. In an aspect, at least one female corn plant provided herein comprises at least one ear or an average ear height between 14 and 25 inches above ground level. In an aspect, at least one female corn plant provided herein comprises at least one ear or an average ear height between 14 and 20 inches above ground level. In an aspect, at least one female corn plant provided herein comprises at least one ear or an average ear height between 14 and 18 inches above ground level. In an aspect, at least one female corn plant provided herein comprises at least one ear or an average ear height between 14 and 16 inches above ground level.

In an aspect, at least one female corn plant provided herein comprises at least one ear or an average ear height between 16 and 40 inches above ground level. In an aspect, at least one female corn plant provided herein comprises at least one ear or an average ear height between 16 and 35 inches above ground level. In an aspect, at least one female corn plant provided herein comprises at least one ear or an average ear height between 16 and 30 inches above ground level. In an aspect, at least one female corn plant provided herein comprises at least one ear or an average ear height between 16 and 25 inches above ground level. In an aspect, at least one female corn plant provided herein comprises at least one ear or an average ear height between 16 and 20 inches above ground level. In another aspect, at least one female corn plant provided herein comprises at least one ear or an average ear height between 16 and 18 inches above ground level.

In an aspect, at least one female corn plant provided herein comprises at least one ear or an average ear height between 18 and 40 inches above ground level. In an aspect, at least one female corn plant provided herein comprises at least one ear or an average ear height between 18 and 35 inches above ground level. In an aspect, at least one female corn plant provided herein comprises at least one ear or an average ear height between 18 and 30 inches above ground level. In an aspect, at least one female corn plant provided herein comprises at least one ear or an average ear height between 18 and 25 inches above ground level. In an aspect, at least one female corn plant provided herein comprises at least one ear or an average ear height between 18 and 22 inches above ground level. In another aspect, at least one female corn plant provided herein comprises at least one ear or an average ear height between 18 and 20 inches above ground level.

In an aspect, at least one female corn plant provided herein comprises at least one ear or an average ear height between 20 and 40 inches above ground level. In an aspect, at least one female corn plant provided herein comprises at least one ear or an average ear height between 20 and 35 inches above ground level. In an aspect, at least one female corn plant provided herein comprises at least one ear or an average ear height between 20 and 30 inches above ground level. In an aspect, at least one female corn plant provided herein comprises at least one ear or an average ear height between 20 and 25 inches above ground level. In another aspect, at least one female corn plant provided herein comprises at least one ear or an average ear height between 20 and 22 inches above ground level.

The description above for a female corn plant having at least one ear at or above a height, or within a height range, can also be applied to a plurality, row(s) or population of female corn plants used for seed production.

As used herein, the term "pollination" refers to the transfer of pollen from a male corn plant, or male floret, to a receptive structure of a female corn plant, or female floret. An example of a receptive structure of a female corn plant is a silk. It is appreciated in the art that a corn plant can pollinate itself (e.g., it is capable of self-pollination) if not detasseled, etc. In an aspect, a corn plant provided herein is not capable of self-pollination.

As used herein, the term "fertilization" refers to the union of a male gamete and a female gamete to produce a kernel, or fertilized egg, following pollination. In an aspect, fertilization is performed by wind. In another aspect, fertilization is performed by human intervention. In another aspect, fertilization is performed by an animal or insect.

As used herein, the term "crossing" refers to the deliberate mating of two plants. The two types of plants can be distantly related, closely related, or identical. In an aspect, crossing comprises pollination and/or fertilization of a plurality or population of female inbred corn plants with pollen from at least one male inbred corn plant. In another aspect, crossing comprises pollination and/or fertilization of a plurality or population of female corn plants with pollen from at least one male corn plant. In another aspect, crossing comprises pollination and/or fertilization of a female corn plant or inbred with pollen from at least one male corn plant.

As used herein, a male corn plant and a female corn plant are in "proximity" or "near" to one other if they are physically separated by a distance short enough to allow cross-pollination to occur.

As used herein, a "hybrid corn seed" is considered to be a seed which is produced by the fertilization of a female corn plant of a first variety, line, or cultivar with the pollen of a male corn plant of a different variety, line, or cultivar (i.e., a seed produced by a hybrid corn plant).

As used herein, a "field" or a "corn field" refers to an outdoor location that is suitable for growing corn. The location can be irrigated or non-irrigated. A corn field can comprise a land area planted with corn seed and/or at least one corn plant or a plurality of corn plants, which can be at one or more stages of development. In an aspect, a corn plant provided herein is planted in a field. In another aspect, a corn plant provided herein is planted indoors, such as in a greenhouse, and/or in a container holding a growth medium or soil.

In an aspect, a field comprises a single plot. In another aspect, a field comprises multiple plots. In another aspect, one or more edges of a field are bordered by a fence. In another aspect, one or more edges of a field are unfenced. In another aspect, one or more edges of a field are bordered by hedges. In an aspect, a field comprises a physically contiguous space. In another aspect, the field comprises a physically non-contiguous space. In still another aspect, the field comprises a biologically contiguous space. As used herein, a "biologically contiguous space" refers to a space or field wherein the pollen can move from one section of the space or field to another section of the space or field. In an aspect, a biologically contiguous field is physically contiguous. In another aspect, a biologically contiguous field is physically non-contiguous (e.g., plots within the field or a single plot within the field can be separated by one or more structures, such as, without being limiting, a road, creek, irrigation ditch, trail, hedgerow, fence, irrigation pipes, fallow field, empty field, non-corn plants).

In an aspect, a field comprises at least 0.5 acres. In an aspect, a field comprises at least 1 acre. In another aspect, a field comprises at least 5 acres. In another aspect, a field comprises at least 10 acres. In another aspect, a field comprises at least 15 acres. In another aspect, a field comprises at least 20 acres. In another aspect, a field comprises at least 25 acres. In another aspect, a field comprises at least 30 acres. In another aspect, a field comprises at least 35 acres. In another aspect, a field comprises at least 40 acres. In another aspect, a field comprises at least 45 acres. In another aspect, a field comprises at least 50 acres. In another aspect, a field comprises at least 75 acres. In another aspect, a field comprises at least 100 acres. In another aspect, a field comprises at least 150 acres. In another aspect, a field comprises at least 200 acres. In another aspect, a field comprises at least 250 acres. In another aspect, a field comprises at least 300 acres. In another aspect, a field comprises at least 350 acres. In another aspect, a field comprises at least 400 acres. In another aspect, a field comprises at least 450 acres. In another aspect, a field comprises at least 500 acres. In another aspect, a field comprises at least 750 acres. In another aspect, a field comprises at least 1000 acres. In another aspect, a field comprises at least 1500 acres. In another aspect, a field comprises at least 2000 acres. In another aspect, a field comprises at least 2500 acres. In another aspect, a field comprises at least 3000 acres. In another aspect, a field comprises at least 4000 acres. In another aspect, a field comprises at least 5000 acres. In another aspect, a field comprises at least 10,000 acres.

In an aspect, a field comprises between 0.5 acres and 10,000 acres. In another aspect, a field comprises between 1 acre and 10,000 acres. In another aspect, a field comprises between 5 acres and 10,000 acres. In another aspect, a field comprises between 10 acres and 10,000 acres. In another aspect, a field comprises between 15 acres and 10,000 acres. In another aspect, a field comprises between 20 acres and 10,000 acres. In another aspect, a field comprises between 25 acres and 10,000 acres. In another aspect, a field comprises between 30 acres and 10,000 acres. In another aspect, a field comprises between 35 acres and 10,000 acres. In another aspect, a field comprises between 40 acres and 10,000 acres. In another aspect, a field comprises between 45 acres and 10,000 acres. In another aspect, a field comprises between 50 acres and 10,000 acres. In another aspect, a field comprises between 75 acres and 10,000 acres. In another aspect, a field comprises between 100 acres and 10,000 acres. In another aspect, a field comprises between 150 acres and 10,000 acres. In another aspect, a field comprises between 200 acres and 10,000 acres. In another aspect, a field comprises between 250 acres and 10,000 acres. In another aspect, a field comprises between 300 acres and 10,000 acres. In another aspect, a field comprises between 350 acres and 10,000 acres. In another aspect, a field comprises between 400 acres and 10,000 acres. In another aspect, a field comprises between 450 acres and 10,000 acres. In another aspect, a field comprises between 500 acres and 10,000 acres. In another aspect, a field comprises between 750 acres and 10,000 acres. In another aspect, a field comprises between 1000 acres and 10,000 acres. In another aspect, a field comprises between 1500 acres and 10,000 acres. In another aspect, a field comprises between 2000 acres and 10,000 acres. In another aspect, a field comprises between 2500 acres and 10,000 acres. In another aspect, a field comprises between 3000 acres and 10,000 acres. In another aspect, a field comprises between 4000 acres and 10,000 acres. In another aspect, a field comprises between 5000 acres and 10,000 acres. In another aspect, a field comprises between 1 acre and 5000 acres. In another aspect, a field comprises between 1 acre and 2500 acres. In another aspect, a field comprises between 1 acre and 1000 acres. In another aspect, a field comprises between 1 acre and 500 acres. In another aspect, a field comprises between 1 acre and 250 acres. In another aspect, a field comprises between 1 acre and 100 acres. In another aspect, a field comprises between 1 acre and 75 acres. In another aspect, a field comprises between 1 acre and 50 acres. In another aspect, a field comprises between 1 acre and 25 acres. In another aspect, a field comprises between 1 acre and 10 acres.

In an aspect, the corn plants provided herein are grown in a field. According to aspects of the present disclosure, a field may comprise male and female corn plants of different inbreds or varieties for hybrid corn seed production. In another aspect, the female inbred corn plants and at least one male inbred corn plant provided herein are grown in a field. In another aspect, the corn plants provided herein are grown in a greenhouse. In another aspect, the female inbred corn plants and at least one male inbred corn plant provided herein are grown in a greenhouse. According to some aspects, a corn field can comprise two or more pluralities of corn plants with the pluralities of corn plants being planted with different corn varieties, at different times, at different densities, in different arrangements (e.g., in rows or scattered or random placement), and/or at different row spacings and/or row lengths, such that the pluralities of corn plants have different heights, spacings, etc., at different time points during the growing season, although each plurality of corn plants can be relatively uniform with respect to plant height and other growth metrics. Typically, corn plants are planted in rows of approximately equal spacing, which may comprise male and female rows for corn seed production. The female and male rows may be present in a regular or repeating pattern or in an irregular or non-repeating pattern, and/or male plants may be interplanted between female rows. As yet another alternative, the female and male plants may be planted randomly or not in rows.

In an aspect, a corn field can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds. In another aspect, a greenhouse and/or in a container holding a growth medium or soil can further comprise plants other than corn plants including, without being limiting, cotton, alfalfa, sunflowers, sorghum, wheat, barley, oat, rice, rye, soybean, vegetables (e.g., potato, tomato, carrot), grass (e.g., bluegrass, Triticale), and weeds.

In an aspect, a corn field comprises at least two corn plants. In another aspect, a corn field comprises at least 10 corn plants. In another aspect, a corn field comprises at least 100 corn plants. In another aspect, a corn field comprises at least 200 corn plants. In another aspect, a corn field comprises at least 500 corn plants. In another aspect, a corn field comprises at least 1,000 corn plants. In another aspect, a corn field comprises at least 2,000 corn plants. In another aspect, a corn field comprises at least 5,000 corn plants. In another aspect, a corn field comprises at least 10,000 corn plants. In another aspect, a corn field comprises at least 20,000 corn plants. In another aspect, a corn field comprises at least 50,000 corn plants. In another aspect, a corn field comprises at least 100,000 corn plants. In another aspect, a corn field comprises at least 200,000 corn plants. In another aspect, a corn field comprises at least 500,000 corn plants. In another aspect, a corn field comprises at least 1,000,000 corn plants. In another aspect, a corn field comprises at least 2,000,000 corn plants. In another aspect, a corn field comprises at least 5,000,000 corn plants. In another aspect, a corn field comprises at least 10,000,000 corn plants.

In an aspect, a corn field comprises between 1 and 10 corn plants. In another aspect, a corn field comprises between 1 and 100 corn plants. In another aspect, a corn field comprises between 1 and 200 corn plants. In another aspect, a corn field comprises between 1 and 500 corn plants. In another aspect, a corn field comprises between 1 and 1,000 corn plants. In another aspect, a corn field comprises between 1 and 2,000 corn plants. In another aspect, a corn field comprises between 1 and 5,000 corn plants. In another aspect, a corn field comprises between 1 and 10,000 corn plants. In another aspect, a corn field comprises between 1 and 20,000 corn plants. In another aspect, a corn field comprises between 1 and 50,000 corn plants. In another aspect, a corn field comprises between 1 and 100,000 corn plants. In another aspect, a corn field comprises between 1 and 200,000 corn plants. In another aspect, a corn field comprises between 1 and 500,000 corn plants. In another aspect, a corn field comprises between 1 and 1,000,000 corn plants. In another aspect, a corn field comprises between 1 and 2,000,000 corn plants. In another aspect, a corn field comprises between 1 and 5,000,000 corn plants. In another aspect, a corn field comprises between 1 and 10,000,000 corn plants. In another aspect, a corn field comprises between 10 and 10,000,000 corn plants. In another aspect, a corn field comprises between 100 and 10,000,000 corn plants. In another aspect, a corn field comprises between 200 and 10,000,000 corn plants. In another aspect, a corn field comprises between 500 and 10,000,000 corn plants. In another aspect, a corn field comprises between 1,000 and 10,000,000 corn plants. In another aspect, a corn field comprises between 2,000 and 10,000,000 corn plants. In another aspect, a corn field comprises between 5,000 and 10,000,000 corn plants. In another aspect, a corn field comprises between 10,000 and 10,000,000 corn plants. In another aspect, a corn field comprises between 20,000 and 10,000,000 corn plants. In another aspect, a corn field comprises between 50,000 and 10,000,000 corn plants. In another aspect, a corn field comprises between 100,000 and 10,000,000 corn plants. In another aspect, a corn field comprises between 200,000 and 10,000,000 corn plants. In another aspect, a corn field comprises between 500,000 and 10,000,000 corn plants. In another aspect, a corn field comprises between 1,000,000 and 10,000,000 corn plants. In another aspect, a corn field comprises between 2,000,000 and 10,000,000 corn plants. In another aspect, a corn field comprises between 5,000,000 and 10,000,000 corn plants. In another aspect, a corn field comprises between 1,000 and 10,000 corn plants. In another aspect, a corn field comprises between 1,000 and 100,000 corn plants. In another aspect, a corn field comprises between 10,000 and 50,000 corn plants. In another aspect, a corn field comprises between 10,000 and 100,000 corn plants. In another aspect, a corn field comprises between 10,000 and 1,000,000 corn plants. In another aspect, a corn field comprises between 100,000 and 1,000,000 corn plants. In another aspect, a corn field comprises between 100,000 and 2,000,000 corn plants. In another aspect, a corn field comprises between 100,000 and 5,000,000 corn plants. In another aspect, a corn field comprises between 1,000,000 and 2,000,000 corn plants. In another aspect, a corn field comprises between 1,000,000 and 5,000,000 corn plants. In another aspect, a corn field comprises between 2,000,000 and 5,000,000 corn plants.

As used herein, a "row" comprises at least one corn plant. In an aspect, a row comprises at least two corn plants. Without being limiting, a row of corn plants is planted in a line or in a generally or approximately linear arrangement, and if a corn field comprises two or more rows, they are typically planted parallel or nearly parallel to each other. A corn field can comprise one or more rows of corn plants where the rows are of the same or different lengths. Without being limiting, a corn field can comprise at least 1 row of corn plants. In another aspect, a corn field comprises at least 10 rows of corn plants. In another aspect, a corn field comprises at least 50 rows of corn plants. In another aspect, a corn field comprises at least 500 rows of corn plants. In another aspect, a corn field comprises at least 1,000 rows of corn plants. In another aspect, a corn field comprises at least 5,000 rows of corn plants. In another aspect, a corn field comprises at least 10,000 rows of corn plants.

In an aspect, a corn field comprises rows that are spaced at least 5 inches apart. In another aspect, a corn field comprises rows that are spaced at least 10 inches apart. In another aspect, a corn field comprises rows that are spaced at least 15 inches apart. In another aspect, a corn field comprises rows of corn plants that are spaced at least 20 inches apart. In another aspect, a corn field comprises rows of corn that are spaced at least 25 inches apart. In another aspect, a corn field comprises rows of corn that are spaced at least 30 inches apart. In another aspect, a corn field comprises rows of corn that are spaced at least 35 inches apart. In another aspect, a corn field comprises rows of corn that are spaced at least 40 inches apart.

As used herein, the term "density" refers to the number of individual plants that occur within a given unit area. In an aspect, a corn field comprises a density of at least 9,000 corn plants per acre. In another aspect, a corn field comprises a density of at least 12,000 corn plants per acre. In another aspect, a corn field comprises a density of at least 15,000 corn plants per acre. In another aspect, a corn field comprises a density of at least 18,000 corn plants per acre. In another aspect, a corn field comprises a density of at least 21,000 corn plants per acre. In another aspect, a corn field comprises a density of at least 24,000 corn plants per acre. In another aspect, a corn field comprises a density of at least 27,000 corn plants per acre. In another aspect, a corn field comprises a density of at least 30,000 corn plants per acre. In another aspect, a corn field comprises a density of at least 33,000 corn plants per acre. In another aspect, a corn field comprises a density of at least 36,000 corn plants per acre. In another aspect, a corn field comprises a density of at least 39,000 corn plants per acre. In another aspect, a corn field comprises a density of at least 42,000 corn plants per acre. In another aspect, a corn field comprises a density of at least 45,000 corn plants per acre. In another aspect, a corn field comprises a density of at least 48,000 corn plants per acre. In another aspect, a corn field comprises a density of at least 51,000 corn plants per acre. In another aspect, a corn field comprises a density of at least 54,000 corn plants per acre. In another aspect, a corn field comprises a density of at least 57,000 corn plants per acre. In another aspect, a corn field comprises a density of at least 60,000 corn plants per acre. In another aspect, a corn field comprises a density of at least 63,000 corn plants per acre. In another aspect, a corn field comprises a density of at least 66,000 corn plants per acre. In another aspect, a corn field comprises a density of at least 69,000 corn plants per acre. In another aspect, a corn field comprises a density of at least 72,000 corn plants per acre. In another aspect, a corn field comprises a density of at least 75,000 corn plants per acre.

In an aspect, a corn field comprises a density of between 20,000 corn plants and 60,000 corn plants per acre. In another aspect, a corn field comprises a density of between 20,000 corn plants and 55,000 corn plants per acre. In another aspect, a corn field comprises a density of between 20,000 corn plants and 50,000 corn plants per acre. In another aspect, a corn field comprises a density of between 20,000 corn plants and 45,000 corn plants per acre. In another aspect, a corn field comprises a density of between 20,000 corn plants and 40,000 corn plants per acre. In another aspect, a corn field comprises a density of between 20,000 corn plants and 35,000 corn plants per acre. In another aspect, a corn field comprises a density of between 20,000 corn plants and 30,000 corn plants per acre. In another aspect, a corn field comprises a density of between 24,000 corn plants and 58,000 corn plants per acre. In another aspect, a corn field comprises a density of between 38,000 corn plants and 60,000 corn plants per acre. In another aspect, a corn field comprises a density of between 38,000 corn plants and 50,000 corn plants per acre. In an aspect, a corn field comprises a density of less than 10,000 corn plants per acre. In another aspect, a corn field comprises a density of less than 20,000 corn plants per acre. In another aspect, a corn field comprises a density of less than 30,000 corn plants per acre.

In an aspect, a corn field comprises at least one corn plant and further comprises a density of at least 9,000 corn plants per acre. In another aspect, a corn field comprises at least one corn plant and further comprises a density of at least 12,000 corn plants per acre. In another aspect, a corn field comprises at least one corn plant and further comprises a density of at least 15,000 corn plants per acre. In another aspect, a corn field comprises at least one corn plant and further comprises a density of at least 18,000 corn plants per acre. In another aspect, a corn field comprises at least one corn plant and further comprises a density of at least 21,000 corn plants per acre. In another aspect, a corn field comprises at least one corn plant and further comprises a density of at least 24,000 corn plants per acre. In another aspect, a corn field comprises at least one corn plant and further comprises a density of at least 27,000 corn plants per acre. In another aspect, a corn field comprises at least one corn plant and further comprises a density of at least 30,000 corn plants per acre. In another aspect, a corn field comprises at least one corn plant and further comprises a density of at least 33,000 corn plants per acre. In another aspect, a corn field comprises at least one corn plant and further comprises a density of at least 36,000 corn plants per acre. In another aspect, a corn field comprises at least one corn plant and further comprises a density of at least one corn plant per acre. In another aspect, a corn field comprises at least one corn plant and further comprises a density of at least 42,000 corn plants per acre. In another aspect, a corn field comprises at least one corn plant and further comprises a density of at least 45,000 corn plants per acre. In another aspect, a corn field comprises at least one corn plant and further comprises a density of at least 48,000 corn plants per acre. In another aspect, a corn field comprises at least one corn plant and further comprises a density of at least 51,000 corn plants per acre. In another aspect, a corn field comprises at least one corn plant and further comprises a density of at least 54,000 corn plants per acre. In another aspect, a corn field comprises at least one corn plant and further comprises a density of at least 57,000 corn plants per acre. In another aspect, a corn field comprises at least one corn plant and further comprises a density of at least 60,000 corn plants per acre. In another aspect, a corn field comprises at least one corn plant and further comprises a density of at least 63,000 corn plants per acre. In another aspect, a corn field comprises at least one corn plant and further comprises a density of at least 66,000 corn plants per acre. In another aspect, a corn field comprises at least one corn plant and further comprises a density of at least 69,000 corn plants per acre. In another aspect, a corn field comprises at least one corn plant and further comprises a density of at least 72,000 corn plants per acre. In another aspect, a corn field comprises at least one corn plant and further comprises a density of at least 75,000 corn plants per acre.

In an aspect, a corn field comprises at least 1,000 corn plants and further comprises a density of at least 9,000 corn plants per acre. In another aspect, a corn field comprises at least 1,000 corn plants and further comprises a density of at least 12,000 corn plants per acre. In another aspect, a corn field comprises at least 1,000 corn plants and further comprises a density of at least 15,000 corn plants per acre. In another aspect, a corn field comprises at least 1,000 corn plants and further comprises a density of at least 18,000 corn plants per acre. In another aspect, a corn field comprises at least 1,000 corn plants and further comprises a density of at least 21,000 corn plants per acre. In another aspect, a corn field comprises at least 1,000 corn plants and further comprises a density of at least 24,000 corn plants per acre. In another aspect, a corn field comprises at least 1,000 corn plants and further comprises a density of at least 27,000 corn plants per acre. In another aspect, a corn field comprises at least 1,000 corn plants and further comprises a density of at least 30,000 corn plants per acre. In another aspect, a corn field comprises at least 1,000 corn plants and further comprises a density of at least 33,000 corn plants per acre. In another aspect, a corn field comprises at least 1,000 corn plants and further comprises a density of at least 36,000 corn plants per acre. In another aspect, a corn field comprises at least 1,000 corn plants and further comprises a density of at least 39,000 corn plants per acre. In another aspect, a corn field comprises at least 1,000 corn plants and further comprises a density of at least 42,000 corn plants per acre. In another aspect, a corn field comprises at least 1,000 corn plants and further comprises a density of at least 45,000 corn plants per acre. In another aspect, a corn field comprises at least 1,000 corn plants and further comprises a density of at least 48,000 corn plants per acre. In another aspect, a corn field comprises at least 1,000 corn plants and further comprises a density of at least 51,000 corn plants per acre. In another aspect, a corn field comprises at least 1,000 corn plants and further comprises a density of at least 54,000 corn plants per acre. In another aspect, a corn field comprises at least 1,000 corn plants and further comprises a density of at least 57,000 corn plants per acre. In another aspect, a corn field comprises at least 1,000 corn plants and further comprises a density of at least 60,000 corn plants per acre. In another aspect, a corn field comprises at least 1,000 corn plants and further comprises a density of at least 63,000 corn plants per acre. In another aspect, a corn field comprises at least 1,000 corn plants and further comprises a density of at least 66,000 corn plants per acre. In another aspect, a corn field comprises at least 1,000 corn plants and further comprises a density of at least 69,000 corn plants per acre. In another aspect, a corn field comprises at least 1,000 corn plants and further comprises a density of at least 72,000 corn plants per acre. In another aspect, a corn field comprises at least 1,000 corn plants and further comprises a density of at least 75,000 corn plants per acre.

In an aspect, a corn field comprises at least 10,000 corn plants and further comprises a density of at least 9,000 corn plants per acre. In another aspect, a corn field comprises at least 10,000 corn plants and further comprises a density of at least 12,000 corn plants per acre. In another aspect, a corn field comprises at least 10,000 corn plants and further comprises a density of at least 15,000 corn plants per acre. In another aspect, a corn field comprises at least 10,000 corn plants and further comprises a density of at least 18,000 corn plants per acre. In another aspect, a corn field comprises at least 10,000 corn plants and further comprises a density of at least 21,000 corn plants per acre. In another aspect, a corn field comprises at least 10,000 corn plants and further comprises a density of at least 24,000 corn plants per acre. In another aspect, a corn field comprises at least 10,000 corn plants and further comprises a density of at least 27,000 corn plants per acre. In another aspect, a corn field comprises at least 10,000 corn plants and further comprises a density of at least 30,000 corn plants per acre. In another aspect, a corn field comprises at least 10,000 corn plants and further comprises a density of at least 33,000 corn plants per acre. In another aspect, a corn field comprises at least 10,000 corn plants and further comprises a density of at least 36,000 corn plants per acre. In another aspect, a corn field comprises at least 10,000 corn plants and further comprises a density of at least 39,000 corn plants per acre. In another aspect, a corn field comprises at least 10,000 corn plants and further comprises a density of at least 42,000 corn plants per acre.

In another aspect, a corn field comprises at least 10,000 corn plants and further comprises a density of at least 45,000 corn plants per acre. In another aspect, a corn field comprises at least 10,000 corn plants and further comprises a density of at least 48,000 corn plants per acre. In another aspect, a corn field comprises at least 10,000 corn plants and further comprises a density of at least 51,000 corn plants per acre. In another aspect, a corn field comprises at least 10,000 corn plants and further comprises a density of at least 54,000 corn plants per acre. In another aspect, a corn field comprises at least 10,000 corn plants and further comprises a density of at least 57,000 corn plants per acre. In another aspect, a corn field comprises at least 10,000 corn plants and further comprises a density of at least 60,000 corn plants per acre. In another aspect, a corn field comprises at least 10,000 corn plants and further comprises a density of at least 63,000 corn plants per acre. In another aspect, a corn field comprises at least 10,000 corn plants and further comprises a density of at least 66,000 corn plants per acre. In another aspect, a corn field comprises at least 10,000 corn plants and further comprises a density of at least 69,000 corn plants per acre. In another aspect, a corn field comprises at least 10,000 corn plants and further comprises a density of at least 72,000 corn plants per acre. In another aspect, a corn field comprises at least 10,000 corn plants and further comprises a density of at least 75,000 corn plants per acre.

In an aspect, a corn field comprises at least 100,000 corn plants and further comprises a density of at least 9,000 corn plants per acre. In another aspect, a corn field comprises at least 100,000 corn plants and further comprises a density of at least 12,000 corn plants per acre. In another aspect, a corn field comprises at least 100,000 corn plants and further comprises a density of at least 15,000 corn plants per acre. In another aspect, a corn field comprises at least 100,000 corn plants and further comprises a density of at least 18,000 corn plants per acre. In another aspect, a corn field comprises at least 100,000 corn plants and further comprises a density of at least 21,000 corn plants per acre. In another aspect, a corn field comprises at least 100,000 corn plants and further comprises a density of at least 24,000 corn plants per acre. In another aspect, a corn field comprises at least 100,000 corn plants and further comprises a density of at least 27,000 corn plants per acre. In another aspect, a corn field comprises at least 100,000 corn plants and further comprises a density of at least 30,000 corn plants per acre. In another aspect, a corn field comprises at least 100,000 corn plants and further comprises a density of at least 33,000 corn plants per acre. In another aspect, a corn field comprises at least 100,000 corn plants and further comprises a density of at least 36,000 corn plants per acre. In another aspect, a corn field comprises at least 100,000 corn plants and further comprises a density of at least 39,000 corn plants per acre. In another aspect, a corn field comprises at least 100,000 corn plants and further comprises a density of at least 42,000 corn plants per acre. In another aspect, a corn field comprises at least 100,000 corn plants and further comprises a density of at least 45,000 corn plants per acre. In another aspect, a corn field comprises at least 100,000 corn plants and further comprises a density of at least 48,000 corn plants per acre. In another aspect, a corn field comprises at least 100,000 corn plants and further comprises a density of at least 51,000 corn plants per acre. In another aspect, a corn field comprises at least 100,000 corn plants and further comprises a density of at least 54,000 corn plants per acre. In another aspect, a corn field comprises at least 100,000 corn plants and further comprises a density of at least 57,000 corn plants per acre. In another aspect, a corn field comprises at least 100,000 corn plants and further comprises a density of at least 60,000 corn plants per acre. In another aspect, a corn field comprises at least 100,000 corn plants and further comprises a density of at least 63,000 corn plants per acre. In another aspect, a corn field comprises at least 100,000 corn plants and further comprises a density of at least 66,000 corn plants per acre. In another aspect, a corn field comprises at least 100,000 corn plants and further comprises a density of at least 69,000 corn plants per acre. In another aspect, a corn field comprises at least 100,000 corn plants and further comprises a density of at least 72,000 corn plants per acre. In another aspect, a corn field comprises at least 100,000 corn plants and further comprises a density of at least 75,000 corn plants per acre.

In an aspect, a corn field comprises at least 1,000,000 corn plants and further comprises a density of at least 9,000 corn plants per acre. In another aspect, a corn field comprises at least 1,000,000 corn plants and further comprises a density of at least 12,000 corn plants per acre. In another aspect, a corn field comprises at least 1,000,000 corn plants and further comprises a density of at least 15,000 corn plants per acre. In another aspect, a corn field comprises at least 1,000,000 corn plants and further comprises a density of at least 18,000 corn plants per acre. In another aspect, a corn field comprises at least 1,000,000 corn plants and further comprises a density of at least 21,000 corn plants per acre. In another aspect, a corn field comprises at least 1,000,000 corn plants and further comprises a density of at least 24,000 corn plants per acre. In another aspect, a corn field comprises at least 1,000,000 corn plants and further comprises a density of at least 27,000 corn plants per acre. In another aspect, a corn field comprises at least 1,000,000 corn plants and further comprises a density of at least 30,000 corn plants per acre. In another aspect, a corn field comprises at least 1,000,000 corn plants and further comprises a density of at least 33,000 corn plants per acre. In another aspect, a corn field comprises at least 1,000,000 corn plants and further comprises a density of at least 36,000 corn plants per acre. In another aspect, a corn field comprises at least 1,000,000 corn plants and further comprises a density of at least 39,000 corn plants per acre. In another aspect, a corn field comprises at least 1,000,000 corn plants and further comprises a density of at least 42,000 corn plants per acre. In another aspect, a corn field comprises at least 1,000,000 corn plants and further comprises a density of at least 45,000 corn plants per acre. In another aspect, a corn field comprises at least 1,000,000 corn plants and further comprises a density of at least 48,000 corn plants per acre. In another aspect, a corn field comprises at least 1,000,000 corn plants and further comprises a density of at least 51,000 corn plants per acre. In another aspect, a corn field comprises at least 1,000,000 corn plants and further comprises a density of at least 54,000 corn plants per acre. In another aspect, a corn field comprises at least 1,000,000 corn plants and further comprises a density of at least 57,000 corn plants per acre. In another aspect, a corn field comprises at least 1,000,000 corn plants and further comprises a density of at least 60,000 corn plants per acre. In another aspect, a corn field comprises at least 1,000,000 corn plants and further comprises a density of at least 63,000 corn plants per acre. In another aspect, a corn field comprises at least 1,000,000 corn plants and further comprises a density of at least 66,000 corn plants per acre. In another aspect, a corn field comprises at least 1,000,000 corn plants and further comprises a density of at least 69,000 corn plants per acre. In another aspect, a corn field comprises at least 1,000,000 corn plants and further comprises a density of at least 72,000 corn plants per acre. In another aspect, a corn field comprises at least 1,000,000 corn plants and further comprises a density of at least 75,000 corn plants per acre.

In an aspect, a corn field comprises at least 10,000,000 corn plants and further comprises a density of at least 9,000 corn plants per acre. In another aspect, a corn field comprises at least 10,000,000 corn plants and further comprises a density of at least 12,000 corn plants per acre. In another aspect, a corn field comprises at least 10,000,000 corn plants and further comprises a density of at least 15,000 corn plants per acre. In another aspect, a corn field comprises at least 10,000,000 corn plants and further comprises a density of at least 18,000 corn plants per acre. In another aspect, a corn field comprises at least 10,000,000 corn plants and further comprises a density of at least 21,000 corn plants per acre. In another aspect, a corn field comprises at least 10,000,000 corn plants and further comprises a density of at least 24,000 corn plants per acre. In another aspect, a corn field comprises at least 10,000,000 corn plants and further comprises a density of at least 27,000 corn plants per acre. In another aspect, a corn field comprises at least 10,000,000 corn plants and further comprises a density of at least 30,000 corn plants per acre. In another aspect, a corn field comprises at least 10,000,000 corn plants and further comprises a density of at least 33,000 corn plants per acre. In another aspect, a corn field comprises at least 10,000,000 corn plants and further comprises a density of at least 36,000 corn plants per acre. In another aspect, a corn field comprises at least 10,000,000 corn plants and further comprises a density of at least 39,000 corn plants per acre. In another aspect, a corn field comprises at least 10,000,000 corn plants and further comprises a density of at least 42,000 corn plants per acre. In another aspect, a corn field comprises at least 10,000,000 corn plants and further comprises a density of at least 45,000 corn plants per acre. In another aspect, a corn field comprises at least 10,000,000 corn plants and further comprises a density of at least 48,000 corn plants per acre. In another aspect, a corn field comprises at least 10,000,000 corn plants and further comprises a density of at least 51,000 corn plants per acre. In another aspect, a corn field comprises at least 10,000,000 corn plants and further comprises a density of at least 54,000 corn plants per acre. In another aspect, a corn field comprises at least 10,000,000 corn plants and further comprises a density of at least 57,000 corn plants per acre. In another aspect, a corn field comprises at least 10,000,000 corn plants and further comprises a density of at least 60,000 corn plants per acre. In another aspect, a corn field comprises at least 10,000,000 corn plants and further comprises a density of at least 63,000 corn plants per acre. In another aspect, a corn field comprises at least 10,000,000 corn plants and further comprises a density of at least 66,000 corn plants per acre. In another aspect, a corn field comprises at least 10,000,000 corn plants and further comprises a density of at least 69,000 corn plants per acre. In another aspect, a corn field comprises at least 10,000,000 corn plants and further comprises a density of at least 72,000 corn plants per acre. In another aspect, a corn field comprises at least 10,000,000 corn plants and further comprises a density of at least 75,000 corn plants per acre.

In an aspect, a corn field comprises at least one corn plant and further comprises a density of between 20,000 corn plants and 55,000 corn plants per acre. In another aspect, a corn field comprises at least one corn plant and further comprises a density of between 20,000 corn plants and 50,000 corn plants per acre. In another aspect, a corn field comprises at least one corn plant and further comprises a density of between 20,000 corn plants and 45,000 corn plants per acre. In another aspect, a corn field comprises at least one corn plant and further comprises a density of between 20,000 corn plants and 40,000 corn plants per acre. In another aspect, a corn field comprises at least one corn plant and further comprises a density of between 20,000 corn plants and 35,000 corn plants per acre. In another aspect, a corn field comprises at least one corn plant and further comprises a density of between 20,000 corn plants and 30,000 corn plants per acre. In another aspect, a corn field comprises at least one corn plant and further comprises a density of between 24,000 corn plants and 58,000 corn plants per acre. In another aspect, a corn field comprises at least one corn plant and further comprises a density of between 38,000 corn plants and 60,000 corn plants per acre. In another aspect, a corn field comprises at least one corn plant and further comprises a density of between 38,000 corn plants and 50,000 corn plants per acre. In another aspect, a corn field comprises at least one corn plant and further comprises a density of less than 10,000 corn plants per acre. In another aspect, a corn field comprises at least one corn plant and further comprises a density of less than 20,000 corn plants per acre. In another aspect, a corn field comprises at least one corn plant and further comprises a density of less than 30,000 corn plants per acre.

In an aspect, a corn field comprises at least 1,000 corn plants and further comprises a density of between 20,000 corn plants and 55,000 corn plants per acre. In another aspect, a corn field comprises at least 1,000 corn plants and further comprises a density of between 20,000 corn plants and 50,000 corn plants per acre. In another aspect, a corn field comprises at least 1,000 corn plants and further comprises a density of between 20,000 corn plants and 45,000 corn plants per acre. In another aspect, a corn field comprises at least 1,000 corn plants and further comprises a density of between 20,000 corn plants and 40,000 corn plants per acre. In another aspect, a corn field comprises at least 1,000 corn plants and further comprises a density of between 20,000 corn plants and 35,000 corn plants per acre. In another aspect, a corn field comprises at least 1,000 corn plants and further comprises a density of between 20,000 corn plants and 30,000 corn plants per acre. In another aspect, a corn field comprises at least 1,000 corn plants and further comprises a density of between 24,000 corn plants and 58,000 corn plants per acre. In another aspect, a corn field comprises at least 1,000 corn plants and further comprises a density of between 38,000 corn plants and 60,000 corn plants per acre. In another aspect, a corn field comprises at least 1,000 corn plants and further comprises a density of between 38,000 corn plants and 50,000 corn plants per acre. In another aspect, a corn field comprises at least 1,000 corn plants and further comprises a density of less than 10,000 corn plants per acre. In another aspect, a corn field comprises at least 1,000 corn plants and further comprises a density of less than 20,000 corn plants per acre. In another aspect, a corn field comprises at least 1,000 corn plants and further comprises a density of less than 30,000 corn plants per acre.

In an aspect, a corn field comprises at least 10,000 corn plants and further comprises a density of between 20,000 corn plants and 55,00 corn plants per acre. In another aspect, a corn field comprises at least 10,000 corn plants and further comprises a density of between 20,000 corn plants and 50,000 corn plants per acre. In another aspect, a corn field comprises at least 10,000 corn plants and further comprises a density of between 20,000 corn plants and 45,000 corn plants per acre. In another aspect, a corn field comprises at least 10,000 corn plants and further comprises a density of between 20,000 corn plants and 40,000 corn plants per acre.

In another aspect, a corn field comprises at least 10,000 corn plants and further comprises a density of between 20,000 corn plants and 35,000 corn plants per acre. In another aspect, a corn field comprises at least 10,000 corn plants and further comprises a density of between 20,000 corn plants and 30,000 corn plants per acre. In another aspect, a corn field comprises at least 10,000 corn plants and further comprises a density of between 24,000 corn plants and 58,000 corn plants per acre. In another aspect, a corn field comprises at least 10,000 corn plants and further comprises a density of between 38,000 corn plants and 60,000 corn plants per acre. In another aspect, a corn field comprises at least 10,000 corn plants and further comprises a density of between 38,000 corn plants and 50,000 corn plants per acre. In another aspect, a corn field comprises at least 10,000 corn plants and further comprises a density of less than 10,000 corn plants per acre. In another aspect, a corn field comprises at least 10,000 corn plants and further comprises a density of less than 20,000 corn plants per acre. In another aspect, a corn field comprises at least 10,000 corn plants and further comprises a density of less than 30,000 corn plants per acre.

In an aspect, a corn field comprises at least 100,000 corn plants and further comprises a density of between 20,000 corn plants and 55,000 corn plants per acre. In another aspect, a corn field comprises at least 100,000 corn plants and further comprises a density of between 20,000 corn plants and 50,000 corn plants per acre. In another aspect, a corn field comprises at least 100,000 corn plants and further comprises a density of between 20,000 corn plants and 45,000 corn plants per acre. In another aspect, a corn field comprises at least 100,000 corn plants and further comprises a density of between 20,000 corn plants and 40,000 corn plants per acre. In another aspect, a corn field comprises at least 100,000 corn plants and further comprises a density of between 20,000 corn plants and 35,000 corn plants per acre. In another aspect, a corn field comprises at least 100,000 corn plants and further comprises a density of between 20,000 corn plants and 30,000 corn plants per acre. In another aspect, a corn field comprises at least 100,000 corn plants and further comprises a density of between 24,000 corn plants and 58,000 corn plants per acre. In another aspect, a corn field comprises at least 100,000 corn plants and further comprises a density of between 38,000 corn plants and 60,000 corn plants per acre. In another aspect, a corn field comprises at least 100,000 corn plants and further comprises a density of between 38,000 corn plants and 50,000 corn plants per acre. In another aspect, a corn field comprises at least 100,000 corn plants and further comprises a density of less than 10,000 corn plants per acre. In another aspect, a corn field comprises at least 100,000 corn plants and further comprises a density of less than 20,000 corn plants per acre. In another aspect, a corn field comprises at least 100,000 corn plants and further comprises a density of less than 30,000 corn plants per acre.

In an aspect, a corn field comprises at least 1,000,000 corn plants and further comprises a density of between 20,000 corn plants and 55,000 corn plants per acre. In another aspect, a corn field comprises at least 1,000,000 corn plants and further comprises a density of between 20,000 corn plants and 50,000 corn plants per acre. In another aspect, a corn field comprises at least 1,000,000 corn plants and further comprises a density of between 20,000 corn plants and 45,000 corn plants per acre. In another aspect, a corn field comprises at least 1,000,000 corn plants and further comprises a density of between 20,000 corn plants and 40,000 corn plants per acre. In another aspect, a corn field comprises at least 1,000,000 corn plants and further comprises a density of between 20,000 corn plants and 35,000 corn plants per acre. In another aspect, a corn field comprises at least 1,000,000 corn plants and further comprises a density of between 20,000 corn plants and 30,000 corn plants per acre. In another aspect, a corn field comprises at least 1,000,000 corn plants and further comprises a density of between 24,000 corn plants and 58,000 corn plants per acre. In another aspect, a corn field comprises at least 1,000,000 corn plants and further comprises a density of between 38,000 corn plants and 60,000 corn plants per acre. In another aspect, a corn field comprises at least 1,000,000 corn plants and further comprises a density of between 38,000 corn plants and 50,000 corn plants per acre. In another aspect, a corn field comprises at least 1,000,000 corn plants and further comprises a density of less than 10,000 corn plants per acre. In another aspect, a corn field comprises at least 1,000,000 corn plants and further comprises a density of less than 20,000 corn plants per acre. In another aspect, a corn field comprises at least 1,000,000 corn plants and further comprises a density of less than 30,000 corn plants per acre.

In an aspect, a corn field comprises at least 10,000,000 corn plants and further comprises a density of between 20,000 corn plants and 55,000 corn plants per acre. In another aspect, a corn field comprises at least 10,000,000 corn plants and further comprises a density of between 20,000 corn plants and 50,000 corn plants per acre. In another aspect, a corn field comprises at least 10,000,000 corn plants and further comprises a density of between 20,000 corn plants and 45,000 corn plants per acre. In another aspect, a corn field comprises at least 10,000,000 corn plants and further comprises a density of between 20,000 corn plants and 40,000 corn plants per acre. In another aspect, a corn field comprises at least 10,000,000 corn plants and further comprises a density of between 20,000 corn plants and 35,000 corn plants per acre. In another aspect, a corn field comprises at least 10,000,000 corn plants and further comprises a density of between 20,000 corn plants and 30,000 corn plants per acre. In another aspect, a corn field comprises at least 10,000,000 corn plants and further comprises a density of between 24,000 corn plants and 58,000 corn plants per acre. In another aspect, a corn field comprises at least 10,000,000 corn plants and further comprises a density of between 38,000 corn plants and 60,000 corn plants per acre. In another aspect, a corn field comprises at least 10,000,000 corn plants and further comprises a density of between 38,000 corn plants and 50,000 corn plants per acre. In another aspect, a corn field comprises at least 10,000,000 corn plants and further comprises a density of less than 10,000 corn plants per acre. In another aspect, a corn field comprises at least 10,000,000 corn plants and further comprises a density of less than 20,000 corn plants per acre. In another aspect, a corn field comprises at least 10,000,000 corn plants and further comprises a density of less than 30,000 corn plants per acre.

In an aspect, a corn field comprises between one and 1,000 corn plants and further comprises a density of at least 9,000 corn plants per acre. In another aspect, a corn field comprises between one and 1,000 corn plants and further comprises a density of at least 12,000 corn plants per acre. In another aspect, a corn field comprises between one and 1,000 corn plants and further comprises a density of at least 15,000 corn plants per acre. In another aspect, a corn field comprises between one and 1,000 corn plants and further comprises a density of at least 18,000 corn plants per acre. In another aspect, a corn field comprises between one and 1,000 corn plants and further comprises a density of at least 21,000 corn plants per acre. In another aspect, a corn field comprises between one and 1,000 corn plants and further comprises a density of at least 24,000 corn plants per acre. In another aspect, a corn field comprises between one and 1,000 corn plants and further comprises a density of at least 27,000 corn plants per acre. In another aspect, a corn field comprises between one and 1,000 corn plants and further comprises a density of at least 30,000 corn plants per acre. In another aspect, a corn field comprises between one and 1,000 corn plants and further comprises a density of at least 33,000 corn plants per acre. In another aspect, a corn field comprises between one and 1,000 corn plants and further comprises a density of at least 36,000 corn plants per acre. In another aspect, a corn field comprises between one and 1,000 corn plants and further comprises a density of at least 39,000 corn plants per acre. In another aspect, a corn field comprises between one and 1,000 corn plants and further comprises a density of at least 42,000 corn plants per acre. In another aspect, a corn field comprises between one and 1,000 corn plants and further comprises a density of at least 45,000 corn plants per acre. In another aspect, a corn field comprises between one and 1,000 corn plants and further comprises a density of at least 48,000 corn plants per acre. In another aspect, a corn field comprises between one and 1,000 corn plants and further comprises a density of at least 51,000 corn plants per acre. In another aspect, a corn field comprises between one and 1,000 corn plants and further comprises a density of at least 54,000 corn plants per acre. In another aspect, a corn field comprises between one and 1,000 corn plants and further comprises a density of at least 57,000 corn plants per acre. In another aspect, a corn field comprises between one and 1,000 corn plants and further comprises a density of at least 60,000 corn plants per acre. In another aspect, a corn field comprises between one and 1,000 corn plants and further comprises a density of at least 63,000 corn plants per acre. In another aspect, a corn field comprises between one and 1,000 corn plants and further comprises a density of at least 66,000 corn plants per acre. In another aspect, a corn field comprises between one and 1,000 corn plants and further comprises a density of at least 69,000 corn plants per acre. In another aspect, a corn field comprises between one and 1,000 corn plants and further comprises a density of at least 72,000 corn plants per acre. In another aspect, a corn field comprises between one and 1,000 corn plants and further comprises a density of at least 75,000 corn plants per acre.

In an aspect, a corn field comprises between 1,000 and 10,000 corn plants and further comprises a density of at least 9,000 corn plants per acre. In another aspect, a corn field comprises between 1,000 and 10,000 corn plants and further comprises a density of at least 12,000 corn plants per acre. In another aspect, a corn field comprises between 1,000 and 10,000 corn plants and further comprises a density of at least 15,000 corn plants per acre. In another aspect, a corn field comprises between 1,000 and 10,000 corn plants and further comprises a density of at least 18,000 corn plants per acre. In another aspect, a corn field comprises between 1,000 and 10,000 corn plants and further comprises a density of at least 21,000 corn plants per acre. In another aspect, a corn field comprises between 1,000 and 10,000 corn plants and further comprises a density of at least 24,000 corn plants per acre. In another aspect, a corn field comprises between 1,000 and 10,000 corn plants and further comprises a density of at least 27,000 corn plants per acre. In another aspect, a corn field comprises between 1,000 and 10,000 corn plants and further comprises a density of at least 30,000 corn plants per acre. In another aspect, a corn field comprises between 1,000 and 10,000 corn plants and further comprises a density of at least 33,000 corn plants per acre. In another aspect, a corn field comprises between 1,000 and 10,000 corn plants and further comprises a density of at least 36,000 corn plants per acre. In another aspect, a corn field comprises between 1,000 and 10,000 corn plants and further comprises a density of at least 39,000 corn plants per acre. In another aspect, a corn field comprises between 1,000 and 10,000 corn plants and further comprises a density of at least 42,000 corn plants per acre. In another aspect, a corn field comprises between 1,000 and 10,000 corn plants and further comprises a density of at least 45,000 corn plants per acre. In another aspect, a corn field comprises between 1,000 and 10,000 corn plants and further comprises a density of at least 48,000 corn plants per acre. In another aspect, a corn field comprises between 1,000 and 10,000 corn plants and further comprises a density of at least 51,000 corn plants per acre. In another aspect, a corn field comprises between 1,000 and 10,000 corn plants and further comprises a density of at least 54,000 corn plants per acre. In another aspect, a corn field comprises between 1,000 and 10,000 corn plants and further comprises a density of at least 57,000 corn plants per acre. In another aspect, a corn field comprises between 1,000 and 10,000 corn plants and further comprises a density of at least 60,000 corn plants per acre. In another aspect, a corn field comprises between 1,000 and 10,000 corn plants and further comprises a density of at least 63,000 corn plants per acre. In another aspect, a corn field comprises between 1,000 and 10,000 corn plants and further comprises a density of at least 66,000 corn plants per acre. In another aspect, a corn field comprises between 1,000 and 10,000 corn plants and further comprises a density of at least 69,000 corn plants per acre. In another aspect, a corn field comprises between 1,000 and 10,000 corn plants and further comprises a density of at least 72,000 corn plants per acre. In another aspect, a corn field comprises between 1,000 and 10,000 corn plants and further comprises a density of at least 75,000 corn plants per acre.

In an aspect, a corn field comprises between 10,000 and 100,000 corn plants and further comprises a density of at least 9,000 corn plants per acre. In another aspect, a corn field comprises between 10,000 and 100,000 corn plants and further comprises a density of at least 12,000 corn plants per acre. In another aspect, a corn field comprises between 10,000 and 100,000 corn plants and further comprises a density of at least 15,000 corn plants per acre. In another aspect, a corn field comprises between 10,000 and 100,000 corn plants and further comprises a density of at least 18,000 corn plants per acre. In another aspect, a corn field comprises between 10,000 and 100,000 corn plants and further comprises a density of at least 21,000 corn plants per acre. In another aspect, a corn field comprises between 10,000 and 100,000 corn plants and further comprises a density of at least 24,000 corn plants per acre. In another aspect, a corn field comprises between 10,000 and 100,000 corn plants and further comprises a density of at least 27,000 corn plants per acre. In another aspect, a corn field comprises between 10,000 and 100,000 corn plants and further comprises a density of at least 30,000 corn plants per acre. In another aspect, a corn field comprises between 10,000 and 100,000 corn plants and further comprises a density of at least 33,000 corn plants per acre. In another aspect, a corn field comprises between 10,000 and 100,000 corn plants and further comprises a density of at least 36,000 corn plants per acre. In another aspect, a corn field comprises between 10,000 and 100,000 corn plants and further comprises a density of at least 39,000 corn plants per acre. In another aspect, a corn field comprises between 10,000 and 100,000 corn plants and further comprises a density of at least 42,000 corn plants per acre. In another aspect, a corn field comprises between 10,000 and 100,000 corn plants and further comprises a density of at least 45,000 corn plants per acre. In another aspect, a corn field comprises between 10,000 and 100,000 corn plants and further comprises a density of at least 48,000 corn plants per acre. In another aspect, a corn field comprises between 10,000 and 100,000 corn plants and further comprises a density of at least 51,000 corn plants per acre. In another aspect, a corn field comprises between 10,000 and 100,000 corn plants and further comprises a density of at least 54,000 corn plants per acre. In another aspect, a corn field comprises between 10,000 and 100,000 corn plants and further comprises a density of at least 57,000 corn plants per acre. In another aspect, a corn field comprises between 10,000 and 100,000 corn plants and further comprises a density of at least 60,000 corn plants per acre. In another aspect, a corn field comprises between 10,000 and 100,000 corn plants and further comprises a density of at least 63,000 corn plants per acre. In another aspect, a corn field comprises between 10,000 and 100,000 corn plants and further comprises a density of at least 66,000 corn plants per acre. In another aspect, a corn field comprises between 10,000 and 100,000 corn plants and further comprises a density of at least 69,000 corn plants per acre. In another aspect, a corn field comprises between 10,000 and 100,000 corn plants and further comprises a density of at least 72,000 corn plants per acre. In another aspect, a corn field comprises between 10,000 and 100,000 corn plants and further comprises a density of at least 75,000 corn plants per acre.

In an aspect, a corn field comprises between 100,000 and 1,000,000 corn plants and further comprises a density of at least 9,000 corn plants per acre. In another aspect, a corn field comprises between 100,000 and 1,000,000 corn plants and further comprises a density of at least 12,000 corn plants per acre. In another aspect, a corn field comprises between 100,000 and 1,000,000 corn plants and further comprises a density of at least 15,000 corn plants per acre. In another aspect, a corn field comprises between 100,000 and 1,000,000 corn plants and further comprises a density of at least 18,000 corn plants per acre. In another aspect, a corn field comprises between 100,000 and 1,000,000 corn plants and further comprises a density of at least 21,000 corn plants per acre. In another aspect, a corn field comprises between 100,000 and 1,000,000 corn plants and further comprises a density of at least 24,000 corn plants per acre. In another aspect, a corn field comprises between 100,000 and 1,000,000 corn plants and further comprises a density of at least 27,000 corn plants per acre. In another aspect, a corn field comprises between 100,000 and 1,000,000 corn plants and further comprises a density of at least 30,000 corn plants per acre. In another aspect, a corn field comprises between 100,000 and 1,000,000 corn plants and further comprises a density of at least 33,000 corn plants per acre. In another aspect, a corn field comprises between 100,000 and 1,000,000 corn plants and further comprises a density of at least 36,000 corn plants per acre. In another aspect, a corn field comprises between 100,000 and 1,000,000 corn plants and further comprises a density of at least 39,000 corn plants per acre. In another aspect, a corn field comprises between 100,000 and 1,000,000 corn plants and further comprises a density of at least 42,000 corn plants per acre. In another aspect, a corn field comprises between 100,000 and 1,000,000 corn plants and further comprises a density of at least 45,000 corn plants per acre. In another aspect, a corn field comprises between 100,000 and 1,000,000 corn plants and further comprises a density of at least 48,000 corn plants per acre. In another aspect, a corn field comprises between 100,000 and 1,000,000 corn plants and further comprises a density of at least 51,000 corn plants per acre. In another aspect, a corn field comprises between 100,000 and 1,000,000 corn plants and further comprises a density of at least 54,000 corn plants per acre. In another aspect, a corn field comprises between 100,000 and 1,000,000 corn plants and further comprises a density of at least 57,000 corn plants per acre. In another aspect, a corn field comprises between 100,000 and 1,000,000 corn plants and further comprises a density of at least 60,000 corn plants per acre. In another aspect, a corn field comprises between 100,000 and 1,000,000 corn plants and further comprises a density of at least 63,000 corn plants per acre. In another aspect, a corn field comprises between 100,000 and 1,000,000 corn plants and further comprises a density of at least 66,000 corn plants per acre. In another aspect, a corn field comprises between 100,000 and 1,000,000 corn plants and further comprises a density of at least 69,000 corn plants per acre. In another aspect, a corn field comprises between 100,000 and 1,000,000 corn plants and further comprises a density of at least 72,000 corn plants per acre. In another aspect, a corn field comprises between 100,000 and 1,000,000 corn plants and further comprises a density of at least 75,000 corn plants per acre.

In an aspect, a corn field comprises between 1,000,000 and 10,000,000 corn plants and further comprises a density of at least 9,000 corn plants per acre. In another aspect, a corn field comprises between 1,000,000 and 10,000,000 corn plants and further comprises a density of at least 12,000 corn plants per acre. In another aspect, a corn field comprises between 1,000,000 and 10,000,000 corn plants and further comprises a density of at least 15,000 corn plants per acre. In another aspect, a corn field comprises between 1,000,000 and 10,000,000 corn plants and further comprises a density of at least 18,000 corn plants per acre. In another aspect, a corn field comprises between 1,000,000 and 10,000,000 corn plants and further comprises a density of at least 21,000 corn plants per acre. In another aspect, a corn field comprises between 1,000,000 and 10,000,000 corn plants and further comprises a density of at least 24,000 corn plants per acre. In another aspect, a corn field comprises between 1,000,000 and 10,000,000 corn plants and further comprises a density of at least 27,000 corn plants per acre. In another aspect, a corn field comprises between 1,000,000 and 10,000,000 corn plants and further comprises a density of at least 30,000 corn plants per acre. In another aspect, a corn field comprises between 1,000,000 and 10,000,000 corn plants and further comprises a density of at least 33,000 corn plants per acre. In another aspect, a corn field comprises between 1,000,000 and 10,000,000 corn plants and further comprises a density of at least 36,000 corn plants per acre. In another aspect, a corn field comprises between 1,000,000 and 10,000,000 corn plants and further comprises a density of at least 39,000 corn plants per acre. In another aspect, a corn field comprises between 1,000,000 and 10,000,000 corn plants and further comprises a density of at least 42,000 corn plants per acre. In another aspect, a corn field comprises between 1,000,000 and 10,000,000 corn plants and further comprises a density of at least 45,000 corn plants per acre. In another aspect, a corn field comprises between 1,000,000 and 10,000,000 corn plants and further comprises a density of at least 48,000 corn plants per acre. In another aspect, a corn field comprises between 1,000,000 and 10,000,000 corn plants and further comprises a density of at least 51,000 corn plants per acre. In another aspect, a corn field comprises between 1,000,000 and 10,000,000 corn plants and further comprises a density of at least 54,000 corn plants per acre. In another aspect, a corn field comprises between 1,000,000 and 10,000,000 corn plants and further comprises a density of at least 57,000 corn plants per acre. In another aspect, a corn field comprises between 1,000,000 and 10,000,000 corn plants and further comprises a density of at least 60,000 corn plants per acre. In another aspect, a corn field comprises between 1,000,000 and 10,000,000 corn plants and further comprises a density of at least 63,000 corn plants per acre. In another aspect, a corn field comprises between 1,000,000 and 10,000,000 corn plants and further comprises a density of at least 66,000 corn plants per acre. In another aspect, a corn field comprises between 1,000,000 and 10,000,000 corn plants and further comprises a density of at least 69,000 corn plants per acre. In another aspect, a corn field comprises between 1,000,000 and 10,000,000 corn plants and further comprises a density of at least 72,000 corn plants per acre. In another aspect, a corn field comprises between 1,000,000 and 10,000,000 corn plants and further comprises a density of at least 75,000 corn plants per acre.

In an aspect, a corn field comprises between one and 1,000 corn plants and further comprises a density of between 20,000 corn plants and 55,000 corn plants per acre. In another aspect, a corn field comprises between one and 1,000 corn plants and further comprises a density of between 20,000 corn plants and 50,000 corn plants per acre. In another aspect, a corn field comprises between one and 1,000 corn plants and further comprises a density of between 20,000 corn plants and 45,000 corn plants per acre. In another aspect, a corn field comprises between one and 1,000 corn plants and further comprises a density of between 20,000 corn plants and 40,000 corn plants per acre. In another aspect, a corn field comprises between one and 1,000 corn plants and further comprises a density of between 20,000 corn plants and 35,000 corn plants per acre. In another aspect, a corn field comprises between one and 1,000 corn plants and further comprises a density of between 20,000 corn plants and 30,000 corn plants per acre. In another aspect, a corn field comprises between one and 1,000 corn plants and further comprises a density of between 24,000 corn plants and 58,000 corn plants per acre. In another aspect, a corn field comprises between one and 1,000 corn plants and further comprises a density of between 38,000 corn plants and 60, 000 corn plants per acre. In another aspect, a corn field comprises between one and 1,000 corn plants and further comprises a density of between 38,000 corn plants and 50,000 corn plants per acre. In another aspect, a corn field comprises between one and 1,000 corn plants and further comprises a density of less than 10,000 corn plants per acre. In another aspect, a corn field comprises between one and 1,000 corn plants and further comprises a density of less than 20,000 corn plants per acre. In another aspect, a corn field comprises between one and 1,000 corn plants and further comprises a density of less than 30,000 corn plants per acre.

In an aspect, a corn field comprises between 1,000 and 10,000 corn plants and further comprises a density of between 20,000 corn plants and 55,000 corn plants per acre. In another aspect, a corn field comprises between 1,000 and 10,000 corn plants and further comprises a density of between 20,000 corn plants and 50,000 corn plants per acre. In another aspect, a corn field comprises between 1,000 and 10,000 corn plants and further comprises a density of between 20,000 corn plants and 45,000 corn plants per acre. In another aspect, a corn field comprises between 1,000 and 10,000 corn plants and further comprises a density of between 20,000 corn plants and 40,000 corn plants per acre. In another aspect, a corn field comprises between 1,000 and 10,000 corn plants and further comprises a density of between 20,000 corn plants and 35,000 corn plants per acre. In another aspect, a corn field comprises between 1,000 and 10,000 corn plants and further comprises a density of between 20,000 corn plants and 30,000 corn plants per acre. In another aspect, a corn field comprises between 1,000 and 10,000 corn plants and further comprises a density of between 24,000 corn plants and 58,000 corn plants per acre. In another aspect, a corn field comprises between 1,000 and 10,000 corn plants and further comprises a density of between 38,000 corn plants and 60,000 corn plants per acre. In another aspect, a corn field comprises between 1,000 and 10,000 corn plants and further comprises a density of between 38,000 corn plants and 50, 000 corn plants per acre. In another aspect, a corn field comprises between 1,000 and 10,000 corn plants and further comprises a density of less than 10,000 corn plants per acre. In another aspect, a corn field comprises between 1,000 and 10,000 corn plants and further comprises a density of less than 20,000 corn plants per acre. In another aspect, a corn field comprises between 1,000 and 10,000 corn plants and further comprises a density of less than 30,000 corn plants per acre.

In an aspect, a corn field comprises between 10,000 and 100,000 corn plants and further comprises a density of between 20,000 corn plants and 55,000 corn plants per acre. In another aspect, a corn field comprises between 10,000 and 100,000 corn plants and further comprises a density of between 20,000 corn plants and 50,000 corn plants per acre. In another aspect, a corn field comprises between 10,000 and 100,000 corn plants and further comprises a density of between 20,000 corn plants and 45,000 corn plants per acre. In another aspect, a corn field comprises between 10,000 and 100,000 corn plants and further comprises a density of between 20,000 corn plants and 40,000 corn plants per acre. In another aspect, a corn field comprises between 10,000 and 100,000 corn plants and further comprises a density of between 20,000 corn plants and 35,000 corn plants per acre. In another aspect, a corn field comprises between 10,000 and 100,000 corn plants and further comprises a density of between 20,000 corn plants and 30,000 corn plants per acre. In another aspect, a corn field comprises between 10,000 and 100,000 corn plants and further comprises a density of between 24,000 corn plants and 58,000 corn plants per acre. In another aspect, a corn field comprises between 10,000 and 100,000 corn plants and further comprises a density of between 38,000 corn plants and 60,000 corn plants per acre. In another aspect, a corn field comprises between 10,000 and 100,000 corn plants and further comprises a density of between 38,000 corn plants and 50,000 corn plants per acre. In another aspect, a corn field comprises between 10,000 and 100,000 corn plants and further comprises a density of less than 10,000 corn plants per acre. In another aspect, a corn field comprises between 10,000 and 100,000 corn plants and further comprises a density of less than 20,000 corn plants per acre. In another aspect, a corn field comprises between 10,000 and 100,000 corn plants and further comprises a density of less than 30,000 corn plants per acre.

In an aspect, a corn field comprises between 100,000 and 1,000,000 corn plants and further comprises a density of between 20,000 corn plants and 55,000 corn plants per acre. In another aspect, a corn field comprises between 100,000 and 1,000,000 corn plants and further comprises a density of between 20,000 corn plants and 50,000 corn plants per acre. In another aspect, a corn field comprises between 100,000 and 1,000,000 corn plants and further comprises a density of between 20,000 corn plants and 45,000 corn plants per acre. In another aspect, a corn field comprises between 100,000 and 1,000,000 corn plants and further comprises a density of between 20,000 corn plants and 40,000 corn plants per acre. In another aspect, a corn field comprises between 100,000 and 1,000,000 corn plants and further comprises a density of between 20,000 corn plants and 35,000 corn plants per acre. In another aspect, a corn field comprises between 100,000 and 1,000,000 corn plants and further comprises a density of between 20,000 corn plants and 30,000 corn plants per acre. In another aspect, a corn field comprises between 100,000 and 1,000,000 corn plants and further comprises a density of between 24,000 corn plants and 58,000 corn plants per acre. In another aspect, a corn field comprises between 100,000 and 1,000,000 corn plants and further comprises a density of between 38,000 corn plants and 60,000 corn plants per acre. In another aspect, a corn field comprises between 100,000 and 1,000,000 corn plants and further comprises a density of between 38,000 corn plants and 50,000 corn plants per acre. In another aspect, a corn field comprises between 100,000 and 1,000,000 corn plants and further comprises a density of less than 10,000 corn plants per acre. In another aspect, a corn field comprises between 100,000 and 1,000,000 corn plants and further comprises a density of less than 20,000 corn plants per acre. In another aspect, a corn field comprises between 100,000 and 1,000,000 corn plants and further comprises a density of less than 30,000 corn plants per acre.

In an aspect, a corn field comprises between 1,000,000 and 10,000,000 corn plants and further comprises a density of between 20,000 corn plants and 55,000 corn plants per acre. In another aspect, a corn field comprises between 1,000,000 and 10,000,000 corn plants and further comprises a density of between 20,000 corn plants and 50,000 corn plants per acre. In another aspect, a corn field comprises between 1,000,000 and 10,000,000 corn plants and further comprises a density of between 20,000 corn plants and 45,000 corn plants per acre. In another aspect, a corn field comprises between 1,000,000 and 10,000,000 corn plants and further comprises a density of between 20,000 corn plants and 40,000 corn plants per acre. In another aspect, a corn field comprises between 1,000,000 and 10,000,000 corn plants and further comprises a density of between 20,000 corn plants and 35,000 corn plants per acre. In another aspect, a corn field comprises between 1,000,000 and 10,000,000 corn plants and further comprises a density of between 20,000 corn plants and 30,000 corn plants per acre. In another aspect, a corn field comprises between 1,000,000 and 10,000,000 corn plants and further comprises a density of between 24,000 corn plants and 58,000 corn plants per acre. In another aspect, a corn field comprises between 1,000,000 and 10,000,000 corn plants and further comprises a density of between 38,000 corn plants and 60,000 corn plants per acre. In another aspect, a corn field comprises between 1,000,000 and 10,000,000 corn plants and further comprises a density of between 38,000 corn plants and 50,000 corn plants per acre. In another aspect, a corn field comprises between 1,000,000 and 10,000,000 corn plants and further comprises a density of less than 10,000 corn plants per acre. In another aspect, a corn field comprises between 1,000,000 and 10,000,000 corn plants and further comprises a density of less than 20,000 corn plants per acre. In another aspect, a corn field comprises between 1,000,000 and 10,000,000 corn plants and further comprises a density of less than 30,000 corn plants per acre.

As used herein, the term "planting pattern" refers to the spatial arrangement of corn plants within a field. In an aspect, the planting pattern within a field is described as the ratio of female plants to male plants. In an aspect, the planting pattern of plants in a field within a field is random. In another aspect, the planting pattern of plants in a field are arranged in rows of male plants and rows of female plants, and the planting pattern is described as the ratio of male plant rows to female plant rows, or vice versa, within the field. In another aspect, the planting pattern within a field is described by the spacing between rows of plants. In another aspect, the planting pattern within a field is described by the spacing between plants within a given row. In an aspect, the planting pattern of plants in a field are arranged in a regular and repeating pattern of rows, which may comprise one or more rows of male plants or two or more contiguous rows of male plants separated by two or more contiguous rows of female plants, three or more contiguous rows of female plants, four or more contiguous rows of female plants, five or more contiguous rows of female plants, six or more contiguous rows of female plants, seven or more contiguous rows of female plants, eight or more contiguous rows of female plants, nine or more contiguous rows of female plants, or ten or more contiguous rows of female plants, wherein the rows of female and/or male plants are separated by equal (or approximately equal) spacing. In another aspect, the planting pattern of plants in a field are arranged in an irregular and non-repeating pattern of rows. In another aspect, the planting pattern within a field is described by a combination of two or more of the arrangements described above.

In an aspect, a corn field provided herein comprises a ratio of at least 1 female inbred corn plant for every male inbred corn plant. In another aspect, a corn field provided herein comprises a ratio of at least 2 female inbred corn plants for every male inbred corn plant. In another aspect, a corn field provided herein comprises a ratio of at least 3 female inbred corn plants for every male inbred corn plant. In another aspect, a corn field provided herein comprises a ratio of at least 4 female corn inbred plants for every male inbred corn plant. In another aspect, a corn field provided herein comprises a ratio of at least 5 female inbred corn plants for every male inbred corn plant. In another aspect, a corn field provided herein comprises a ratio of at least 6 female inbred corn plants for every male inbred corn plant. In another aspect, a corn field provided herein comprises a ratio of at least 7 female inbred corn plants for every male inbred corn plant. In another aspect, a corn field provided herein comprises a ratio of at least 8 female inbred corn plants for every male inbred corn plant. In another aspect, a corn field provided herein comprises a ratio of at least 9 female inbred corn plants for every male inbred corn plant. In another aspect, a corn field provided herein comprises a ratio of at least 10 female inbred corn plants for every male inbred corn plant. In another aspect, a corn field provided herein comprises a ratio of at least 15 female inbred corn plants for every male inbred corn plant. In another aspect, a corn field provided herein comprises a ratio of at least 20 female inbred corn plants for every male inbred corn plant. In another aspect, a corn field provided herein comprises a ratio of at least 25 female inbred corn plants for every male inbred corn plant. In another aspect, a corn field provided herein comprises a ratio of at least 30 female inbred corn plants for every male inbred corn plant. In another aspect, a corn field provided herein comprises a ratio of at least 35 female inbred corn plants for every male inbred corn plant. In another aspect, a corn field provided herein comprises a ratio of at least 40 female inbred corn plants for every male inbred corn plant. In another aspect, a corn field provided herein comprises a ratio of at least 45 female inbred corn plants for every male inbred corn plant. In another aspect, a corn field provided herein comprises a ratio of at least 50 female inbred corn plants for every male inbred corn plant. In another aspect, a corn field provided herein comprises a ratio of at least 55 female inbred corn plants for every male inbred corn plant. In another aspect, a corn field provided herein comprises a ratio of at least 60 female inbred corn plants for every male inbred corn plant. In another aspect, a corn field provided herein comprises a ratio of at least 65 female inbred corn plants for every male inbred corn plant. In another aspect, a corn field provided herein comprises a ratio of at least 70 female inbred corn plants for every male inbred corn plant. In another aspect, a corn field provided herein comprises a ratio of at least 75 female inbred corn plants for every male inbred corn plant. In another aspect, a corn field provided herein comprises a ratio of at least 80 female inbred corn plants for every male inbred corn plant. In another aspect, a corn field provided herein comprises a ratio of at least 85 female inbred corn plants for every male inbred corn plant. In another aspect, a corn field provided herein comprises a ratio of at least 90 female inbred corn plants for every male inbred corn plant. In another aspect, a corn field provided herein comprises a ratio of at least 95 female inbred corn plants for every male inbred corn plant. In another aspect, a corn field provided herein comprises a ratio of at least 100 female inbred corn plants for every male inbred corn plant. In another aspect, a corn field provided herein comprises a ratio of at least 105 female inbred corn plants for every male inbred corn plant. In another aspect, a corn field provided herein comprises a ratio of at least 110 female inbred corn plants for every male inbred corn plant. In another aspect, a corn field provided herein comprises a ratio of at least 115 female inbred corn plants for every male inbred corn plant. In another aspect, a corn field provided herein comprises a ratio of at least 120 female inbred corn plants for every male inbred corn plant.

In an aspect, a corn field provided herein comprises between 1 and 10 female inbred corn plants for every male inbred corn plant. In another aspect, a corn field provided herein comprises between 5 and 10 female inbred corn plants for every male inbred corn plant. In another aspect, a corn field provided herein comprises between 1 and 20 female inbred corn plants for every male inbred corn plant. In another aspect, a corn field provided herein comprises between 5 and 20 female inbred corn plants for every male inbred corn plant. In another aspect, a corn field provided herein comprises between 5 and 15 female inbred corn plants for every male inbred corn plant. In another aspect, a corn field provided herein comprises between 5 and 10 female inbred corn plants for every two male inbred corn plants. In another aspect, a corn field provided herein comprises between 5 and 20 female inbred corn plants for every two male inbred corn plants. In another aspect, a corn field provided herein comprises between 5 and 15 female inbred corn plants for every two male inbred corn plants. In another aspect, a corn field provided herein comprises between 1 and 30 female inbred corn plants for every male inbred corn plant. In another aspect, a corn field provided herein comprises between 1 and 40 female inbred corn plants for every male inbred corn plant. In another aspect, a corn field provided herein comprises between 1 and 50 female inbred corn plants for every male inbred corn plant. In another aspect, a corn field provided herein comprises between 1 and 60 female inbred corn plants for every male inbred corn plant. In another aspect, a corn field provided herein comprises between 1 and 80 female inbred corn plants for every male inbred corn plant. In another aspect, a corn field provided herein comprises between 1 and 100 female inbred corn plants for every male inbred corn plant. In another aspect, a corn field provided herein comprises between 1 and 120 female inbred corn plants for every male inbred corn plant. In another aspect, a corn field provided herein comprises between 10 and 20 female inbred corn plants for every male inbred corn plant. In another aspect, a corn field provided herein comprises between 20 and 30 female inbred corn plants for every male inbred corn plant. In another aspect, a corn field provided herein comprises between 30 and 40 female inbred corn plants for every male inbred corn plant. In another aspect, a corn field provided herein comprises between 40 and 50 female inbred corn plants for every male inbred corn plant. In another aspect, a corn field provided herein comprises between 50 and 60 female inbred corn plants for every male inbred corn plant. In another aspect, a corn field provided herein comprises between 60 and 70 female inbred corn plants for every male inbred corn plant. In another aspect, a corn field provided herein comprises between 70 and 80 female inbred corn plants for every male inbred corn plant. In another aspect, a corn field provided herein comprises between 80 and 90 female inbred corn plants for every male inbred corn plant. In another aspect, a corn field provided herein comprises between 90 and 100 female inbred corn plants for every male inbred corn plant. In another aspect, a corn field provided herein comprises between 100 and 110 female inbred corn plants for every male inbred corn plant. In another aspect, a corn field provided herein comprises between 110 and 120 female inbred corn plants for every male inbred corn plant. In another aspect, a corn field provided herein comprises between 20 and 40 female inbred corn plants for every male inbred corn plant. In another aspect, a corn field provided herein comprises between 40 and 60 female inbred corn plants for every male inbred corn plant. In another aspect, a corn field provided herein comprises between 60 and 80 female inbred corn plants for every male inbred corn plant. In another aspect, a corn field provided herein comprises between 80 and 100 female inbred corn plants for every male inbred corn plant. In another aspect, a corn field provided herein comprises between 100 and 120 female inbred corn plants for every male inbred corn plant. In another aspect, a corn field provided herein comprises between 20 and 80 female inbred corn plants for every male inbred corn plant. In another aspect, a corn field provided herein comprises between 40 and 100 female inbred corn plants for every male inbred corn plant. In another aspect, a corn field provided herein comprises between 60 and 120 female inbred corn plants for every male inbred corn plant.

In an aspect, a corn field provided herein comprises a ratio of at least 1 female corn plant for every male corn plant. In another aspect, a corn field provided herein comprises a ratio of at least 2 female corn plants for every male corn plant. In another aspect, a corn field provided herein comprises a ratio of at least 3 female corn plants for every male corn plant. In another aspect, a corn field provided herein comprises a ratio of at least 4 female corn plants for every male corn plant. In another aspect, a corn field provided herein comprises a ratio of at least 5 female corn plants for every male corn plant. In another aspect, a corn field provided herein comprises a ratio of at least 6 female corn plants for every male corn plant. In another aspect, a corn field provided herein comprises a ratio of at least 7 female corn plants for every male corn plant. In another aspect, a corn field provided herein comprises a ratio of at least 8 female corn plants for every male corn plant. In another aspect, a corn field provided herein comprises a ratio of at least 9 female corn plants for every male corn plant. In another aspect, a corn field provided herein comprises a ratio of at least 10 female corn plants for every male corn plant. In another aspect, a corn field provided herein comprises a ratio of at least 15 female corn plants for every male corn plant. In another aspect, a corn field provided herein comprises a ratio of at least 20 female corn plants for every male corn plant. In another aspect, a corn field provided herein comprises a ratio of at least 25 female corn plants for every male corn plant. In another aspect, a corn field provided herein comprises a ratio of at least 30 female corn plants for every male corn plant. In another aspect, a corn field provided herein comprises a ratio of at least 35 female corn plants for every male corn plant. In another aspect, a corn field provided herein comprises a ratio of at least 40 female corn plants for every male corn plant. In another aspect, a corn field provided herein comprises a ratio of at least 45 female corn plants for every male corn plant. In another aspect, a corn field provided herein comprises a ratio of at least 50 female corn plants for every male corn plant. In another aspect, a corn field provided herein comprises a ratio of at least 55 female corn plants for every male corn plant. In another aspect, a corn field provided herein comprises a ratio of at least 60 female corn plants for every male corn plant. In another aspect, a corn field provided herein comprises a ratio of at least 65 female corn plants for every male corn plant. In another aspect, a corn field provided herein comprises a ratio of at least 70 female corn plants for every male corn plant. In another aspect, a corn field provided herein comprises a ratio of at least 75 female corn plants for every male corn plant. In another aspect, a corn field provided herein comprises a ratio of at least 80 female corn plants for every male corn plant. In another aspect, a corn field provided herein comprises a ratio of at least 85 female corn plants for every male corn plant. In another aspect, a corn field provided herein comprises a ratio of at least 90 female corn plants for every male corn plant. In another aspect, a corn field provided herein comprises a ratio of at least 95 female corn plants for every male corn plant. In another aspect, a corn field provided herein comprises a ratio of at least 100 female corn plants for every male corn plant. In another aspect, a corn field provided herein comprises a ratio of at least 105 female corn plants for every male corn plant. In another aspect, a corn field provided herein comprises a ratio of at least 110 female corn plants for every male corn plant. In another aspect, a corn field provided herein comprises a ratio of at least 115 female corn plants for every male corn plant. In another aspect, a corn field provided herein comprises a ratio of at least 120 female corn plants for every male corn plant.

In an aspect, a corn field provided herein comprises between 1 and 10 female corn plants for every male corn plant. In another aspect, a corn field provided herein comprises between 5 and 10 female corn plants for every male corn plant. In another aspect, a corn field provided herein comprises between 1 and 20 female corn plants for every male corn plant. In another aspect, a corn field provided herein comprises between 5 and 20 female corn plants for every male corn plant. In another aspect, a corn field provided herein comprises between 5 and 15 female corn plants for every male corn plant. In another aspect, a corn field provided herein comprises between 5 and 10 female corn plants for every two male corn plants. In another aspect, a corn field provided herein comprises between 5 and 20 female corn plants for every two male corn plants. In another aspect, a corn field provided herein comprises between 5 and 15 female corn plants for every two male corn plants. In another aspect, a corn field provided herein comprises between 1 and 30 female corn plants for every male corn plant. In another aspect, a corn field provided herein comprises between 1 and 40 female corn plants for every male corn plant. In another aspect, a corn field provided herein comprises between 1 and 50 female corn plants for every male corn plant. In another aspect, a corn field provided herein comprises between 1 and 60 female corn plants for every male corn plant. In another aspect, a corn field provided herein comprises between 1 and 80 female corn plants for every male corn plant. In another aspect, a corn field provided herein comprises between 1 and 100 female corn plants for every male corn plant. In another aspect, a corn field provided herein comprises between 1 and 120 female corn plants for every male corn plant. In another aspect, a corn field provided herein comprises between 10 and 20 female corn plants for every male corn plant. In another aspect, a corn field provided herein comprises between 20 and 30 female corn plants for every male corn plant. In another aspect, a corn field provided herein comprises between 30 and 40 female corn plants for every male corn plant. In another aspect, a corn field provided herein comprises between 40 and 50 female corn plants for every male corn plant. In another aspect, a corn field provided herein comprises between 50 and 60 female corn plants for every male corn plant. In another aspect, a corn field provided herein comprises between 60 and 70 female corn plants for every male corn plant. In another aspect, a corn field provided herein comprises between 70 and 80 female corn plants for every male corn plant. In another aspect, a corn field provided herein comprises between 80 and 90 female corn plants for every male corn plant. In another aspect, a corn field provided herein comprises between 90 and 100 female corn plants for every male corn plant. In another aspect, a corn field provided herein comprises between 100 and 110 female corn plants for every male corn plant. In another aspect, a corn field provided herein comprises between 110 and 120 female corn plants for every male corn plant. In another aspect, a corn field provided herein comprises between 20 and 40 female corn plants for every male corn plant. In another aspect, a corn field provided herein comprises between 40 and 60 female corn plants for every male corn plant. In another aspect, a corn field provided herein comprises between 60 and 80 female corn plants for every male corn plant. In another aspect, a corn field provided herein comprises between 80 and 100 female corn plants for every male corn plant. In another aspect, a corn field provided herein comprises between 100 and 120 female corn plants for every male corn plant. In another aspect, a corn field provided herein comprises between 20 and 80 female corn plants for every male corn plant. In another aspect, a corn field provided herein comprises between 40 and 100 female corn plants for every male corn plant. In another aspect, a corn field provided herein comprises between 60 and 120 female corn plants for every male corn plant.

In an aspect, a corn field provided herein comprises at least one row of female inbred corn plants and at least one row of male inbred corn plants. In another aspect, a corn field provided herein comprises multiple rows of female inbred corn plants and at least one row of male inbred corn plants. In another aspect, a corn field provided herein comprises multiple rows of female inbred corn plants and multiple rows of male inbred corn plants.

In an aspect, a corn field provided herein comprises at least one row of female corn plants and at least one row of male corn plants. In another aspect, a corn field provided herein comprises multiple rows of female corn plants and at least one row of male corn plants. In another aspect, a corn field provided herein comprises multiple rows of female corn plants and multiple rows of male corn plants.

In an aspect, a corn field provided herein comprises rows of female inbred corn plants and rows of male inbred corn plants where the overall female-to-male corn plant ratio (or the ratio of female-to-male corn plant rows) within the field is 2:2. In another aspect, a corn field provided herein comprises rows of female inbred corn plants and rows of male inbred corn plants where the overall female-to-male corn plant ratio (or the ratio of female-to-male corn plant rows) within the field is 3:1. In another aspect, a corn field provided herein comprises rows of female inbred corn plants and rows of male inbred corn plants where the overall female-to-male corn plant ratio (or the ratio of female-to-male corn plant rows) within the field is 3:2. In another aspect, a corn field provided herein comprises rows of female inbred corn plants and rows of male inbred corn plants where the overall female-to-male corn plant ratio (or the ratio of female-to-male corn plant rows) within the field is 4:1. In another aspect, a corn field provided herein comprises rows of female inbred corn plants and rows of male inbred corn plants where the overall female-to-male corn plant ratio (or the ratio of female-to-male corn plant rows) within the field is 4:2. In another aspect, a corn field provided herein comprises rows of female inbred corn plants and rows of male inbred corn plants where the overall female-to-male corn plant ratio (or the ratio of female-to-male corn plant rows) within the field is 4:3. In another aspect, a corn field provided herein comprises rows of female inbred corn plants and rows of male inbred corn plants where the overall female-to-male corn plant ratio (or the ratio of female-to-male corn plant rows) within the field is 5:1. In another aspect, a corn field provided herein comprises rows of female inbred corn plants and rows of male inbred corn plants where the overall female-to-male corn plant ratio (or the ratio of female-to-male corn plant rows) within the field is 5:2. In another aspect, a corn field provided herein comprises rows of female inbred corn plants and rows of male inbred corn plants where the overall female-to-male corn plant ratio (or the ratio of female-to-male corn plant rows) within the field is 6:1. In another aspect, a corn field provided herein comprises rows of female inbred corn plants and rows of male inbred corn plants where the overall female-to-male corn plant ratio (or the ratio of female-to-male corn plant rows) within the field is 6:2. In another aspect, a corn field provided herein comprises rows of female inbred corn plants and rows of male inbred corn plants where the overall female-to-male corn plant ratio (or the ratio of female-to-male corn plant rows) within the field is 7:1. In another aspect, a corn field provided herein comprises rows of female inbred corn plants and rows of male inbred corn plants where the overall female-to-male corn plant ratio (or the ratio of female-to-male corn plant rows) within the field is 7:2. In another aspect, a corn field provided herein comprises rows of female inbred corn plants and rows of male inbred corn plants where the overall female-to-male corn plant ratio (or the ratio of female-to-male corn plant rows) within the field is 8:1. In another aspect, a corn field provided herein comprises rows of female inbred corn plants and rows of male inbred corn plants where the overall female-to-male corn plant ratio (or the ratio of female-to-male corn plant rows) within the field is 8:2.

In an aspect, a corn field provided herein comprises rows of female corn plants and rows of male corn plants where the overall female-to-male corn plant ratio (or the ratio of female-to-male corn plant rows) within the field is 2:2. In another aspect, a corn field provided herein comprises rows of female inbred corn plants and rows of male inbred corn plants where the overall female-to-male corn plant ratio (or the ratio of female-to-male corn plant rows) within the field is 3:1. In another aspect, a corn field provided herein comprises rows of female corn plants and rows of male corn plants where the overall female-to-male corn plant ratio (or the ratio of female-to-male corn plant rows) within the field is 3:2. In another aspect, a corn field provided herein comprises rows of female corn plants and rows of male corn plants where the overall female-to-male corn plant ratio (or the ratio of female-to-male corn plant rows) within the field is 4:1. In another aspect, a corn field provided herein comprises rows of female corn plants and rows of male corn plants where the overall female-to-male corn plant ratio (or the ratio of female-to-male corn plant rows) within the field is 4:2. In another aspect, a corn field provided herein comprises rows of female corn plants and rows of male corn plants where the overall female-to-male corn plant ratio (or the ratio of female-to-male corn plant rows) within the field is 4:3. In another aspect, a corn field provided herein comprises rows of female corn plants and rows of male corn plants where the overall female-to-male corn plant ratio (or the ratio of female-to-male corn plant rows) within the field is 5:1. In another aspect, a corn field provided herein comprises rows of female corn plants and rows of male corn plants where the overall female-to-male corn plant ratio (or the ratio of female-to-male corn plant rows) within the field is 5:2. In another aspect, a corn field provided herein comprises rows of female corn plants and rows of male corn plants where the overall female-to-male corn plant ratio (or the ratio of female-to-male corn plant rows) within the field is 6:1. In another aspect, a corn field provided herein comprises rows of female corn plants and rows of male corn plants where the overall female-to-male corn plant ratio (or the ratio of female-to-male corn plant rows) within the field is 6:2. In another aspect, a corn field provided herein comprises rows of female corn plants and rows of male corn plants where the overall female-to-male corn plant ratio (or the ratio of female-to-male corn plant rows) within the field is 7:1. In another aspect, a corn field provided herein comprises rows of female corn plants and rows of male corn plants where the overall female-to-male corn plant ratio (or the ratio of female-to-male corn plant rows) within the field is 7:2. In another aspect, a corn field provided herein comprises rows of female corn plants and rows of male corn plants where the overall female-to-male corn plant ratio (or the ratio of female-to-male corn plant rows) within the field is 8:1. In another aspect, a corn field provided herein comprises rows of female corn plants and rows of male corn plants where the overall female-to-male corn plant ratio (or the ratio of female-to-male corn plant rows) within the field is 8:2.

In an aspect, a corn field provided herein comprises at least 1 female corn plant row for every male corn plant row. In another aspect, a corn field provided herein comprises at least 2 female corn plant rows for every male corn plant row. In another aspect, a corn field provided herein comprises at least 3 female corn plant rows for every male corn plant row. In another aspect, a corn field provided herein comprises at least 4 female corn plant rows for every male corn plant row. In another aspect, a corn field provided herein comprises at least 5 female corn plant rows for every male corn plant row. In another aspect, a corn field provided herein comprises at least 6 female corn plant rows for every male corn plant row.

In another aspect, a corn field provided herein comprises at least 7 female corn plant rows for every male corn plant row. In another aspect, a corn field provided herein comprises at least 8 female corn plant rows for every male corn plant row. In another aspect, a corn field provided herein comprises at least 9 female corn plant rows for every male corn plant row. In another aspect, a corn field provided herein comprises at least 10 female corn plant rows for every male corn plant row. In another aspect, a corn field provided herein comprises at least 11 female corn plant rows for every male corn plant row. In another aspect, a corn field provided herein comprises at least 12 female corn plant rows for every male corn plant row.

In an aspect, a corn field provided herein comprises between 1 female row and 2 female rows for every male row. In another aspect, a corn field provided herein comprises between 2 female rows and 3 female rows for every male row. In another aspect, a corn field provided herein comprises between 3 female rows and 4 female rows for every male row. In another aspect, a corn field provided herein comprises between 4 female rows and 5 female rows for every male row. In another aspect, a corn field provided herein comprises between 5 female rows and 6 female rows for every male row. In another aspect, a corn field provided herein comprises between 6 female rows and 7 female rows for every male row. In another aspect, a corn field provided herein comprises between 7 female rows and 8 female rows for every male row. In another aspect, a corn field provided herein comprises between 8 female rows and 9 female rows for every male row. In another aspect, a corn field provided herein comprises between 9 female rows and 10 female rows for every male row. In another aspect, a corn field provided herein comprises between 10 female rows and 11 female rows for every male row. In another aspect, a corn field provided herein comprises between 11 female rows and 12 female rows for every male row. In another aspect, a corn field provided herein comprises between 1 female row and 4 female rows for every male row. In another aspect, a corn field provided herein comprises between 4 female rows and 8 female rows for every male row. In another aspect, a corn field provided herein comprises between 8 female rows and 12 female rows for every male row. In another aspect, a corn field provided herein comprises between 1 female row and 10 female rows for every male row. In another aspect, a corn field provided herein comprises between 1 female row and 12 female rows for every male row.

In an aspect, a corn field provided herein comprises a regular and repeating pattern of two contiguous rows of female corn plants followed by two contiguous rows of male corn plants. In an aspect, a corn field provided herein comprises a regular and repeating pattern of three contiguous rows of female corn plants followed by one row of male corn plants. In an aspect, a corn field provided herein comprises a regular and repeating pattern of three contiguous rows of female corn plants followed by two rows of male corn plants. In an aspect, a corn field provided herein comprises a regular and repeating pattern of four contiguous rows of female corn plants followed by one row of male corn plants. In an aspect, a corn field provided herein comprises a regular and repeating pattern of four contiguous rows of female corn plants followed by two contiguous rows of male corn plants. In an aspect, a corn field provided herein comprises a regular and repeating pattern of four contiguous rows of female corn plants followed by three contiguous rows of male corn plants. In an aspect, a corn field provided herein comprises a regular and repeating pattern of five contiguous rows of female corn plants followed by one row of male corn plants. In an aspect, a corn field provided herein comprises a regular and repeating pattern of five contiguous rows of female corn plants followed by two contiguous rows of male corn plants. In an aspect, a corn field provided herein comprises a regular and repeating pattern of six contiguous rows of female corn plants followed by one row of male corn plants. In an aspect, a corn field provided herein comprises a regular and repeating pattern of six contiguous rows of female corn plants followed by two contiguous rows of male corn plants. In an aspect, a corn field provided herein comprises a regular and repeating pattern of seven contiguous rows of female corn plants followed by one row of male corn plants. In an aspect, a corn field provided herein comprises a regular and repeating pattern of seven contiguous rows of female corn plants followed by two contiguous rows of male corn plants. In an aspect, a corn field provided herein comprises a regular and repeating pattern of eight contiguous rows of female corn plants followed by one row of male corn plants. In an aspect, a corn field provided herein comprises a regular and repeating pattern of eight contiguous rows of female corn plants followed by two contiguous rows of male corn plants.

In an aspect, a corn field provided herein comprises at least two rows of corn plants, where any two adjacent rows are spaced at least 10 inches apart. In another aspect, a corn field provided herein comprises at least two rows of corn plants, where any two adjacent rows are spaced at least 12 inches apart. In another aspect, a corn field provided herein comprises at least two rows of corn plants, where any two adjacent rows are spaced at least 14 inches apart. In another aspect, a corn field provided herein comprises at least two rows of corn plants, where any two adjacent rows are spaced at least 16 inches apart. In another aspect, a corn field provided herein comprises at least two rows of corn plants, where any two adjacent rows are spaced at least 18 inches apart. In another aspect, a corn field provided herein comprises at least two rows of corn plants, where any two adjacent rows are spaced at least 20 inches apart. In another aspect, a corn field provided herein comprises at least two rows of corn plants, where any two adjacent rows are spaced at least 22 inches apart. In another aspect, a corn field provided herein comprises at least two rows of corn plants, where any two adjacent rows are spaced at least 24 inches apart. In another aspect, a corn field provided herein comprises at least two rows of corn plants, where any two adjacent rows are spaced at least 26 inches apart. In another aspect, a corn field provided herein comprises at least two rows of corn plants, where any two adjacent rows are spaced at least 28 inches apart. In another aspect, a corn field provided herein comprises at least two rows of corn plants, where any two adjacent rows are spaced at least 30 inches apart. In another aspect, a corn field provided herein comprises at least two rows of corn plants, where any two adjacent rows are spaced at least 32 inches apart. In another aspect, a corn field provided herein comprises at least two rows of corn plants, where any two adjacent rows are spaced at least 34 inches apart. In another aspect, a corn field provided herein comprises at least two rows of corn plants, where any two adjacent rows are spaced at least 36 inches apart. In another aspect, a corn field provided herein comprises at least two rows of corn plants, where any two adjacent rows are spaced at least 38 inches apart. In another aspect, a corn field provided herein comprises at least two rows of corn plants, where any two adjacent rows are spaced at least 40 inches apart. In another aspect, a corn field provided herein comprises at least two rows of corn plants, where different adjacent rows of the corn field have variable and/or irregular spacing.

In an aspect, a corn field provided herein comprises an average of at least 10 inches between adjacent rows of corn plants. In an aspect, a corn field provided herein comprises an average of at least 12 inches between adjacent rows of corn plants. In an aspect, a corn field provided herein comprises an average of at least 14 inches between adjacent rows of corn plants. In an aspect, a corn field provided herein comprises an average of at least 16 inches between adjacent rows of corn plants. In an aspect, a corn field provided herein comprises an average of at least 18 inches between adjacent rows of corn plants. In an aspect, a corn field provided herein comprises an average of at least 20 inches between adjacent rows of corn plants. In an aspect, a corn field provided herein comprises an average of at least 22 inches between adjacent rows of corn plants. In an aspect, a corn field provided herein comprises an average of at least 24 inches between adjacent rows of corn plants. In an aspect, a corn field provided herein comprises an average of at least 26 inches between adjacent rows of corn plants. In an aspect, a corn field provided herein comprises an average of at least 28 inches between adjacent rows of corn plants. In an aspect, a corn field provided herein comprises an average of at least 30 inches between adjacent rows of corn plants. In an aspect, a corn field provided herein comprises an average of at least 32 inches between adjacent rows of corn plants. In an aspect, a corn field provided herein comprises an average of at least 34 inches between adjacent rows of corn plants. In an aspect, a corn field provided herein comprises an average of at least 36 inches between adjacent rows of corn plants. In an aspect, a corn field provided herein comprises an average of at least 38 inches between adjacent rows of corn plants. In an aspect, a corn field provided herein comprises an average of at least 40 inches between adjacent rows of corn plants.

In an aspect, a corn field provided herein comprises at least two rows of corn plants, where any two adjacent rows are spaced between 10 and 12 inches apart. In another aspect, a corn field provided herein comprises at least two rows of corn plants, where any two adjacent rows are spaced between 12 and 14 inches apart. In another aspect, a corn field provided herein comprises at least two rows of corn plants, where any two adjacent rows are spaced between 14 and 16 inches apart. In another aspect, a corn field provided herein comprises at least two rows of corn plants, where any two adjacent rows are spaced between 16 and 18 inches apart. In another aspect, a corn field provided herein comprises at least two rows of corn plants, where any two adjacent rows are spaced between 18 and 20 inches apart. In another aspect, a corn field provided herein comprises at least two rows of corn plants, where any two adjacent rows are spaced between 20 and 22 inches apart. In another aspect, a corn field provided herein comprises at least two rows of corn plants, where any two adjacent rows are spaced between 22 and 24 inches apart. In another aspect, a corn field provided herein comprises at least two rows of corn plants, where any two adjacent rows are spaced between 24 and 26 inches apart. In another aspect, a corn field provided herein comprises at least two rows of corn plants, where any two adjacent rows are spaced between 26 and 28 inches apart. In another aspect, a corn field provided herein comprises at least two rows of corn plants, where any two adjacent rows are spaced between 28 and 30 inches apart. In another aspect, a corn field provided herein comprises at least two rows of corn plants, where any two adjacent rows are spaced between 30 and 32 inches apart. In another aspect, a corn field provided herein comprises at least two rows of corn plants, where any two adjacent rows are spaced between 32 and 34 inches apart. In another aspect, a corn field provided herein comprises at least two rows of corn plants, where any two adjacent rows are spaced between 34 and 36 inches apart. In another aspect, a corn field provided herein comprises at least two rows of corn plants, where any two adjacent rows are spaced between 36 and 38 inches apart. In another aspect, a corn field provided herein comprises at least two rows of corn plants, where any two adjacent rows are spaced between 38 and 40 inches apart. In another aspect, a corn field provided herein comprises at least two rows of corn plants, where any two adjacent rows are spaced between 10 and 15 inches apart. In another aspect, a corn field provided herein comprises at least two rows of corn plants, where any two adjacent rows are spaced between 15 and 20 inches apart. In another aspect, a corn field provided herein comprises at least two rows of corn plants, where any two adjacent rows are spaced between 20 and 25 inches apart. In another aspect, a corn field provided herein comprises at least two rows of corn plants, where any two adjacent rows are spaced between 25 and 30 inches apart. In another aspect, a corn field provided herein comprises at least two rows of corn plants, where any two adjacent rows are spaced between 30 and 35 inches apart. In another aspect, a corn field provided herein comprises at least two rows of corn plants, where any two adjacent rows are spaced between 35 and 40 inches apart. In another aspect, a corn field provided herein comprises at least two rows of corn plants, where any two adjacent rows are spaced between 12 and 24 inches apart. In another aspect, a corn field provided herein comprises at least two rows of corn plants, where any two adjacent rows are spaced between 24 and 36 inches apart. In another aspect, a corn field provided herein comprises at least two rows of corn plants, where any two adjacent rows are spaced between 12 and 36 inches apart. In another aspect, a corn field provided herein comprises at least two rows of corn plants, where any two adjacent rows are spaced between 10 and 40 inches apart.

In an aspect, a corn field provided herein comprises an average of between 10 and 12 inches between adjacent rows of corn plants. In an aspect, a corn field provided herein comprises an average of between 10 and 14 inches between adjacent rows of corn plants. In an aspect, a corn field provided herein comprises an average of between 10 and 16 inches between adjacent rows of corn plants. In an aspect, a corn field provided herein comprises an average of between 10 and 18 inches between adjacent rows of corn plants. In an aspect, a corn field provided herein comprises an average of between 10 and 20 inches between adjacent rows of corn plants. In an aspect, a corn field provided herein comprises an average of between 10 and 22 inches between adjacent rows of corn plants. In an aspect, a corn field provided herein comprises an average of between 10 and 24 inches between adjacent rows of corn plants. In an aspect, a corn field provided herein comprises an average of between 10 and 26 inches between adjacent rows of corn plants. In an aspect, a corn field provided herein comprises an average of between 10 and 28 inches between adjacent rows of corn plants. In an aspect, a corn field provided herein comprises an average of between 10 and 30 inches between adjacent rows of corn plants. In an aspect, a corn field provided herein comprises an average of between 10 and 32 inches between adjacent rows of corn plants. In an aspect, a corn field provided herein comprises an average of between 10 and 34 inches between adjacent rows of corn plants. In an aspect, a corn field provided herein comprises an average of between 10 and 36 inches between adjacent rows of corn plants. In an aspect, a corn field provided herein comprises an average of between 10 and 38 inches between adjacent rows of corn plants. In an aspect, a corn field provided herein comprises an average of between 10 and 40 inches between adjacent rows of corn plants. In an aspect, a corn field provided herein comprises an average of between 12 and 18 inches between adjacent rows of corn plants. In an aspect, a corn field provided herein comprises an average of between 12 and 20 inches between adjacent rows of corn plants. In an aspect, a corn field provided herein comprises an average of between 12 and 22 inches between adjacent rows of corn plants. In an aspect, a corn field provided herein comprises an average of between 12 and 24 inches between adjacent rows of corn plants. In an aspect, a corn field provided herein comprises an average of between 12 and 36 inches between adjacent rows of corn plants. In an aspect, a corn field provided herein comprises an average of between 18 and 24 inches between adjacent rows of corn plants. In an aspect, a corn field provided herein comprises an average of between 18 and 36 inches between adjacent rows of corn plants.

As used herein, the term "harvesting" refers to the process of removing or gathering at least one ear of corn from a corn plant. A corn field is considered to be "harvested" when at least one ear has been removed from at least 50% of the corn plants in the corn field. As such, an "unharvested" corn plant has not had any ears purposely removed. In an aspect, a corn field provided herein is an unharvested corn field. In another aspect, at least 50% of the corn plants in a corn field provided herein are unharvested. In another aspect, at least 60% of the corn plants in a corn field provided herein are unharvested. In another aspect, at least 70% of the inbred corn plants in a corn field provided herein are unharvested. In another aspect, at least 80% of the corn plants in a corn field provided herein are unharvested. In another aspect, at least 90% of the corn plants in a corn field provided herein are unharvested. In another aspect, 100% of the corn plants in a corn field provided herein are unharvested.

As used herein, the term "yield" refers to the amount of harvested plant material, such as kernels or seeds, per harvested field or cultivated area. In an aspect, yield is measured in bushels per acre. Yield can be dependent on average kernel weight and the average number of kernels per ear. As used herein, "seed yield" refers to the number of seeds or kernels harvested per harvested field or cultivated area. In an aspect, seed yield is measured in Standard Seed Units (SSU) per acre. One SSU for corn is equivalent to 80,000 corn seed kernels. In an aspect, seed yield is measured in terms of the average number of kernels or seeds per ear. The number of Standard Seed Units (SSUs) or the average number of kernels per ear is/are appropriate for seed production since they quantify the number of seeds or kernels that can be produced, harvested or collected from a seed production field or from female corn plant(s), and thus the number of hybrid corn seeds or kernels that can potentially be sold and planted from the quantity of seeds or kernels produced, whereas yield takes into account both seed number and seed size.

In an aspect, the yield of hybrid corn seed provided herein comprises an average of at least 60 bushels per acre. In an aspect, the yield of hybrid corn seed provided herein comprises an average of at least 80 bushels per acre. In an aspect, the yield of hybrid corn seed provided herein comprises an average of at least 100 bushels per acre. In another aspect, the yield of hybrid corn seed provided herein comprises an average of at least 120 bushels per acre. In another aspect, the yield of hybrid corn seed provided herein comprises an average of at least 140 bushels per acre. In another aspect, the yield of hybrid corn seed provided herein comprises an average of at least 160 bushels per acre. In another aspect, the yield of hybrid corn seed provided herein comprises an average of at least 180 bushels per acre. In another aspect, the yield of hybrid corn seed provided herein comprises an average of at least 200 bushels per acre. In another aspect, the yield of hybrid corn seed provided herein comprises an average of at least 220 bushels per acre. In another aspect, the yield of hybrid corn seed provided herein comprises an average of at least 240 bushels per acre. In another aspect, the yield of hybrid corn seed provided herein comprises an average of at least 260 bushels per acre. In another aspect, the yield of hybrid corn seed provided herein comprises an average of at least 300 bushels per acre. In another aspect, the yield of hybrid corn seed provided herein comprises an average of at least 400 bushels per acre. In another aspect, the yield of hybrid corn seed provided herein comprises an average of at least 500 bushels per acre.

In an aspect, the yield of hybrid corn seed provided herein comprises an average of between 100 and 120 bushels per acre. In another aspect, the yield of hybrid corn seed provided herein comprises an average of between 120 and 140 bushels per acre. In another aspect, the yield of hybrid corn seed provided herein comprises an average of between 140 and 160 bushels per acre. In another aspect, the yield of hybrid corn seed provided herein comprises an average of between 160 and 180 bushels per acre. In another aspect, the yield of hybrid corn seed provided herein comprises an average of between 180 and 200 bushels per acre. In another aspect, the yield of hybrid corn seed provided herein comprises an average of between 200 and 220 bushels per acre. In another aspect, the yield of hybrid corn seed provided herein comprises an average of between 220 and 240 bushels per acre. In another aspect, the yield of hybrid corn seed provided herein comprises an average of between 240 and 260 bushels per acre. In another aspect, the yield of hybrid corn seed provided herein comprises an average of between 100 and 140 bushels per acre. In another aspect, the yield of hybrid corn seed provided herein comprises an average of between 140 and 180 bushels per acre. In another aspect, the yield of hybrid corn seed provided herein comprises an average of between 180 and 220 bushels per acre. In another aspect, the yield of hybrid corn seed provided herein comprises an average of between 220 and 260 bushels per acre. In another aspect, the yield of hybrid corn seed provided herein comprises an average of between 100 and 180 bushels per acre. In another aspect, the yield of hybrid corn seed provided herein comprises an average of between 180 and 260 bushels per acre. In another aspect, the yield of hybrid corn seed provided herein comprises an average of between 100 and 500 bushels per acre. In another aspect, the yield of hybrid corn seed provided herein comprises an average of between 100 and 400 bushels per acre. In another aspect, the yield of hybrid corn seed provided herein comprises an average of between 100 and 350 bushels per acre. In another aspect, the yield of hybrid corn seed provided herein comprises an average of between 100 and 300 bushels per acre. In another aspect, the yield of hybrid corn seed provided herein comprises an average of between 100 and 260 bushels per acre. In another aspect, the yield of hybrid corn seed provided herein comprises an average of between 100 and 200 bushels per acre.

In an aspect, the yield of hybrid corn seed provided herein comprises at least 100 bushels per acre. In another aspect, the yield of hybrid corn seed provided herein comprises at least 120 bushels per acre. In another aspect, the yield of hybrid corn seed provided herein comprises at least 140 bushels per acre. In another aspect, the yield of hybrid corn seed provided herein comprises at least 160 bushels per acre. In another aspect, the yield of hybrid corn seed provided herein comprises at least 180 bushels per acre. In another aspect, the yield of hybrid corn seed provided herein comprises at least 200 bushels per acre. In another aspect, the yield of hybrid corn seed provided herein comprises at least 220 bushels per acre. In another aspect, the yield of hybrid corn seed provided herein comprises at least 240 bushels per acre. In another aspect, the yield of hybrid corn seed provided herein comprises at least 260 bushels per acre. In another aspect, the yield of hybrid corn seed provided herein comprises at least 300 bushels per acre. In another aspect, the yield of hybrid corn seed provided herein comprises at least 350 bushels per acre. In another aspect, the yield of hybrid corn seed provided herein comprises at least 400 bushels per acre. In another aspect, the yield of hybrid corn seed provided herein comprises at least 450 bushels per acre. In another aspect, the yield of hybrid corn seed provided herein comprises at least 500 bushels per acre.

In an aspect, the yield of hybrid corn seed provided herein comprises between 100 and 120 bushels per acre. In another aspect, the yield of hybrid corn seed provided herein comprises between 120 and 140 bushels per acre. In another aspect, the yield of hybrid corn seed provided herein comprises between 140 and 160 bushels per acre. In another aspect, the yield of hybrid corn seed provided herein comprises between 160 and 180 bushels per acre. In another aspect, the yield of hybrid corn seed provided herein comprises between 180 and 200 bushels per acre. In another aspect, the yield of hybrid corn seed provided herein comprises between 200 and 220 bushels per acre. In another aspect, the yield of hybrid corn seed provided herein comprises between 220 and 240 bushels per acre. In another aspect, the yield of hybrid corn seed provided herein comprises between 240 and 260 bushels per acre. In another aspect, the yield of hybrid corn seed provided herein comprises between 100 and 140 bushels per acre. In another aspect, the yield of hybrid corn seed provided herein comprises between 140 and 180 bushels per acre. In another aspect, the yield of hybrid corn seed provided herein comprises between 180 and 220 bushels per acre. In another aspect, the yield of hybrid corn seed provided herein comprises between 220 and 260 bushels per acre. In another aspect, the yield of hybrid corn seed provided herein comprises between 100 and 180 bushels per acre. In another aspect, the yield of hybrid corn seed provided herein comprises between 180 and 260 bushels per acre. In another aspect, the yield of hybrid corn seed provided herein comprises between 100 and 500 bushels per acre. In another aspect, the yield of hybrid corn seed provided herein comprises between 100 and 450 bushels per acre. In another aspect, the yield of hybrid corn seed provided herein comprises between 100 and 400 bushels per acre. In another aspect, the yield of hybrid corn seed provided herein comprises between 100 and 350 bushels per acre. In another aspect, the yield of hybrid corn seed provided herein comprises between 100 and 300 bushels per acre. In another aspect, the yield of hybrid corn seed provided herein comprises between 100 and 260 bushels per acre. In another aspect, the yield of hybrid corn seed provided herein comprises between 100 and 200 bushels per acre.

In an aspect, the hybrid corn seed yield provided herein comprises an average of at least 200 kernels per ear. In another aspect, the hybrid corn seed yield provided herein comprises an average of at least 300 kernels per ear. In another aspect, the hybrid corn seed yield provided herein comprises an average of at least 400 kernels per ear. In another aspect, the hybrid corn seed yield provided herein comprises an average of at least 500 kernels per ear. In another aspect, the hybrid corn seed yield provided herein comprises an average of at least 600 kernels per ear. In another aspect, the hybrid corn seed yield provided herein comprises an average of at least 700 kernels per ear. In another aspect, the hybrid corn seed yield provided herein comprises an average of at least 800 kernels per ear. In another aspect, the hybrid corn seed yield provided herein comprises an average of at least 900 kernels per ear. In another aspect, the hybrid corn seed yield provided herein comprises an average of at least 1,000 kernels per ear. In another aspect, the hybrid corn seed yield provided herein comprises an average of at least 1,100 kernels per ear. In another aspect, the hybrid corn seed yield provided herein comprises an average of at least 1,200 kernels per ear. In another aspect, the hybrid corn seed yield provided herein comprises an average of at least 1,300 kernels per ear. In another aspect, the hybrid corn seed yield provided herein comprises an average of at least 1,400 kernels per ear. In another aspect, the hybrid corn seed yield provided herein comprises an average of at least 1,500 kernels per ear.

In an aspect, the hybrid corn seed yield provided herein comprises an average of between 200 and 300 kernels per ear. In another aspect, the hybrid corn seed yield provided herein comprises an average of between 300 and 400 kernels per ear. In another aspect, the hybrid corn seed yield provided herein comprises an average of between 400 and 500 kernels per ear. In another aspect, the hybrid corn seed yield provided herein comprises an average of between 500 and 600 kernels per ear. In another aspect, the hybrid corn seed yield provided herein comprises an average of between 600 and 700 kernels per ear. In another aspect, the hybrid corn seed yield provided herein comprises an average of between 700 and 800 kernels per ear. In another aspect, the hybrid corn seed yield provided herein comprises an average of between 800 and 900 kernels per ear. In another aspect, the hybrid corn seed yield provided herein comprises an average of between 900 and 1,000 kernels per ear. In another aspect, the hybrid corn seed yield provided herein comprises an average of between 1,000 and 1,100 kernels per ear. In another aspect, the hybrid corn seed yield provided herein comprises an average of between 1,100 and 1,200 kernels per ear. In another aspect, the hybrid corn seed yield provided herein comprises an average of between 200 and 400 kernels per ear. In another aspect, the hybrid corn seed yield provided herein comprises an average of between 400 and 600 kernels per ear. In another aspect, the hybrid corn seed yield provided herein comprises an average of between 600 and 800 kernels per ear. In another aspect, the hybrid corn seed yield provided herein comprises an average of between 800 and 1,000 kernels per ear. In another aspect, the hybrid corn seed yield provided herein comprises an average of between 1,000 and 1,200 kernels per ear. In another aspect, the hybrid corn seed yield provided herein comprises an average of between 200 and 700 kernels per ear. In another aspect, the hybrid corn seed yield provided herein comprises an average of between 700 and 1,200 kernels per ear. In another aspect, the hybrid corn seed yield provided herein comprises an average of between 200 and 1,500 kernels per ear. In another aspect, the hybrid corn seed yield provided herein comprises an average of between 200 and 1,400 kernels per ear. In another aspect, the hybrid corn seed yield provided herein comprises an average of between 200 and 1,300 kernels per ear. In another aspect, the hybrid corn seed yield provided herein comprises an average of between 200 and 1,200 kernels per ear.

In an aspect, the hybrid corn seed yield provided herein comprises at least 200 kernels per ear. In another aspect, the hybrid corn seed yield provided herein comprises at least 300 kernels per ear. In another aspect, the hybrid corn seed yield provided herein comprises at least 400 kernels per ear. In another aspect, the hybrid corn seed yield provided herein comprises at least 500 kernels per ear. In another aspect, the hybrid corn seed yield provided herein comprises at least 600 kernels per ear. In another aspect, the hybrid corn seed yield provided herein comprises at least 700 kernels per ear. In another aspect, the hybrid corn seed yield provided herein comprises at least 800 kernels per ear. In another aspect, the hybrid corn seed yield provided herein comprises at least 900 kernels per ear. In another aspect, the hybrid corn seed yield provided herein comprises at least 1,000 kernels per ear. In another aspect, the hybrid corn seed yield provided herein comprises at least 1,100 kernels per ear. In another aspect, the hybrid corn seed yield provided herein comprises at least 1,200 kernels per ear. In another aspect, the hybrid corn seed yield provided herein comprises at least 1,300 kernels per ear. In another aspect, the hybrid corn seed yield provided herein comprises at least 1,400 kernels per ear. In another aspect, the hybrid corn seed yield provided herein comprises at least 1,500 kernels per ear.

In an aspect, the hybrid corn seed yield provided herein comprises between 200 and 300 kernels per ear. In another aspect, the hybrid corn seed yield provided herein comprises between 300 and 400 kernels per ear. In another aspect, the hybrid corn seed yield provided herein comprises between 400 and 500 kernels per ear. In another aspect, the hybrid corn seed yield provided herein comprises between 500 and 600 kernels per ear. In another aspect, the hybrid corn seed yield provided herein comprises between 600 and 700 kernels per ear. In another aspect, the hybrid corn seed yield provided herein comprises between 700 and 800 kernels per ear. In another aspect, the hybrid corn seed yield provided herein comprises between 800 and 900 kernels per ear. In another aspect, the hybrid corn seed yield provided herein comprises between 900 and 1,000 kernels per ear. In another aspect, the hybrid corn seed yield provided herein comprises between 1,000 and 1,100 kernels per ear. In another aspect, the hybrid corn seed yield provided herein comprises between 1,100 and 1,200 kernels per ear. In another aspect, the hybrid corn seed yield provided herein comprises between 200 and 400 kernels per ear. In another aspect, the hybrid corn seed yield provided herein comprises between 400 and 600 kernels per ear. In another aspect, the hybrid corn seed yield provided herein comprises between 600 and 800 kernels per ear. In another aspect, the hybrid corn seed yield provided herein comprises between 800 and 1,000 kernels per ear. In another aspect, the hybrid corn seed yield provided herein comprises between 1,000 and 1,200 kernels per ear. In another aspect, the hybrid corn seed yield provided herein comprises between 200 and 700 kernels per ear. In another aspect, the hybrid corn seed yield provided herein comprises between 700 and 1,200 kernels per ear. In another aspect, the hybrid corn seed yield provided herein comprises between 200 and 1,200 kernels per ear.

In an aspect, the hybrid corn seed provided herein comprises an average of at least 0.2 grams per dry kernel. In another aspect, the hybrid corn seed provided herein comprises an average of at least 0.25 grams per dry kernel. In another aspect, the hybrid corn seed provided herein comprises an average of at least 0.3 grams per dry kernel. In another aspect, the hybrid corn seed provided herein comprises an average of at least 0.35 grams per dry kernel. In another aspect, the hybrid corn seed provided herein comprises an average of at least 0.4 grams per dry kernel. In another aspect, the hybrid corn seed provided herein comprises an average of at least 0.45 grams per dry kernel. In another aspect, the hybrid corn seed provided herein comprises an average of at least 0.5 grams per dry kernel. In another aspect, the hybrid corn seed provided herein comprises an average of at least 0.55 grams per dry kernel. In another aspect, the hybrid corn seed provided herein comprises an average of at least 0.6 grams per dry kernel.

In an aspect, the hybrid corn seed provided herein comprises an average of between 0.2 and 0.25 grams per dry kernel. In another aspect, the hybrid corn seed provided herein comprises an average of between 0.25 and 0.3 grams per dry kernel. In another aspect, the hybrid corn seed provided herein comprises an average of between 0.3 and 0.35 grams per dry kernel. In another aspect, the hybrid corn seed provided herein comprises an average of between 0.35 and 0.4 grams per dry kernel. In another aspect, the hybrid corn seed provided herein comprises an average of between 0.4 and 0.45 grams per dry kernel. In another aspect, the hybrid corn seed provided herein comprises an average of between 0.45 and 0.5 grams per dry kernel. In another aspect, the hybrid corn seed provided herein comprises an average of between 0.5 and 0.55 grams per dry kernel. In another aspect, the hybrid corn seed provided herein comprises an average of between 0.55 and 0.6 grams per dry kernel. In another aspect, the hybrid corn seed provided herein comprises an average of between 0.2 and 0.3 grams per dry kernel. In another aspect, the hybrid corn seed provided herein comprises an average of between 0.3 and 0.4 grams per dry kernel. In another aspect, the hybrid corn seed provided herein comprises an average of between 0.4 and 0.5 grams per dry kernel. In another aspect, the hybrid corn seed provided herein comprises an average of between 0.5 and 0.6 grams per dry kernel. In another aspect, the hybrid corn seed provided herein comprises an average of between 0.2 and 0.4 grams per dry kernel. In another aspect, the hybrid corn seed provided herein comprises an average of between 0.4 and 0.6 grams per dry kernel. In another aspect, the hybrid corn seed provided herein comprises an average of between 0.2 and 0.6 grams per dry kernel.

In an aspect, the hybrid corn seed provided herein comprises at least 0.2 grams per dry kernel. In another aspect, the hybrid corn seed provided herein comprises at least 0.25 grams per dry kernel. In another aspect, the hybrid corn seed provided herein comprises at least 0.3 grams per dry kernel. In another aspect, the hybrid corn seed provided herein comprises at least 0.35 grams per dry kernel. In another aspect, the yield corn seed provided herein comprises at least 0.4 grams per dry kernel. In another aspect, the hybrid corn seed provided herein comprises at least 0.45 grams per dry kernel. In another aspect, the hybrid corn seed provided herein comprises at least 0.5 grams per dry kernel. In another aspect, the hybrid corn seed provided herein comprises at least 0.55 grams per dry kernel. In another aspect, the hybrid corn seed provided herein comprises at least 0.6 grams per dry kernel.

In an aspect, the hybrid corn seed provided herein comprises between 0.2 and 0.25 grams per dry kernel. In another aspect, the hybrid corn seed provided herein comprises between 0.25 and 0.3 grams per dry kernel. In another aspect, the hybrid corn seed provided herein comprises between 0.3 and 0.35 grams per dry kernel. In another aspect, the hybrid corn seed provided herein comprises between 0.35 and 0.4 grams per dry kernel. In another aspect, the hybrid corn seed provided herein comprises between 0.4 and 0.45 grams per dry kernel. In another aspect, the hybrid corn seed provided herein comprises between 0.45 and 0.5 grams per dry kernel. In another aspect, the hybrid corn seed provided herein comprises between 0.5 and 0.55 grams per dry kernel. In another aspect, the hybrid corn seed provided herein comprises between 0.55 and 0.6 grams per dry kernel. In another aspect, the hybrid corn seed provided herein comprises between 0.2 and 0.3 grams per dry kernel. In another aspect, the hybrid corn seed provided herein comprises between 0.3 and 0.4 grams per dry kernel. In another aspect, the hybrid corn seed provided herein comprises between 0.4 and 0.5 grams per dry kernel. In another aspect, the hybrid corn seed provided herein comprises between 0.5 and 0.6 grams per dry kernel. In another aspect, the hybrid corn seed provided herein comprises between 0.2 and 0.4 grams per dry kernel. In another aspect, the hybrid corn seed provided herein comprises between 0.4 and 0.6 grams per dry kernel. In another aspect, the hybrid corn seed provided herein comprises between 0.2 and 0.6 grams per dry kernel.

In an aspect, the yield of hybrid corn seed provided herein comprises at least 80 SSUs per acre. In an aspect, the yield of hybrid corn seed provided herein comprises at least 90 SSUs per acre. In an aspect, the yield of hybrid corn seed provided herein comprises at least 100 SSUs per acre. In an aspect, the yield of hybrid corn seed provided herein comprises at least 105 SSUs per acre. In an aspect, the yield of hybrid corn seed provided herein comprises at least 110 SSUs per acre. In an aspect, the yield of hybrid corn seed provided herein comprises at least 115 SSUs per acre. In an aspect, the yield of hybrid corn seed provided herein comprises at least 120 SSUs per acre. In an aspect, the yield of hybrid corn seed provided herein comprises at least 125 SSUs per acre. In an aspect, the yield of hybrid corn seed provided herein comprises at least 130 SSUs per acre. In an aspect, the yield of hybrid corn seed provided herein comprises at least 135 SSUs per acre. In an aspect, the yield of hybrid corn seed provided herein comprises at least 140 SSUs per acre. In an aspect, the yield of hybrid corn seed provided herein comprises at least 145 SSUs per acre. In an aspect, the yield of hybrid corn seed provided herein comprises at least 150 SSUs per acre. In an aspect, the yield of hybrid corn seed provided herein comprises at least 155 SSUs per acre. In an aspect, the yield of hybrid corn seed provided herein comprises at least 160 SSUs per acre. In an aspect, the yield of hybrid corn seed provided herein comprises at least 170 SSUs per acre. In an aspect, the yield of hybrid corn seed provided herein comprises at least 180 SSUs per acre. In an aspect, the yield of hybrid corn seed provided herein comprises at least 190 SSUs per acre. In an aspect, the yield of hybrid corn seed provided herein comprises at least 200 SSUs per acre.

In an aspect, the hybrid corn seed yield provided herein comprises between 80 SSUs per acre and 200 SSUs per acre. In an aspect, the hybrid corn seed yield provided herein comprises between 80 SSUs per acre and 190 SSUs per acre. In an aspect, the hybrid corn seed yield provided herein comprises between 80 SSUs per acre and 180 SSUs per acre. In an aspect, the hybrid corn seed yield provided herein comprises between 80 SSUs per acre and 170 SSUs per acre. In an aspect, the hybrid corn seed yield provided herein comprises between 80 SSUs per acre and 160 SSUs per acre. In an aspect, the hybrid corn seed yield provided herein comprises between 80 SSUs per acre and 150 SSUs per acre. In an aspect, the hybrid corn seed yield provided herein comprises between 80 SSUs per acre and 140 SSUs per acre. In an aspect, the hybrid corn seed yield provided herein comprises between 80 SSUs per acre and 130 SSUs per acre. In an aspect, the hybrid corn seed yield provided herein comprises between 80 SSUs per acre and 120 SSUs per acre. In an aspect, the hybrid corn seed yield provided herein comprises between 80 SSUs per acre and 110 SSUs per acre. In an aspect, the hybrid corn seed yield provided herein comprises between 80 SSUs per acre and 100 SSUs per acre. In an aspect, the hybrid corn seed yield provided herein comprises between 80 SSUs per acre and 90 SSUs per acre.

In an aspect, the hybrid corn seed yield provided herein comprises between 90 SSUs per acre and 200 SSUs per acre. In an aspect, the hybrid corn seed yield provided herein comprises between 90 SSUs per acre and 190 SSUs per acre. In an aspect, the hybrid corn seed yield provided herein comprises between 90 SSUs per acre and 180 SSUs per acre. In an aspect, the hybrid corn seed yield provided herein comprises between 90 SSUs per acre and 170 SSUs per acre. In an aspect, the hybrid corn seed yield provided herein comprises between 90 SSUs per acre and 160 SSUs per acre. In an aspect, the hybrid corn seed yield provided herein comprises between 90 SSUs per acre and 150 SSUs per acre. In an aspect, the hybrid corn seed yield provided herein comprises between 90 SSUs per acre and 140 SSUs per acre. In an aspect, the hybrid corn seed yield provided herein comprises between 90 SSUs per acre and 130 SSUs per acre. In an aspect, the hybrid corn seed yield provided herein comprises between 90 SSUs per acre and 120 SSUs per acre. In an aspect, the hybrid corn seed yield provided herein comprises between 90 SSUs per acre and 110 SSUs per acre. In an aspect, the hybrid corn seed yield provided herein comprises between 90 SSUs per acre and 100 SSUs per acre.

In an aspect, the hybrid corn seed yield provided herein comprises between 100 SSUs per acre and 200 SSUs per acre. In an aspect, the hybrid corn seed yield provided herein comprises between 100 SSUs per acre and 190 SSUs per acre. In an aspect, the hybrid corn seed yield provided herein comprises between 100 SSUs per acre and 180 SSUs per acre. In an aspect, the hybrid corn seed yield provided herein comprises between 100 SSUs per acre and 170 SSUs per acre. In an aspect, the hybrid corn seed yield provided herein comprises between 100 SSUs per acre and 160 SSUs per acre. In an aspect, the hybrid corn seed yield provided herein comprises between 100 SSUs per acre and 150 SSUs per acre. In an aspect, the hybrid corn seed yield provided herein comprises between 100 SSUs per acre and 140 SSUs per acre. In an aspect, the hybrid corn seed yield provided herein comprises between 100 SSUs per acre and 130 SSUs per acre. In an aspect, the hybrid corn seed yield provided herein comprises between 100 SSUs per acre and 120 SSUs per acre. In an aspect, the hybrid corn seed yield provided herein comprises between 100 SSUs per acre and 110 SSUs per acre.

In an aspect, the hybrid corn seed yield provided herein comprises between 110 SSUs per acre and 200 SSUs per acre. In an aspect, the hybrid corn seed yield provided herein comprises between 110 SSUs per acre and 190 SSUs per acre. In an aspect, the hybrid corn seed yield provided herein comprises between 110 SSUs per acre and 180 SSUs per acre. In an aspect, the hybrid corn seed yield provided herein comprises between 110 SSUs per acre and 170 SSUs per acre. In an aspect, the hybrid corn seed yield provided herein comprises between 110 SSUs per acre and 160 SSUs per acre. In an aspect, the hybrid corn seed yield provided herein comprises between 110 SSUs per acre and 150 SSUs per acre. In an aspect, the hybrid corn seed yield provided herein comprises between 110 SSUs per acre and 140 SSUs per acre. In an aspect, the hybrid corn seed yield provided herein comprises between 110 SSUs per acre and 130 SSUs per acre. In an aspect, the hybrid corn seed yield provided herein comprises between 110 SSUs per acre and 120 SSUs per acre.

In an aspect, the hybrid corn seed yield provided herein comprises between 120 SSUs per acre and 200 SSUs per acre. In an aspect, the hybrid corn seed yield provided herein comprises between 120 SSUs per acre and 190 SSUs per acre. In an aspect, the hybrid corn seed yield provided herein comprises between 120 SSUs per acre and 180 SSUs per acre. In an aspect, the hybrid corn seed yield provided herein comprises between 120 SSUs per acre and 170 SSUs per acre. In an aspect, the hybrid corn seed yield provided herein comprises between 120 SSUs per acre and 160 SSUs per acre. In an aspect, the hybrid corn seed yield provided herein comprises between 120 SSUs per acre and 150 SSUs per acre. In an aspect, the hybrid corn seed yield provided herein comprises between 120 SSUs per acre and 140 SSUs per acre. In an aspect, the hybrid corn seed yield provided herein comprises between 120 SSUs per acre and 130 SSUs per acre.

In an aspect, the hybrid corn seed yield provided herein comprises between 130 SSUs per acre and 200 SSUs per acre. In an aspect, the hybrid corn seed yield provided herein comprises between 130 SSUs per acre and 190 SSUs per acre. In an aspect, the hybrid corn seed yield provided herein comprises between 130 SSUs per acre and 180 SSUs per acre. In an aspect, the hybrid corn seed yield provided herein comprises between 130 SSUs per acre and 170 SSUs per acre. In an aspect, the hybrid corn seed yield provided herein comprises between 130 SSUs per acre and 160 SSUs per acre. In an aspect, the hybrid corn seed yield provided herein comprises between 130 SSUs per acre and 150 SSUs per acre. In an aspect, the hybrid corn seed yield provided herein comprises between 130 SSUs per acre and 140 SSUs per acre.

In an aspect, the hybrid corn seed yield provided herein comprises between 140 SSUs per acre and 200 SSUs per acre. In an aspect, the hybrid corn seed yield provided herein comprises between 140 SSUs per acre and 190 SSUs per acre. In an aspect, the hybrid corn seed yield provided herein comprises between 140 SSUs per acre and 180 SSUs per acre. In an aspect, the hybrid corn seed yield provided herein comprises between 140 SSUs per acre and 170 SSUs per acre. In an aspect, the hybrid corn seed yield provided herein comprises between 140 SSUs per acre and 160 SSUs per acre. In an aspect, the hybrid corn seed yield provided herein comprises between 140 SSUs per acre and 150 SSUs per acre.

In an aspect, the hybrid corn seed yield provided herein comprises between 150 SSUs per acre and 200 SSUs per acre. In an aspect, the hybrid corn seed yield provided herein comprises between 150 SSUs per acre and 190 SSUs per acre. In an aspect, the hybrid corn seed yield provided herein comprises between 150 SSUs per acre and 180 SSUs per acre. In an aspect, the hybrid corn seed yield provided herein comprises between 150 SSUs per acre and 170 SSUs per acre. In an aspect, the hybrid corn seed yield provided herein comprises between 150 SSUs per acre and 160 SSUs per acre.

In an aspect, the hybrid corn seed yield provided herein comprises between 160 SSUs per acre and 200 SSUs per acre. In an aspect, the hybrid corn seed yield provided herein comprises between 160 SSUs per acre and 190 SSUs per acre. In an aspect, the hybrid corn seed yield provided herein comprises between 160 SSUs per acre and 180 SSUs per acre. In an aspect, the hybrid corn seed yield provided herein comprises between 160 SSUs per acre and 170 SSUs per acre. In an aspect, the hybrid corn seed yield provided herein comprises between 170 SSUs per acre and 200 SSUs per acre. In an aspect, the hybrid corn seed yield provided herein comprises between 170 SSUs per acre and 190 SSUs per acre. In an aspect, the hybrid corn seed yield provided herein comprises between 170 SSUs per acre and 180 SSUs per acre. In an aspect, the hybrid corn seed yield provided herein comprises between 180 SSUs per acre and 200 SSUs per acre. In an aspect, the hybrid corn seed yield provided herein comprises between 180 SSUs per acre and 190 SSUs per acre.

In an aspect, the yield of hybrid corn seed provided herein comprises between 190 SSUs per acre and 200 SSUs per acre.

As used herein, "detasseled" corn refers to corn where the pollen-producing flowers, or tassels, have been removed. Detasseling is typically performed before the tassel can shed pollen. Detasseling can be accomplished via machine detasseling, manual detasseling, or a combination of both machine and manual detasseling. Detasseling often removes the uppermost leaves of the corn plant along with the developing tassel. Detasseled corn plants retain their female flowers, which eventually produce kernels on the ear. In an aspect, a corn plant provided herein is a detasseled corn plant.

In an aspect, the female corn plants provided herein have been detasseled. In another aspect, at least 50% of the female corn plants provided herein have been detasseled. In another aspect, at least 60% of the female corn plants provided herein have been detasseled. In another aspect, at least 70% of the female corn plants provided herein have been detasseled. In another aspect, at least 80% of the female corn plants provided herein have been detasseled. In another aspect, at least 90% of the female corn plants provided herein have been detasseled. In another aspect, at least 95% of the female corn plants provided herein have been detasseled. In another aspect, 99% of the female corn plants provided herein have been detasseled. In another aspect, 100% of the female corn plants provided herein have been detasseled.

As an alternative to detasseling, the female corn plants can have sterility through genetic crosses and inheritance and/or use of an inducible system. One system that can be employed to induce male sterility in female corn plants is the Roundup® hybridization system (RHS), wherein the male reproductive tissues or tassels are unable to produce pollen following treatment with glyphosate during an appropriate window of plant development. In one RHS system, corn plants (or female corn plants) in a seed production field have a Roundup® or glyphosate resistant 5-enolpyruvylshikimate-3-phosphate synthase (EPSPS) transgene, but due to the combination expression elements, the expression of the transgene in male reproductive tissues is low. As a result, when these corn plants (or female corn plants) are treated with glyphosate, their male reproductive structures or tassels do not develop to produce pollen. In a second generation RHS system (RHS2), the corn plants (or female corn plants) in a seed production field have a Roundup® or glyphosate resistant 5-enolpyruvylshikimate-3-phosphate synthase (EPSPS) transgene that further contains in its 3' untranslated region (UTR) a target site for an endogenous small interfering RNA (siRNA) expressed specifically in male tissues. Thus, expression of the transgene is suppressed in the male reproductive tissues to render those tissues susceptible to Roundup® or glyphosate treatment. Accordingly, corn plants (or female corn plants) containing this transgene can be made male sterile and unable to produce pollen by Roundup® or glyphosate treatment. According to some embodiments, corn plants (or female corn plants) comprise a RHS event, such as MON 87427 (see, e.g., U.S. Application Pub. No. 2011/0126310, the entire contents and disclosure of which are incorporated herein by reference) or MON 87429 (see, e.g., U.S. Provisional App. No. 62/625,537, the entire contents and disclosure of which are incorporated herein by reference). In addition to the RHS system, other chemical hybridizing agents (CHAs) known in the art could be used to make corn plants male sterile.

As an alternative to chemical treatment, corn plants (or female corn plants) can be made male sterile through genetic crosses and inheritance causing cytoplasmic male sterility. As used herein, the term "cytoplasmic male sterility" or "CMS" refers to a condition where a corn plant is partially or fully incapable of producing functional pollen. As known in the art, cytoplasmic male sterility is a maternally inherited trait that is commonly associated with unusual open reading frames within the mitochondrial genome which cause cytoplasmic dysfunction. In an aspect, a corn plant or female corn plant provided herein is a cytoplasmic male sterile corn plant.

The shorter plant heights of female corn plants in a production field as provided herein are more accessible for over-the-top treatment with a chemical hybridizing agent or glyphosate (or Roundup®) treatment with standard farming equipment without damaging the female corn plants. In an aspect, methods are provided for planting and treating shorter female corn plants in a seed production field as described herein with a chemical hybridizing agent or glyphosate (or Roundup®) to induce male sterility. In another aspect, shorter female corn plants in a seed production field as described herein further have cytoplasmic male sterility.

In an aspect, the female corn plants provided herein exhibit cytoplasmic male sterility. In another aspect, at least 60% of the female corn plants in a corn field provided herein exhibit cytoplasmic male sterility. In another aspect, at least 70% of the female corn plants in a corn field provided herein exhibit cytoplasmic male sterility. In another aspect, at least 80% of the female corn plants in a corn field provided herein exhibit cytoplasmic male sterility. In another aspect, at least 90% of the female corn plants in a corn field provided herein exhibit cytoplasmic male sterility. In another aspect, 100% of the female corn plants in a corn field provided herein exhibit cytoplasmic male sterility.

In an aspect, this disclosure provides a method of fertilizing at least one female inbred corn plant with pollen from at least one male inbred corn plant, where the at least one female inbred corn plant has an average height that is at least 2.5% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants have the same or similar average height or do not differ in average height by more than 1%. In an aspect, this disclosure provides a method of fertilizing at least one female inbred corn plant with pollen from at least one male inbred corn plant, where the at least one female inbred corn plant has an average height that is at least 5% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants have the same or similar average height or do not differ in average height or do not differ in average height by more than 1% or 2.5%. In an aspect, this disclosure provides a method of fertilizing at least one female inbred corn plant with pollen from at least one male inbred corn plant, where the at least one female inbred corn plant has an average height that is at least 10% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants have the same or similar average height or do not differ in average height by more than 1%, 2.5% or 5%. In another aspect, this disclosure provides a method of fertilizing a plurality of female inbred corn plants with pollen from at least one male inbred corn plant, where the female inbred corn plants have an average height that is at least 10% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 15% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 20% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 25% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%. In an aspect, this disclosure provides a method of fertilizing a plurality of female inbred corn plants with pollen from at least one male inbred corn plant, where the female inbred corn plants have an average height that is at least 30% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants have the same or similar average height or do not differ in average height by more than 1%, 2.5% or 5%.

In another aspect, this disclosure provides a method of fertilizing a plurality of female inbred corn plants with pollen from at least one male inbred corn plant, where the female inbred corn plants have an average height that is at least 10% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 15% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 20% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 25% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%. In an aspect, this disclosure provides a method of fertilizing a plurality of female inbred corn plants with pollen from at least one male inbred corn plant, where the female inbred corn plants have an average height that is at least 30% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 7.5%.

In an aspect, this disclosure provides a method of fertilizing at least one female inbred corn plant with pollen from at least one male inbred corn plant, where the at least one female inbred corn plant has an average height that is at least 15% lower than the height (or average height) of the at least one male inbred corn plant, and then harvesting the hybrid corn seeds produced by the at least one female inbred corn plant, where the yield and/or seed yield of harvested hybrid corn seeds is greater than the yield and/or seed yield that is obtained by fertilizing at least one control female inbred corn plant with pollen from at least one male control inbred corn plant where the female and male control plants do not differ in average height by more than 10%. In another aspect, this disclosure provides a method of fertilizing a plurality of female inbred corn plants with pollen from at least one male inbred corn plant, where the female inbred corn plants have an average height that is at least 15% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%. In an aspect, this disclosure provides a method of fertilizing a plurality of female inbred corn plants with pollen from at least one male inbred corn plant, where the female inbred corn plants have an average height that is at least 20% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%. In an aspect, this disclosure provides a method of fertilizing a plurality of female inbred corn plants with pollen from at least one male inbred corn plant, where the female inbred corn plants have an average height that is at least 25% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%. In an aspect, this disclosure provides a method of fertilizing a plurality of female inbred corn plants with pollen from at least one male inbred corn plant, where the female inbred corn plants have an average height that is at least 30% lower than the height (or average height) of the at least one male inbred corn plant, and then harvesting the hybrid corn seeds produced by one or more of the female inbred corn plants, where the yield and/or seed yield of harvested hybrid corn seeds is greater than the yield and/or seed yield that is obtained by fertilizing a plurality of control female inbred corn plants with pollen from at least one male control inbred corn plant where the female and male control plants do not differ in average height by more than 10%.

In an aspect, this disclosure provides a method of fertilizing at least one female inbred corn plant with pollen from at least one male inbred corn plant, where the female-to-male plant height ratio is 0.98:1 or less, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one male control inbred corn plant, where the female-to-male control plant height ratio is about 1:1. In an aspect, this disclosure provides a method of fertilizing at least one female inbred corn plant with pollen from at least one male inbred corn plant, where the female-to-male plant height ratio is 0.97:1 or less, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one male control inbred corn plant, where the female-to-male control plant height ratio is about 1:1. In an aspect, this disclosure provides a method of fertilizing at least one female inbred corn plant with pollen from at least one male inbred corn plant, where the female-to-male plant height ratio is 0.96:1 or less, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one male control inbred corn plant, where the female-to-male control plant height ratio is about 1:1. In another aspect, this disclosure provides a method of fertilizing a plurality of female inbred corn plants with pollen from at least one male inbred corn plant, where the female-to-male plant height ratio is 0.95:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1. In an aspect, this disclosure provides a method of fertilizing at least one female inbred corn plant with pollen from at least one male inbred corn plant, where the female-to-male plant height ratio is 0.9:1 or less, and then harvesting the hybrid corn seeds produced by the at least one female inbred corn plant, where the yield, seed yield or SSUs of harvested hybrid corn seeds is greater than the yield or SSUs that is obtained by fertilizing at least one control female inbred corn plant with pollen from at least one male control inbred corn plant, where the female-to-male control plant height ratio is about 1:1 or between 0.95:1 and 1:1. In another aspect, this disclosure provides a method of fertilizing a plurality of female inbred corn plants with pollen from at least one male inbred corn plant, where the female-to-male plant height ratio is 0.9:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In another aspect, this disclosure provides a method of fertilizing a plurality of female inbred corn plants with pollen from at least one male inbred corn plant, where the female-to-male plant height ratio is 0.85:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.8:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.75:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.7:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is 0.6:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1.

In an aspect, this disclosure provides a method of fertilizing a plurality of female inbred corn plants with pollen from at least one male inbred corn plant, where the female-to-male plant height ratio is between 0.6:1 and 0.95:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is between 0.7:1 and 0.95:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1. In an aspect, this disclosure provides a method of fertilizing a plurality of female inbred corn plants with pollen from at least one male inbred corn plant, where the female-to-male plant height ratio is between 0.8:1 and 0.95:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.95:1 and 1:1.

In an aspect, this disclosure provides a method of fertilizing a plurality of female inbred corn plants with pollen from at least one male inbred corn plant, where the female-to-male plant height ratio is 0.85:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.8:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.75:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.7:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is 0.6:1 or less, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1. In an aspect, this disclosure provides a method of fertilizing a plurality of female inbred corn plants with pollen from at least one male inbred corn plant, where the female-to-male plant height ratio is between 0.6:1 and 0.9:1, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the female-to-male control plant height ratio is about 1:1 or between 0.9:1 and 1:1.

In an aspect, this disclosure provides a method of fertilizing at least one female inbred corn plant with pollen from at least one male inbred corn plant, where the at least one female-inbred corn plant has a height (or average height) that is at least 2.0 meters shorter, at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter than the height (or average height) of the at least one male inbred corn plant, and then harvesting the hybrid corn seeds produced by the at least one female inbred corn plant, where the yield, seed yield or SSUs of harvested hybrid corn seeds is greater than the yield, seed yield or SSUs that is obtained by fertilizing at least one control female inbred corn plant with pollen from at least one control male inbred corn plant, where the female control plant height is no more than 0.25 meters shorter than the height of the at least one male control plant. In an aspect, this disclosure provides a method of fertilizing a plurality of female inbred corn plants with pollen from at least one male inbred corn plant, where the average female-inbred corn plant height is at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter, or at least 0.2 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one control male inbred corn plant, where the average female control plant height is about the same as, or is no more than 0.2 meters shorter than, the height of the at least one male control plant. In an aspect, this disclosure provides a method of fertilizing a plurality of female inbred corn plants with pollen from at least one male inbred corn plant, where the average female-inbred corn plant height is at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter, at least 0.2 meters shorter, or at least 0.1 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one control male inbred corn plant, where the average female control plant height is about the same as, or is no more than 0.15 meters shorter than, the height of the at least one male control plant. In an aspect, this disclosure provides a method of fertilizing a plurality of female inbred corn plants with pollen from at least one male inbred corn plant, where the average female-inbred corn plant height is at least 1.5 meters shorter, at least 1.4 meters shorter, at least 1.3 meters shorter, at least 1.2 meters shorter, at least 1.1 meters shorter, at least 1.0 meters shorter, at least 0.9 meters shorter, at least 0.8 meters shorter, at least 0.7 meters shorter, at least 0.6 meters shorter, at least 0.5 meters shorter, at least 0.4 meters shorter, at least 0.3 meters shorter, at least 0.2 meters shorter, or at least 0.1 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one control male inbred corn plant, where the average female control plant height is about the same as, or is no more than 0.1 meters shorter than the height of the at least one male control plant.

In an aspect, this disclosure provides a method of fertilizing a plurality of female inbred corn plants with pollen from at least one male inbred corn plant, where the average female inbred corn plant height is between 0.1 and 1.0 meters shorter, between 0.2 and 1.0 meters shorter, or between 0.2 and 0.5 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In an aspect, this disclosure provides a method of fertilizing a plurality of female inbred corn plants with pollen from at least one male inbred corn plant, where the average female-inbred corn plant height is between 0.5 and 1.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 1.0 and 1.5 meters shorter than the height (or average height) of the male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 1.5 and 2.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the male control plant. In another aspect, this disclosure provides a method of fertilizing a plurality of female inbred corn plants with pollen from at least one male inbred corn plant, where the average female-inbred corn plant height is between 0.5 and 1.5 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 1.0 and 2.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant. In another aspect, this disclosure provides a method of fertilizing a plurality of female inbred corn plants with pollen from at least one male inbred corn plant, where the average female-inbred corn plant height is between 0.5 and 2.0 meters shorter than the height (or average height) of the at least one male inbred corn plant, and then harvesting the hybrid corn seeds produced by one or more of the female inbred corn plants, where the yield, seed yield or SSUs of harvested hybrid corn seeds is greater than the yield, seed yield or SSUs that is obtained by fertilizing a plurality of control female inbred corn plants with pollen from at least one male control inbred corn plant, where the average female control plant height is the same or similar as, or is no more than 0.25 meters, 0.2 meters, 0.15 meters, or 0.1 meters shorter than, the height (or average height) of the at least one male control plant.

In an aspect, the yield, seed yield or SSUs of hybrid corn seed is increased by at least 1.0%. In an aspect, the yield, seed yield or SSUs of hybrid corn seed is increased by at least 1.5%. In an aspect, the yield, seed yield or SSUs of hybrid corn seed is increased by at least 2.0%. In an aspect, the yield, seed yield or SSUs of hybrid corn seed is increased by at least 2.5%. In an aspect, the yield, seed yield or SSUs of hybrid corn seed is increased by at least 3.0%. In another aspect, the yield, seed yield or SSUs of hybrid corn seed is increased by at least 3.5%. In another aspect, the yield, seed yield or SSUs of hybrid corn seed is increased by at least 4.0%. In another aspect, the yield, seed yield or SSUs of hybrid corn seed is increased by at least 4.5%. In another aspect, the yield, seed yield or SSUs of hybrid corn seed is increased by at least 5.0%. In another aspect, the yield, seed yield or SSUs of hybrid corn seed is increased by at least 5.5%. In another aspect, the yield, seed yield or SSUs of hybrid corn seed is increased by at least 6.0%. In another aspect, the yield, seed yield or SSUs of hybrid corn seed is increased by at least 6.5%. In another aspect, the yield, seed yield or SSUs of hybrid corn seed is increased by at least 7.0%. In another aspect, the yield, seed yield or SSUs of hybrid corn seed is increased by at least 7.5%. In another aspect, the yield, seed yield or SSUs of hybrid corn seed is increased by at least 8.0%. In another aspect, the yield, seed yield or SSUs of hybrid corn seed is increased by at least 8.5%. In another aspect, the yield, seed yield or SSUs of hybrid corn seed is increased by at least 9.0%. In another aspect, the yield, seed yield or SSUs of hybrid corn seed is increased by at least 9.5%. In another aspect, the yield, seed yield or SSUs of hybrid corn seed is increased by at least 10%. In another aspect, the yield, seed yield of hybrid corn seed is increased by at least 11%. In another aspect, the yield, seed yield or SSUs of hybrid corn seed is increased by at least 12%. In another aspect, the yield, seed yield or SSUs of hybrid corn seed is increased by at least 13%. In another aspect, the yield, seed yield or SSUs of hybrid corn seed is increased by at least 14%. In another aspect, the yield, seed yield or SSUs of hybrid corn seed is increased by at least 15%. In another aspect, the yield, seed yield or SSUs of hybrid corn seed is increased by at least 16%. In another aspect, the yield, seed yield or SSUs of hybrid corn seed is increased by at least 17%. In another aspect, the yield, seed yield or SSUs of hybrid corn seed is increased by at least 18%. In another aspect, the yield, seed yield or SSUs of hybrid corn seed is increased by at least 19%. In another aspect, the yield, seed yield or SSUs of hybrid corn seed is increased by at least 20%.

In another aspect, the yield, seed yield or SSUs of hybrid corn seed is increased by between 1% and 20%. In another aspect, the yield, seed yield or SSUs of hybrid corn seed is increased by between 1% and 15%. In another aspect, the yield, seed yield or SSUs of hybrid corn seed is increased by between 1% and 10%. In another aspect, the yield, seed yield or SSUs of hybrid corn seed is increased by between 1% and 5%. In another aspect, the yield, seed yield or SSUs of hybrid corn seed is increased by between 3% and 6%. In another aspect, the yield, seed yield or SSUs of hybrid corn seed is increased by between 6% and 9%. In another aspect, the yield, seed yield or SSUs of hybrid corn seed is increased by between 9% and 12%. In another aspect, the yield, seed yield or SSUs of hybrid corn seed is increased by between 12% and 15%. In another aspect, the yield, seed yield or SSUs of hybrid corn seed is increased by between 15% and 18%. In another aspect, the yield, seed yield or SSUs of hybrid corn seed is increased by between 18% and 20%. In another aspect, the yield, seed yield or SSUs of hybrid corn seed is increased by between 3% and 12%. In another aspect, the yield, seed yield or SSUs of hybrid corn seed is increased by between 12% and 20%. In another aspect, the yield, seed yield or SSUs of hybrid corn seed is increased by between 3% and 20%. Any other range of increased yield, seed yield or SSUs of hybrid corn seed above 1% is contemplated herein.

In an aspect, this disclosure provides a method of crossing at least one male inbred corn plant with at least one female inbred corn plant to produce hybrid corn seeds, where the at least one female inbred corn plant has an average height that is at least 2.5% lower than the height (or average height) of the at least one male inbred corn plant, and then harvesting the hybrid corn seeds produced by the at least one female inbred corn plant. In an aspect, this disclosure provides a method of crossing at least one male inbred corn plant with at least one female inbred corn plant to produce hybrid corn seeds, where the at least one female inbred corn plant has an average height that is at least 5% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 7.5% lower than the height (or average height) of the at least one male inbred corn plant, and then harvesting the hybrid corn seeds produced by the at least one female inbred corn plant. In an aspect, this disclosure provides a method of crossing at least one male inbred corn plant with at least one female inbred corn plant to produce hybrid corn seeds, where the at least one female inbred corn plants has an average height that is at least 10% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 12.5% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 15% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 17.5% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 20% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 25% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant have an average height that is at least 30% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant have an average height that is at least 35% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 40% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 45% lower than the height (or average height) of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has an average height that is at least 50% lower than the height (or average height) of the at least one male inbred corn plant, and then harvesting the hybrid corn seeds produced by one or more of the female inbred corn plants.

In an aspect, this disclosure provides a method of crossing at least one male inbred corn plant with at least one female inbred corn plant to produce hybrid corn seeds, where the female-to-male plant height ratio is 0.95:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.95:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.9:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.9:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.85:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.85:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.8:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.8:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.75:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.75:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.7:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.7:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.65:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.65:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.6:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.6:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.55:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.55:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the female-to-male plant height ratio is 0.5:1 or less, and then harvesting the hybrid corn seeds produced by the at least one female inbred corn plant. In an aspect, this disclosure provides a method of crossing at least one male inbred corn plant with a plurality of female inbred corn plants to produce hybrid corn seeds, where the female-to-male plant height ratio is 0.5:1 or less, and then harvesting the hybrid corn seeds produced by one or more of the female inbred corn plants.

In an aspect, this disclosure provides a method of crossing at least one male inbred corn plant with at least one female inbred corn plant to produce hybrid corn seeds, where the at least one female inbred corn plant has a height that is at least 0.1 meters shorter or at least 0.2 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.1 meters shorter or at least 0.2 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 0.3 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.3 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 0.4 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.4 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 0.5 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 0.5 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 1.0 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 1.0 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 1.5 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 1.5 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds, where the at least one female inbred corn plant has a height that is at least 2.0 meters shorter than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds, where the female inbred corn plants have an average height that is at least 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to a plurality of female inbred corn plants to produce hybrid corn seeds, where the female inbred corn plants have an average height that is between 0.1 and 0.5 meters or between 0.2 and 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds, where the female inbred corn plants have an average height that is between 1.0 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds, where the female inbred corn plants have an average height that is between 1.5 and 2.0 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds, where the female inbred corn plants have an average height that is between 0.5 and 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to at least one female inbred corn plant to produce hybrid corn seeds, where the at least one female inbred corn plant has an average height that is at least 2.5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 2.5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 10% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 10% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 12.5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 12.5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 15% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 15% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 17.5% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 17.5% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 20% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 20% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 25% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 25% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 30% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 30% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 35% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 35% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 40% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 40% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 45% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 45% lower than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has an average height that is at least 50% lower than the height of the at least one male inbred corn plant, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female inbred corn plants have an average height that is at least 50% lower than the height of the at least one male inbred corn plant, and then harvesting the hybrid corn seeds produced by one or more of the female inbred corn plants.

In an aspect, this disclosure provides a method of planting at least one male inbred corn plant in proximity to at least one female inbred corn plant to produce hybrid corn seeds, where the female-to-male plant height ratio is 0.98:1 or less, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female-to-male plant height ratio is 0.98:1 or less, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the female-to-male plant height ratio is 0.95:1 or less, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female-to-male plant height ratio is 0.95:1 or less, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the female-to-male plant height ratio is 0.9:1 or less, and then harvesting the hybrid corn seeds produced by the at least one female inbred corn plant. In another aspect, this disclosure provides a method of planting at least one male inbred corn plant in proximity to a plurality of female inbred corn plants to produce hybrid corn seeds, where the female-to-male plant height ratio is 0.9:1 or less, and then harvesting the hybrid corn seeds produced by one or more of the female inbred corn plants. In another aspect, this disclosure provides a method of planting at least one male inbred corn plant in proximity to a plurality of female inbred corn plants to produce hybrid corn seeds, where the female-to-male plant height ratio is 0.85:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.8:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.75:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.7:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.65:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.6:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.55:1 or less, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female-to-male plant height ratio is 0.5:1 or less, and then harvesting the hybrid corn seeds produced by one or more of the female inbred corn plants.

In an aspect, this disclosure provides a method of planting at least one male inbred corn plant in proximity to at least one female inbred corn plant to produce hybrid corn seeds, where the at least one female inbred corn plant has a height that is at least 0.1 meters or at least 0.2 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.1 meters or at least 0.2 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has a height that is at least 0.3 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.3 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has a height that is at least 0.4 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.4 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to at least one female inbred corn plant to produce hybrid corn seeds, where the at least one female inbred corn plant has a height that is at least 0.5 meters shorter than the height of the at least one male inbred corn plant, and then harvesting the hybrid corn seeds produced by the at least one female inbred corn plant. In an aspect, this disclosure provides a method of planting at least one male inbred corn plant in proximity to a plurality of female inbred corn plants to produce hybrid corn seeds, where the female inbred corn plants have an average height that is at least 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is at least 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is at least 1.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is at least 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to a plurality of female inbred corn plants to produce hybrid corn seeds, where the female inbred corn plants have an average height that is between 0.1 and 0.5 meters or between 0.2 and 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 1.0 and 1.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 1.5 and 2.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 2.0 meters shorter than the height of the at least one male inbred corn plant, and then harvesting the hybrid corn seeds produced by one or more of the female inbred corn plants. According to some of these aspect, the at least one male inbred corn plant and the plurality of female inbred corn plants may be planted in rows as provided herein.

In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 2.5% lower than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 2.5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 5% lower than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 10% lower than the height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 10% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 12.5% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 12.5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 15% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 15% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 17.5% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 17.5% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 20% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 20% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 25% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 25% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 30% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 30% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 35% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 35% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 40% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 40% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 45% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 45% lower than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has an average height that is at least 50% lower than the height of the at least one male inbred corn plant, and then harvesting the hybrid corn seeds produced by the at least one female inbred corn plant. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 50% lower than the height of the at least one male inbred corn plant, and then harvesting the hybrid corn seeds produced by one or more of the female inbred corn plants.

In an aspect, this disclosure provides a method of crossing at least one male inbred corn plant with at least one female inbred corn plant to produce hybrid corn seeds by fertilizing the at least one female inbred corn plant with pollen from the at least one male corn plant, where the female-to-male plant height ratio is 0.98:1 or less, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.98:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the female-to-male plant height ratio is 0.95:1 or less, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.95:1 or less, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the female-to-male plant height ratio is 0.9:1 or less, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.9:1 or less, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.85:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.8:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.75:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.7:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.65:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.6:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.55:1 or less, and then harvesting the hybrid corn seeds produced by one or more of the female inbred corn plants. In an aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female-to-male plant height ratio is 0.5:1 or less, and then harvesting the hybrid corn seeds produced by one or more of the female inbred corn plants.

In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.1 meters or at least 0.2 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.1 meters or at least 0.2 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.3 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.3 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.4 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.4 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 0.5 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 0.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the female inbred corn plants with pollen from the at least one male corn plant, where the plurality of female inbred corn plants have an average height that is at least 1.0 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 1.0 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 1.5 meters shorter than the height of the at least one male inbred corn plant, and then harvesting the hybrid corn seeds produced by one or more of the female inbred corn plants. In an aspect, this disclosure provides a method of crossing at least one male inbred corn plant with at least one female inbred corn plant to produce hybrid corn seeds by fertilizing the at least one female inbred corn plant with pollen from the at least one male corn plant, where the at least one female inbred corn plant has a height (or average height) that is at least 1.5 meters shorter than the average height of the at least one male inbred corn plant, and then harvesting the hybrid corn seeds produced by the at least one female inbred corn plant. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is at least 2.0 meters shorter than the height of the at least one male inbred corn plant, and then harvesting the hybrid corn seeds produced by one or more of the female inbred corn plants.

In an aspect, this disclosure provides a method of planting at least one male inbred corn plant in proximity to a plurality of female inbred corn plants to produce hybrid corn seeds, where the female inbred corn plants have an average height that is between 0.1 and 0.5 meters or between 0.2 and 0.5 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.0 meters shorter than the height of the at least one male inbred corn plant, and then harvesting the hybrid corn seeds produced by one or more of the female inbred corn plants. In an aspect, this disclosure provides a method of planting at least one male inbred corn plant in proximity to a plurality of female inbred corn plants to produce hybrid corn seeds, where the female inbred corn plants have an average height that is between 0.5 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is between 1.0 and 1.5 meters shorter than the height of the at least one male inbred corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is between 1.5 and 2.0 meters shorter than the height of the at least one male inbred corn plant by fertilizing the plurality of female inbred corn plants with pollen from the at least one male corn plant, and then harvesting the hybrid corn seeds produced by one or more of the female inbred corn plants. In another aspect, this disclosure provides a method of crossing at least one male inbred corn plant with a plurality of female inbred corn plants to produce hybrid corn seeds by fertilizing the plurality of female inbred corn plants with pollen from the at least one male corn plant, where the female inbred corn plants have an average height that is between 0.5 and 2.0 meters shorter than the height of the at least one male inbred corn plant, and then harvesting the hybrid corn seeds produced by one or more of the female inbred corn plants.

As used herein, the term "tassel skeletonization" (TSK) refers to under-developed male tassels or spikelets that become "skeletonized" by producing little to no pollen. Tassel skeletonization can result in fewer if any anthers developing on the affected parts of the tassel. Tassel skeletonization negatively impacts crop productivity and yield as the reproductive capacity of male corn plants to produce pollen is curtailed or eliminated. If the pollen shed is reduced from male plants, then fertilization of females and seed production will likely be reduced. In an aspect, TSK can be measured by the percentage of anthers that undergo dehiscence. As used herein, "dehiscence" refers to the release of pollen from an anther.

In an aspect, at least one male corn plant provided herein comprises at least 5% greater anther dehiscence as compared to a control male corn plant. In another aspect, a male corn plant provided herein comprises at least 10% greater anther dehiscence as compared to a control male corn plant. In another aspect, at least one male corn plant provided herein comprises at least 15% greater anther dehiscence as compared to a control male corn plant. In another aspect, at least one male corn plant provided herein comprises at least 20% greater anther dehiscence as compared to a control male corn plant. In another aspect, at least one male corn plant provided herein comprises at least 25% greater anther dehiscence as compared to a control male corn plant. In another aspect, at least one male corn plant provided herein comprises at least 30% greater anther dehiscence as compared to a control male corn plant. In another aspect, at least one male corn plant provided herein comprises at least 35% greater anther dehiscence as compared to a control male corn plant. In another aspect, at least one male corn plant provided herein comprises at least 40% greater anther dehiscence as compared to a control male corn plant. In another aspect, at least one male corn plant provided herein comprises at least 45% greater anther dehiscence as compared to a control male corn plant. In another aspect, at least one male corn plant provided herein comprises at least 50% greater anther dehiscence as compared to a control male corn plant. In another aspect, at least one male corn plant provided herein comprises at least 60% greater anther dehiscence as compared to a control male corn plant. In another aspect, at least one male corn plant provided herein comprises at least 70% greater anther dehiscence as compared to a control male corn plant. In another aspect, at least one male corn plant provided herein comprises at least 80% greater anther dehiscence as compared to a control male corn plant. In another aspect, at least one male corn plant provided herein comprises at least 90% greater anther dehiscence as compared to a control male corn plant. In another aspect, at least one male corn plant provided herein comprises at least 100% greater anther dehiscence as compared to a control male corn plant. In another aspect, at least one male corn plant provided herein comprises at least 150% greater anther dehiscence as compared to a control male corn plant. In another aspect, at least one male corn plant provided herein comprises at least 200% greater anther dehiscence as compared to a control male corn plant. In another aspect, at least one male corn plant provided herein comprises at least 250% greater anther dehiscence as compared to a control male corn plant. In another aspect, at least one male corn plant provided herein comprises at least 300% greater anther dehiscence as compared to a control male corn plant. In another aspect, at least one male corn plant provided herein comprises at least 400% greater anther dehiscence as compared to a control male corn plant. In another aspect, at least one male corn plant provided herein comprises at least 500% greater anther dehiscence as compared to a control male corn plant.

According to embodiments of the present disclosure, the anther dehiscence of a male corn plant and the average anther dehiscence of male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the anther dehiscence of a male corn plant or the average anther dehiscence of male corn plants is at R1 stage.

In an aspect, TSK can be measured by the total number of anthers present on the tassel. In an aspect, at least one male corn plant provided herein comprises at least 5% more anthers as compared to a control male corn plant. In another aspect, at least one male corn plant provided herein comprises at least 10% more anthers as compared to a control male corn plant. In another aspect, at least one male corn plant provided herein comprises at least 15% more anthers as compared to a control male corn plant. In another aspect, at least one male corn plant provided herein comprises at least 20% more anthers as compared to a control male corn plant. In another aspect, at least one male corn plant provided herein comprises at least 25% more anthers as compared to a control male corn plant. In another aspect, at least one male corn plant provided herein comprises at least 30% more anthers as compared to a control male corn plant. In another aspect, at least one male corn plant provided herein comprises at least 35% more anthers as compared to a control male corn plant. In another aspect, at least one male corn plant provided herein comprises at least 40% more anthers as compared to a control male corn plant. In another aspect, at least one male corn plant provided herein comprises at least 45% more anthers as compared to a control male corn plant. In another aspect, at least one male corn plant provided herein comprises at least 50% more anthers as compared to a control male corn plant. In another aspect, at least one male corn plant provided herein comprises at least 60% more anthers as compared to a control male corn plant. In another aspect, at least one male corn plant provided herein comprises at least 70% more anthers as compared to a control male corn plant. In another aspect, at least one male corn plant provided herein comprises at least 80% more anthers as compared to a control male corn plant. In another aspect, at least one male corn plant provided herein comprises at least 90% more anthers as compared to a control male corn plant. In another aspect, at least one male corn plant provided herein comprises at least 100% more anthers as compared to a control male corn plant. In another aspect, at least one male corn plant provided herein comprises at least 150% more anthers as compared to a control male corn plant. In another aspect, at least one male corn plant provided herein comprises at least 200% more anthers as compared to a control male corn plant. In another aspect, at least one male corn plant provided herein comprises at least 250% more anthers as compared to a control male corn plant. In another aspect, at least one male corn plant provided herein comprises at least 300% more anthers as compared to a control male corn plant. In another aspect, at least one male corn plant provided herein comprises at least 400% more anthers as compared to a control male corn plant. In another aspect, at least one male corn plant provided herein comprises at least 500% more anthers as compared to a control male corn plant.

According to embodiments of the present disclosure, the number of anthers of (or on) a male corn plant and the average number of anthers of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the number of anthers of (or on) a male corn plant or the average number of anthers of (or on) male corn plants is at R1 stage.

Tassel skeletonization can result in a reduced number of tassel branches. In an aspect, TSK can be measured by the total number of tassel branches. In an aspect, at least one male corn plant provided herein comprises at least 5% more tassel branches as compared to a control male corn plant. In another aspect, at least one male corn plant provided herein comprises at least 10% more tassel branches as compared to a control male corn plant. In another aspect, at least one male corn plant provided herein comprises at least 15% more tassel branches as compared to a control male corn plant. In another aspect, at least one male corn plant provided herein comprises at least 20% more tassel branches as compared to a control male corn plant. In another aspect, at least one male corn plant provided herein comprises at least 25% more tassel branches as compared to a control male corn plant. In another aspect, at least one male corn plant provided herein comprises at least 30% more tassel branches as compared to a control male corn plant. In another aspect, at least one male corn plant provided herein comprises at least 35% more tassel branches as compared to a control male corn plant. In another aspect, at least one male corn plant provided herein comprises at least 40% more tassel branches as compared to a control male corn plant. In another aspect, at least one male corn plant provided herein comprises at least 45% more tassel branches as compared to a control male corn plant. In another aspect, at least one male corn plant provided herein comprises at least 50% more tassel branches as compared to a control male corn plant. In another aspect, at least one male corn plant provided herein comprises at least 60% more tassel branches as compared to a control male corn plant. In another aspect, at least one male corn plant provided herein comprises at least 70% more tassel branches as compared to a control male corn plant. In another aspect, at least one male corn plant provided herein comprises at least 80% more tassel branches as compared to a control male corn plant. In another aspect, at least one male corn plant provided herein comprises at least 90% more tassel branches as compared to a control male corn plant. In another aspect, at least one male corn plant provided herein comprises at least 100% more tassel branches as compared to a control male corn plant. In another aspect, at least one male corn plant provided herein comprises at least 150% more tassel branches as compared to a control male corn plant. In another aspect, at least one male corn plant provided herein comprises at least 200% more tassel branches as compared to a control male corn plant. In another aspect, at least one male corn plant provided herein comprises at least 250% more tassel branches as compared to a control male corn plant. In another aspect, at least one male corn plant provided herein comprises at least 300% more tassel branches as compared to a control male corn plant. In another aspect, at least one male corn plant provided herein comprises at least 400% more tassel branches as compared to a control male corn plant. In another aspect, at least one male corn plant provided herein comprises at least 500% more tassel branches as compared to a control male corn plant.

According to embodiments of the present disclosure, the number of tassel branches of (or on) a male corn plant and the average number of tassel branches of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the number of tassel branches of (or on) a male corn plant or the average number of tassel branches of (or on) male corn plants is at R1 stage.

Tassel skeletonization can result in a reduction of tassel branch length. In an aspect, TSK can be measured by the average length of tassel branches. In an aspect, at least one male corn plant provided herein comprises at least 5% longer tassel branches as compared to a control male corn plant. In another aspect, at least one male corn plant provided herein comprises at least 10% longer tassel branches as compared to a control male corn plant. In another aspect, at least one male corn plant provided herein comprises at least 15% longer tassel branches compared to a control male corn plant. In another aspect, at least one male corn plant provided herein comprises at least 20% longer tassel branches as compared to a control male corn plant. In another aspect, at least one male corn plant provided herein comprises at least 25% longer tassel branches as compared to a control male corn plant. In another aspect, at least one male corn plant provided herein comprises at least 30% longer tassel branches as compared to a control male corn plant. In another aspect, at least one male corn plant provided herein comprises at least 35% longer tassel branches as compared to a control male corn plant. In another aspect, at least one male corn plant provided herein comprises at least 40% longer tassel branches as compared to a control male corn plant. In another aspect, at least one male corn plant provided herein comprises at least 45% longer tassel branches as compared to a control male corn plant. In another aspect, at least one male corn plant provided herein comprises at least 50% longer tassel branches as compared to a control male corn plant. In another aspect, at least one male corn plant provided herein comprises at least 60% longer tassel branches as compared to a control male corn plant. In another aspect, at least one male corn plant provided herein comprises at least 70% longer tassel branches as compared to a control male corn plant. In another aspect, at least one male corn plant provided herein comprises at least 80% longer tassel branches as compared to a control male corn plant. In another aspect, at least one male corn plant provided herein comprises at least 90% longer tassel branches as compared to a control male corn plant. In another aspect, at least one male corn plant provided herein comprises at least 100% longer tassel branches as compared to a control male corn plant. In another aspect, at least one male corn plant provided herein comprises at least 150% longer tassel branches as compared to a control male corn plant. In another aspect, at least one male corn plant provided herein comprises at least 200% longer tassel branches as compared to a control male corn plant. In another aspect, at least one male corn plant provided herein comprises at least 250% longer tassel branches as compared to a control male corn plant. In another aspect, at least one male corn plant provided herein comprises at least 300% longer tassel branches as compared to a control male corn plant. In another aspect, at least one male corn plant provided herein comprises at least 400% longer tassel branches as compared to a control male corn plant. In another aspect, at least one male corn plant provided herein comprises at least 500% longer tassel branches as compared to a control male corn plant.

According to embodiments of the present disclosure, the length of tassel branches of (or on) a male corn plant and the average length of tassel branches of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the length of tassel branches of (or on) a male corn plant or the average length of tassel branches of (or on) male corn plants is at R1 stage.

In an aspect, TSK can be measured using a "TSK scoring guide," which scores corn plants on a 1-10 scale based on the percentage of tassels on the plant that are skeletonized (e.g., a corn plant with less than or equal to 10% of its tassels being skeletonized is given a score of 1, a plant with approximately 50% of its tassels being skeletonized is given a score of 5, a plant with about 90% of its tassels being skeletonized is given a score of 9, etc.). In an aspect, at least one male corn plant that is planted near one or more female corn plants of a lesser height as provided herein has a TSK score that is improved (decreased) by at least 1 unit according to the TSK scoring guide, in comparison to at least one male control corn plant (i.e., at least one male corn plant of the same inbred line that is planted at the same density next to, and surrounded by, other corn plants of the same or similar height). In an aspect, at least one male corn plant provided herein has a TSK score that is improved (decreased) by at least 2 units as measured by using the TSK scoring guide in comparison to a control plant. In an aspect, at least one male corn plant provided herein has a TSK score that is improved (decreased) by at least 3 units as measured by using the TSK scoring guide in comparison to a control plant. In an aspect, at least one male corn plant provided herein has a TSK score that is improved (decreased) by at least 4 units as measured by using the TSK scoring guide in comparison to a control plant. In an aspect, at least one male corn plant provided herein has a TSK score that is improved (decreased) by at least 5 units as measured by using the TSK scoring guide in comparison to a control plant. In an aspect, at least one male corn plant provided herein has a TSK score that is improved (decreased) by at least 6 units as measured by using the TSK scoring guide in comparison to a control plant. In an aspect, at least one male corn plant provided herein has a TSK score that is improved (decreased) by at least 7 units as measured by using the TSK scoring guide in comparison to a control plant. In an aspect, at least one male corn plant provided herein has a TSK score that is improved (decreased) by at least 8 units as measured by using the TSK scoring guide in comparison to a control plant. In an aspect, at least one male corn plant provided herein has a TSK score that is improved (decreased) by at least 9 units as measured by using the TSK scoring guide in comparison to a control plant.

According to embodiments of the present disclosure, the TSK score of (or on) a male corn plant and the average TSK score of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the TSK score of (or on) a male corn plant or the average TSK score of (or on) male corn plants is at R1 stage.

In an aspect, this disclosure provides a corn field comprising at least two male inbred corn plants and at least two female inbred corn plants, where the female inbred corn plants are at least 10% shorter in average height than the male inbred corn plants, and further where the male inbred corn plants exhibit at least 10% less tassel skeletonization as compared to the tassel skeletonization exhibited by control male inbred corn plants in a corn field comprising at least two control male inbred corn plants and at least two control female inbred corn plants where the control male and female inbred corn plants do not differ in height by more than 5%. In an aspect, male inbred corn plants provided herein exhibit at least 12.5% less tassel skeletonization as compared to control male inbred corn plants. In an aspect, male inbred corn plants provided herein exhibit at least 15% less tassel skeletonization as compared to control male inbred corn plants. In an aspect, male inbred corn plants provided herein exhibit at least 17.5% less tassel skeletonization as compared to control male inbred corn plants. In an aspect, male inbred corn plants provided herein exhibit at least 20% less tassel skeletonization as compared to control male inbred corn plants. In an aspect, male inbred corn plants provided herein exhibit at least 25% less tassel skeletonization as compared to control male inbred corn plants. In an aspect, male inbred corn plants provided herein exhibit at least 30% less tassel skeletonization as compared to control male inbred corn plants. In an aspect, male inbred corn plants provided herein exhibit at least 35% less tassel skeletonization as compared to control male inbred corn plants. In an aspect, male inbred corn plants provided herein exhibit at least 40% less tassel skeletonization as compared to control male inbred corn plants. In an aspect, male inbred corn plants provided herein exhibit at least 45% less tassel skeletonization as compared to control male inbred corn plants. In an aspect, male inbred corn plants provided herein exhibit at least 50% less tassel skeletonization as compared to control male inbred corn plants. In an aspect, male inbred corn plants provided herein exhibit at least 55% less tassel skeletonization as compared to control male inbred corn plants. In an aspect, male inbred corn plants provided herein exhibit at least 60% less tassel skeletonization as compared to control male inbred corn plants. In an aspect, male inbred corn plants provided herein exhibit at least 65% less tassel skeletonization as compared to control male inbred corn plants. In an aspect, male inbred corn plants provided herein exhibit at least 70% less tassel skeletonization as compared to control male inbred corn plants. In an aspect, male inbred corn plants provided herein exhibit at least 75% less tassel skeletonization as compared to control male inbred corn plants. In an aspect, male inbred corn plants provided herein exhibit at least 80% less tassel skeletonization as compared to control male inbred corn plants. In an aspect, male inbred corn plants provided herein exhibit at least 85% less tassel skeletonization as compared to control male inbred corn plants. In an aspect, male inbred corn plants provided herein exhibit at least 90% less tassel skeletonization as compared to control male inbred corn plants. In an aspect, male inbred corn plants provided herein exhibit at least 95% less tassel skeletonization as compared to control male inbred corn plants. In an aspect, male inbred corn plants provided herein exhibit 100% less tassel skeletonization as compared to control male inbred corn plants.

According to embodiments of the present disclosure, the tassel skeletonization of (or on) a male corn plant and the average tassel skeletonization of (or on) male corn plants as described herein may be at or during a late vegetative and/or a reproductive stage of development when tassel formation and extension, pollen shed, silking, pollination, and/or kernel or ear development occurs, such as V12, V13, V14, V15, Vn, VT, R1, R2, R3, R4, R5, and/or R6 stage, such as VT or R1 stage. If the developmental stage is not specified or stated, then the tassel skeletonization of (or on) a male corn plant or the average tassel skeletonization of (or on) male corn plants is at R1 stage.

In an aspect, this disclosure provides a method of reducing tassel skeletonization by providing a corn field comprising at least two male inbred corn plants and at least two female inbred corn plants, where the female inbred corn plants are 10% shorter in average height than the male inbred corn plants, and further where the male inbred corn plants exhibit between 10% and 20% less tassel skeletonization as compared to the tassel skeletonization exhibited by control male inbred corn plants in a corn field comprising control male inbred corn plants and control female inbred corn plants where the control male and female inbred corn plants do not differ in height by more than 5%. In an aspect, male inbred corn plants provided herein exhibit between 10% and 30% less tassel skeletonization as compared to control male inbred corn plants. In an aspect, male inbred corn plants provided herein exhibit between 10% and 40% less tassel skeletonization as compared to control male inbred corn plants. In an aspect, male inbred corn plants provided herein exhibit between 10% and 50% less tassel skeletonization as compared to control male inbred corn plants. In an aspect, male inbred corn plants provided herein exhibit between 10% and 60% less tassel skeletonization as compared to control male inbred corn plants. In an aspect, male inbred corn plants provided herein exhibit between 10% and 70% less tassel skeletonization as compared to control male inbred corn plants. In an aspect, male inbred corn plants provided herein exhibit between 10% and 80% less tassel skeletonization as compared to control male inbred corn plants. In an aspect, male inbred corn plants provided herein exhibit between 10% and 90% less tassel skeletonization as compared to control male inbred corn plants. In an aspect, male inbred corn plants provided herein exhibit between 10% and 100% less tassel skeletonization as compared to control male inbred corn plants. In an aspect, male inbred corn plants provided herein exhibit between 20% and 30% less tassel skeletonization as compared to control male inbred corn plants. In an aspect, male inbred corn plants provided herein exhibit between 20% and 40% less tassel skeletonization as compared to control male inbred corn plants. In an aspect, male inbred corn plants provided herein exhibit between 20% and 50% less tassel skeletonization as compared to control male inbred corn plants. In an aspect, male inbred corn plants provided herein exhibit between 20% and 60% less tassel skeletonization as compared to control male inbred corn plants. In an aspect, male inbred corn plants provided herein exhibit between 20% and 70% less tassel skeletonization as compared to control male inbred corn plants. In an aspect, male inbred corn plants provided herein exhibit between 20% and 80% less tassel skeletonization as compared to control male inbred corn plants. In an aspect, male inbred corn plants provided herein exhibit between 20% and 90% less tassel skeletonization as compared to control male inbred corn plants. In an aspect, male inbred corn plants provided herein exhibits between 20% and 100% less tassel skeletonization as compared to control male inbred corn plants. In an aspect, male inbred corn plants provided herein exhibit between 30% and 50% less tassel skeletonization as compared to control male inbred corn plants. In an aspect, male inbred corn plants provided herein exhibit between 30% and 80% less tassel skeletonization as compared to control male inbred corn plants. In an aspect, male inbred corn plants provided herein exhibit between 30% and 100% less tassel skeletonization as compared to control male inbred corn plants. In an aspect, male inbred corn plants provided herein exhibit between 50% and 70% less tassel skeletonization as compared to control male inbred corn plants. In an aspect, male inbred corn plants provided herein exhibit between 60% and 80% less tassel skeletonization as compared to control male inbred corn plants. In an aspect, male inbred corn plants provided herein exhibit between 70% and 90% less tassel skeletonization as compared to control male inbred corn plants. In an aspect, male inbred corn plants provided herein exhibit between 50% and 100% less tassel skeletonization as compared to control male inbred corn plants.

According to an aspect of the present disclosure, one or more male corn plants can be made "taller" or higher by raising the male plants (or base of the male plants) relative to the female corn plants. This could be done regardless of whether the female plants are shorter than the male plants— i.e., the female plants may be taller or shorter than, or about the same height as, the male plants when the male plants have not been raised, but the top(s) of the male plants would be higher than the tops of the female plants when the male plants are raised relative to the surrounding soil or ground. For example, male plants may be planted in ground, earth or soil that is mounded or raised relative to the ground, earth or soil in which the female plants are planted, such that the tassels of the male plants are higher than the tops of the female plants. As another example, male plants may be planted in pots or containers to raise their height relative to the female plants. Conversely, a similar effect could be achieved if the female corn plant(s) are lowered relative to the male corn plant(s). For example, the female corn plants may be planted in furrows or valleys or at lower elevations or downslope relative to the male corn plants.

According to these embodiments, when a male plant(s) is/are raised relative to one or more female plants, the effective height(s) or effective average height(s) of the male plants is/are calculated and defined as including the raised height relative to the top surface of the surrounding soil or ground in addition to the actual height of the male plant(s). Likewise, if female corn plants are lowered relative to one or more male plants, the effective height(s) or effective average height(s) of the female plants is/are calculated and defined by subtracting from the actual height of the female plant, the lowered height of the female plant(s) relative to the top surface of the surrounding soil or ground (e.g., the surrounding soil or ground where the male plants are located or planted). For example, if the actual height of a corn plant is 3 meters, but the corn plant is raised 0.5 meters above the top surface of the surrounding soil or ground, then the effective height of the corn plant is 3.5 meters, but if such a plant is not raised relative to the top surface of the surrounding soil or ground, then the effective height of the plant is equal to its actual height. As another example, if the actual height of a corn plant is 3 meters, but the corn plant is lowered 0.5 meters below the top surface of the surrounding soil or ground, then the effective height of the corn plant is 2.5 meters. According to present embodiments, all of the description provided herein in reference to individual or average plant height(s), and relative plant height(s) of male and female corn plants, shall be equally and fully applicable to the effective plant height(s) or average effective plant height(s) of raised or lowered plants.

According to some aspects, the difference in plant height and/or placement (or average plant height and/or placement) between the male and female corn plants may be described as the difference in height or elevation of a particular structural or anatomical feature. In terms of placement, the relative height or elevation of the particular structural or anatomical feature, such as the ligule or collar or uppermost leaf surface, may provide an alternative or additional basis to describe the effective height of a plant that is raised or lowered relative to other plants. In an aspect, the average height of the ligule or collar of the uppermost fully expanded leaf and/or the uppermost leaf surface of the female inbred corn plants is at least 2% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 2.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 3% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 3.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 4% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 4.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 7.5% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 10% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 15% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 20% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 25% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 30% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 35% less or lower than the height (or average height) of the ligule or collar of at least one male inbred corn plant(s) (or the average plant height of male inbred corn plants). In an aspect, the average height of the ligule or collar of the uppermost fully expanded leaf and/or the uppermost leaf surface of the female inbred corn plants is at least 40% less or lower than the height (or average height) of the ligule or collar of at least one male inbred corn plant(s) (or the average plant height of male inbred corn plants).

The following are non-limiting exemplary embodiments of the present disclosure:

1. A method comprising: (a) fertilizing a plurality of female inbred corn plants with pollen from at least one male inbred corn plant to produce hybrid corn seeds, wherein the female inbred corn plants have an average height that is at least 2.5% lower than the average height of the at least one male inbred corn plant.

2. A method comprising: (a) crossing at least one male inbred corn plant with a plurality of female inbred corn plants to produce hybrid corn seeds, wherein the plurality of female inbred corn plants have an average height that is at least 2.5% lower than the height or average height of the at least one male inbred corn plant; and (b) harvesting said hybrid corn seeds from one or more of the female inbred corn plants.

3. A method comprising: (a) planting at least one male inbred corn plant in proximity to a plurality of female inbred corn plants to produce hybrid corn seeds, wherein the female inbred corn plants have an average height that is at least 2.5% lower than the height of the at least one male inbred corn plant; and (b) harvesting said hybrid corn seeds from one or more of the female inbred corn plants.

4. The method of embodiment 1, wherein the yield or seed yield of hybrid corn seeds produced in step (b) is greater than the yield or seed yield of control hybrid corn seeds obtained from fertilizing a plurality of control female inbred corn plants with pollen from at least one control male inbred corn plant and harvesting said control hybrid corn seeds from one or more of said control female inbred corn plants, wherein said control hybrid corn seeds are harvested from the same number of female inbred corn plants as in step (b), and wherein the average height of said plurality of control female inbred corn plants is the same or similar to the average height of said at least one control male inbred corn plants.

5. The method of any one of embodiments 1-4, wherein said female inbred corn plants have an average height that is at least 5%, at least 10%, at least 15%, at least 20%, at least 25%, at least 30%, at least 35%, at least 40%, at least 45%, at least 50%, at least 55%, at least 60%, or at least 70% shorter than said at least one male inbred corn plant.

6. The method of any one of the embodiments 1-5, wherein said female inbred corn plants have an average height that is between 2.5% and 50% shorter than said at least one male inbred corn plant.

7. The method of any one of the embodiments 1-6, wherein said female inbred corn plants are dwarf corn plants, semi-dwarf corn plants, or brachytic mutant corn plant.

8. The method of any one of the embodiments 1-7, wherein said female inbred corn plants comprise one or more ears at least 18 inches, at least 19 inches, at least 20 inches, at least 21 inches, at least 22 inches, at least 23 inches, or at least 24 inches above ground level.

9. The method of any one of the embodiments 1-8, wherein said female inbred corn plants comprise at least one ear that is at least 18 inches above ground level.

10. The method of any one of the embodiments 1-9, wherein said female inbred corn plants comprise at least one ear that is at least 24 inches above ground level.

11. The method of any one of the embodiments 1-10, wherein said female inbred corn plants comprise a mutation in a brachytic2 (br2) locus as compared to a wildtype br2 locus.

12. The method of any one of the embodiments 1-11, wherein said female inbred corn plants comprise a heterologous polynucleotide encoding an RNA molecule that suppresses expression of a brachytic2 (br2) gene or an mRNA transcribed therefrom.

13. The method of any one of the embodiments 1-12, wherein said female inbred corn plants comprise a mutation in a GA20 oxidase locus as compared to a wildtype GA20 oxidase locus.

14. The method of any one of the embodiments 1-13, wherein said female inbred corn plants comprise a heterologous polynucleotide encoding an RNA molecule that suppresses expression of a GA20 oxidase gene or an mRNA transcribed therefrom.

15. The method of embodiment 4, wherein the yield and/or seed yield is increased by at least 3.0%, at least 3.5%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10%, at least 11%, at least 12%, at least 13%, at least 14%, at least 15%, at least 16%, at least 17%, at least 18%, at least 19%, or at least 20% relative to the yield of hybrid corn seeds obtained from fertilizing a plurality of control female inbred corn plants with pollen from at least one control male inbred corn plant, wherein the female and male control plants do not differ in average height by more than 5%.

16. The method of embodiments 4 or 15, wherein the yield and/or seed yield said hybrid corn seeds is increased by between 3% and 20% relative to the yield of hybrid corn seeds obtained from fertilizing a plurality of control female inbred corn plants with pollen from at least one control male inbred corn plant, wherein the female and male control plants do not differ in average height by more than 5%.

17. The method of any one of the embodiments 1-16, wherein said female inbred corn plants and said at least one male inbred corn plant are grown in a corn field.

18. The method of any one of the embodiments 1-16, wherein said female inbred corn plants and said at least one male inbred corn plant are grown in a greenhouse.

19. The method of any one of the embodiments 1-18, wherein said female inbred corn plants are detasseled.

20. The method of any one of the embodiments 1-19, wherein said female inbred corn plants have cytoplasmic male sterility.

21. The method of any one of the embodiments 1-20, wherein the heights of said female inbred corn plants and said at least one male inbred corn plant are measured as the distance between the soil and the ligule of the uppermost fully-expanded leaf.

22. The method of any one of the embodiments 1-20, wherein the heights of said female inbred corn plants and said at least one male inbred corn plant are measured as the distance between the soil and the upper leaf surface of the leaf farthest from the soil.

23. The method of any one of the embodiments 1-20, wherein the heights of said female inbred corn plants and said at least one male inbred corn plant are measured as the distance between the soil and the arch of the highest corn leaf that is at least 50% developed.

24. The method of any one of the embodiments 1-23, wherein the heights of said female inbred corn plants and said at least one male inbred corn plant are measured at R1 stage.

25. The method of any one of the embodiments 4, 15, or 16, wherein the yield is measured in bushels per acre.

26. The method of any one of the embodiments 4, 15, 16, or 25, wherein the yield is at least 100 bushels per acre, at least 120 bushels per acre, at least 140 bushels per acre, at least 160 bushels per acre, at least 180 bushels per acre, at least 200 bushels per acre, at least 220 bushels per acre, at least 240 bushels per acre, or at least 260 bushels per acre.

27. The method of any one of the embodiments 4, 15, 16, 25, or 26, wherein the yield is between 100 and 260 bushels per acre.
28. The method of any one of the embodiments, 4, 15, or 16, wherein the seed yield is measured in standard seed units (SSUs) per acre.
29. The method of any one of the embodiments 4, 15, 16, or 28, wherein the seed yield is at least 80 SSUs per acre, at least 90 SSUs per acre, at least 100 SSUs per acre, at least 110 SSUs per acre, at least 120 SSUs per acre, at least 130 SSUs per acre, at least 140 SSUs per acre, at least 150 SSUs per acre, at least 160 SSUs per acre, at least 170 SSUs per acre, at least 180 SSUs per acre, at least 190 SSUs per acre, or at least 200 SSUs per acre.
30. The method of any one of the embodiments 4, 15, or 16, wherein the seed yield is measured in average number of kernels per ear.
31. The method of any one of the embodiments 4, 15, 16, or 30, wherein the seed yield is at least 200 kernels per ear, at least 300 kernels per ear, at least 400 kernels per ear, at least 500 kernels per ear, at least 600 kernels per ear, at least 700 kernels per ear, at least 800 kernels per ear, at least 900 kernels per ear, at least 1,000 kernels per ear, at least 1100 kernels per ear, or at least 1,200 kernels per ear.
32. The method of any one of the embodiments 4, 15, 16, 30, or 31, wherein the yield is between 200 and 1,200 kernels per ear.
33. The method of any one of the embodiments 4, 15, or 16, wherein the seed yield is measured in dry weight of kernels.
34. The method of any one of the embodiments 4, 15, 16, or 33, wherein the seed yield is at least 0.2 grams per dry kernel, at least 0.25 grams per dry kernel, at least 0.3 grams per dry kernel, at least 0.35 grams per dry kernel, at least 0.4 grams per dry kernel, at least 0.45 grams per dry kernel, at least 0.5 grams per dry kernel, at least 0.55 grams per dry kernel, or at least 0.6 grams per dry kernel.
35. The method of any one of the embodiments 4, 15, 16, 33, or 34, wherein the seed yield is between 0.2 and 0.6 grams per dry kernel.
36. The method of embodiment 17, wherein the field comprises at least one row of female inbred corn plants and at least one row of male inbred corn plants.
37. The method of embodiments 17 or 36, wherein the field comprises multiple rows of female inbred corn plants and at least one row of male inbred corn plants.
38. The method of any one of the embodiments 17, 36, or 37, wherein the field comprises multiple rows of female inbred corn plants and multiple rows of male inbred corn plants.
39. The method of any one of the embodiments 36-38, wherein the ratio of female inbred corn plant rows to male inbred corn plant rows is selected from the group consisting of 2:2, 3:2, 4:1, 4:2, 4:3, 6:1, and 6:2.
40. The method of any one of the embodiments 36-39, wherein the corn field comprises between 1 female row and 10 female rows for every male row.
41. The method of any one of the embodiments 36-40, wherein the corn field comprises at least 1, at least 2, at least 3, at least 4, at least 5, at least 6, at least 7, at least 8, at least 9, or at least 10 female rows for every male row.
42. The method of any one of the embodiments 17 or 36-41, wherein the corn field further comprises at least two rows of inbred corn plants, and wherein said at least two rows of inbred corn plants are spaced at least 12 inches, at least 14 inches, at least 16 inches, at least 18 inches, at least 20 inches, at least 22 inches, at least 24 inches, at least 26 inches, at least 28 inches, at least 30 inches, at least 32 inches, at least 34 inches, or at least 36 inches apart.
43. The method of any one of the embodiments 17 or 36-42, wherein the corn field further comprises at least two rows of inbred corn plants, and wherein said at least two rows are spaced between 12 and 36 inches apart.
44. The method of any one of the embodiments 17 or 36-43, wherein the corn field comprises a ratio of at least 1 female inbred corn plant, at least 2 female inbred corn plants, at least 3 female inbred corn plants, at least 4 female inbred corn plants, at least 5 female inbred corn plants, at least 6 female inbred corn plants, at least 7 female inbred corn plants, at least 8 female inbred corn plants, at least 9 female inbred corn plants, at least 10 female inbred corn plants, at least 15 female inbred corn plants, at least 20 female inbred corn plants, at least 25 female inbred corn plants, at least 30 female inbred corn plants, at least 35 female inbred corn plants, at least 40 female inbred corn plants, at least 45 female inbred corn plants, at least 50 female inbred corn plants, at least 60 female inbred corn plants, at least 70 female inbred corn plants, at least 80 female inbred corn plants, at least 90 female inbred corn plants, or at least 100 female inbred corn plants for every male inbred corn plant.
45. The method of any one of the embodiments 17 or 36-44, wherein the corn field comprises between 1 female inbred corn plant and 100 female inbred corn plants for every male inbred corn plant.
46. The method of any one of the embodiments 17 or 36-45, wherein the corn field comprises a planting density of at least 12,000 corn plants per acre, at least 15,000 corn plants per acre, at least 18,000 corn plants per acre, at least 21,000 corn plants per acre, at least 24,000 corn plants per acre, at least 27,000 corn plants per acre, at least 30,000 corn plants per acre, at least 33,000 corn plants per acre, at least 36,000 corn plants per acre, at least 39,000 corn plants per acre, at least 42,000 corn plants per acre, at least 45,000 corn plants per acre, at least 48,000 corn plants per acre, at least 51,000 corn plants per acre, at least 54,000 corn plants per acre, at least 57,000 corn plants per acre, or at least 60,000 corn plants per acre.
47. The method of any one of the embodiments 17 or 36-46, wherein the corn field comprises a planting density of between 12,000 and 60,000 corn plants per acre.
48. The method of any one of the embodiments 17 or 36-47, wherein the corn field comprises at least two male inbred corn plants and at least two female inbred corn plants, wherein said female inbred corn plants comprise an average height that is at least 10% shorter than the average height of said male inbred corn plants, and wherein said male inbred corn plants exhibit at least 2.5% less tassel skeletonization as compared to a control corn field comprising at least two control male inbred corn plants and at least two control female inbred corn plants, wherein said male and female control plants have the same or similar plant heights.
49. The method of embodiment 48, wherein tassel skeletonization is measured based on the percentage of tassels that are skeletonized.
50. The method of embodiments 48 or 49, wherein said male inbred corn plants exhibit at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less tassel skeletonization.

51. The method of embodiment 2, wherein the crossing comprises fertilization of said plurality of female inbred corn plants with pollen from said at least one male inbred corn plant.

EXAMPLES

Example 1. Comparison of Corn Seed Yield Distribution, as Grouped by Height of Female Parental Line Relative to Male, for Varying Hybrid Combinations To understand the effects on corn seed yield due to the relative height differences of male and female parental inbred lines, over 400 hybrid combinations of varying parental plant heights were studied. The study comprised US hybrid seed production from different parental inbred combinations in diverse growth environments from 2008-2016. Although each of the 400 hybrid combinations may not be equally represented across all testing years and environments, the large data set provides a good indication of yield trends across all female rows in the field in relation to the relative male/female plant heights. Seed yield is defined by Standard Seed Units (SSU) per acre. One SSU for corn is equivalent to 80,000 corn seed kernels.

In this experiment, the yield data (expressed in total SSU's per acre) was separated into two groups: (a) Shorter Female Bucket (where the female parent line comprised a height at least 10% shorter than that of the male line), and (b) Taller Female Bucket (comprising the remainder of the crosses). Three hundred seventy-nine hybrid combinations were grouped into the Taller Female Bucket, and 36 hybrid combinations were grouped in the Shorter Female Bucket. The height difference between each male/female parent pair does not take into account the effect of detasseling the female plants, which was typically done in these fields over this time period. Although the effective female plant height at pollination was shortened after detasseling, the yield data is still meaningful in that relative height differences between female plants should still be present after detasseling.

The seed yield in this analysis (expressed in total SSUs per acre) was measured for each hybrid combination in the study and grouped into the Taller Female or Shorter Female buckets or groups as described above. The distribution of seed yields per acre for the Taller and Shorter Female Buckets is shown in the box and whisker plots in FIG. 1. Each whisker marks the first point outside the box that is larger or smaller than 1.5 times the inner quartile range (IQR), where the IQR is the middle 50% of the data. The 75th percentile and the 25th percentile of the data are marked by the upper and lower ends of the box, respectively, with the median indicated by the dividing line of the box in between the two ends of the box. Most of the data points are expected to fall between the whisker boundaries, although a few additional data points are shown above and below the upper and lower whiskers, respectively.

This data shows that seed yield in the Shorter Female Bucket was less variable than that of the Taller Female Bucket. As shown in FIG. 1, if the female parent line is at least 10% shorter than the pairing male parent line, hybrid seed production stability was significantly improved as demonstrated by a decrease in variation.

Example 2. Distribution of Corn Seed Yield by Height Ratio of Male/Female Parental Lines for Hybrid Combinations of a Single Female Parental Line Corn seed yield is primarily determined by the female parental line in hybrid seed production. To control for variation in genetic potential with corn seed yields, the female parental line in this example was held constant and the male parental lines were varied. The effects of the relative plant heights of the male and female parental lines upon corn seed yield were studied by leveraging the normal variation of plant heights of various male parental lines. Twenty-five different hybrid combinations using various male parental lines for each female line were analyzed in this study.

Figure 2:
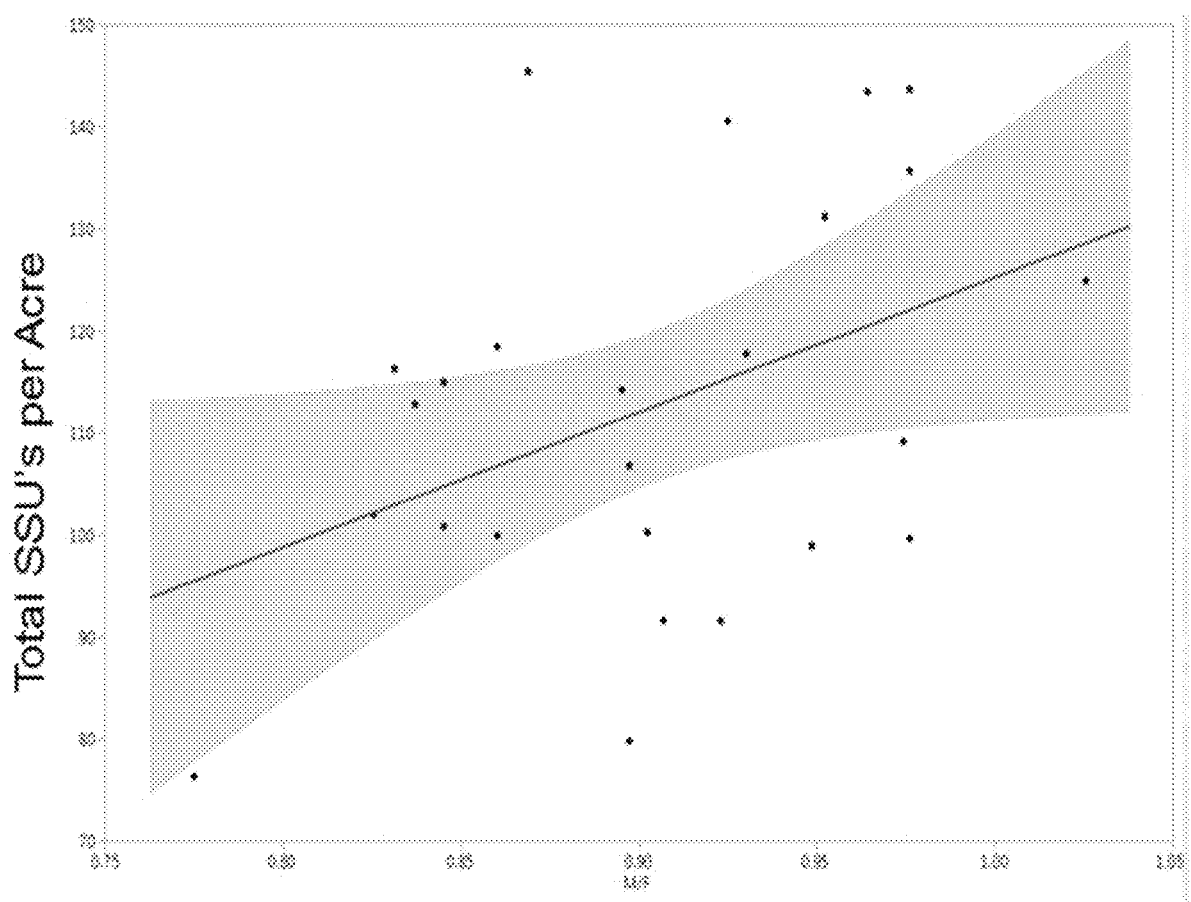
FIG. 2 is a plot comparing male-to-female (M/F) parent corn plant height ratio (x-axis) to hybrid corn seed yield (y-axis, measured in Standard Seed Units (SSUs)) for 25 different hybrid corn combinations.

Although the height difference between each pair of male/female parents does not take into account the effect of detasseling the female plants, which was employed in most of the production practice, the relative plant heights should still be present after detasseling. The seed yield in this analysis (total SSUs per acre) measures the overall seed yield over all female rows. The data presented in FIG. 2 compares corn seed yield, expressed as total SSUs per acre, to the ratio of characteristic heights of male/female parental lines (M/F). Each data point is the average seed yield for each male/female hybrid combination. The linear regression line is shown. The shaded area covers 95% confidence for the regression line.

While seed yield varies significantly for individual male/female hybrid combinations, FIG. 2 shows an overall trend of higher corn seed yield when the female parental line is shorter relative to the male parental line. In this example, seed yield is an average over the field, and does not distinguished between different rows of females, although it is expected that the more interior female rows further away from the male plants would most benefit from the shorter plant height and improved pollen flow as discussed herein.

Example 3. Short Female Parental Lines Allow for Improved Seed Yield and More Efficient Use of Planting Area Approximately 19% of the male inbreds used in commercial corn production today are considered high risk males due to their tendency for tassel skeletonization and/or reduced pollen load relative to other male lines. Indeed, tassel skeletonization (TSK) can cause male inbred corn plants to have a reduced pollen load. TSK is one of the phenotypes that is taken into account during male risk assessment and selection of male lines for commercial seed production. One of the major inducers of TSK can be shading of male plants by neighboring females.

Figure 3:
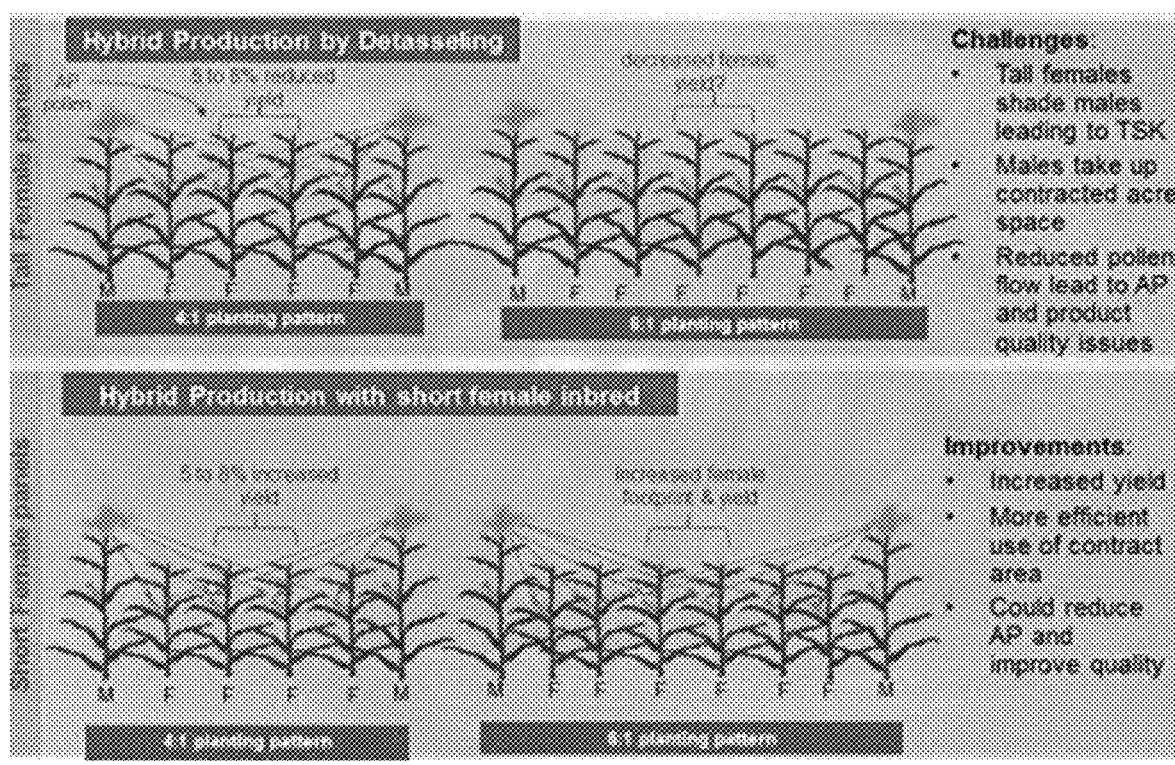
FIG. 3 is a visual representation of two common planting patterns (4:1 and 6:1) incorporating rows of either tall female inbred corn plants (upper panel) or short female inbred plants (lower panel). Abbreviations: TSK: tassel skeletonization; AP: adventitious presence; M: male; F: female.

As introduced above, by reducing the shading of adjacent male plants, shorter female plants reduce the risk of TSK in males and could thereby improve overall seed yield. Historically, the middle two rows in a 4:1 female-to-male row configuration exhibit a 5% to 8% reduction in seed yield relative to the two outer rows due to poor pollen distribution and/or a lack of pollen availability to these rows. In addition to improving yield in the center panels of female rows, shorter female inbred plants could also enable an increase in the ratio of female-to-male rows to 6:1 or some other higher ratio of female-to-male rows than is used currently, which may improve seed yield per acre and/or reduce the overall field production footprint. Having an improved pollen flow with shorter female inbreds can also help ensure that the females are pollinated by the male plants, thus reducing the possibility and/or occurrence rate of adventitious presence (AP) of unwanted transgenes or genetics due to unintended pollination and fertilization events from other pollen sources. A diagram of how shorter female plants can improve pollen flow in a 6:1 and 4:1 arrangement ratio of female-to-male rows is shown in FIG. 3, relative to male and female plants of a similar height.

Example 4. Improved Seed Yield with Short Female Parental Line

Field trials are described in this example demonstrating improved seed yield in hybrid corn seed production by utilizing a shorter female parental line. These corn seed production field trials were conducted over one growing season at two field sites in Illinois, U.S.A., which are approximately 100 miles away from each other, with one of the two sites (first field site) being further north than the other (second) field site. The two sites have similar soil conditions, but the second site received less rainfall than the other (first) site during the trial season.

To produce hybrid corn seeds, a tall inbred male parental line was used with a shorter inbred (transgenic) female parental line. A corresponding tall inbred (non-transgenic) female line was used as a control. The inbred lines were planted with two ratio arrangements of females to males: one with 4:1 female/male row configuration and 30-inch row spacing, and another with 6:1 female/male row configuration and 20-inch row spacing. Each arrangement of female-to-male row ratio had a medium planting density of 34,400 plants/acre for 20-inch row field or 27,200 plants/acre for 30-inch row field, and a high planting density of 39,560 plants/acre for 20-inch row field or 32,000 plants/acres for 30-inch row field. The tall and short female plants were planted with approximately equal spacing along each row. Mature corn ears were hand harvested in these trials, and results were collected from 5 interior plants of each 17.5-inch plot row, with 24 replicates for the 30-inch row spacing plots, and 36 replicates for the 20-inch row spacing plots, respectively. Seed yield was measured as the number of SSUs per acre where the number of acres took into account only the area of female plants. One Standard Seed Unit (SSU) is defined as 80,000 corn seed kernels.

Figure 4:
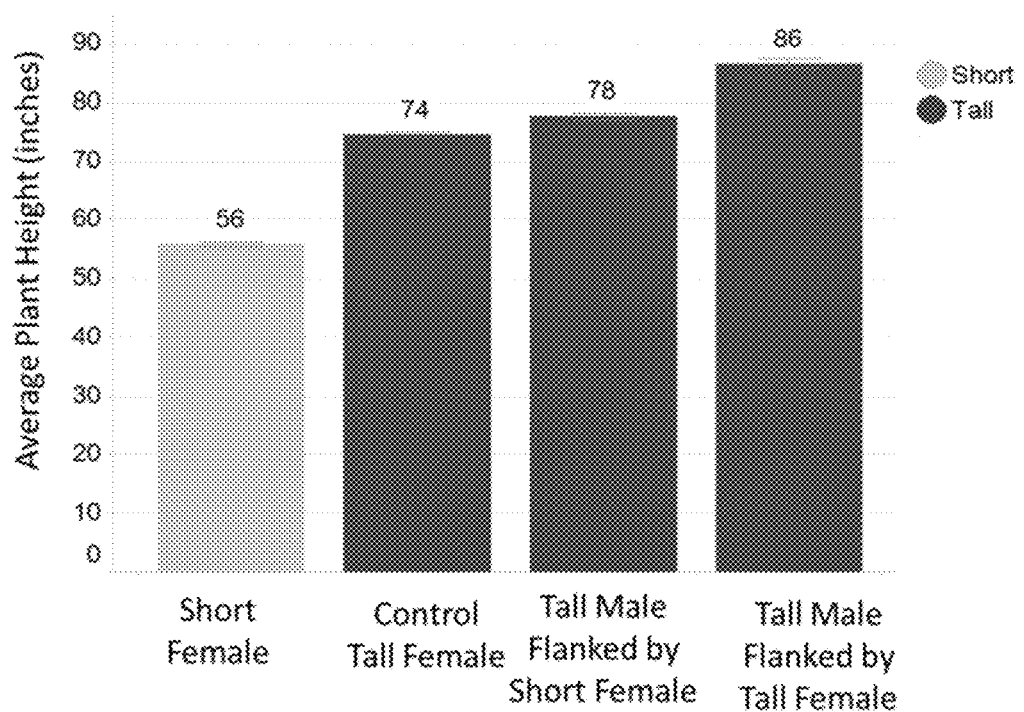
FIG. 4 shows the average plant height (PHT) of the inbred corn plants grown in the present field trials: (1) short female, (2) the control tall female, (3) tall male flanked by short female, and (4) tall male flanked by tall female.

FIG. 4 shows the average plant height (PHT) of the inbred corn plants grown in the present field trials: (1) short female, (2) the control tall female, (3) tall male flanked by short female, and (4) tall male flanked by tall female. In this experiment, the plant height is measured from the ground to the base of the uppermost collared leaf. The vertical error bars indicate the standard errors for PHT. Note that for the same inbred male line, the heights of the male plants flanked by shorter female plants are significantly reduced relative to those flanked by the control tall female plants. Without being bound by theory, the reduced male plant height may result from having less need for competitive vertical growth due to the surrounding female plants being shorter. The reduced vertical growth may improve male corn plant robustness, lodging resistance and stability, as well as male tassel formation and pollen shed.

Figure 5:
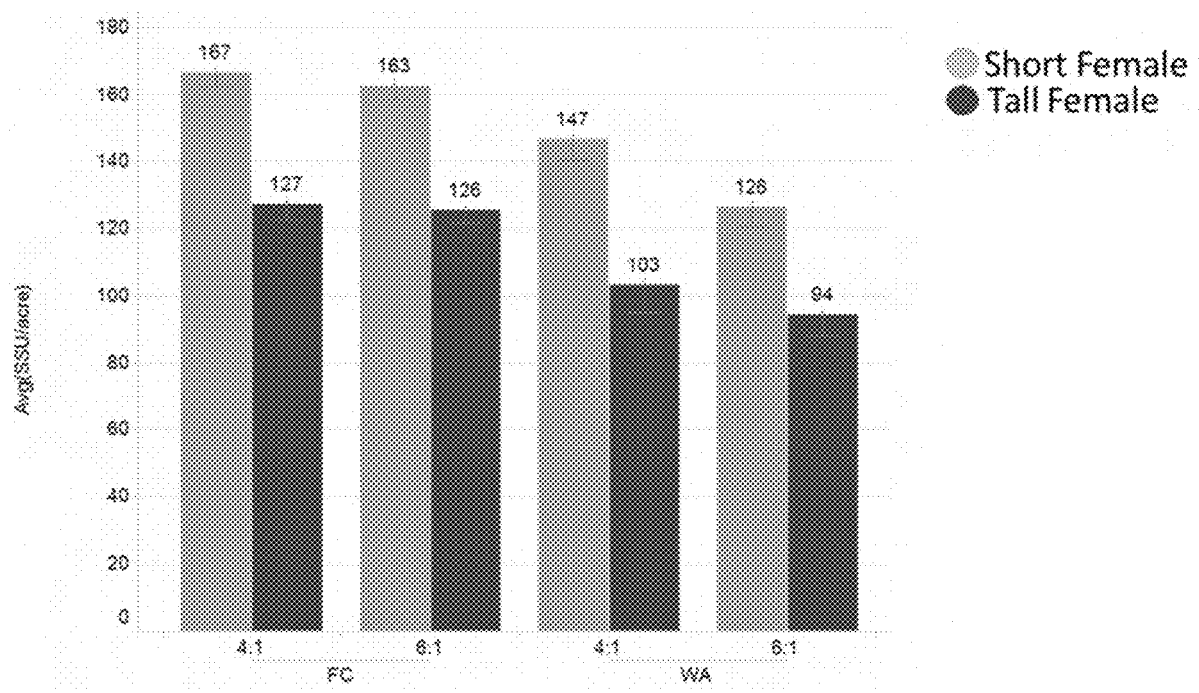
FIG. 5 shows the seed yield in SSU/acre at two testing sites, for both 4:1 and 6:1 female:male row ratio arrangements, averaged over two planting densities.

FIG. 5 shows the seed yield in SSU/acre at the two testing sites, for both 4:1 and 6:1 female:male row ratio arrangements. Seed yield was averaged over the 2 planting densities (described above). In these examples, "WA" is an abbreviation for the first field site, and "FC" is an abbreviation for the second field site. The vertical error bars indicate standard errors for the seed yields. Note the significant improvement in seed yield with shorter female lines, across row planting arrangements at both sites.

Figure 6:
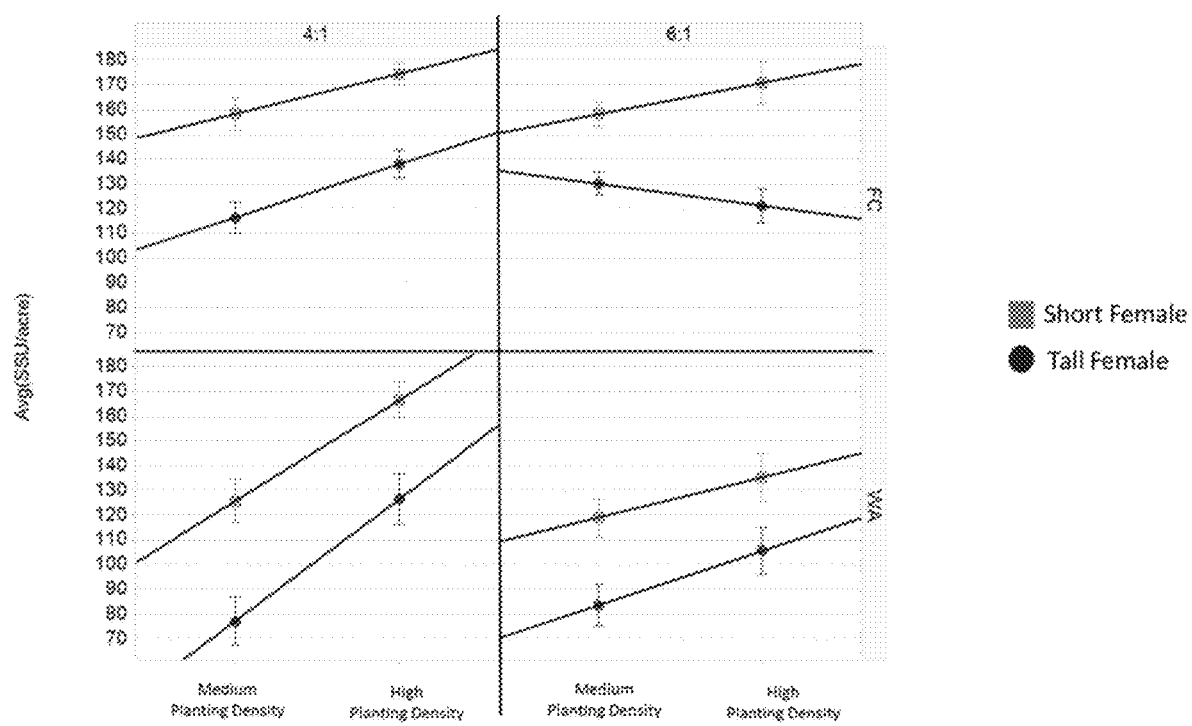
FIG. 6 compares the seed yields of short and tall female lines at two testing sites with 4:1 and 6:1 female-to-male row ratio arrangements, and with two planting densities.

FIG. 6 compares the seed yields of short and tall female lines at two testing sites with 4:1 and 6:1 female-to-male row ratio arrangements, and with two planting densities. "M" indicates medium planting density, and "H" for high planting density. For this experiment, "WA" is an abbreviation for the first site, and "FC" is an abbreviation for the second site. The vertical error bars indicate standard error for the seed yields. Note that the average seed yield is consistently and significantly higher with shorter females than with taller females, at both sites and with both 4:1 and 6:1 female-to-male ratio arrangements of rows, and at both medium and high planting densities. Furthermore, the average seed yield with shorter females is consistently higher at high density relative to medium density planting at both sites and for both of the female-to-male row ratio arrangements.

Example 5. Improved Pollen Production and Distribution with Short Female Parental Line Utilizing short female parental lines in hybrid corn seed production is shown in this example to have direct positive effects on pollen production and dispersion. Without being bound by theory, these positive effects may result from reduced shading of the taller male plants and less physical or wind obstruction to pollen flow from the male tassels by the shorter female plants, resulting in higher seed yields. In this example, direct pollen count measurements are provided over 5 consecutive days of the pollination period, at various female row positions. The "pollination period" is defined as the consecutive five-day period wherein the first day is when the male tassels in the field have reached 10% anthesis. These five consecutive pollination days can be referred to herein as "Day 1", Day 2", etc.

Pollen trap plates of ~5-inch diameter were placed on level platforms positioned adjacent to the female corn plants in different row positions relative to the closest male row at a height similar to the height of the female corn ears. For the 4:1 female-to-male row ratio planting arrangement, the female rows adjacent to male rows are called the "4-1" position, and the two adjacent inner female rows further away from male rows are called the "4-2" position. Likewise, within the 6:1 female-to-male row ratio planting, the "6-1" position includes the female rows adjacent to male rows, the "6-2" position includes the females rows that are two rows away from the closest male rows, and the "6-3" position includes the two adjacent innermost female rows furthest away from male rows.

600 plates were collected daily from each testing site, with 120 plates collected for each of 5 consecutive days of pollination period, of which 48 plates were collected from plots of 30-inch row spacing, and the other 72 plates from 20-inch plots. To count the number of pollen grains collected on each plate, the collected plates were imaged using a commercial multispectral imaging system, with high-resolution images under strobed LED lights of 19 discrete wavelengths from 365 to 970 nm. The images were further combined into a single multispectral image. An image analysis software was developed to count the number of pollen grains for each plate, and to run the subsequent statistical analysis.

The following experiments and accompanying figures show the average daily pollen counts at different row positions based on the placement of the collection plates. These experiments were carried out at both locations with 4:1 or 6:1 female-to-male row arrangements. The measurements were averaged over all plates for a specific day, at one of the two sites, and for a specific female row position and ratio. The vertical error bars indicate standard errors for the average daily pollen counts.

Figure 7:
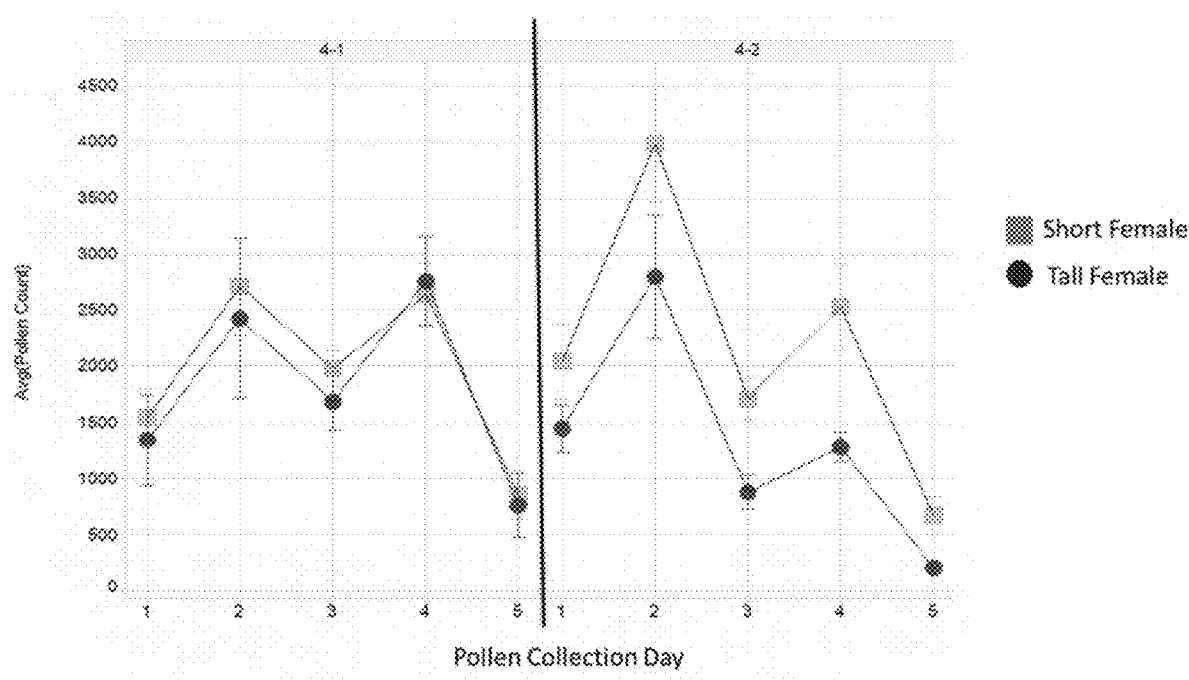
FIG. 7 shows average daily pollen count results for the 4-1 and 4-2 positions at a first field location site with a 4:1 planting arrangement.
Figure 8:
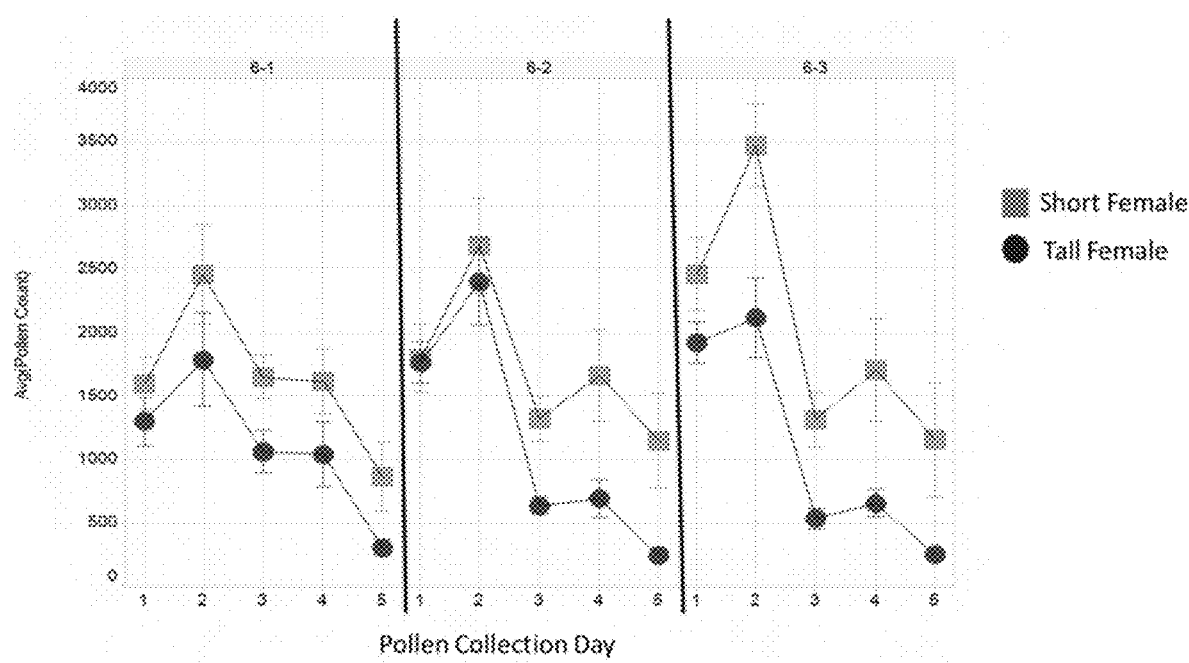
FIG. 8 shows average daily pollen count results for the 6-1, 6-2 and 6-3 positions at a first field location site with a 6:1 planting arrangement.
Figure 9:
FIG. 9 shows average daily pollen count results for the 4-1 and 4-2 positions at a second field location site with a 4:1 planting arrangement.
Figure 10:
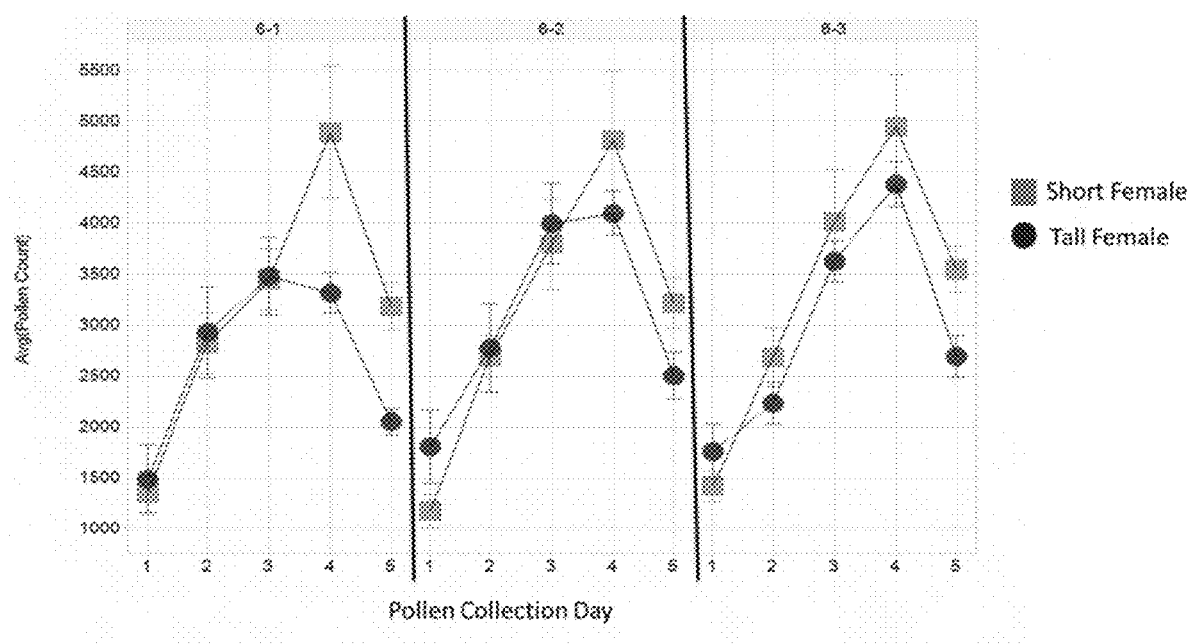
FIG. 10 shows average daily pollen count results for the 6-1, 6-2 and 6-3 positions at a second field location site with a 6:1 planting arrangement.

FIG. 7 shows average daily pollen count results for the 4-1 and 4-2 positions at the first field location site with a 4:1 planting arrangement. In this experiment, position 4-2 showed a significant increase in pollen count with shorter female corn plants, throughout Days 1 to 5. FIG. 8 shows average daily pollen count results for the 6-1, 6-2 and 6-3 positions at the first field location site with a 6:1 planting arrangement. Note the significant increase in pollen count with shorter female corn plants for all positions on Days 3 to 5 and for position 6-3 on Days 1 and 2. FIG. 9 shows average daily pollen count results for the 4-1 and 4-2 positions at the second field location site with a 4:1 planting arrangement. In this experiment, both 4-1 and 4-2 position showed a significant increase in pollen count with shorter female corn plants during Day 5, as well as a significant increase in pollen count with shorter female corn plants at position 4-1 during Day 4. FIG. 10 shows average daily pollen count results for the 6-1, 6-2 and 6-3 positions at the second field location site with a 6:1 planting arrangement. Note the significant increase in pollen count with shorter female corn plants at all row positions (6-1, 6-2 and 6-3) during Day 5 and at row position 6-1 during Day 4. These results show increased pollen collection overall with shorter female plants at both 4:1 and 6:1 female-to-male row ratio planting, with the amounts depending on the ratio of female-to-male rows and the row position.

Without being bound by theory, the increased pollen flow and collection in the rows of shorter female corn plants may at least partially explain and support the increased seed production (SSU/acre) in the production field as shown above.

Example 6. Reduced Male Tassel Skeletonization with Short Female Parental Line Effective pollen production and shedding in hybrid seed production can depend on overall tassel size as well as how fully the tassel develops. In this example, tassel size and development of male inbred plants are observed and measured with either short or tall females. Larger and more developed tassels should produce more pollen leading to greater pollination and seed yields of females. In these experiments, male corn plants next to, or flanked by, shorter female corn plants had larger (data not shown) and more developed tassels with less tassel skeletonization (TSK) (see below), as compared to male corn plants next to, or flanked by, taller female corn plants. Without being bound by theory, it is proposed that the shorter female plants next to the taller male plants permit the male plants to receive more light, perhaps without having to grow as tall, which may improve the development of male reproductive structures.

Tassel skeletonization (TSK), also called "tassel blasting", describes the abortion of glumes and anthers on tassel branches and the main spikelet. It results from an underdevelopment of the tassel and causes reduced pollen production. As known in the art, skeletonization can be measured on the tassels of male parental plants, by a visual rating at 50% pollination stage (P50), on a SKLP scale from 1 to 9, to estimate the level of increasing severity at a plot level. A score of "1" indicates no skeletonization, whereas a score of "9" indicates that the entire tassel is skeletonized. Tassel skeletonization of male corn plants next to either tall or short females was observed and scored according to the above scale. Average SKLP ratings were determined for tassels of male inbred plants flanked in a seed production field by either short female plants (Short) or tall female control plants (Tall) planted at either 20-inch or 30-inch row spacings. For male plants next to taller females, 23 replicates were used for measurement of plants in 30-inch rows, and 26 replicates were used for measurement of plants in 20-inch rows. For male plants next to shorter females, 19 replicates were used for measurement of plants in 30-inch rows, and 26 replicates were used for measurement of plants in 20-inch rows.

Figure 11:
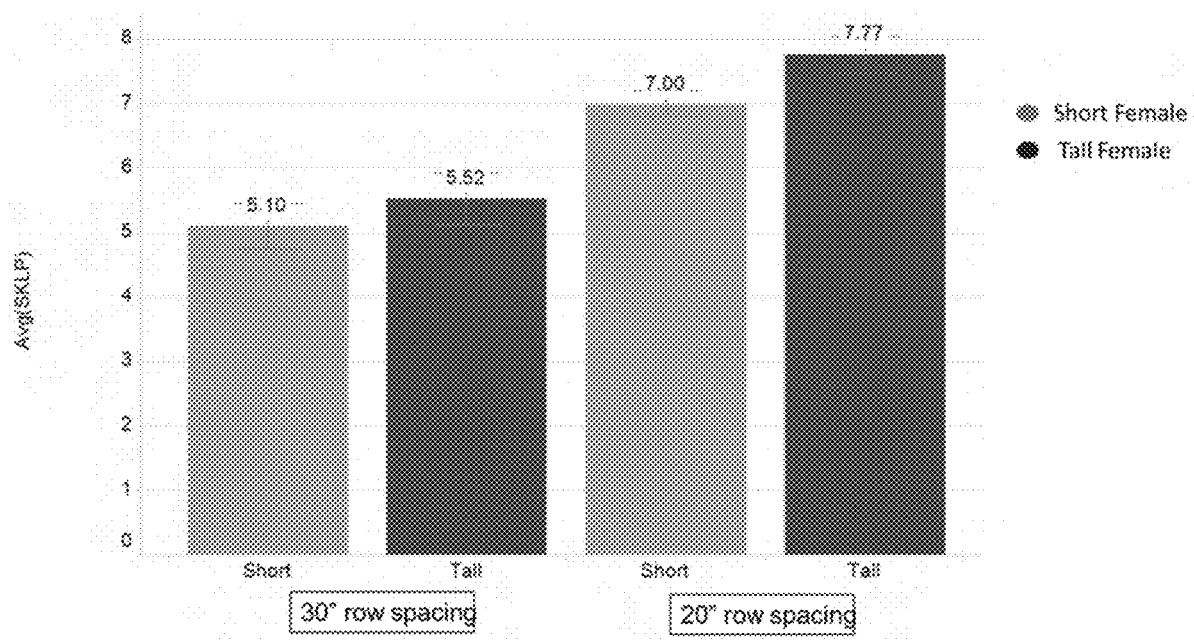
FIG. 11 shows average tassel skeletonization (SKLP) scores of male plants flanked by shorter or taller female plants at 20-inch row spacing and 30-inch row spacing, respectively.

As shown in FIG. 11 for these experiments, male plants flanked by shorter females at 20-inch row spacing had significantly improved (lower) average tassel skeletonization (SKLP) scores (e.g., about 7.0) relative to females planted next to taller females at the same row spacing (e.g., about 7.77). At 30-inch row spacing, average tassel skeletonization (SKLP) scores trended positive toward improvement (e.g., about 5.1), relative to females planted next to taller females at the same row spacing (e.g., 5.52), although the change was not statistically significant. These data indicate that tassel skeletonization of male plants can be reduced with shorter females in corn production fields, which can lead to increased pollen production and shedding.

Without being bound by theory, decreased tassel skeletonization may at least partially explain and support the increased pollen flow and collection in the rows of shorter female corn plants in the production field as shown above.

Example 7. Reduced Plant Lodging with Short Female Parent Line

Corn seed production can be improved if plant lodging is reduced in the production field. It is proposed that the shorter stature female corn plants can have increased lodging resistance relative to taller females, thus leading to improved seed yields in the production field. The shorter stature corn plant may also be more accessible during the growing season with standard height agricultural equipment allowing for over-the-top applications of fertilizer, pesticides, water, etc., to further improve seed yields.

Figure 12:
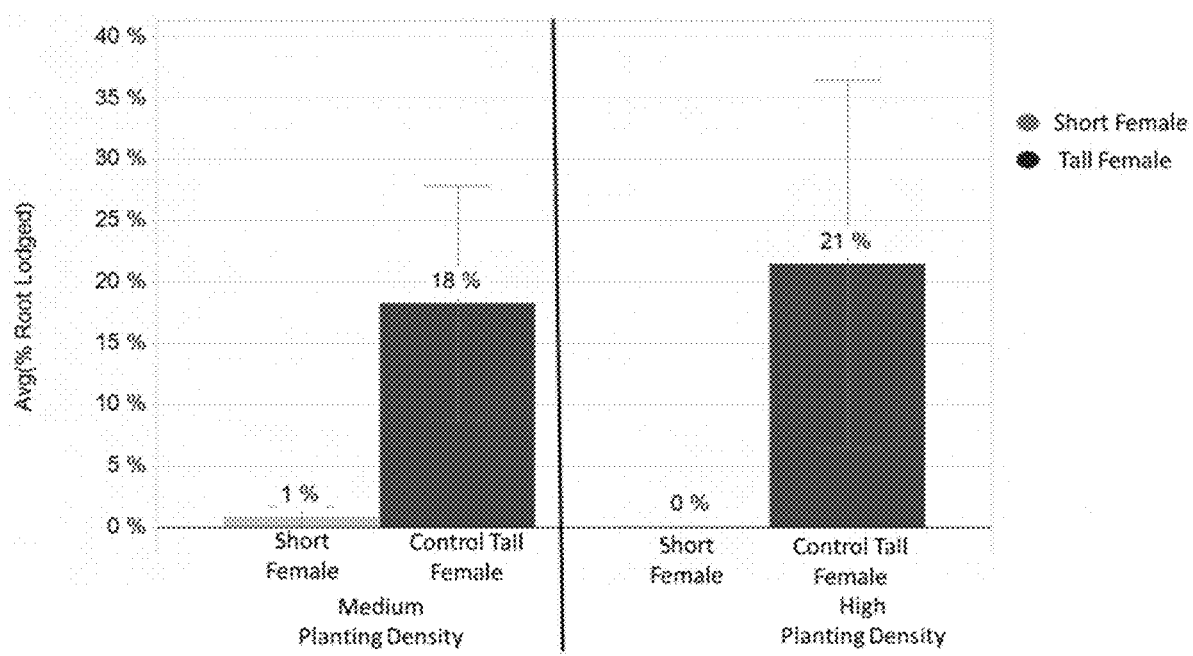
FIG. 12 shows average percentage of root lodged short female plants and root lodged control tall female plants at high and low planting densities.

At one of the corn production field sites, a thunderstorm with high winds caused plant root lodging, particularly among the taller female corn plants in the field. However, the shorter female corn plants exhibited much less lodging at this testing location. Root lodging of female corn plants was measured in a field affected by the storm at both medium (M) and high (H) planting densities. Root lodging data was collected on four female plant rows over the length of the field. A plant was counted as root lodged if it leaned at least 45 degrees from a vertical orientation in the row. 52 replicates were included for both tall and short female corn plants. As shown in FIG. 12, where lodging was significant for the tall control female plants, it was greatly reduced for the short female plants in both medium and high planting density plots. The vertical error bars indicate standard error of average percentage of lodged plants.

Without being bound by theory, the increased lodging resistance of shorter stature female corn plants, in addition to increased pollen flow, may further help to explain and support the increased seed production (SSU/acre) in the production field as shown above.

Having described the present disclosure and inventions in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

The invention claimed is:

1. A method of hybrid corn seed production, said method comprising:
   (a) fertilizing a plurality of female inbred corn plants with pollen from at least one male inbred corn plant to produce hybrid corn seeds, wherein the female inbred corn plants have an average height that is at least 2.5% lower than the average height of the at least one male inbred corn plant, and wherein the female inbred corn plants comprise a recombinant polynucleotide encoding an RNA molecule that suppresses expression of an endogenous GA3 oxidase gene; and
   (b) harvesting said hybrid corn seeds from one or more of the female inbred corn plants.

2. The method of claim 1, wherein the yield or seed yield of hybrid corn seeds produced in step (b) is greater than the yield or seed yield of control hybrid corn seeds obtained from fertilizing a plurality of control female inbred corn plants with pollen from at least one control male inbred corn plant and harvesting said control hybrid corn seeds from one or more of said control female inbred corn plants, wherein said control hybrid corn seeds are harvested from the same number of female inbred corn plants as in step (b), and wherein the average height of said plurality of control female inbred corn plants is the same or similar to the average height of said at least one control male inbred corn plants.

3. The method of claim 1, wherein said female inbred corn plants have an average height that is at least 5% shorter than said at least one male inbred corn plant.

4. The method of claim 1, wherein said female inbred corn plants have an average height that is between 2.5% and 50% shorter than said at least one male inbred corn plant.

5. The method of claim 1, wherein said female inbred corn plants are dwarf corn plants or semi-dwarf corn plants.

6. The method of claim 1, wherein said female inbred corn plants comprise at least one ear that is at least 18 inches above ground level.

7. The method of claim 2, wherein the yield or seed yield of hybrid corn seeds produced in step (b) is increased by at least 3.0% relative to the yield or seed yield of the control hybrid corn seeds.

8. The method of claim 2, wherein said female inbred corn plants and said at least one male inbred corn plant are grown in a corn field.

9. The method of claim 2, wherein the heights of said female inbred corn plants and said at least one male inbred corn plant are measured at R1 stage.

10. The method of claim 8, wherein the field comprises multiple rows of female inbred corn plants and at least one row of male inbred corn plants.

11. The method of claim 10, wherein the ratio of female inbred corn plant rows to the at least one male inbred corn plant row is selected from the group consisting of 2:2, 3:2, 4:1, 4:2, 4:3, 6:1, and 6:2.

12. The method of claim 10, wherein the corn field comprises between 1 female row and 10 female rows for every male row.

13. The method of claim 8, wherein the corn field comprises between 1 female inbred corn plant and 100 female inbred corn plants for every male inbred corn plant.

14. The method of claim 8, wherein the corn field comprises at least two male inbred corn plants and at least two female inbred corn plants, wherein said female inbred corn plants comprise an average height that is at least 2.5% shorter than the average height of said male inbred corn plants, and wherein said male inbred corn plants exhibit at least 10% less tassel skeletonization as compared to a control corn field comprising at least two control male inbred corn plants and at least two control female inbred corn plants, wherein said male and female control plants have the same or similar plant heights, and wherein said tassel skeletonization is measured by the percentage of anthers that undergo dehiscence.

15. The method of claim 14, wherein said male inbred corn plants exhibit at least 5% less tassel skeletonization.

16. A method of hybrid corn seed production, said method comprising:
   (a) crossing at least one male inbred corn plant with a plurality of female inbred corn plants to produce hybrid corn seeds, wherein the plurality of female inbred corn plants have an average height that is at least 2.5% lower than the height or average height of the at least one male inbred corn plant, and wherein said female inbred corn plants comprise a recombinant polynucleotide encoding an RNA molecule that suppresses expression of an endogenous GA3 oxidase gene; and
   (b) harvesting said hybrid corn seeds from one or more of the female inbred corn plants.

17. A method of hybrid corn seed production, said method comprising:
   (a) planting at least one male inbred corn plant in proximity to a plurality of female inbred corn plants to produce hybrid corn seeds, wherein the female inbred corn plants have an average height that is at least 2.5% lower than the height or average height of the at least one male inbred corn plant, and wherein said female inbred corn plants comprise a recombinant polynucleotide encoding an RNA molecule that suppresses expression of an endogenous GA3 oxidase gene; and
   (b) harvesting said hybrid corn seeds from one or more of the female inbred corn plants.

18. The method of claim 1, wherein said RNA molecule comprises a sequence that is at least 90% complementary to at least 19 consecutive nucleotides of said endogenous GA3 oxidase gene, wherein said endogenous GA3 oxidase gene encodes an amino acid sequence at least 90% identical to an amino acid sequence selected from the group consisting of SEQ ID NOs: 30 and 33.

19. The method of claim 1, wherein said endogenous GA3 oxidase gene encodes an amino acid sequence at least 95% identical to an amino acid sequence selected from the group consisting of SEQ ID NOs: 30 and 33.

20. The method of claim 1, wherein said recombinant polynucleotide is operably linked to a plant-expressible promoter.

21. The method of claim 20, wherein the plant-expressible promoter is a vascular promoter.

22. The method of claim 20, wherein said plant-expressible promoter is a leaf promoter.

23. The method of claim 20, wherein said plant-expressible promoter is a constitutive promoter.

24. The method of claim 1, wherein the female inbred corn plants have an average height that is at least 10% lower than the average height of the at least one male inbred corn plant.

25. The method of claim 1, wherein the female inbred corn plants have an average height that is at least 15% lower than the average height of the at least one male inbred corn plant.

26. The method of claim 1, wherein the female inbred corn plants have an average height that is at least 20% lower than the average height of the at least one male inbred corn plant.

27. The method of claim 1, wherein the female inbred corn plants have an average height that is at least 30% lower than the average height of the at least one male inbred corn plant.

28. The method of claim 2, wherein the yield or seed yield of hybrid corn seeds produced in step (b) is increased by at least 5.0%, relative to the yield or seed yield of the control hybrid corn seeds.

29. The method of claim 2, wherein the yield or seed yield of hybrid corn seeds produced in step (b) is increased by at least 7.5%, relative to the yield or seed yield of the control hybrid corn seeds.

30. The method of claim 2, wherein the yield or seed yield of hybrid corn seeds produced in step (b) is increased by at least 10%, relative to the yield or seed yield of the control hybrid corn seeds.

31. The method of claim 2, wherein the yield or seed yield of hybrid corn seeds produced in step (b) is increased by at least 20%, relative to the yield or seed yield of the control hybrid corn seeds.

32. The method of claim 2, wherein the yield or seed yield of hybrid corn seeds produced in step (b) is increased by at least 30%, relative to the yield or seed yield of the control hybrid corn seeds.

33. The method of claim 8, wherein the corn field comprises at least 100 corn plants.

34. The method of claim 8, wherein the corn field comprises at least 1,000 corn plants.

35. The method of claim 8, wherein the corn field comprises at least 10,000 corn plants.

36. The method of claim 1, wherein the corn field comprises at least 100,000 corn plants.

37. The method of claim 1, wherein step (a) comprises fertilizing the plurality of female inbred corn plants with a plurality of male inbred corn plants.

\* \* \* \* \*

SEQUENCE LISTING

<160> NUMBER OF SEQ ID NOS: 131

<210> SEQ ID NO 1
<211> LENGTH: 1741
<212> TYPE: DNA
<213> ORGANISM: Zea mays

<400> SEQUENCE: 1

| | |
|---|---|
| gacggtagtt ttcatctaaa gtttattctt cgtcacatgg gatggccgtt tgcttgtttg | 60 |
| ttgcttccgg gaggcggtgg tgaattgaag cagatcgaca agcatggctg cccactggtc | 120 |
| tcgatcgatc ggcctgccat gccatgccat gccactagag tccgtcctga ctggccgccc | 180 |
| gttccccccgt ataaaaaggc aggcaggcag gcagagcggg gacgagcaag caagcagttg | 240 |
| cagttgcagc ggcctcctcc tctgcttcct ccctcctcct cctcaccatg gtgctggctg | 300 |
| cgcacgatcc ccctcccctt gtgttcgacg ctgcccgcct gagcggcctc tccgacatcc | 360 |
| cgcagcagtt catctggccg gcggacgaga gccccacccc ggactccgcc gaggagctgg | 420 |
| ccgtgccgct catcgacctc tccggggacg ccgccgaggt ggtccggcag gtccggcgcg | 480 |
| cctgcgacct gcacggcttc ttccaggtgg tggggcacgg catcgacgcg cgcgctgacgg | 540 |
| cggaggccca ccgctgcatg gacgccttct tcacgctgcc gctcccggac aagcagcgcg | 600 |
| cgcagcgccg ccagggggac agctgcggct acgccagcag cttcacgggc cggttcgcgt | 660 |
| ccaagctgcc ctggaaggag acgctgtcgt ccgctacac cgacgacgac gacggcgaca | 720 |
| agtccaagga cgtcgtggcg tcctacttcg tggacaagct gggcgagggg taccggcacc | 780 |
| acggggaggt gtacgggcgc tactgctctg agatgagccg tctgtcgctg gagctcatgg | 840 |
| aggtgctagg cgagagcctg ggcgtgggcc ggcgccactt ccggcgcttc ttccagggga | 900 |
| acgactccat catgcgcctc aactactacc gccgtgcca gcggccctac gacacgctgg | 960 |
| gcacggggcc gcattgcgac cccacgtcgc tcaccatcct gcaccaggac gacgtgggcg | 1020 |
| gactccaggt gttcgacgcc gccacgctcg cgtggcgctc catcaggccc cgcccgggcg | 1080 |
| ccttcgtcgt caacatcggc gacaccttca tggcgctctc caacgggcgc tacaggagct | 1140 |
| gcctccaccg cgccgtcgtc aacagccggg tggcacgccg ctcgctcgcc ttcttcctgt | 1200 |
| gcccggagat ggacaaggtg gtcaggccgc ccaaggagct ggtggacgac gccaacccga | 1260 |
| gggcgtaccc ggacttcacg tggaggacgc tgctggactt caccatgagg cactacaggt | 1320 |
| cggacatgag gacgctcgag gccttctcca actggctcag caccagtagc aatggcggac | 1380 |
| agcacctgct ggagaagaag taggcatgct atttgggtat ggaagatggt ggatgtaagc | 1440 |
| aaacaaagcc aaattaagca gagtaggtta attaaggttg gctgatgatc catttaggga | 1500 |
| aggagctgat ctccctgact ccctcctcca attttctcaa ccaaatttat atagtataat | 1560 |
| aataataata aaatagcaag taatagttgt atcgtattat tattaattaa tttattagct | 1620 |
| ggtaggcaag tagtattaaa taccatttgt agtacgatgg gcgtatttct attttggcgt | 1680 |
| tttgctctgt gttttttgac gtttcctttg gatttggggg gacctcagat cagctcggcc | 1740 |
| t | 1741 |

<210> SEQ ID NO 2
<211> LENGTH: 1116
<212> TYPE: DNA
<213> ORGANISM: Zea mays

<400> SEQUENCE: 2

| | |
|---|---|
| atggtgctgg ctgcgcacga tccccctccc cttgtgttcg acgctgcccg cctgagcggc | 60 |

-continued

| | |
|---|---|
| ctctccgaca tcccgcagca gttcatctgg ccggcggacg agagccccac cccggactcc | 120 |
| gccgaggagc tggccgtgcc gctcatcgac ctctccgggg acgccgccga ggtggtccgg | 180 |
| caggtccggc gcgcctgcga cctgcacggc ttcttccagg tggtgggca cggcatcgac | 240 |
| gcggcgctga cggcggaggc ccaccgctgc atggacgcct tcttcacgct gccgctcccg | 300 |
| gacaagcagc gcgcgcagcg ccgccagggg acagctgcg gctacgccag cagcttcacg | 360 |
| ggccggttcg cgtccaagct gccctggaag agacgctgt cgttccgcta caccgacgac | 420 |
| gacgacggcg acaagtccaa ggacgtcgtg gcgtcctact tcgtggacaa gctgggcgag | 480 |
| gggtaccggc accacgggga ggtgtacggg cgctactgct ctgagatgag ccgtctgtcg | 540 |
| ctggagctca tggaggtgct aggcgagagc ctgggcgtgg gccggcgcca cttccggcgc | 600 |
| ttcttccagg ggaacgactc catcatgcgc ctcaactact acccgccgtg ccagcggccc | 660 |
| tacgacacgc tgggcacggg gccgcattgc gaccccacgt cgctcaccat cctgcaccag | 720 |
| gacgacgtgg gcggactcca ggtgttcgac gccgccacgc tcgcgtggcg ctccatcagg | 780 |
| ccccgcccgg gcgccttcgt cgtcaacatc ggcgacacct tcatggcgct ctccaacggg | 840 |
| cgctacagga gctgcctcca ccgcgccgtc gtcaacagcc gggtggcacg ccgctcgctc | 900 |
| gccttcttcc tgtgcccgga gatggacaag gtggtcaggc cgcccaagga gctggtggac | 960 |
| gacgccaacc cgagggcgta cccggacttc acgtggagga cgctgctgga cttcaccatg | 1020 |
| aggcactaca ggtcggacat gaggacgctc gaggccttct ccaactggct cagcaccagt | 1080 |
| agcaatggcg acagcacct gctggagaag aagtag | 1116 |

<210> SEQ ID NO 3
<211> LENGTH: 371
<212> TYPE: PRT
<213> ORGANISM: Zea mays

<400> SEQUENCE: 3

```
Met Val Leu Ala Ala His Asp Pro Pro Leu Val Phe Asp Ala Ala
1               5                   10                  15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Glu Leu Ala Val Pro Leu
        35                  40                  45

Ile Asp Leu Ser Gly Asp Ala Ala Glu Val Val Arg Gln Val Arg Arg
    50                  55                  60

Ala Cys Asp Leu His Gly Phe Phe Gln Val Val His Gly Ile Asp
65                  70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Tyr Thr Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
```

```
                    180                 185                 190
Val Gly Arg Arg His Phe Arg Arg Phe Phe Gln Gly Asn Asp Ser Ile
            195                 200                 205
Met Arg Leu Asn Tyr Tyr Pro Pro Cys Gln Arg Pro Tyr Asp Thr Leu
        210                 215                 220
Gly Thr Gly Pro His Cys Asp Pro Thr Ser Leu Thr Ile Leu His Gln
225                 230                 235                 240
Asp Asp Val Gly Gly Leu Gln Val Phe Asp Ala Ala Thr Leu Ala Trp
                245                 250                 255
Arg Ser Ile Arg Pro Arg Pro Gly Ala Phe Val Val Asn Ile Gly Asp
            260                 265                 270
Thr Phe Met Ala Leu Ser Asn Gly Arg Tyr Arg Ser Cys Leu His Arg
        275                 280                 285
Ala Val Val Asn Ser Arg Val Ala Arg Arg Ser Leu Ala Phe Phe Leu
        290                 295                 300
Cys Pro Glu Met Asp Lys Val Val Arg Pro Lys Glu Leu Val Asp
305                 310                 315                 320
Asp Ala Asn Pro Arg Ala Tyr Pro Asp Phe Thr Trp Arg Thr Leu Leu
                325                 330                 335
Asp Phe Thr Met Arg His Tyr Arg Ser Asp Met Arg Thr Leu Glu Ala
            340                 345                 350
Phe Ser Asn Trp Leu Ser Thr Ser Ser Asn Gly Gly Gln His Leu Leu
        355                 360                 365
Glu Lys Lys
    370

<210> SEQ ID NO 4
<211> LENGTH: 1517
<212> TYPE: DNA
<213> ORGANISM: Zea mays

<400> SEQUENCE: 4
caggaataaa ataagcctcc gcccggcttc gttgcatcca cgcacgcagc aagcgatcgg      60
atttcgccag catggcggcg gcggccgtgg tgttcgacgc cgaggcgctg agccgggagg     120
agcacatccc ggcgcagttc gtgtggccca ccgaggagcg ggcgccggcg gcggcgtgg     180 aggaggtcgc catccccgtg gtcgacctcg gcgagttcct ccgccgcggg gtgctcccgc     240
gcggcgtggc ggaggcgtgc gagcgccacg gcgtcttcca ggtggtgaac cacggcgtgg     300
gcgccgcgct gctcgccgag gcctaccgct gttgcgacgc cttttacgcg ctcccgctcg     360
cggacaagca gcgcgcgcag cgccggcacg gggagaacca cggctacgcc agcagcttca     420
cgggccgctt ccactgctgc ctgccgtgga aggagacgct gtccttcaac tgccccgccg     480
gtgccgggac tgcgcgcgcc gtcgtcggct acttcgtcga cgtcctcggc gaggactacc     540
gccacatggg ggaggtgtac caggagtact gcgacgcgat gacgcgtctg gcgctggacg     600
tgacggaggt gctggcggca gcgctggggc tggaccgcgg cgcactgcgc ggcttcttcg     660
agggcggcga ctccgtcatg cggctgaacc actacccggc gtgccggcag ccgcacctga     720
cgctggggac gggcccgcac cgggacccga cgtcgctgac gctgctgcac caggacgacg     780
tgggcgggct gcaggtgcgc gccggcggcg gccgtggcg cgcggtgcgg cccgcgcgg     840 acgcgttcgt ggtcaacatt ggcgacacct tcgccgcgct caccgacggg cgtcacacca     900
gctgcctgca ccgcgccgtg gtgaccggcg cggctcccg ccgtcgctc gccttcttcc     960 tcaacccgcc gctggaccgc gtcgtccgcc cgccgggcgc gctcctccag gagaacaagc    1020
```

```
aggcgggccg cccgcgcgcg ttcccggact tcacgtggcg cgagttcctc gagttcacgc   1080
agaagcacta ccggtcggac gcgggcacca tggacgcctt cgtgtcgtgg atcgcgggag   1140
gccgccgcca ccatggcgga caggaggagg gcaactgaga tcgatgcatc tctagctgta   1200
ggcagcagcg cagcagctac caagaataat ggccggcgac ggagatgcag ctacgacgca   1260
caaataaatt gagtgtttgt ggtacaataa ggacgaggac gatcaatggc gacctgtaac   1320
cggtgcagtt ttagttaatc tttcatggcg atatggcatt aaccaatcgt tggtgtaaaa   1380
tgcgtgcatg ctttgcatgc caatgttggc catgtgatgg cacagcgtga gtgtagctca   1440
cccaccgtga caacgtgcta atttcgtgtg gtcctagata ccaaggtcgt ctaatgaact   1500
tgatggattg atgattt                                                 1517

<210> SEQ ID NO 5
<211> LENGTH: 1107
<212> TYPE: DNA
<213> ORGANISM: Zea mays

<400> SEQUENCE: 5
atggcggcgg cggccgtggt gttcgacgcc gaggcgctga gccggaggga gcacatcccg     60
gcgcagttcg tgtggcccac cgaggagcgg gcgccggcgg gcggcgtgga ggaggtcgcc    120
atccccgtgg tcgacctcgg cgagttcctc cgccgcgggg tgctcccgcg cggcgtggcg    180
gaggcgtgcg agcgccacgg cgtcttccag gtggtgaacc acgcgtgggc gccgcgctg    240 ctcgccgagg cctaccgctg ttgcgacgcc ttttacgcgc tcccgctcgc ggacaagcag    300
cgcgcgcagc gccggcacgg ggagaaccac ggctacgcca gcagcttcac gggccgcttc    360
cactgctgcc tgccgtggaa ggagacgctg tccttcaact gccccgccgg tgccgggact    420
gcgcgcgccg tcgtcggcta cttcgtcgac gtcctcggcg aggactaccg ccacatgggg    480
gaggtgtacc aggagtactg cgacgcgatg acgcgtctgg cgctggacgt gacggaggtg    540
ctggcggcag cgctggggct ggaccgcggc gcactgcgcg gcttcttcga gggcggcgac    600
tccgtcatgc ggctgaacca ctaccgggcg tgccggcagc cgcacctgac gctggggacg    660
ggcccgcacc gggacccgac gtcgctgacg ctgctgcacc aggacgacgt gggcgggctg    720
caggtgcgcg ccggcggcgg gccgtggcgc gcggtgcggc cccgcgcgga cgcgttcgtg    780
gtcaacattg gcgacacctt cgccgcgctc accgacgggg tcacaccag ctgcctgcac    840 cgcgccgtgg tgaccggcgg cggctcccgc cggtcgctcg ccttcttcct caacccgccg    900
ctggaccgct cgtccgcccc gccgggcgcg ctcctccagg agaacaagca ggcgggccgc    960
ccgcgcgcgt tcccggactt cacgtggcgc gagttcctcg agttcacgca gaagcactac   1020
cggtcggacg cgggcaccat ggacgccttc gtgtcgtgga tcgcgggagg ccgccgccac   1080
catggcggac aggaggaggg caactga                                       1107

<210> SEQ ID NO 6
<211> LENGTH: 368
<212> TYPE: PRT
<213> ORGANISM: Zea mays

<400> SEQUENCE: 6

Met Ala Ala Ala Ala Val Val Phe Asp Ala Glu Ala Leu Ser Arg Glu
 1               5                  10                  15

Glu His Ile Pro Ala Gln Phe Val Trp Pro Thr Glu Glu Arg Ala Pro
            20                  25                  30
```

```
Ala Gly Gly Val Glu Val Ala Ile Pro Val Val Asp Leu Gly Glu
         35                  40                  45

Phe Leu Arg Arg Gly Val Leu Pro Arg Gly Val Ala Glu Ala Cys Glu
 50                  55                  60

Arg His Gly Val Phe Gln Val Val Asn His Gly Val Gly Ala Ala Leu
 65                  70                  75                  80

Leu Ala Glu Ala Tyr Arg Cys Cys Asp Ala Phe Tyr Ala Leu Pro Leu
                 85                  90                  95

Ala Asp Lys Gln Arg Ala Gln Arg His Gly Glu Asn His Gly Tyr
             100                 105                 110

Ala Ser Ser Phe Thr Gly Arg Phe His Cys Cys Leu Pro Trp Lys Glu
         115                 120                 125

Thr Leu Ser Phe Asn Cys Pro Ala Gly Ala Gly Thr Ala Arg Ala Val
 130                 135                 140

Val Gly Tyr Phe Val Asp Val Leu Gly Glu Asp Tyr Arg His Met Gly
145                 150                 155                 160

Glu Val Tyr Gln Glu Tyr Cys Asp Ala Met Thr Arg Leu Ala Leu Asp
                 165                 170                 175

Val Thr Glu Val Leu Ala Ala Ala Leu Gly Leu Asp Arg Gly Ala Leu
             180                 185                 190

Arg Gly Phe Phe Glu Gly Gly Asp Ser Val Met Arg Leu Asn His Tyr
         195                 200                 205

Pro Ala Cys Arg Gln Pro His Leu Thr Leu Gly Thr Gly Pro His Arg
 210                 215                 220

Asp Pro Thr Ser Leu Thr Leu Leu His Gln Asp Val Gly Gly Leu
225                 230                 235                 240

Gln Val Arg Ala Gly Gly Pro Trp Arg Ala Val Arg Pro Arg Ala
             245                 250                 255

Asp Ala Phe Val Val Asn Ile Gly Asp Thr Phe Ala Ala Leu Thr Asp
         260                 265                 270

Gly Arg His Thr Ser Cys Leu His Arg Ala Val Thr Gly Gly Gly
 275                 280                 285

Ser Arg Arg Ser Leu Ala Phe Phe Leu Asn Pro Pro Leu Asp Arg Val
290                 295                 300

Val Arg Pro Pro Gly Ala Leu Leu Gln Glu Asn Lys Gln Ala Gly Arg
305                 310                 315                 320

Pro Arg Ala Phe Pro Asp Phe Thr Trp Arg Glu Phe Leu Glu Phe Thr
                 325                 330                 335

Gln Lys His Tyr Arg Ser Asp Ala Gly Thr Met Asp Ala Phe Val Ser
             340                 345                 350

Trp Ile Ala Gly Gly Arg Arg His His Gly Gly Gln Glu Glu Gly Asn
         355                 360                 365
```

<210> SEQ ID NO 7
<211> LENGTH: 1522
<212> TYPE: DNA
<213> ORGANISM: Zea mays

<400> SEQUENCE: 7

```
gcacactcgc agctcgcaca tctcatggtg tcctaagaac ggcaagagcc agctctgcct      60
agcagcagcg cacagccaca tccatggacg ccagcccgac ccaccgctc  ccctccgcg     120 ccccaactcc cagcattgac ctccccgctg gcaaggacag ggccgacgcg gcggctaaca    180
aggccgcggc tgtgttcgac ctgcgccggg agcccaagat cccggagcca ttcctgtggc    240
```

```
cgcacgaaga ggcgcggccg acctcggccg cggagctgga ggtgccggtg gtggacgtgg    300
gcgtgctgcg caatggcgac ggcgcggggc tccgccgcgc cgcggcgcaa gtggcggcgg    360
cgtgcgcgac gcacgggttc ttccaggtgt gcgggcacgg cgtggacgcg cgctggggc     420 gcgccgcgct ggacggcgcc agcgacttct tccggctgcc gctggctgag aagcagcggg    480
cccggcgcgt ccccggcacc gtgtccgggt acacgagcgc gcacgccgac cggttcgcgt    540
ccaagctccc ctggaaggag accctgtcct tcggcttcca cgacggcgcc gcggcgcccg    600
tcgtcgtgga ctacttcacc ggcaccctcg gccaagattt cgagccagtg gggcgggtgt    660
accagaggta ctgcgaggag atgaaggagc tgtcgctgac gatcatggag ctgctggagc    720
tgagcctggg cgtggagcgc ggctactacc gggagttctt cgaggacagc cgctccatca    780
tgcggtgcaa ctactacccg ccgtgccggg tgcggagcg cacgctgggc acgggcccgc     840
actgcgaccc cacggcgctg accatcctcc tgcaggacga cgtcggcggg ctggaggtcc    900
tggtggacgg cgagtggcgc cccgtccggc ccgtcccagg cgccatggtc atcaacatcg    960
gcgacacctt catggcgctg tccaacgggc ggtacaagag ctgcctgcac cgcgcggtgg   1020
tgaaccggcg gcaggagcgg caatcgctgg ccttcttcct gtgcccgcgc gaggaccggg   1080
tggtgcgccc gccggccagc gccgcgccgc ggcagtaccc ggacttcacc tgggccgacc   1140
tcatgcgctt cacgcagcgc cactaccgcg ccgacacccg cacgctggac gccttcaccc   1200
gctggctctc ccacgcccg gcggcggcgg ctccctgcac ctaacgagcc ggccgtctct    1260
ttcgccgggg cccgcgcggg gttcgcccac gtggtgatca ggtggcagac atgtggccca   1320 cgggcccccgc gccgccttcc ccattttttgg acgaccctac tgctactact actagtgtac   1380
atatgcaaaa aaatacatat atatataggt actttctcta atattttat atataagcaa     1440 ggcggcctgg tgttcttttc tttgttttgt cgacaactgt ttgatcccat cctatggacg   1500
atggatagtt caatgtttgt ac                                            1522
```

<210> SEQ ID NO 8
<211> LENGTH: 1161
<212> TYPE: DNA
<213> ORGANISM: Zea mays

<400> SEQUENCE: 8

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg cggcgcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
accctcggcc aagatttcga gccagtgggg cgggtgtacc agaggtactg cgaggagatg    600
aaggagctgt cgctgacgat catggagctg ctggagctga gcctgggcgt ggagcgcggc    660
tactaccggg agttcttcga ggacagccgc tccatcatgc ggtgcaacta ctacccgccg    720
tgcccggtgc ggagcgcac gctgggcacg ggcccgcact gcgaccccac ggcgctgacc     780
atcctcctgc aggacgacgt cggcgggctg gaggtcctgg tggacggcga gtggcgcccc    840
```

-continued

```
gtccggcccg tcccaggcgc catggtcatc aacatcggcg acaccttcat ggcgctgtcc      900
aacgggcggt acaagagctg cctgcaccgc gcggtggtga accggcggca ggagcggcaa      960
tcgctggcct tcttcctgtg cccgcgcgag gaccgggtgg tgcgcccgcc ggccagcgcc     1020
gcgccgcggc agtaccccga cttcacctgg gccgacctca tgcgcttcac gcagcgccac     1080
taccgcgccg acaccgcac gctggacgcc ttcacccgct ggctctccca cggcccggcg      1140
gcggcggctc cctgcaccta a                                               1161
```

<210> SEQ ID NO 9
<211> LENGTH: 386
<212> TYPE: PRT
<213> ORGANISM: Zea mays

<400> SEQUENCE: 9

```
Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

Ala Gly Leu Arg Arg Ala Ala Ala Gln Val Ala Ala Cys Ala Thr
                85                  90                  95

His Gly Phe Phe Gln Val Cys Gly His Gly Val Asp Ala Ala Leu Gly
            100                 105                 110

Arg Ala Ala Leu Asp Gly Ala Ser Asp Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Ala Pro Val Val Val Asp
                165                 170                 175

Tyr Phe Thr Gly Thr Leu Gly Gln Asp Phe Glu Pro Val Gly Arg Val
            180                 185                 190

Tyr Gln Arg Tyr Cys Glu Glu Met Lys Glu Leu Ser Leu Thr Ile Met
        195                 200                 205

Glu Leu Leu Glu Leu Ser Leu Gly Val Glu Arg Gly Tyr Tyr Arg Glu
    210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
            260                 265                 270

Leu Val Asp Gly Glu Trp Arg Pro Val Arg Pro Val Pro Gly Ala Met
        275                 280                 285

Val Ile Asn Ile Gly Asp Thr Phe Met Ala Leu Ser Asn Gly Arg Tyr
    290                 295                 300

Lys Ser Cys Leu His Arg Ala Val Val Asn Arg Arg Gln Glu Arg Gln
```

```
              305                 310                 315                 320
Ser Leu Ala Phe Phe Leu Cys Pro Arg Glu Asp Arg Val Val Arg Pro
                325                 330                 335
Pro Ala Ser Ala Ala Pro Arg Gln Tyr Pro Asp Phe Thr Trp Ala Asp
                340                 345                 350
Leu Met Arg Phe Thr Gln Arg His Tyr Arg Ala Asp Thr Arg Thr Leu
                355                 360                 365
Asp Ala Phe Thr Arg Trp Leu Ser His Gly Pro Ala Ala Ala Pro
                370                 375                 380
Cys Thr
385

<210> SEQ ID NO 10
<211> LENGTH: 1457
<212> TYPE: DNA
<213> ORGANISM: Zea mays

<400> SEQUENCE: 10
taatcacctc atcacaggtc cccccagcct cactctcgcg ccggctcaag gtacattgcg      60
tgtcctagcc aagacacgca gctcatctca gcctcacacg cacagcaaga gcgaggcgtg     120
attcgccatg ggcggcctca ctatggacca ggccttcgtg caggcccccg agcaccgccc     180
caagcccatc gtcaccgagg ccaccggcat ccctctcatc gacctctcgc tctggccgc      240 cagcggcggc gccgtggacg cgctggccgc cgaggtgggc gcggcgagcc gggactgggg     300
cttcttcgtg gtcgtgggcc acggcgtgcc cgcagagacc gtggcgcgcg cgacggaggc     360
gcagcgagcg ttcttcgcgc tgccggcaga gcggaaggcc gccgtgcgga ggaacgaggc     420
ggagccgctc gggtactacg agtcggagca caccaagaac gtgagggact ggaaggaggt     480
gtacgacctc gtgccgcgcg agccgccgcc gccggcagcc gtggccgacg gcgagcttgt     540
gttcgataac aagtgccccc aggatctacc gggcttcaga gaggcgctgg aggagtacgc     600
gaaagcgatg gaagagctgg cgttcaagct gctggagctg atcgcccgga gcctgaagct     660
gaggcccgac cggctgcacg gcttcttcaa ggaccagacg accttcatcc ggctgaacca     720
ctaccctcct tgcccgagcc ccgacctggc cctcggcgtg gggcggcaca aggacgccgg     780
cgccctgacc atcctgtacc aggacgacgt cggggggctc gacgtccggc ggcgctccga     840
cggcgagtgg gtccgcgtca ggcccgtgcc cgactcgttc atcatcaacg tcggcgacct     900
catccaggta cgagagcgcg gagcaccggg tgtcggtgaa ctcggcgagg gagaggttct     960
ccatgcccta cttcttcaac ccggcgacct acaccatggt ggagccggtg gaggagctgg    1020
tgagcaagga cgatccgccc aggtacgacg cctacaactg gggcgacttc ttcagcacca    1080
ggaagaacag caacttcaag aagctcaacg tggagaacat tcagatcgcg catttcaaga    1140
agagcctcgt cctcgcctaa ctactgctac tgctaggatc catgccattg ccatgtcgtc    1200
ttcagattca gagcacgcca tgtcgtcgct agcttcgtgg tagaacaaat aatgatgtgc    1260
gtgctgtgtg taagcatgga tatggatgtg aatatgtaat atgatgagca ctcctacttt    1320
ggtatgtttg ggaataacag acttgtgttg gtctggttca ttatttgtaa gaaaatcaaa    1380
aagagttagt agggcaggag gctaaccaca gtcatgctgc accacatccc tggtggaaag    1440
ctggccgggt tacgcta                                                   1457

<210> SEQ ID NO 11
<211> LENGTH: 1116
<212> TYPE: DNA
```

<213> ORGANISM: Zea mays

<400> SEQUENCE: 11

```
atgggcggcc tcactatgga ccaggccttc gtgcaggccc cgagcaccg ccccaagccc    60
atcgtcaccg aggccaccgg catccctctc atcgacctct cgcctctggc cgccagcggc   120
ggcgccgtgg acgcgctggc cgccgaggtg ggcgcggcga ccgggactg gggcttcttc    180
gtggtcgtgg ccacggcgt gcccgcagag accgtggcgc gcgcgacgga ggcgcagcga   240
gcgttcttcg cgctgccggc agagcggaag ccgccgtgc ggaggaacga ggcggagccg    300
ctcgggtact acgagtcgga gcacaccaag aacgtgaggg actggaagga ggtgtacgac   360
ctcgtgccgc gcgagccgcc gccgccggca gccgtggccg acggcgagct tgtgttcgat   420
aacaagtggc cccaggatct accgggcttc agagaggcgc tggaggagta cgcgaaagcg   480
atggaagagc tggcgttcaa gctgctggag ctgatcgccc ggagcctgaa gctgaggccc   540
gaccggctgc acggcttctt caaggaccag acgaccttca tccggctgaa ccactaccct   600
ccttgcccga gccccgacct ggccctcggc gtggggcggc acaaggacgc cggcgccctg   660
accatcctgt accaggacga cgtcgggggg ctcgacgtcc ggcggcgctc cgacggcgag   720
tgggtccgcg tcaggcccgt gcccgactcg ttcatcatca acgtcggcga cctcatccag   780
gtacgagagc gcggagcacc gggtgtcggt gaactcggcg agggagaggt tctccatgcc   840
ctacttcttc aacccggcga cctacaccat ggtggagccg gtggaggagc tggtgagcaa   900
ggacgatccg cccaggtacg acgcctacaa ctggggcgac ttcttcagca ccaggaagaa   960
cagcaacttc aagaagctca acgtggagaa cattcagatc gcgcatttca agaagagcct  1020
cgtcctcgcc taactactgc tactgctagg atccatgcca ttgccatgtc gtcttcagat  1080
tcagagcacg ccatgtcgtc gctagcttcg tggtag                           1116
```

<210> SEQ ID NO 12
<211> LENGTH: 371
<212> TYPE: PRT
<213> ORGANISM: Zea mays

<400> SEQUENCE: 12

```
Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
            20                  25                  30

Leu Ser Pro Leu Ala Ala Ser Gly Gly Ala Val Asp Ala Leu Ala Ala
        35                  40                  45

Glu Val Gly Ala Ala Ser Arg Asp Trp Gly Phe Phe Val Val Val Gly
    50                  55                  60

His Gly Val Pro Ala Glu Thr Val Ala Arg Thr Glu Ala Gln Arg
65                  70                  75                  80

Ala Phe Phe Ala Leu Pro Ala Glu Arg Lys Ala Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro
        115                 120                 125

Pro Ala Ala Val Ala Asp Gly Glu Leu Val Phe Asp Asn Lys Trp Pro
    130                 135                 140

Gln Asp Leu Pro Gly Phe Arg Glu Ala Leu Glu Glu Tyr Ala Lys Ala
145                 150                 155                 160
```

```
Met Glu Glu Leu Ala Phe Lys Leu Leu Glu Leu Ile Ala Arg Ser Leu
                165                 170                 175

Lys Leu Arg Pro Asp Arg Leu His Gly Phe Phe Lys Asp Gln Thr Thr
            180                 185                 190

Phe Ile Arg Leu Asn His Tyr Pro Pro Cys Pro Ser Pro Asp Leu Ala
        195                 200                 205

Leu Gly Val Gly Arg His Lys Asp Ala Gly Ala Leu Thr Ile Leu Tyr
    210                 215                 220

Gln Asp Asp Val Gly Gly Leu Asp Val Arg Arg Ser Asp Gly Glu
225                 230                 235                 240

Trp Val Arg Val Arg Pro Val Pro Asp Ser Phe Ile Ile Asn Val Gly
                245                 250                 255

Asp Leu Ile Gln Val Arg Glu Arg Gly Ala Pro Gly Val Gly Glu Leu
                260                 265                 270

Gly Glu Gly Glu Val Leu His Ala Leu Leu Leu Gln Pro Gly Asp Leu
            275                 280                 285

His His Gly Gly Ala Gly Gly Gly Ala Gly Glu Gln Gly Arg Ser Ala
        290                 295                 300

Gln Val Arg Arg Leu Gln Leu Gly Arg Leu Leu Gln His Gln Glu Glu
305                 310                 315                 320

Gln Gln Leu Gln Glu Ala Gln Arg Gly Glu His Ser Asp Arg Ala Phe
                325                 330                 335

Gln Glu Glu Pro Arg Pro Arg Leu Thr Thr Ala Thr Ala Arg Ile His
            340                 345                 350

Ala Ile Ala Met Ser Ser Ser Asp Ser Glu His Ala Met Ser Ser Leu
        355                 360                 365

Ala Ser Trp
    370

<210> SEQ ID NO 13
<211> LENGTH: 1733
<212> TYPE: DNA
<213> ORGANISM: Zea mays

<400> SEQUENCE: 13
atgaggccgc gcctccctcc aaatgttccc tccctgcctt cgtctttgtc gttgctcgca    60
aactccctgt cctcccctgt tacaaatacc cccacccgcc cggacagctt ccctgcatac   120
ttgcagctcg cacatctcat ggtgtcgcag gaacgacaag agccagctgt gcctagcagc   180
agcagcagca gcgccaagcg cgcagccacg tccatggacg ccagcccggc ccgccgctc    240
ctcctccgcg cccccactcc cagccccagc attgacctcc ccgctggcaa ggacaaggcc   300
gacgcggcgg ccagcaaggc cggcgcggcc gtgttcgacc tgcgccggga gcccaagatc   360
cccgcgccat tcctgtggcc gcaggaagag gcgcggccgt cctcggccgc ggagctggag   420
gtgccgatgg tggacgtggg cgtgctcgcg aatggcgacc gcgcgggct gcggcgcgcc   480
gcggcgcagg tggccgcggc gtgcgcgacg cacgggttct tccaggtgtg cgggcacggc   540
gtggacgcgg cgctgggcg cgccgcgctg gacggcgcca cgacttctt ccggctgccg   600
ctcgccgaga agcagcgcgc ccggcgcgtc cccggcaccg tgtccgggta cgagcgcg    660
cacgccgacc ggttcgcggc caagctcccc tggaaggaga ccctgtcgtt cggctaccac   720
gacgcgccg cgtcgcctgt cgtcgtggac tacttcgtcg caccctcgg ccaggatttc   780
gagccaatgg ggtgggtgta ccagaggtac tgcgaggaga tgaaggagct gtcgctgacg   840
```

```
atcatggagc tgctggagct gagcctgggc gtggagctgc gcggctacta ccgggagttc    900
ttcgaggaca gccggtccat catgcggtgc aactactacc cgccgtgccc ggagccggag    960
cgcacgctgg gcacgggccc gcactgcgac cccacggcgc tcaccatcct cctgcaggac   1020
gacgtgggcg gctggaggt gctggtggac ggtgagtggc ccccgtccg gcccgtcccg    1080 ggcgccatgg tcatcaacat cggcgacacc ttcatggcgc tgtcgaacgg gaggtacaag   1140
agctgcctgc accgcgcggt ggtgaaccag cggcgggcg gcggtcgct ggccttcttc    1200 ctgtgcccgc gcgaggaccg ggtggtgcgc ccgccggcca gtgctgcgcc gcggcgctac   1260
ccggacttca cctgggccga cctcatgcgc ttcacgcagc gccactaccg cgccgacacc   1320
cgcacgctgg acgccttcac ccgctggctc tcccacggcc cggcccaggc ggcggcgcct   1380
ccctgcacct agcgagccgg gccaaggcg tctctttcgc cccacgtgcg cgcccagctg   1440
ggcaggtggc cagacacgcg gcccgcgggc cccgcgccgc cttgccattt tttgacgctg   1500
gccctactgc tgtgctacta gtgtacatat gcaagagtac atatatatat atatatatac   1560
gtattttcta tatattatat ataaaagcaa ggcggcccgg tgcccttctc ttgttttgtc    1620
cacaactgtt tgatcccatt attctatgga ccatggatac ttcaatgttt gtactaagac   1680
cgtgaacgtg ggattctttt ccttcctctg tgttttttct gagaaaaatt aaa            1733

<210> SEQ ID NO 14
<211> LENGTH: 1392
<212> TYPE: DNA
<213> ORGANISM: Zea mays

<400> SEQUENCE: 14
atgaggccgc gcctccctcc aaatgttccc tccctgcctt cgtctttgtc gttgctcgca     60
aactccctgt cctcccctgt tacaaatacc cccacccgcc cggacagctt ccctgcatac    120
ttgcagctcg cacatctcat ggtgtcgcag gaacgacaag agccagctgt gcctagcagc    180
agcagcagca gcgccaagcg cgcagccacg tccatggacg ccagcccggc cccgccgctc   240
ctcctccgcg cccccactcc cagccccagc attgacctcc ccgctggcaa ggacaaggcc   300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag   420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc   540
gtggacgcgg cgctggggcg cgccgcgctg gacggcgcca gcgacttctt ccggctgccg   600
ctcgccgaga agcagcgcgc ccggcgcgtc cccggcaccg tgtccgggta cacgagcgcg   660
cacgccgacc ggttcgcggc caagctcccc tggaaggaga ccctgtcgtt cggctaccac   720
gacggcgccg cgtcgcctgt cgtcgtggac tacttcgtcg gcaccctcgg ccaggatttc    780
gagccaatgg ggtgggtgta ccagaggtac tgcgaggaga tgaaggagct gtcgctgacg    840
atcatggagc tgctggagct gagcctgggc gtggagctgc gcggctacta ccgggagttc    900
ttcgaggaca gccggtccat catgcggtgc aactactacc cgccgtgccc ggagccggag    960
cgcacgctgg gcacgggccc gcactgcgac cccacggcgc tcaccatcct cctgcaggac   1020
gacgtgggcg gctggaggt gctggtggac ggtgagtggc ccccgtccg gcccgtcccg    1080 ggcgccatgg tcatcaacat cggcgacacc ttcatggcgc tgtcgaacgg gaggtacaag   1140
agctgcctgc accgcgcggt ggtgaaccag cggcgggcg gcggtcgct ggccttcttc    1200 ctgtgcccgc gcgaggaccg ggtggtgcgc ccgccggcca gtgctgcgcc gcggcgctac   1260
```

```
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct ag                                                        1392
```

<210> SEQ ID NO 15
<211> LENGTH: 463
<212> TYPE: PRT
<213> ORGANISM: Zea mays

<400> SEQUENCE: 15

```
Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ser Lys Ala Gly Ala Ala Val Phe
            100                 105                 110

Asp Leu Arg Arg Glu Pro Lys Ile Pro Ala Pro Phe Leu Trp Pro Gln
        115                 120                 125

Glu Glu Ala Arg Pro Ser Ser Ala Ala Glu Leu Glu Val Pro Met Val
    130                 135                 140

Asp Val Gly Val Leu Arg Asn Gly Asp Arg Ala Gly Leu Arg Arg Ala
145                 150                 155                 160

Ala Ala Gln Val Ala Ala Ala Cys Ala Thr His Gly Phe Phe Gln Val
                165                 170                 175

Cys Gly His Gly Val Asp Ala Ala Leu Gly Arg Ala Ala Leu Asp Gly
            180                 185                 190

Ala Ser Asp Phe Phe Arg Leu Pro Leu Ala Glu Lys Gln Arg Ala Arg
        195                 200                 205

Arg Val Pro Gly Thr Val Ser Gly Tyr Thr Ser Ala His Ala Asp Arg
    210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Val Asp Tyr Phe Val Gly Thr Leu
                245                 250                 255

Gly Gln Asp Phe Glu Pro Met Gly Trp Val Tyr Gln Arg Tyr Cys Glu
            260                 265                 270

Glu Met Lys Glu Leu Ser Leu Thr Ile Met Glu Leu Leu Glu Leu Ser
        275                 280                 285

Leu Gly Val Glu Leu Arg Gly Tyr Tyr Arg Glu Phe Phe Glu Asp Ser
    290                 295                 300

Arg Ser Ile Met Arg Cys Asn Tyr Tyr Pro Pro Cys Pro Glu Pro Glu
305                 310                 315                 320

Arg Thr Leu Gly Thr Gly Pro His Cys Asp Pro Thr Ala Leu Thr Ile
                325                 330                 335

Leu Leu Gln Asp Asp Val Gly Gly Leu Glu Val Leu Val Asp Gly Glu
```

```
              340                 345                 350
Trp Arg Pro Val Arg Pro Val Pro Gly Ala Met Val Ile Asn Ile Gly
        355                 360                 365

Asp Thr Phe Met Ala Leu Ser Asn Gly Arg Tyr Lys Ser Cys Leu His
    370                 375                 380

Arg Ala Val Val Asn Gln Arg Arg Ala Arg Arg Ser Leu Ala Phe Phe
385                 390                 395                 400

Leu Cys Pro Arg Glu Asp Arg Val Val Arg Pro Ala Ser Ala Ala
                405                 410                 415

Pro Arg Arg Tyr Pro Asp Phe Thr Trp Ala Asp Leu Met Arg Phe Thr
                420                 425                 430

Gln Arg His Tyr Arg Ala Asp Thr Arg Thr Leu Asp Ala Phe Thr Arg
            435                 440                 445

Trp Leu Ser His Gly Pro Ala Gln Ala Ala Ala Pro Pro Cys Thr
        450                 455                 460

<210> SEQ ID NO 16
<211> LENGTH: 1510
<212> TYPE: DNA
<213> ORGANISM: Zea mays

<400> SEQUENCE: 16
```

| | | | | | |
|---|---|---|---|---|---|
| aaagagcgcg | cgacggcggc | ccctgggaga | gccatgcgag | actggaggcg | gaaccgcgca | 60 |
| cgacaccaag | ctgccgcgcc | ggactgctgc | acgcaagcgc | agcgcaggac | cgaccgacct | 120 |
| ccgtaggcac | gcacggcgcc | ggcggcatgg | cggagcacct | cctgtcgacg | gccgtgcacg | 180 |
| acacgctgcc | ggggagctac | gtgcggccgg | agccggagcg | cccgcgcctc | gcggaggtcg | 240 |
| tgaccggcgc | gcgcatcccc | gtcgtggacc | tgggcagccc | cgaccgcggc | gcggtcgtgg | 300 |
| ccgccgtcgg | cgacgcctgc | cgctcgcacg | gcttcttcca | ggtcgtcaac | cacgggatac | 360 |
| acgccgccct | ggtcgcggcg | gtgatggccc | ggggcgcgg | cttcttccgg | ctgcccccg | 420 |
| aggagaaggc | caagctctac | tccgacgacc | ccgccaggaa | gatccggctg | tccaccagct | 480 |
| tcaacgtgcg | caaggagacg | gtgcacaact | ggcgcgacta | cctccgcctg | cactgccatc | 540 |
| ccctcgacga | gttcctgccc | gattggccgt | ccaacccgcc | cgatttcaag | gagaccatgg | 600 |
| gcacctactg | caaggaggtc | cgggagctcg | ggttcaggct | gtacgccgcg | atctcggaga | 660 |
| gcctgggcct | agaggcgagc | tacatgaagg | aagcgctggg | ggagcaggag | cagcacatgg | 720 |
| cggtcaactt | ctacccgccg | tgcccggagc | cggagctcac | ctacggcctc | ccggcgcaca | 780 |
| ccgaccccaa | cgcgctcacc | atcctgctca | tggaccggga | cgtcgccggc | ctgcaggtgc | 840 |
| tccacgccgg | ccagtgggtc | gccgtcaacc | cgcagcccgg | cgcgctcatc | atcaacatcg | 900 |
| gcgaccagct | gcaggcgctg | agcaacgggc | agtaccggag | cgtgtggcac | gcgcggtgg | 960 |
| tgaactcgga | ccgggagcgc | atgtccgtgg | cgtcgttcct | gtgcccgtgc | aaccacgtcg | 1020 |
| tgctcggccc | cgcgcggaag | ctcgtcaccg | aggacacccc | ggccgtgtac | aggaactaca | 1080 |
| cgtacgacaa | gtactacgcc | aagttctgga | gcaggaacct | ggaccaggag | cactgcctcg | 1140 |
| agctcttcag | aacctagcga | atcggatacg | gatggatgga | tacattacat | acgcgccctc | 1200 |
| tgtttttctc | catgacgtta | gaagaacacg | ttctgcaatg | tttgtccatt | caaggtggta | 1260 |
| tcaatcaagg | ctgtggtcgt | tgcaattctt | ccgctccata | tacatgatta | aatgctttga | 1320 |
| aagaaaaaga | aaaaaaagaa | acacaagtat | tatggcacta | ctagtgtttt | taggaacaag | 1380 |
| gaaagagggg | ttgcccctgc | tggctatata | tattaaatat | aaataaaggt | aaggctgtag | 1440 |

```
acattggtga ataagagaaa gtatttgagt ttctctattg tcactccaga acagactcct   1500
ttgcctcgat                                                         1510
```

<210> SEQ ID NO 17
<211> LENGTH: 1011
<212> TYPE: DNA
<213> ORGANISM: Zea mays

<400> SEQUENCE: 17

```
atggcggagc acctcctgtc gacggccgtg cacgacacgc tgccggggag ctacgtgcgg    60
ccggagccgg agcgcccgcg cctcgcggag gtcgtgaccg gcgcgcgcat ccccgtcgtg   120
gacctgggca gccccgaccg cggcgcggtc gtggccgccg tcggcgacgc ctgccgctcg   180
cacggcttct tccaggtcgt caaccacggg atacacgccg ccctggtcgc ggcggtgatg   240
gccgcggggc gcggcttctt ccggctgccc ccgaggaga aggccaagct ctactccgac   300
gaccccgcca ggaagatccg gctgtccacc agcttcaacg tgcgcaagga gacggtgcac   360
aactggcgcg actacctccg cctgcactgc catcccctcg acgagttcct gcccgattgg   420
ccgtccaacc cgcccgattt caaggagacc atgggcacct actgcaagga ggtccgggag   480
ctcgggttca ggctgtacgc cgcgatctcg gagagcctgg cctagaggc gagctacatg   540 aaggaagcgc tgggggagca ggagcagcac atggcggtca acttctaccc gccgtgcccg   600
gagccggagc tcacctacgg cctcccggcg cacaccgacc ccaacgcgct caccatcctg   660
ctcatggacc cggacgtcgc cggcctgcag gtgctccacg ccggccagtg ggtcgccgtc   720
aacccgcagc ccggcgcgct catcatcaac atcggcgacc agctgcaggc gctgagcaac   780
gggcagtacc ggagcgtgtg caccgcgcg gtggtgaact cggaccggga gcgcatgtcc   840
gtggcgtcgt tcctgtgccc gtgcaaccac gtcgtgctcg gccccgcgcg gaagctcgtc   900
accgaggaca ccccggccgt gtacaggaac tacacgtacg acaagtacta cgccaagttc   960
tggagcagga acctggacca ggagcactgc ctcgagctct tcagaaccta g            1011
```

<210> SEQ ID NO 18
<211> LENGTH: 336
<212> TYPE: PRT
<213> ORGANISM: Zea mays

<400> SEQUENCE: 18

```
Met Ala Glu His Leu Leu Ser Thr Ala Val His Asp Thr Leu Pro Gly
1               5                  10                  15

Ser Tyr Val Arg Pro Glu Pro Glu Arg Pro Arg Leu Ala Glu Val Val
            20                  25                  30

Thr Gly Ala Arg Ile Pro Val Val Asp Leu Gly Ser Pro Asp Arg Gly
        35                  40                  45

Ala Val Val Ala Ala Val Gly Asp Ala Cys Arg Ser His Gly Phe Phe
    50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Leu Pro Asp Trp Pro Ser Asn Pro
```

```
                        130                 135                 140
Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Pro
    210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Arg Lys Leu Val Thr Glu Asp Thr
    290                 295                 300

Pro Ala Val Tyr Arg Asn Tyr Thr Tyr Asp Lys Tyr Tyr Ala Lys Phe
305                 310                 315                 320

Trp Ser Arg Asn Leu Asp Gln Glu His Cys Leu Glu Leu Phe Arg Thr
                325                 330                 335

<210> SEQ ID NO 19
<211> LENGTH: 1387
<212> TYPE: DNA
<213> ORGANISM: Zea mays

<400> SEQUENCE: 19
gttttctttt tgaacgtaac tgacagaagc tatctgccta gctacggcgt gtcggttgct     60
tgtctcacca aagcagcgac atggaagcct acagctcgt cgcgtcgcgc catttccacc    120
caacaaagcg gcggcgccag cacgcactgc ttctgcttgt gcgtgctcct ccgttccggg    180
cacgcctcta agtctatac agcctcgaat ccatcccggc cgccgctcct gggggatact    240
acagcgagcc gaagcgggga tggcggagat ccctgtgatc gacctgcgcg tcgccggctc    300
ggcggccgag gagtccgcgc ggctgcgggc gcgtgcgag cgcctgggct gcttccgggt    360
gaccggccac ggcgtgccct cggtgctcct ggcagagatg aaggccgccg tgcgcgcgct    420
cttcgacctc cccgacgacg ccaagcgccg caacgccgac gtcatcaccg gcagcggcta    480
cgtcgccccc agcccgacca cccgctctca cgaggccttc gggctcctcg acgccgccgt    540
gcccaccgac gtcgacgcct tttgcgcgct cctcgacgcg ccgcccaaca tcagggagac    600
cgtcaaggcc tacgcggaga agatgcacga tgtgatcgtt ggcgtcgccc gcgagctggc    660
gtctagcctg gggctagtcg aggagcactc gttccaggac tggccgtgcc agttccgcat    720
caacaggtac aactacacgc gggagacggt gggctcctcc ggcgtgcaga cccacacgga    780
ctcgggcttc ctcaccgtgc tccatgagga cgagtgtgtc ggcggcctcg aggtcctgga    840
cccgggcacc ggcgagttcg tgcccgtgga ccccgtcgcg ggctcctttc tcgtaaacat    900
cggcgacgtc ggcacggcgt ggagcaacgg gaggctgcac aacgtgaagc accgggtgcg    960
gtgcgtcgca cccgtgccgc gcatctccat cgccatgttc ctgctcgcac ccaaggacga   1020
```

-continued

```
cagcgtgagc gcaccggcgg cgttcgtgga cgcggaccac ccgcgcaggt acaaggtgtt    1080
caactacaac gactatcgga ggctcagact gtccaccggc gagcacgcag gcgaggcgct    1140
cgcacggatg gcggcgtgac gtggctggag ctgcaaattg gattggaagc cgagacaagc    1200
cgttagttat ttaccatgcc cgtgcgttca ccgcacacaa tcatattcaa aagccataaa    1260
ataaaaaata attttaatat cagtcaacat atggtttaaa tatcatatgg agtacaatat    1320
tccgaatttt tttttgtaat ttagtctgtc ttttgaaaaa aatgcacatc tagacctccg    1380
gatgact                                                              1387
```

<210> SEQ ID NO 20
<211> LENGTH: 900
<212> TYPE: DNA
<213> ORGANISM: Zea mays

<400> SEQUENCE: 20

```
atggcggaga tccctgtgat cgacctgcgc gtcgccggct cggcggccga ggagtccgcg     60
cggctgcggg ccgcgtgcga gcgcctgggc tgcttccggg tgaccggcca cggcgtgccc    120
tcggtgctcc tggcagagat gaaggccgcc gtgcgcgcgc tcttcgacct ccccgacgac    180
gccaagcgcc gcaacgccga cgtcatcacc ggcagcggct acgtcgcccc cagcccgacc    240
aacccgctct acgaggcctt cgggctcctc gacgccgccg tgcccaccga cgtcgacgcc    300
ttttgcgcgc tcctcgacgc gccgcccaac atcagggaga ccgtcaaggc ctacgcggag    360
aagatgcacg atgtgatcgt tggcgtcgcc cgcgagctgg cgtctagcct ggggctagtc    420
gaggagcact cgttccagga ctggccgtgc cagttccgca tcaacaggta caactacacg    480
cgggagacgg tgggctcctc cggcgtgcag acccacacgg actcgggctt cctcaccgtg    540
ctccatgagg acgagtgtgt cggcggcctc gaggtcctgg accgggcac cggcgagttc    600 gtgcccgtgg accccgtcgc gggctccttt ctcgtaaaca tcggcgacgt cggcacggcg    660
tggagcaacg ggaggctgca caacgtgaag caccgggtgc ggtgcgtcgc acccgtgccg    720
cgcatctcca tcgccatgtt cctgctcgca cccaaggacg acagcgtgag cgcaccggcg    780
gcgttcgtgg acgcggacca cccgcgcagg tacaaggtgt tcaactacaa cgactatcgg    840
aggctcagac tgtccaccgg cgagcacgca ggcgaggcgc tcgcacggat ggcggcgtga    900
```

<210> SEQ ID NO 21
<211> LENGTH: 299
<212> TYPE: PRT
<213> ORGANISM: Zea mays

<400> SEQUENCE: 21

```
Met Ala Glu Ile Pro Val Ile Asp Leu Arg Val Ala Gly Ser Ala Ala
1               5                   10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95
```

```
Asp Val Asp Ala Phe Cys Ala Leu Leu Asp Ala Pro Pro Asn Ile Arg
                100                 105                 110

Glu Thr Val Lys Ala Tyr Ala Glu Lys Met His Asp Val Ile Val Gly
            115                 120                 125

Val Ala Arg Glu Leu Ala Ser Ser Leu Gly Leu Val Glu Glu His Ser
        130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175

Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
            260                 265                 270

Val Phe Asn Tyr Asn Asp Tyr Arg Arg Leu Arg Leu Ser Thr Gly Glu
        275                 280                 285

His Ala Gly Glu Ala Leu Ala Arg Met Ala Ala
    290                 295

<210> SEQ ID NO 22
<211> LENGTH: 1496
<212> TYPE: DNA
<213> ORGANISM: Zea mays

<400> SEQUENCE: 22
gtcggtctct tgtctcacca aaccggcgac atggtacatg gaggccagcc cgtcgcttgg      60
cgccacaagt ctcggtgccg tccgtccgac aagcggcgcc agcgcacgct ggctgctcgt     120
gcacgcctct aaatacggcc ccggacccgc caccaagcga aggccaatcc cgtccgccgc     180
cccccaccaa ccacgaacca cgcaagcgaa cccggccggc gcggggcagc ggcgatggcg     240
gagatcccgg tgatcgacct cgcctcgcc ggctcgtcgc ccgacgagtc ggcgcggctg     300
cgcgacgcgt gcgagcgcct gggctgcttt cgggtgaccg ccacggcgc gcccgcgggg     360 ctcctggccg acatgaaggc cgccgtgcgc gcgctcttcg acctccccga cgacgccaag     420
cgccgcaacg ccgacgtcat ccccggcagc ggctacgtcg cgccctgccc cgccaacccg     480
ctctacgagg ccttcgggct cctcgacgcc gccgcgcccg ccgacgtcga cgccttctgc     540
gcgcgcctcg acgcgccgcc caaagtcagg gagaccgtca agacctacgc ggagaagatg     600
cacgacgtga tcgtcggcgt cgccggcgag ctggccacca gcctggggct gggcctggag     660
gagcactcgt tccaggactg gccgtgccag ttccgcatca acaggtacaa ctacacgcag     720
gagacggtgg gctcctccgg cgtgcagacc cacacggact cgggcttcct caccgtgctc     780
caggaggacg agtgcgtcgg cggcctcgag gtgctggacc ccgccgccgg tgagttcgtg     840
cccgtggacc ccgtcgccgg ctccttcctc gtcaacatcg gcgacgtcgg cacggcgtgg     900
agcaacggga ggctccacaa cgtgaagcac cgggtgcggt gcgtcgcgcc cgtgccgcgc     960
```

```
atctccatcg ccatgttcct gctggcgccc aaggacgacc gcgtgagcgc cccggaggcg      1020
ttggtcgacg cgggccaccc gcgtcggtac aagccgttca actacgacga ctaccggagg      1080
ctccggctgt ccaccggcga gcgcgcaggc gaggcgctcg cgcggatggc ggcgtgatgt      1140
cgtcacgcac gtgcaagccg ttaattatag gctcgcgcat gcatacgcct acacgagagg      1200
ttgtctcgtt aagccgttct attaaaatgt gtgggggaga aagatgacta ccgtggtgcc      1260
atgtggattg ctatcgggtc tgatcaataa aatcttgcaa cacttgcacg tgcgattcca      1320
tatcctagca cgggtgggcg ccacgctagt aggtagagac cggagcggcc aaaaaatggc      1380
tacagcacca gtaggtgaac tctcaagcaa cactggctat cccacttctg acgttgtctc      1440
tctcatcact atgtatgacc agcgaatgaa gtgtttaaaa atctgacgcc gtgaaa         1496
```

<210> SEQ ID NO 23
<211> LENGTH: 903
<212> TYPE: DNA
<213> ORGANISM: Zea mays

<400> SEQUENCE: 23

```
atggcggaga tcccggtgat cgacctgcgc ctcgccggct cgtcgcccga cgagtcggcg      60
cggctgcgcg acgcgtgcga gcgcctgggc tgctttcggg tgaccggcca cggcgcgccc     120
gcggggctcc tggccgacat gaaggccgcc gtgcgcgcgc tcttcgacct ccccgacgac     180
gccaagcgcc gcaacgccga cgtcatcccc ggcagcggct acgtcgcgcc ctgccccgcc     240
aacccgctct acgaggcctt cgggctcctc gacgccgccg cgcccgccga cgtcgacgcc     300
ttctgcgcgc gcctcgacgc gccgcccaaa gtcaggggaga ccgtcaagac ctacgcggag    360
aagatgcacg acgtgatcgt cggcgtcgcc ggcgagctgg ccaccagcct ggggctgggc     420
ctggaggagc actcgttcca ggactggccg tgccagttcc gcatcaacag gtacaactac     480
acgcaggaga cggtgggctc ctccggcgtg cagacccaca cggactcggg cttcctcacc     540
gtgctccagg aggacgagtg cgtcggcggc ctcgaggtgc tggaccccgc cgccggtgag     600
ttcgtgcccg tggaccccgt cgccggctcc ttcctcgtca catcggcga cgtcggcacg      660 gcgtggagca cgggaggct ccacaacgtg aagcaccggg tgcggtgcgt cgcgcccgtg      720
ccgcgcatct ccatcgccat gttcctgctg gcgcccaagg acgaccgcgt gagcgccccg     780
gaggcgttgg tcgacgcggg ccacccgcgt cggtacaagc cgttcaacta cgacgactac     840
cggaggctcc ggctgtccac cggcgagcgc gcaggcgagg cgctcgcgcg gatggcggcg     900
tga                                                                   903
```

<210> SEQ ID NO 24
<211> LENGTH: 300
<212> TYPE: PRT
<213> ORGANISM: Zea mays

<400> SEQUENCE: 24

```
Met Ala Glu Ile Pro Val Ile Asp Leu Arg Leu Ala Gly Ser Ser Pro
1               5                   10                  15

Asp Glu Ser Ala Arg Leu Arg Asp Ala Cys Glu Arg Leu Gly Cys Phe
            20                  25                  30

Arg Val Thr Gly His Gly Ala Pro Ala Gly Leu Leu Ala Asp Met Lys
        35                  40                  45

Ala Ala Val Arg Ala Leu Phe Asp Leu Pro Asp Asp Ala Lys Arg Arg
    50                  55                  60

Asn Ala Asp Val Ile Pro Gly Ser Gly Tyr Val Ala Pro Cys Pro Ala
```

```
            65                  70                  75                  80

Asn Pro Leu Tyr Glu Ala Phe Gly Leu Leu Asp Ala Ala Pro Ala
                85                  90                  95

Asp Val Asp Ala Phe Cys Ala Arg Leu Asp Ala Pro Pro Lys Val Arg
            100                 105                 110

Glu Thr Val Lys Thr Tyr Ala Glu Lys Met His Asp Val Ile Val Gly
            115                 120                 125

Val Ala Gly Glu Leu Ala Thr Ser Leu Gly Leu Gly Leu Glu Glu His
        130                 135                 140

Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
                165                 170                 175

Gly Phe Leu Thr Val Leu Gln Glu Asp Glu Cys Val Gly Gly Leu Glu
            180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
    210                 215                 220

Gly Arg Leu His Asn Val Lys His Arg Val Arg Cys Val Ala Pro Val
225                 230                 235                 240

Pro Arg Ile Ser Ile Ala Met Phe Leu Leu Ala Pro Lys Asp Asp Arg
                245                 250                 255

Val Ser Ala Pro Glu Ala Leu Val Asp Ala Gly His Pro Arg Arg Tyr
            260                 265                 270

Lys Pro Phe Asn Tyr Asp Asp Tyr Arg Arg Leu Arg Leu Ser Thr Gly
            275                 280                 285

Glu Arg Ala Gly Glu Ala Leu Ala Arg Met Ala Ala
        290                 295                 300

<210> SEQ ID NO 25
<211> LENGTH: 1614
<212> TYPE: DNA
<213> ORGANISM: Zea mays

<400> SEQUENCE: 25
accacacgaa ttgcacatct ccacagctca cgattccaac actagctaca tatatatgta      60
gctttctagg ctactatata cactcaccac caagtgtgaa gtgtgtatat atagtgacag     120
ctactgcaat atatacatac gcgtcaccta tatattagcc aagctagcta tatgagcttg     180
gttgcggcgc caatggcgat cgtcgacgtg gccaacgccc agctgcagca agcagcagca     240
gcagctgcca agaaagacga ggacggccat gagcagcagg agtcgtccta cgactacggc     300
gcgctgatga aaggcgtgag gcacctgtcg gacagcggca ttaccaggct gcccgacagg     360
tacgtcctgc ccgcgtccga ccgccccggc gtccttgccg tctcgtcgtc cgtggcgggc     420
agcggcaggg tcaagctccc tgtcgtcaac ctcgccggcc tccgcgaccc ctgccagcgc     480
gccgccgtgc tggccacgct cgacgccgcg tgccgggagt acggcttctt tcaggtggta     540
aaccacgggt tcgggagcga cgtgagcggc gggatgctgg acgtggcgca gcgcttcttc     600
gagctgccgc tggccgagcg agcgcggcac atgtcggcgg acgtgcgggc gccggtgcgc     660
tacggcacca gcttcaacca ggccaaggac gacgtgctct gctggcgcga cttcctcaag     720
ctcgtctgcc agccgctgca ggcggtgctc ccgtactggc cccagcagcc ggcggacctc     780
agggacgtgg ccaccaggta cgccacggcg agccaccggc tgttcatgga ggtcatggag     840
```

```
gcggcgctgg aggccctggg catccccacg gccggcggcg tgctcgggga gctggcagcg      900
tcgtcgtcgc acatgatgac ggtgaactgc tacccggcgt gcccgcagcc tgagctcacg      960
ctggggatgc cctcgcactc ggactacggc ctcttcacgt tcgtcctgca ggaccacgtc     1020
gagggcctcc aggtcatgca cgacggccgc tggctcacca tcgacccat cccgggatcg      1080 ttcgtcgtca acgtcggcga ccacctagag atctacagca acgggcggta caagagcgcg     1140
ctgcaccggg tgcacgtgaa ctccacgcgg ccgcgcatct cggtggcgtc gttccacagc     1200
ctgccggcgg agcgagtgat cgggccggcg ccggagctgg tggacgacga ggccggcaac     1260
ccgcggcggt acatggacac cgacttcgct accttcctcg cctacctcgc atccgcggac     1320
ggcaagaaca agaccttcct ccagtcaagg aagctgcctg ctgctgctcc tccatgcctc     1380
tagctaacta gatagctgct tattaatctg acagaataaa attaatcagt tcagcgcaca     1440
attccacaag cgaaaacaaa cctggatttg ttttaattag ctctgcccct cattattaca     1500
ttcaagctag ctcttggtca acgcatgcac acaagcttga gcattgactg gtccctttc      1560 aatcggttgc attgtactcc ctccgtacca aaattggttg tcgctatagt attt           1614
```

<210> SEQ ID NO 26
<211> LENGTH: 1212
<212> TYPE: DNA
<213> ORGANISM: Zea mays

<400> SEQUENCE: 26

```
atgagcttgg ttgcggcgcc aatggcgatc gtcgacgtgg ccaacgccca gctgcagcaa       60
gcagcagcag cagctgccaa gaaagacgag gacggccatg agcagcagga gtcgtcctac      120
gactacggcg cgctgatgaa ggcgtgagg cacctgtcgg cagcggcat taccaggctg       180 cccgacaggt acgtcctgcc cgcgtccgac cgccccggcg tccttgccgt ctcgtcgtcc      240
gtggcgggca cggcagggt caagctccct gtcgtcaacc tcgccggcct ccgcgacccc       300
tgccagcgcg ccgccgtgct ggccacgctc gacgccgcgt gcgggagta cggcttcttt      360 caggtggtaa accacgggtt cgggagcgac gtgagcggcg ggatgctgga cgtggcgcag      420
cgcttcttcg agctgccgct ggccgagcga gcgcggcaca tgtcggcgga cgtgcgggcg      480
ccggtgcgct acggcaccag cttcaaccag gccaaggacg acgtgctctg ctggcgcgac      540
ttcctcaagc tcgtctgcca gccgctgcag gcggtgctcc cgtactggcc ccagcagccg      600
gcggacctca gggacgtggc caccaggtac gccacggcga ccaccggct gttcatggag       660 gtcatggagg cggcgctgga ggccctgggc atccccacgg ccggcggcgt gctcggggag      720
ctggcagcgt cgtcgtcgca catgatgacg gtgaactgct acccggcgtg cccgcagcct      780
gagctcacgc tggggatgcc ctcgcactcg gactacggcc tcttcacgtt cgtcctgcag      840
gaccacgtcg agggcctcca ggtcatgcac gacggccgct ggctcaccat cgacccatc      900 ccgggatcgt tcgtcgtcaa cgtcggcgac cacctagaga tctacagcaa cgggcggtac     960
aagagcgcgc tgcaccgggt gcacgtgaac tccacgcggc cgcgcatctc ggtggcgtcg     1020
ttccacagcc tgccggcgga gcgagtgatc gggccggcgc cggagctggt ggacgacgag     1080
gccggcaacc gcggcggta catggacacc gacttcgcta ccttcctcgc ctacctcgca      1140
tccgcggacg gcaagaacaa gaccttcctc cagtcaagga agctgcctgc tgctgctcct     1200
ccatgcctct ag                                                         1212
```

<210> SEQ ID NO 27

```
<211> LENGTH: 403
<212> TYPE: PRT
<213> ORGANISM: Zea mays

<400> SEQUENCE: 27

Met Ser Leu Val Ala Ala Pro Met Ala Ile Val Asp Val Ala Asn Ala
1               5                   10                  15

Gln Leu Gln Gln Ala Ala Ala Ala Ala Lys Lys Asp Glu Asp Gly
            20                  25                  30

His Glu Gln Gln Glu Ser Ser Tyr Asp Tyr Gly Ala Leu Met Lys Gly
            35                  40                  45

Val Arg His Leu Ser Asp Ser Gly Ile Thr Arg Leu Pro Asp Arg Tyr
50                  55                  60

Val Leu Pro Ala Ser Asp Arg Pro Gly Val Leu Ala Val Ser Ser Ser
65                  70                  75                  80

Val Ala Gly Ser Gly Arg Val Lys Leu Pro Val Val Asn Leu Ala Gly
                85                  90                  95

Leu Arg Asp Pro Cys Gln Arg Ala Ala Val Leu Ala Thr Leu Asp Ala
            100                 105                 110

Ala Cys Arg Glu Tyr Gly Phe Phe Gln Val Val Asn His Gly Phe Gly
        115                 120                 125

Ser Asp Val Ser Gly Gly Met Leu Asp Val Ala Gln Arg Phe Phe Glu
130                 135                 140

Leu Pro Leu Ala Glu Arg Ala Arg His Met Ser Ala Asp Val Arg Ala
145                 150                 155                 160

Pro Val Arg Tyr Gly Thr Ser Phe Asn Gln Ala Lys Asp Asp Val Leu
                165                 170                 175

Cys Trp Arg Asp Phe Leu Lys Leu Val Cys Gln Pro Leu Gln Ala Val
            180                 185                 190

Leu Pro Tyr Trp Pro Gln Pro Ala Asp Leu Arg Asp Val Ala Thr
        195                 200                 205

Arg Tyr Ala Thr Ala Ser His Arg Leu Phe Met Glu Val Met Glu Ala
210                 215                 220

Ala Leu Glu Ala Leu Gly Ile Pro Thr Ala Gly Gly Val Leu Gly Glu
225                 230                 235                 240

Leu Ala Ala Ser Ser Ser His Met Met Thr Val Asn Cys Tyr Pro Ala
                245                 250                 255

Cys Pro Gln Pro Glu Leu Thr Leu Gly Met Pro Ser His Ser Asp Tyr
            260                 265                 270

Gly Leu Phe Thr Phe Val Leu Gln Asp His Val Glu Gly Leu Gln Val
        275                 280                 285

Met His Asp Gly Arg Trp Leu Thr Ile Asp Pro Ile Pro Gly Ser Phe
290                 295                 300

Val Val Asn Val Gly Asp His Leu Glu Ile Tyr Ser Asn Gly Arg Tyr
305                 310                 315                 320

Lys Ser Ala Leu His Arg Val His Val Asn Ser Thr Arg Pro Arg Ile
                325                 330                 335

Ser Val Ala Ser Phe His Ser Leu Pro Ala Glu Arg Val Ile Gly Pro
            340                 345                 350

Ala Pro Glu Leu Val Asp Asp Glu Ala Gly Asn Pro Arg Arg Tyr Met
        355                 360                 365

Asp Thr Asp Phe Ala Thr Phe Leu Ala Tyr Leu Ala Ser Ala Asp Gly
370                 375                 380

Lys Asn Lys Thr Phe Leu Gln Ser Arg Lys Leu Pro Ala Ala Ala Pro
```

385         390         395         400
Pro Cys Leu

<210> SEQ ID NO 28
<211> LENGTH: 1863
<212> TYPE: DNA
<213> ORGANISM: Zea mays

<400> SEQUENCE: 28

| | | | | | |
|---|---|---|---|---|---|
| tgccaccata | ccactagtgc | aaggtcctag | atttacactt | ggtgctacac | cttgcttcgc | 60 |
| cccctteett | ccttccttcc | ttccttccct | ccttccttgg | tctctaggca | gctagcagtg | 120 |
| tggtgctgct | gccggccgcc | tattggccgc | ctgggactgg | gatccattaa | ttactgcgcg | 180 |
| cgcgcggcta | accaaccaat | cccagcgtgc | gtaatctatt | gcccacatgc | cgacgccgtc | 240 |
| gcacctcaac | aagaacccgc | gctacctgga | cttccgggcg | gcgcggcggg | tgccggagtc | 300 |
| gcacgcctgg | ccgggcctgc | acgaccaccc | cgtcgtggac | ggcggcgcgc | cgggccccga | 360 |
| cgccgtgccg | gtggtggacc | tgggcgccgc | ggacccggcg | ccggcgccgg | cggcggcggt | 420 |
| ggcccgcgcc | gccgagcaat | ggggcgcgtt | cctgctcacg | gccacggcg | tcccgcgga | 480 |
| cctgctggcg | cgcgtggagg | accggatcgc | caccatgttc | gcgctgccgg | ccgacgacaa | 540 |
| gatgcgcgcc | gtgcgcgggc | ccggcgacgc | ctgcggctac | ggctccccgc | ccatctcctc | 600 |
| cttcttctcc | aagtgcatgt | ggtccgaggg | ctacaccttc | tcgccggcct | ccctccgcgc | 660 |
| cgacctccgc | aagctctggc | ccaaggccgg | cgacgactac | accagcttct | gtgatgtgat | 720 |
| ggaggagttc | cacaagcaca | tgcgcgccct | cgcggacaag | ctgctggagc | tgttcctcat | 780 |
| ggcgctgggg | ctcaccgacg | agcaggccag | cgccgtcgag | gccgagcgga | ggatcgccga | 840 |
| gacgatgacc | gccaccatgc | atctcaactg | gtacccgagg | tgcccggacc | cgcggcgcgc | 900 |
| gctggggctg | atcgcgcaca | ccgactcggg | cttcttcacc | ttcgtgatgc | agagcctcgt | 960 |
| gcccgggctg | cagctcttcc | gccacgcccc | ggaccggtgg | gtggcggtgc | cggccgtgcc | 1020 |
| gggcgccttc | gtcgtcaacg | tgggcgacct | cttccacatc | ctcaccaacg | gccggttcca | 1080 |
| cagcgtgtac | caccgcgccg | tcgtgaaccg | ggacctcgac | aggatctcgc | tcggctactt | 1140 |
| cctcggcccg | ccgccgcacg | ccaaggtggc | gccgctgcgc | gaggccgtgc | cgcccggccg | 1200 |
| ggcccccgcg | taccgcgccg | tcacgtggcc | cgagtacatg | ggcgtccgca | agaaggcctt | 1260 |
| caccaccggc | gcctccgcgc | tcaagatggt | cgccctcgcc | gccgccgccg | acctcgacga | 1320 |
| cgacggcgac | gccgccgtcg | tccatcagca | gcagcagcta | gtcgtctcgt | cgtagccgag | 1380 |
| accgatcgcc | ggagactgat | gctgatgatg | atgcatatat | acatgagaga | aatcgtcgag | 1440 |
| tagactagcc | gattgcaaaa | gcaaccccag | ctgccgaaac | ctggcatatc | gatcccattc | 1500 |
| tctgctgcgc | acatgtatgc | atgcatgcgc | ttcgtccgtt | cgactcgtgt | gtgcttgctt | 1560 |
| gcttgcgcgt | gcagcagaac | taattccgtt | ccgcagctag | ctgctctgct | ctgctctgct | 1620 |
| ggaatgtaat | taagtagtag | tatatggtag | tagagaaaag | attagctagg | cgatcgatat | 1680 |
| agatgacggg | ccggggaaga | agacgaatta | attaagatcg | atcgacgacg | acgagctgtg | 1740 |
| cgtggctggc | tgtgttcttc | tctagcctag | ttacagaggc | cggctgctgc | tgcttccaat | 1800 |
| cgggctgctt | gtcgctactg | acgatcgtta | gtggatccat | taactaatct | ggaattctgg | 1860 |
| att | | | | | | 1863 |

<210> SEQ ID NO 29
<211> LENGTH: 1149

<212> TYPE: DNA
<213> ORGANISM: Zea mays

<400> SEQUENCE: 29

```
atgccgacgc cgtcgcacct caacaagaac ccgcgctacc tggacttccg ggcggcgcgg      60
cgggtgccgg agtcgcacgc ctggccgggc ctgcacgacc ccccgtcgt ggacggcggc     120
gcgccgggcc ccgacgccgt gccggtggtg gacctgggcg ccgcggaccc ggcgccggcg     180
ccggcggcgg cggtggcccg cgccgccgag caatggggcg cgttcctgct cacgggccac     240
ggcgtccccg cggacctgct ggcgcgcgtg gaggaccgga tcgccaccat gttcgcgctg     300
ccggccgacg acaagatgcg cgccgtgcgc gggcccggcg acgcctgcgg ctacggctcc     360
ccgcccatct cctccttctt ctccaagtgc atgtggtccg agggctacac cttctcgccg     420
gcctccctcc gcgccgacct ccgcaagctc tggcccaagg ccggcgacga ctacaccagc     480
ttctgtgatg tgatggagga gttccacaag cacatgcgcg ccctcgcgga caagctgctg     540
gagctgttcc tcatggcgct ggggctcacc gacgagcagg ccagcgccgt cgaggccgag     600
cggaggatcg ccgagacgat gaccgccacc atgcatctca actggtaccc gaggtgcccg     660
gacccgcggc gcgcgctggg gctgatcgcg cacaccgact cgggcttctt caccttcgtg     720
atgcagagcc tcgtgcccgg gctgcagctc ttccgccacg ccccggaccg gtgggtggcg     780
gtgccggccg tgccgggcgc cttcgtcgtc aacgtgggcg acctcttcca catcctcacc     840
aacggccggt tccacagcgt gtaccaccgc gccgtcgtga accgggacct cgacaggatc     900
tcgctcggct acttcctcgg cccgccgccg cacgccaagg tggcgccgct cgcgcgaggcc     960
gtgccgcccg gcgggccccc cgcgtaccgc gccgtcacgt ggcccgagta catgggcgtc    1020
cgcaagaagg ccttcaccac cggcgcctcc gcgctcaaga tggtcgccct cgccgccgcc    1080
gccgacctcg acgacgacgg cgacgccgcc gtcgtccatc agcagcagca gctagtcgtc    1140
tcgtcgtag                                                             1149
```

<210> SEQ ID NO 30
<211> LENGTH: 382
<212> TYPE: PRT
<213> ORGANISM: Zea mays

<400> SEQUENCE: 30

```
Met Pro Thr Pro Ser His Leu Asn Lys Asn Pro Arg Tyr Leu Asp Phe
 1               5                  10                  15

Arg Ala Ala Arg Arg Val Pro Glu Ser His Ala Trp Pro Gly Leu His
             20                  25                  30

Asp His Pro Val Val Asp Gly Gly Ala Pro Gly Pro Asp Ala Val Pro
         35                  40                  45

Val Val Asp Leu Gly Ala Ala Asp Pro Ala Pro Ala Ala Ala
     50                  55                  60

Val Ala Arg Ala Ala Glu Gln Trp Gly Ala Phe Leu Leu Thr Gly His
 65                  70                  75                  80

Gly Val Pro Ala Asp Leu Leu Ala Arg Val Glu Asp Arg Ile Ala Thr
                 85                  90                  95

Met Phe Ala Leu Pro Ala Asp Asp Lys Met Arg Ala Val Arg Gly Pro
            100                 105                 110

Gly Asp Ala Cys Gly Tyr Gly Ser Pro Pro Ile Ser Ser Phe Phe Ser
        115                 120                 125

Lys Cys Met Trp Ser Glu Gly Tyr Thr Phe Ser Pro Ala Ser Leu Arg
    130                 135                 140
```

```
Ala Asp Leu Arg Lys Leu Trp Pro Lys Ala Gly Asp Tyr Thr Ser
145                 150                 155                 160

Phe Cys Asp Val Met Glu Glu Phe His Lys His Met Arg Ala Leu Ala
                165                 170                 175

Asp Lys Leu Leu Glu Leu Phe Leu Met Ala Leu Gly Leu Thr Asp Glu
            180                 185                 190

Gln Ala Ser Ala Val Glu Ala Glu Arg Arg Ile Ala Glu Thr Met Thr
        195                 200                 205

Ala Thr Met His Leu Asn Trp Tyr Pro Arg Cys Pro Asp Pro Arg Arg
210                 215                 220

Ala Leu Gly Leu Ile Ala His Thr Asp Ser Gly Phe Phe Thr Phe Val
225                 230                 235                 240

Met Gln Ser Leu Val Pro Gly Leu Gln Leu Phe Arg His Ala Pro Asp
                245                 250                 255

Arg Trp Val Ala Val Pro Ala Val Pro Gly Ala Phe Val Val Asn Val
                260                 265                 270

Gly Asp Leu Phe His Ile Leu Thr Asn Gly Arg Phe His Ser Val Tyr
            275                 280                 285

His Arg Ala Val Val Asn Arg Asp Leu Asp Arg Ile Ser Leu Gly Tyr
        290                 295                 300

Phe Leu Gly Pro Pro His Ala Lys Val Ala Pro Leu Arg Glu Ala
305                 310                 315                 320

Val Pro Pro Gly Arg Ala Pro Ala Tyr Arg Ala Val Thr Trp Pro Glu
                325                 330                 335

Tyr Met Gly Val Arg Lys Lys Ala Phe Thr Thr Gly Ala Ser Ala Leu
                340                 345                 350

Lys Met Val Ala Leu Ala Ala Ala Asp Leu Asp Asp Asp Gly Asp
            355                 360                 365

Ala Ala Val Val His Gln Gln Gln Leu Val Val Ser Ser
            370                 375                 380

<210> SEQ ID NO 31
<211> LENGTH: 1439
<212> TYPE: DNA
<213> ORGANISM: Zea mays

<400> SEQUENCE: 31
gacctccatt ttgattatct ctatcctgta cgtgccgaga gtccttcaaa gccgacgacg      60
agacgacgat gcagtcgtcg tcgtcatcag cctcgacgcc ggctgccgct tccggcctcg     120
tcttcgatct cgggtctgcg gcgggcgtgc cggagacaca cgcgtggccg ggggtgaacg     180
agtaccgtcg gtggagtcc gctggccgcg acgtggtccc ggtggtggac atggggggtgg    240 cctgcccgga cgcgacgcgg gcgttggcgc gcgccgcaga cgagtggggc gtgtttctgc     300
tcgtcggcca cggcgtgccc cgggaagtgg cggcgcgtgc cgaggagcag gtcgcgcgcc     360
tgttcgtgct cccggctcct gacaaggccc gcgcggggcg ccgccccggg gagcccacgg     420
ccaccggcta cggcaggccg cccctggcac tccgcttctc caagctcatg tggtccgagg     480
ggtacacgtt ccgcgccgcc accgtccgcg aagagttccg ccgcgtctgg cccgacggcg     540
gcgacgacta cctccgcttc tgcgacgtga tggaggagta cgacagagag atgagggctc     600
tcggtggcag gctgctcgac ctcttcttca tggcgctcgg cctcaccgac gtccagttcg     660
ccaccggcga gacggagcgg aggatccgcg agacctggac ggcgacgatg cacccaatcc     720
tgtgtccgga accggagcgc gccatcgggc tgacggcgca cacggactcg ggcttcatca     780
```

```
cgctcatcat gcagagcccc gtgcccgggc tgcagctgct ccgccgcggg ccggaccggt    840
gggtgacggt gccggcgccg ccgggcgcgc tcatcgtcat gctcggcgac ctgttccagg    900
tgctcacgaa cggccgcttc cggagcccta ccaccgcgc cgtcgtaagc cgagagcgcg    960
agcggatctc cgtgccctac ttcctctgcc cgccggagga catgacgtg gcgccgctcg   1020 cgtccgctct gctgccgggg aggaaggccg tgttccgggc cgtgacgtgg ccagagtaca   1080
tggaggtcaa gcacaaggtg ttcggcacg atgcgccggc cctggagatg ctgcagctgc   1140
aggtggatga ggaagaacaa ggtgaaaggg ccgccaccac ctaagcccta aggaactact   1200
agctgaatcc ataaactaat aaagaattcg tgaataaggg cgttggaaga ctggacacaa   1260
cacaagagag ttgctatata tcgtatttct gaaatttaag gcaaatatct tagttaaaaa   1320
actggtatat ttaaatagac aatatatatc taaaataaag atagttcacc attttttacgg   1380 tcgaacaatg ataaagttat atattgtctg aatagtaaca aattaaagat ttccaggag    1439

<210> SEQ ID NO 32
<211> LENGTH: 1116
<212> TYPE: DNA
<213> ORGANISM: Zea mays

<400> SEQUENCE: 32
atgcagtcgt cgtcgtcatc agcctcgacg ccggctgccg cttccggcct cgtcttcgat     60
ctcgggtctg cggcgggcgt gccggagaca cacgcgtggc cggggggtgaa cgagtacccg    120 tcggtggagt ccgctggccg cgacgtggtc ccggtggtgg acatgggggt ggcctgcccg    180
gacgcgacgc gggcgttggc gcgcgccgca gacgagtggg gcgtgtttct gctcgtcggc    240
cacggcgtgc cccgggaagt ggcggcgcgt gccgaggagc aggtcgcgcg cctgttcgtg    300 ctccccggctc ctgacaaggc ccgcgcgggg cgccgccccg gggagcccac ggccaccggc    360
tacggcaggc cgccccctggc actccgcttc tccaagctca tgtggtccga ggggtacacg    420
ttccgcgccg ccaccgtccg cgaagagttc cgccgcgtct ggcccgacgg cggcgacgac    480
tacctccgct tctgcgacgt gatggaggag tacgacagag agatgagggc tctcggtggc    540
aggctgctcg acctcttctt catggcgctc ggcctcaccg acgtccagtt cgccaccggc    600
gagacggagc ggaggatccg cgagacctgg acggcgacga tgcacccaat cctgtgtccg    660
gaaccggagc gcgccatcgg gctgacggcg cacacggact cgggcttcat cacgctcatc    720
atgcagagcc ccgtgcccgg gctgcagctg ctccgccgcg ggccggaccg gtgggtgacg    780
gtgccggcgc gccgggcgc gctcatcgtc atgctcggcg acctgttcca ggtgctcacg    840
aacggccgct tccggagccc tatccaccgc gccgtcgtaa gccgagagcg cgagcggatc    900
tccgtgccct acttcctctg cccgccggag gacatgacgt ggcgccgct cgcgtccgct    960 ctgctgccgg ggaggaaggc cgtgttccgg gccgtgacgt ggccagagta catggaggtc   1020
aagcacaagg tgttcggcac ggatgcgccg gccctggaga tgctgcagct gcaggtggat   1080
gaggaagaac aaggtgaaag gccgccacc acctaa                              1116

<210> SEQ ID NO 33
<211> LENGTH: 371
<212> TYPE: PRT
<213> ORGANISM: Zea mays

<400> SEQUENCE: 33

Met Gln Ser Ser Ser Ser Ser Ala Ser Thr Pro Ala Ala Ala Ser Gly
1               5                   10                  15
```

Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
        35                  40                  45

Val Val Pro Val Val Asp Met Gly Val Ala Cys Pro Asp Ala Thr Arg
50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
                85                  90                  95

Arg Leu Phe Val Leu Pro Ala Pro Asp Lys Ala Arg Ala Gly Arg Arg
            100                 105                 110

Pro Gly Glu Pro Thr Ala Thr Gly Tyr Gly Arg Pro Pro Leu Ala Leu
        115                 120                 125

Arg Phe Ser Lys Leu Met Trp Ser Glu Gly Tyr Thr Phe Arg Ala Ala
    130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Asp Arg Glu Met Arg
                165                 170                 175

Ala Leu Gly Gly Arg Leu Leu Asp Leu Phe Phe Met Ala Leu Gly Leu
            180                 185                 190

Thr Asp Val Gln Phe Ala Thr Gly Glu Thr Glu Arg Arg Ile Arg Glu
        195                 200                 205

Thr Trp Thr Ala Thr Met His Pro Ile Leu Cys Pro Glu Pro Glu Arg
    210                 215                 220

Ala Ile Gly Leu Thr Ala His Thr Asp Ser Gly Phe Ile Thr Leu Ile
225                 230                 235                 240

Met Gln Ser Pro Val Pro Gly Leu Gln Leu Leu Arg Arg Gly Pro Asp
                245                 250                 255

Arg Trp Val Thr Val Pro Ala Pro Pro Gly Ala Leu Ile Val Met Leu
            260                 265                 270

Gly Asp Leu Phe Gln Val Leu Thr Asn Gly Arg Phe Arg Ser Pro Ile
        275                 280                 285

His Arg Ala Val Val Ser Arg Glu Arg Glu Arg Ile Ser Val Pro Tyr
    290                 295                 300

Phe Leu Cys Pro Pro Glu Asp Met Thr Val Ala Pro Leu Ala Ser Ala
305                 310                 315                 320

Leu Leu Pro Gly Arg Lys Ala Val Phe Arg Ala Val Thr Trp Pro Glu
                325                 330                 335

Tyr Met Glu Val Lys His Lys Val Phe Gly Thr Asp Ala Pro Ala Leu
            340                 345                 350

Glu Met Leu Gln Leu Gln Val Asp Glu Glu Gln Gly Glu Arg Ala
        355                 360                 365

Ala Thr Thr
    370

<210> SEQ ID NO 34
<211> LENGTH: 4095
<212> TYPE: DNA
<213> ORGANISM: Zea mays

<400> SEQUENCE: 34
taaatttgtg atccttgtga agttgttata tcatgaattg tgaacttgtt gcatttgtga      60

```
tcttttgtca actttgttgt attgtgaagt tgatatgtt taccgatcgt attttagatt      120
tcgatcgtta ccggtgtatt ttccgcacca aactttttgtt tccgatgttt tcgaaatacc    180
gatatcgttt ccgttctat agttaccctt tcaatttta tttccgatta aaaatatgaa      240
aacggtaatg gttttagtgt ttatcgaccg ttttcatctc taatcatccc tgccggtgaa    300 gtttaattt tcccttggct aaagagatgc aagctgctgt aaaatacgtt aaaacaggca    360
aggcagcccc agcagccagc atcgcgtgcc cgtctatgta catcagtgga tacgtagcat    420
ctctagtgag taatataacg attgcatttg gctggaggac gtatgttata taagtatgtc    480
atttaccagt tgcattagta tcttccctaa ctcctataat aactctcttc gtggaatgga    540
cgtagacgta tgctatataa gtattaaaaa atagtttttt aagctggtgt cctcaatttt    600
gctattgttc tcgtttttat ctttagttgt gtcacaaatt taatccgtac aacaaatcaa    660
aaataccata cccttcttat attaattttc taacataaca tttgtttaga tattttcagt    720
cgtgaaaata caattctaat tctaacgtcg tagtatcaaa tcaaaccatc cagaatttga    780
ccaagcttaa ttataaaaaa tataaaattt atgatactga atagatagca ttagatttgt    840
tatataatat attttataa aataccattt ttatggtata aatattggta ctcctttact    900
ttaaactata gatagttttg actaaggatg caactagaat tgcatcctct tttcactgca    960
ccttcattag ttttaatatt tatttagatg ggcccttgca aactgtagat atcatctctt   1020
gcaacattct ttctatagca ccacgaaaat gtattgcggc tttgaaatta taattgaatt   1080
agttgtatca tttctttcac cgatgcgtta aattcaaaat taagtgttat atttcttcat   1140
aatttgttaa atatatagac cctataatcc accattattt actataatag catacattaa   1200
cattggtttt agcctacact acgacactcg aggcattgaa ttttcctcta tcaaagaatt   1260
atatgtgtag tagtattgtt cttgacaaaa aggggatta aaattaaact accaatattg   1320
atacttatct tatcacatcc atgaatacaa tcaacactct tacaaaagat aagatacaag   1380
attaaaaagt accatgataa tacattaaga ttattagcaa tgcattaaat taaataaatg   1440
tgcaagtgaa tcatgatttt agttttatct attttacttt taaaatatga tattctctga   1500
ctacttctaa gcataaatgt gattctaagt catgaccgat cgtgcttatt cagaaaaatg   1560
aaggagacac agatttctat aaaaaaaggt tgtcatggga ctattgggtc aaccatctta   1620
ttcatttggg aaaataagtt tagaacacat caacccattt tagatgttga gtttggccct   1680
aatggtccat tgaccttact tttgtgggtt gacatagacc atctatccca agttattgtt   1740
gtgtcacatt ccctgatatc atgaatctat atttagctt tccgttttca tatttttagt   1800
cgttacatat ttttatccg cgtactagat taaaactcta gttgttgcaa tacattttgt   1860 tcatttttt ctatttcttc tttactaaca acatattcta gttcctagct acattcttaa   1920
gtaccatagt gctataaaca tttttatcc tacattattc cacttaagaa attgaatttt   1980
ctgcataaaa aaattatatg tccagtagtg ttgtcttata aaagcataaa gtgattaaaa   2040 ttaaaccat tattgatatc ttatttttca aaaaaaaata taagcttata gaaagtgaat   2100
taatttcatg gtaaattaat atagtttaaa ttgaattatt agtgttatta ctatgtttat   2160
tatcaatgaa acatttttca tggttgatat aacttagtgt tacttatttt agtatttttt   2220
atataattct agttaacttt tagttttga tttaaaaaaa cgagaattgt gtccttttgt   2280
ggagtgagta taaagaaagt aatatctgtt catcataatt tggttttta aggtacgtga   2340 aacttgcttt atatttggac tcaagctatg tctaaataca tagtaaaaaa gcaatatttc   2400
```

```
tagaaaagac aaaacatctt ataatttaga atcaaggaaa tatatagatt ttatgtgcag    2460
tgagaagcca tttacaatgg aacgttcaac gttgggccaa tagatatttt gcgatatgat    2520
gatgggcata tttttgcatg gttgtccctc cactagctat agtttgatga tacgatacgc    2580
tgcacacacc attgggttgt accatgttag tgtagcaaca gtagaaaccc aattgtggcc    2640
gtgaaccatg ataatactag gtagagtgct agctagaggt ttcaggctat tgatgcgtga    2700
attaaacttt ctgttgtgtt gcgaggaaac gagtattgtg aaatatttga aacggttttt    2760
tttgtgaaag atttgaaacg gtattttgt tgtgaaataa agatcaaggc taaataaatt    2820
caaactaata aaacatatta attgacggcc tgaagccccc gccccatgg ccccatgcca    2880 tagcatcagg tcccacatga catgaggccg cgcctccctc tatgttggct ccctgccttc    2940
gccgttgtcg tcgctcccga actccctctc ctcccctgtt acaaataccc ccacccgccc    3000
ggacagcttc cctgcacact cgcagctcgc acatctcatg gtgtcctaag aacggcaaga    3060
gccagctctg cctagcagca gcgcacagcc acatccatgg acgccagccc gaccccaccg    3120
ctccccctcc gcgccccaac tcccagcatt gacctccccg ctggcaagga cagggccgac    3180
gcggcggcta acaaggccgc ggctgtgttc gacctgcgcc gggagcccaa gatcccggag    3240
ccattcctgt ggccgcacga agaggcgcgg ccgacctcgg ccgcggagct ggaggtgccg    3300
gtggtggacg tgggcgtgct gcgcaatggc gacggcgcgg ggctccgccg cgccgcggcg    3360
caagtggcgc cggcgtgcgc gacgcacggg ttcttccagg tgtgcgggca cggcgtggac    3420
gcggcgctgg ggcgcgccgc gctggacggc gccagcgact tcttccggct gccgctggct    3480
gagaagcagc gggcccggcg cgtccccggc accgtgtccg ggtacacgag cgcgcacgcc    3540
gaccggttcg cgtccaagct cccctggaag gagaccctgt ccttcggctt ccacgacggc    3600
gccgcggcgc ccgtcgtcgt ggactacttc accggcaccc tcggccaaga tttcgagcca    3660
gtggggtgag taaagaagaa gatggcgccg aatttacatt tataagtagg accagcagaa    3720 gccccctgccc ctgggggcct tagcattgca ttcgactgat gaatacgcat ggcaggcggg    3780
tgtaccagag gtactgcgag gagatgaagg agctgtcgct gacgatcatg gagctgctgg    3840
agctgagcct gggcgtggag cgcggctact accgggagtt cttcgaggac agccgctcca    3900
tcatgcggtg caactactac ccgccgtgcc cggtgccgga gcgcacgctg gcacgggcc    3960 cgcactgcga ccccacggcg ctgaccatcc tcctgcagga cgacgtcggc gggctggagg    4020
tcctggtgga cggcgagtgg cgccccgtcc ggcccgtccc aggcgccatg gtcatcaaca    4080
tcggcgacac cttca                                                     4095
```

<210> SEQ ID NO 35
<211> LENGTH: 7404
<212> TYPE: DNA
<213> ORGANISM: Zea mays

<400> SEQUENCE: 35

```
cctatttgt gtctaatact cttcttatat taattgtttg gtcaaacttt agataaattt     60
gactaatgat gcaattaaaa ctgcatcacc tttactaagg tactgcttta tatgtttcga    120
caaaattttc aattattctc tatgtgtttt aatctttgcg ctacacctcc attgatttaa    180
atactcattt attttaaacc ataacttaaa ttatatcgga tctttgcatc ctttctatgg    240
caccatacat gaatcgatat tttggctgca aattttttaat catgttagtt ttagcatttt    300
ttcatatcca tgtgttaagt ttgaatcatg tgttgttttt ataataattta ttgaaaatat    360 agatcctaaa cttcactaat acttacaaca atagcatcat catgtgtttt aatccacgcc    420
```

```
acaacactca aggcattgaa ttttcttcta ccaaagagtt gtatgtgtgt attgttcttt    480
aaaaaataga gtgattataa ttaaactacc agtattcata tgtaaaatgt atagacatct    540
aaaataaaat ttgcaaaaaa cattgttgca gactttcaat ataattaaga atgggttta    600 gggtcatgat atatggtttg ttaaagaaac ttgttttttt ttgcaattga taaactataa    660
aatacatttt cactattgtg tgcatatgta cttggtatac atagtggcat atatcatttt    720
tgtttacttt gaggtttgaa ttatctatgt taaaattgga taacatagat acattggtgt    780
gcgtcctttg gcccatttac ttgactgagg agcaatacta taaagtaaaa catatttgga    840
tattttatct taaactccta gcataatatt gatttaatta tgaacaaata tatgtttagg    900
tgatagtttc atgggtggta aactatataa gaaggcttac catgatcttt gcaaactcta    960
ggctatgaaa gagttccatg atttgtctta gaagcataga caaaacagtg ataatgatct   1020
aaatcacact tatggcactg atgaccatat atgcaaagct aaatgcatgt taagttgtat   1080
tatatcatat gttacaatg actatcgcat ataacgagga atacattgtc tatatagata   1140
gctattactg tagtagtgcc aaatgttgga caacatgaat cataatcttc aaacctagag   1200
aaattgtagt cagtcgtaca catatcgtct agtaagttgt ctatacttt tatttattgt   1260 atcaaatttt attgttatct tgcttgcttg tttgtttgta ccatagacac aatatggtca   1320
aaaagtggtc aatcgattcg aagaagattg caattgacga gtgctaacag ttgatccttt   1380
tgttgtgcac gctagcggag tagcatgaaa agagtaaaat atgaaattag cgttctaaac   1440
tgtttgtgct ataggtactt cgtatttaat ggagtgacta actataggaa ggtgagagct   1500
cagaagtcag caccctcaca cagagttcta gagttagtgg tcatcgaacc acgacaaact   1560
acatgatgag cagaagaggc aacatcaaga ctatgatcaa tagtttcggg tcaatgaatg   1620
acatcgtgat gagtatttat ctaactatat agaacaacaa cacatgatgt tttaagtaag   1680
ttcaactgat cttctattgc tatctttaag tatttaacgt agcgaataat gttttatcta   1740
tttcattcat aaataatgtt gtgacaaaag gggataacca tcacttttac catgttctag   1800
ataccacaac catctccacc atcataatgg gttcttcatt ggtgcttgga cctcaaataa   1860
tcatatctat agccaactta gctcaattct aataaaatta ggcaacttgg cttcattgta   1920
gcaaaaatag ccaacttagc tcaattttat ctaaacttag ctaatctagc acaacttaga   1980
tcaatattag gaaaaactaa tcaatctaat ctagctcaac tatagcgaaa gatagatatt   2040
gtagcataac ttagtagatc tatctcaaat tttagcaaaa actaatcaat ttagataaac   2100
tctataaaat tttaatcatt atgacttatt tccaactaat tgtaacttgc atgattttta   2160
tgttccttct ttataattag caacacctaa agacacgaat gatgaggggt ctaacgcatt   2220
cattaaccag ttgttaaata atactctagg tagatgataa gaactctaat tattctatga   2280
atctaagcta aaagatgttt aatatttaag tattggtgtt tattatgtta tttagaacga   2340
ttcatgttac ttaaagattt gttatgattt ttaaatatga ttatgataat ttatgtggtg   2400
tggattaact tgtgaacata tgtgatgtag atgaatatgt atgttgtgga tggaaccata   2460
tgaatatata tacacactca tatactattc gttggtgtag gtaaagcttc atccatcggt   2520
aattactaaa tggtcttcag tcattaccac taggtgaagc ttcacacgac cgataattat   2580
tgaagaacgc tcattaattt ccggtaatgg cttattggcc ttcactagtc ggtgaaaatt   2640
agctattttt ataccaataa aaattagcta atatatgtaa accaggtcta attttatgg    2700 gcctcttacc gaccaaaatt gattagatta ttgttacaat agttttagtc aaaagctagc   2760
```

```
tatgctataa aaattttgaa ttaaagtgag tttcgtaata aaaattgcat acttttaaaa    2820
taaaataatt aaaaaacagt ttttagaaat acaatcaaac accttatgct ataaaaaaat    2880
tgtaatgtac ctacaaatat ataatacttt actttaaaat aggcctgtgc cttctcggct    2940
ctatatgggc tgcctccaac gaagcgccat ggccatgggc tccactgtgt cgggtcccac    3000
atgaggccgc gcctccctcc aaatgttccc tccctgcctt cgtctttgtc gttgctcgca    3060
aactccctgt cctcccctgt tacaaatacc cccacccgcc cggacagctt ccctgcatac    3120
ttgcagctcg cacatctcat ggtgtcgcag gaacgacaag agccagctgt gcctagcagc    3180
agcagcagca gcgccaagcg cgcagccacg tccatggacg ccagcccggc cccgccgctc    3240
ctcctccgcg cccccactcc cagccccagc attgacctcc ccgctggcaa ggacaaggcc    3300
gacgcggcgg ccagcaaggc cggcgcggcc gtgttcgacc tgcgccggga gcccaagatc    3360
cccgcgccat tcctgtggcc gcaggaagag gcgcggccgt cctcggccgc ggagctggag    3420
gtgccgatgg tggacgtggg cgtgctgcgc aatggcgacc gcgcggggct gcggcgcgcc    3480
gcggcgcagg tggccgcggc gtgcgcgacg cacgggttct tccaggtgtg cgggcacggc    3540
gtggacgcgg cgctggggcg cgccgcgctg gacggcgcca gcgacttctt ccggctgccg    3600
ctcgccgaga agcagcgcgc ccggcgcgtc cccggcaccg tgtccgggta cacgagcgcg    3660
cacgccgacc ggttcgcggc caagctcccc tggaaggaga ccctgtcgtt cggctaccac    3720
gacggcgccg cgtcgcctgt cgtcgtggac tacttcgtcg gcaccctcgg ccaggatttc    3780
gagccaatgg ggtaagtaag gtagtaagaa ggagcgccgg tttacattta ccgcacgtcg    3840
gcgtgcggtc gagtcgggac tcgggagacg tatgaacccc cgtcccgtcc catgcatgtg    3900
tggcaggtgg gtgtaccaga ggtactgcga ggagatgaag gagctgtcgc tgacgatcat    3960
ggagctgctg gagctgagcc tgggcgtgga gctgcgcggc tactaccggg agttcttcga    4020
ggacagccgg tccatcatgc ggtgcaacta ctacccgccg tgcccggagc cggagcgcac    4080
gctgggcacg ggcccgcact gcgacccccac ggcgctcacc atcctcctgc aggacgacgt    4140
gggcgggctg gaggtgctgg tggacggtga gtggcgcccc gtccggcccg tcccgggcgc    4200
catggtcatc aacatcggcg acaccttcat ggtaacgaaa cgaaagcgct cgctcctctg    4260
ttttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacggggac gtggcgggga gacgatacga    4680
tgggtgccgg gcaggtttcc gaattccaaa cgttttgtg gcgtgcgtcc atggggcgcc    4740
cccaaacttc ggacgtttcc ggcgctccaa caaatcttct cgcttcacac gtcaccgtcg    4800
tcccggattc atttgcctcg tcgctccacc attcgctgct ctcctctcca cgtactctta    4860
ccctgacctt tgggaaagaa ctgaacattc gagatgcaca acagttcaaa tataacatat    4920
gcagcacaag atcgttcgac tgctatccga caagccaaca acgtgcccag tagaactgaa    4980
tgtacctgtg atttccagca ctaacttaca gcaacgttgt gaaaaaacaa aaacgaaaac    5040
aaacggcaga aaaaacagat gtattgttct acagttacac caaatatttt ctggtccttt    5100
cagcaccaac aagagccata cgcatatcta gaagacaaaa ttcctctaat ttcaccccta    5160
```

```
cgtggtagca gttcctcctc aacacagttc acgtgctagc gtcgagttct ttgggccgcc   5220
acatcgactt ctcgacgcag agcaggccct cgctgccctt ggtgtaggtc atccgcacct   5280
cccactgcac ggacttggcc atgctctcca gctcatttat cgtgtccgcg gtgtccctca   5340
cgatcagctt gccctgtggc ctcagtacac ggtcgacctc ggcgaaaact gcagccagtt   5400
tgcatctgta aacaggcaac acagattttt agtatctaaa acactgcagg caaacgccac   5460
aggttttagt cgcaagaagc aataaaagca tgcaaacaat gctacgtgta cgtatcaaag   5520
gaacatgtca aaactcgttg catgaacgat cattgatgtt tccttgctga actagtcaca   5580
tcagtctgct tcaacttctg ggtttcacta gtagatatac cagaagggta gaataatgtg   5640
aagagcaaga aatacagacc tctttctgag ctttgagaac agatggtccg cgtgcagaag   5700
gtcatacgtt cttgggtaag tgctgaaaga ctcgcaccag tcatggtaca tgccaaacaa   5760
accgcgctcg tagatgatgg gcagcgtgtc tggtgaatcg atcggcacga tattcatgac   5820
ccagaccttt tggtccctca gagctgcagc aaaactgcca tgcaacaatg taaagcatta   5880
gtcaagaaga aggtgtacag tgcatttctc cttgtcaaca gtcttcagta acaaaaaaaa   5940
agtgttatgc ttgactgaat ctttcaaaga aatatgcttg atgacttatg gtggacaagt   6000
tgcctgttat agtgttatgt tttaattaac tatgtgccag cttgggtaac tagtagttat   6060
gtagtgtgat ctgaattacc aaaatataaa taaataaata acatgcccca agaaactacg   6120
aaaaccattt acttaccctc catagacagc tctcatgtcc atgacatttc tcactttgga   6180
ccagtcaatt cccatgccat tcacatacga tttacttaca cccgtttcc agtgggcatt    6240 atctgcctca aaatcttcat ttgcaggctt tccatagaca ccaaccttgg aaccatcaat   6300
ccagaaaggg gtcttctcaa gcctttgcgg ccataactct ggccattttg atcctcggac   6360
ttttgagcca ccaggcagtt tgtgcatgca tgcttccaac ggtacattcc tgcaaatcaa   6420
aaggctgtgt aagcaaagca gagaagcact ttctctccat tgaaaatatac tcttctcaaa   6480 gaaccgaaac cataccaagc agcatctgca tcatcagatt ccttgcacaa tggcgggctg   6540
ttttcagatc ttttctcata gcaaatattg tccattggtt tctgatatat gaccatacca   6600
acttggttta acttatcctt agtcttgttg accatcttcc agcacatgga ctttgtcaaa   6660
gtagacatgg ctgaaaaggg tatgtggcca catgttatgt tagaaataaa attcaatttt   6720
gaacagttgg tccatagcat gtattttgaa caaatgcaat ccttctccat ccatgaaaga   6780
agttgaccct tcatacttag gattattcag tactttcact catgtctgct gaatttgttc   6840
tcttggtagt tgctatacaa gaaagggga agtacagagt agctaaactt atacaagcta    6900
tagtctgata tttgtatgaa acataaattt tggtatggat gtcttattaa aatgggaggt   6960
tgtataatat ttttctagcc tacctcaact tgcttgagac taaaaggctt tgttgttgtt   7020
gttgaggctg tatggtgctt tgactttaca aatcaagtta tcagctaccc tacttatgga   7080
tatacacctc tcataaaatg atggtaagaa gtttcgatat gtcacattaa cataagaact   7140
tcattcagtt agggtacaac gaagttaagt agttacggaa ataccattcc aaatctcaac   7200
atcctctggg agcttttggt aaacaggagt ggcagaccag acaaagtaac caccagggcg   7260
taacaagcgg ttcaattcca gcaaaagcat gccacctaaa agtagcgagc cagcaataag   7320
attcagttct atagcaaatc aataaatgaa aggaggacat gtcaatatgt aaccagcagg   7380
acaaaccttc gatgtgccaa ggga                                         7404
```

<210> SEQ ID NO 36

<211> LENGTH: 1788
<212> TYPE: DNA
<213> ORGANISM: Zea mays

<400> SEQUENCE: 36

```
aatcccagcg tgcgtaatct attgcccaca tgccgacgcc gtcgcacctc aacaagaacc      60
cgcgctacct ggacttccgg gcggcgcggc gggtgccgga gtcgcacgcc tggccgggcc     120
tgcacgacca ccccgtcgtg gacggcggcg cgccgggccc cgacgccgtg ccggtggtgg     180
acctgggcgc cgcggacccg gcgccggcgc cggcggcggc ggtggcccgc gccgccgagc     240
aatgggggcgc gttcctgctc acgggccacg gcgtccccgc ggacctgctg gcgcgcgtgg    300
aggaccggat cgccaccatg ttcgcgctgc cggccgacga caagatgcgc gccgtgcgcg     360
ggcccgcga cgcctgcggc tacgctcccc cgcccatctc ctccttcttc tccaagtgca      420
tgtggtccga gggctacacc ttctcgccgg cctccctccg cgccgacctc cgcaagctct     480
ggcccaaggc cggcgacgac tacaccagct tctggtacgt tgcgttgcgt gcttgtgtgc     540
gcgcacacct gccgaccgcg gccacaccgt acgcaaccca cgcgtacgta cgtgcgctag     600
ctacctgctt cgctcgcttc gctcctctcg cctcgccatg catatgcacg tacggccgta    660
caggtacagc agcaggtcac acgcacgaac gcacgcacgc accagcaccg atatgataca     720
tcatcgacgt gtcgtccccc cgtctaaggc catgcatgca tgcaagcacg cctagctagc     780
cctttttggct tgctagctga cgaggggagc taggacgagc atacttactg tgcgcgtcat    840
gctcaattgc tcacactata ctactacttg ttactacagt gatgtgatgg aggagttcca     900
caagcacatg cgcgcccctcg cggacaagct gctggagctg ttcctcatgg cgctggggct    960
caccgacgag caggccagcg ccgtcgaggc cgagcggagg atcgccgaga cgatgaccgc     1020
caccatgcat ctcaactggt gggtatatat tattgtctgt catgttgtcg tcgtcgtacg     1080
cgttgcggtt gggtgtacat gtatataaca caaacaacaa aaaactaacg ccgtgccgac     1140
gacgacgacg atcatcaggt acccgaggtg cccggaccsg cggcgcgcgc tggggctgat     1200
cgcgcacacc gactcgggct tcttcacctt cgtgatgcag agcctcgtgc ccgggctgca     1260
gctcttccgc cacgccccgg accggtgggt ggcggtgccg ccgtgccgg gcgccttcgt      1320
cgtcaacgtg ggcgacctct tccacatcct caccaacggc cggttccaca gcgtgtacca     1380
ccgcgccgtc gtgaaccggg acctcgacag gatctcgctc ggctacttcc tcggcccgcc     1440
gccgcacgcc aaggtggcgc cgctgcgcga ggccgtgccg cccggccggg ccccgcgta     1500
ccgcgccgtc acgtggcccg agtacatggg cgtccgcaag aaggccttca ccaccggcgc     1560
ctccgcgctc aagatggtcg ccctcgccgc cgccgccgac ctcgacgacg acggcgacgc     1620
cgccgtcgtc catcagcagc agcagctagt cgtctcgtcg tagccgagac cgatcgccgg     1680
agactgatgc tgatgatgat gcatatatac atgagagaaa tcgtcgagta gactagccga     1740
ttgcaaaagc aaccccagct gccgaaacct ggcatatcga tcccattc                 1788
```

<210> SEQ ID NO 37
<211> LENGTH: 1698
<212> TYPE: DNA
<213> ORGANISM: Zea mays

<400> SEQUENCE: 37

```
cgtgccgaga gtccttcaaa gccgacgacg agacgacgat gcagtcgtcg tcgtcatcag      60
cctcgacgcc ggctgccgct tccggcctcg tcttcgatct cgggtctgcg gcgggcgtgc     120
cggagacaca cgcgtggccg ggggtgaacg agtacccgtc ggtggagtcc gctggccgcg     180
```

```
acgtggtccc ggtggtggac atggggtgg cctgcccgga cgcgacgcgg gcgttggcgc    240
gcgccgcaga cgagtggggc gtgtttctgc tcgtcggcca cggcgtgccc cgggaagtgg    300
cggcgcgtgc cgaggagcag gtcgcgcgcc tgttcgtgct cccggctcct gacaaggccc    360
gcgcggggcg ccgccccggg gagcccacgg ccaccggcta cggcaggccg ccctggcac     420 tccgcttctc caagctcatg tggtccgagg ggtacacgtt ccgcgccgcc accgtccgcg    480
aagagttccg ccgcgtctgg cccgacggcg gcgacgacta cctccgcttc tggtacgtac    540
gagcgccatg tcacgtgctt gtgctttcat gcctcgtacc gtcgtcgtgc tgtacgtgtt    600
atgtttatcg gccggtacgt cacgcgtgct acactggtta acgacgtgag cgtgcccacg    660
ttgactgcat gcatgtgcat gcgcgcgccc agcgacgtga tggaggagta cgacagagag    720
atgagggctc tcggtggcag gctgctcgac ctcttcttca tggcgctcgg cctcaccgac    780
gtccagttcg ccaccggcga acggagcgg aggatccgcg agacctggac ggcgacgatg     840
cacccaatcc tgtacgtacg tcaaaaacga atatctgacc aatgcaaacg ttttctgca    900 atgccagtca tccactcatc ctgtacgtac ctctggactc tgcttgtcca tctactgatg    960
acacgtatgg taggtacccc aggtgtccgg aacggagcg cgccatcggg ctgacgcgc     1020 acacggactc gggcttcatc acgctcatca tgcagagccc cgtgcccggg ctgcagctgc    1080
tccgccgcgg gccggaccgg tgggtgacgg tgccggcgcc gccggcgcg ctcatcgtca     1140 tgctcggcga cctgttccag gtgctcacga acggccgctt ccggagccct atccaccgcg    1200
ccgtcgtaag ccgagagcgc gagcggatct ccgtgcccta cttcctctgc ccgccggagg    1260
acatgacggt ggcgccgctc gcgtccgctc tgctgccggg gaggaaggcc gtgttccggg    1320
ccgtgacgtg gccagagtac atggaggtca agcacaaggt gttcggcacg gatgcgccgg    1380
ccctggagat gctgcagctg caggtggatg aggaagaaca aggtgaaagg gccgccacca    1440
cctaagccct aaggaactac tagctgaatc cataaactaa taagaattc gtgaataagg     1500 gcgttggaag actggacaca acacaagaga gttgctatat atcgtatttc tgaaatttaa    1560
ggcaaatatc ttagttaaaa aactggtata tttaaataga caatatatat ctaaaataaa    1620
gatagttcac cattttacg gtcgaacaat gataagtta tatattgtct gaatagtaac      1680
aaattaaaga tttccagg                                                   1698
```

<210> SEQ ID NO 38
<211> LENGTH: 4095
<212> TYPE: DNA
<213> ORGANISM: Zea mays

<400> SEQUENCE: 38

```
cggtctaagt gaccgtttga gagaggaaaa gggttgaaag agaccccggtc tttgtgacca     60 cctcaacggg gagtaggttt ataagaaccg aacctcggta aaacgaatca ccgtgtcatc    120
cgccttattt gcttgtgatt tgttttcgcc ctctctttcg gactcgttta tatttctaac    180
gctaaccccg acttgtagtt gtgcttaaag tttgtaaatt tcagattcgc cctattcacc    240
ccctctaggc gactttcata taaatattgg gagaaatatg aaaacaaat gaaggtcgaa      300 cgagtcagag acaccataaa aaagaggtcg tcttaactag ggtgctaaac ctcaacattg    360
tagtagatct tagtactgag tttgacatct ttgacaccaa caagatggtg atacgttact    420
ttctacgtta acttgggtag gtatatcgac tatagtggcc tataacacta ggctatgtaa    480
tatgatattg tgttgagtct ttataaacat gatttttttt aaaaaaaaga gctaaaataa    540
```

```
aaaatagaaa tcgacggtac gatgcaagtt cttctcaaga caaccaaacg caccccttgcc      600 cctttattga aattgaagta tgtgctttat caaatgttta aatactaatt ataagtatta      660
aatataattt aattataata ctaattatat agataaagac taaataacaa gacaaattta      720
ttaaatataa ttaattcatt attaacaaat acttaatgta gcacgatcga atcatggact      780
aattagtctt gatagactcg tcttaccatt taatcataat tagttttgta tactgtttat      840
aatatttcta actagctagt attaaacttt tgatgtaacc taactaaagt ttagtcacgc      900
caatacataa ggactcggat cgttcgatca cccatgacat cacgtatact aagagcatct      960
ccaaaagctc tccagaagtc tcccctaaat ctattttttt gggaaaaaca caaaaacatg     1020
tctccaacag ttcccttaaa gcgcccccaa cttttttcata gcccttaaaa ctccctcatt     1080
tgtagctaca aatgaggggt tttttgggct ccccagaaac aaactgttga tttaagggat     1140
ctgttggaga aaggattaaa atttaccctc acttattatt tagatgtccc ttaaaactga     1200
ttttgaggag tcgttttatg tagagctctt ggagatgctc taacacaccg agcacaaccg     1260
catcatcaat caaaacaacc caaagtttgt tcggtacaag tcatcagcct gtgtacacac     1320
atcagcctcg gccccgggag aagcgctagc aaacaaggtt cacctaaaaa tccatccaga     1380
ttcattgaat ccaaccagca caaacgtccc atttattaat cacctcatca caggtccccc     1440
cagcctcact ctcgcgccgg ctcaaggtac attgcgtgtc ctagccaaga cacgcagctc     1500
atctcagcct cacacgcaca gcaagagcga ggcgtgattc gccatgggcg gcctcactat     1560
ggaccaggcc ttcgtgcagg cccccgagca ccgccccaag cccatcgtca ccgaggccac     1620
cggcatccct ctcatcgacc tctcgcctct ggccgccagc ggcggcgccg tggacgcgct     1680
ggccgccgag gtgggcgcgg cgagccggga ctggggcttc ttcgtggtcg tgggccacgg     1740
cgtgcccgca gagaccgtgg cgcgcgcgac ggaggcgcag cgagcgttct tcgcgctgcc     1800
ggcagagcgg aaggccgccg tgcggaggaa cgaggcggag ccgctcgggt actacgagtc     1860
ggagcacacc aagaacgtga gggactggaa ggaggtgtac gacctcgtgc cgcgcgagcc     1920
gccgccgccg gcagccgtgg ccgacggcga gcttgtgttc gataacaagt ggccccagga     1980
tctaccgggc ttcaggtgac gaaattaact atatatccct ttcgatcata gttgcgttaa     2040
taaattaagg gaatcgtgag cgtacgtacg taagtttccg cagagaggcg ctggaggagt     2100
acgcgaaagc gatggaagag ctggcgttca agctgctgga gctgatcgcc cggagcctga     2160
agctgaggcc cgaccggctg cacggcttct tcaaggacca gacgaccttc atccggctga     2220
accactaccc tccttgcccg agccccgacc tggccctcgg cgtggggcgg cacaaggacg     2280
ccggcgccct gaccatcctg taccaggacg acgtcggggg gctcgacgtc cggcggcgct     2340
ccgacggcga gtgggtccgc gtcaggcccg tgcccgactc gttcatcatc aacgtcggcg     2400
acctcatcca ggtacgtgcc cacctgatga actgagctga acgtaggttg catgcactgc     2460
atgtgtatag gcttctcaga tcgcttcgtg tggcgtaagg tgtggagcaa cgacaggtac     2520
gagagcgcgg agcaccgggt gtcggtgaac tcggcgaggg agaggttctc catgccctac     2580
ttcttcaacc cggcgaccta caccatggtg gagccggtgg aggagctggt gagcaaggac     2640
gatccgccca ggtacgacgc ctacaactgg ggcgacttct tcagcaccag gaagaacagc     2700
aacttcaaga agctcaacgt ggagaacatt cagatcgcgc atttcaagaa gagcctcgtc     2760
ctcgcctaac tactgctact gctaggatcc atgccattgc catgtcgtct tcagattcag     2820
agcacgccat gtcgtcgcta gcttcgtggt agaacaaata atgatgtgcg tgctgtgtgt     2880
aagcatggat atggatgtga atatgtaata tgatgagcac tcctactttg gtatgtttgg     2940
```

```
gaataacaga cttgtgttgg tctggttcat tatttgtaag aaaatcaaaa agagttagta    3000
gggcaggagg ctaaccacag tcatgctgca ccacatccct ggtggaaagc tggccgggtt    3060
acgctacgct cgtgcagcca gattactgca gggccgggat atgcttccgg tggaaggaag    3120
gggacggtgg ctgaggacca tggggctgga gcctgggaga gaggtcgagc tagaagaaag    3180
ggggagagag aagacgcaca acgaagatgg gtcagccagg gatttcgacc caaggggggag   3240 ctagtggatt ttgggagaaa acagaaaaga gaaaagagaa aagaagaaaa atttgttggt    3300
gtgaacacaa ggttgatttg tcttttctta tttggattga tgatgagtcg tggactaacc    3360
gacccgtgag ctattgtgtc gtataatcat gtctctcggt ttctggtgtg caggtttgaa    3420
gcacagagac ggtggtcgac gcaaaggtga acgtcatgca ggttcgtgcc gatggaccgg    3480
gagcagtgaa agacgagcgt tgggacttga caagggacc agagtcgccg gatgactagc     3540
cgcagtggct gacgcctgga acacgcatag acgtgaggac gtggtagagc aggtgaaaat    3600
cgcctagagg ggggggggt gaatagacaa aacctaaaaa ttataaactt tgaacacaaa     3660
cttaccctga ggttaccgtt agaacgagta ttaatgaaat cggagtgcgg aaggcaagtt    3720
cttcttgcta cgagttgctt aatcaatatt gataactttg ggagtcaact caaaatgatc    3780
acaagcaaaa gaactagaga gagaggagag gaagaatcaa ctcgcaaagt aatgatcaac    3840
acaaatgaac acaatgattt atttctcgag gtttggttcc gaagaaccta ctccccgttc    3900
aggagtccac ataggacatg tctctttcaa cccttctcct ctctcaaatg gtcacataga    3960
ctggttcagt tgagagcacc tagagggggg tgaataggtg atcttgtaaa atcaaacact    4020
aatagccaca aaacttagtt taaagtgtta gtacggctaa gtagctttga agcgagttat    4080
tgtgaacaca acaat                                                      4095
```

<210> SEQ ID NO 39
<211> LENGTH: 726
<212> TYPE: DNA
<213> ORGANISM: Rice tungro bacilliform virus

<400> SEQUENCE: 39

```
tcctacaaaa gggagtagta atatttaatg agcttgaagg aggatatcaa ctctctccaa      60
ggtttattgg agacctttat gctcatggtt ttattaaaca aataaacttc acaaccaagg    120
ttcctgaagg gctaccgcca atcatagcgg aaaaacttca agactataag ttccctggat    180
caaataccgt cttaatagaa cgagagattc ctcgctggaa cttcaatgaa atgaaaagag    240
aaacacagat gaggaccaac ttatatatct tcaagaatta tcgctgtttc tatggctatt    300
caccattaag gccatacgaa cctataactc ctgaagaatt tgggtttgat tactacagtt    360
gggaaaatat ggttgatgaa gacgaaggag aagttgtata catctccaag tatactaaga    420
ttatcaaagt cactaaagag catgcatggg cttggccaga acatgatgga gacacaatgt    480
cctgcaccac atcaatagaa gatgaatgga tccatcgtat ggacaatgct aaagaagct    540 ttatcaaaag caactttaag tacgaatcaa taaagaagga ccagaagata taaagcggga    600
acatcttcac atgctaccac atggctagca tctttacttt agcatctcta ttattgtaag    660
agtgtataat gaccagtgtg cccctggact ccagtatata aggagcacca gagtagtgta    720
atagat                                                                726
```

<210> SEQ ID NO 40
<211> LENGTH: 165
<212> TYPE: DNA

<213> ORGANISM: Rice tungro bacilliform virus

<400> SEQUENCE: 40

```
acgaatcaat aaagaaggac cagaagatat aaagctggaa catcttcaca tgctaccaca 60
tggctagcat ctttacttta gcatctctat tattgtaaga gtgtataatg accagtgtgc 120
ccctggactc cagtatataa ggagcaccag agtagtgtaa tagat 165

<210> SEQ ID NO 41
<211> LENGTH: 2000
<212> TYPE: DNA
<213> ORGANISM: Zea mays

<400> SEQUENCE: 41
ctgcaatata tacaccaaaa gtattataaa ctgtcatata tatgaccaaa accttttttat 60
tttagaaaag tatattaatc atggtatatt aatcaaagtt gttgttgggg ctgcaaaaat 120
cataccccttc ttccacaagc tgttccttga actgcaggta ctcaggaact ctcagctcct 180
caacagcgag ctcactgacg ttgaccctca catactccca gacaccaggc ctagggcgga 240
tggcaagtgc aacccatggg gggatgacaa tcgcctcctg taagataata gagctagaat 300
gattaaagaa ggtgcacact acaaaaggaa cagtgctgtc cagcgagatc tgaatctgat 360
gcaaacctga gctgccctca ggacatcctc aaaagcacca tccttgagct tctcgcgctc 420
agcctcaggg atcgcattgt tgtactcggc aatgatctgg tggggctgca gcataccctt 480
tccaaggttt ttcagcctgc gcaaaacgat gtgccaaata acatcagact atgccagatc 540
tataaactca tcaaacatat acaatttcaa gaaatagttt agacgtatga tcagcagtca 600
gtagcgtggg aacatatgca acatagcgaa gaggcacaac agcaaattca ttcgaaaaaa 660
tgaaaacaaa gattcctctc ttttaactga acttctcgaa accccctttca tgcctacaca 720
tccgatctag tcagatgcct atgcgttcat gctgaacaga acgtgtcaga actaagcata 780
aactggttag caagcattat cgtattcgat agacccttta gtaacaagct atacattggg 840
taagttcaga ctccaatcat tctgttcaga aacatcgtat tgaatataaa actaaagaac 900
acacatgcag gtgcagccag atctaacagc agtttacagt cggtactaaa aaaagcatgg 960
tgtatgtatg tatcatcagt atccagtact aggtttcgac aaaatcctgg atgctaatta 1020
aatactcatc ttattaggga acacaggaac attatgtcta cagcattgaa tgatggccac 1080
atcatgctag atctaacaat acataatatg atggaactgg tcttaaaaag tcgcattcgc 1140
tcaaataata cccgtagcaa aataaatgta aacttgcaga cgaagcgggg gaaatgaggg 1200
cagacctggt gaagacggcg acaagctcat tggggtgggc agagagtgag tcgccaatgc 1260
gctccctgac gctgtggagg cggctcagga cacggtcacc tgcaccttcc cccattgctg 1320
tcctcttcct ggatcctcag gcctgcacag cgaaaccgaa acggaagcgg aagcttcagt 1380
cagcagagaa aactgaaacc gaaaaacggt tcagatccgt tgacataaaa gctgcgatga 1440
catcctaaaa ctaaaacccc tccagcaaga cataaaccca actgccaaca accagtcttt 1500
taagtctcga cacacccttg acgctgcgcc acgaaactat attgcaggca agaaaccaac 1560
agaacctaac tctggaaggg gggaaagaaa cggcagacag gagcaagacc caaaaaaaaa 1620
cgactcagat cctggtacta tagtcctagt acctagacca gaaagaagaa acaaccaata 1680
caacaagagg catacaagaa ctgaatcgat gaactgaaac gcttcagagg accgaggaat 1740
ggcggagaag ggaggcgcct atttatacag atctgacgag agaaccgaac aaaaacacat 1800
cgatgggaac catggagaag aaaagggctg gccgcatggc accaatggcc tcggcctcca 1860
```

| | |
|---|---|
| aaaagccgtt gaatccaaag caggcgagga cgaagcgtga cgcggcaggg tacttctcta | 1920 |
| gaaaagcacg gcatcagcaa ggtgggggg ctggggttcc ttattgcagg caatcacgag | 1980 |
| gtgattagca caaacggaag | 2000 |

<210> SEQ ID NO 42
<211> LENGTH: 2000
<212> TYPE: DNA
<213> ORGANISM: Oryza sativa

<400> SEQUENCE: 42

| | |
|---|---|
| ctgaaatata catcagagat attacaatga catatatatc gataaaagaa aaataataaa | 60 |
| attaagtttt aaattttaag aatatatgtt tttagtatcc caattatgca gatttcatac | 120 |
| ccttcttcca caagctgttc cttgaactgc aagtactcgg ggactgtcag caactcaaca | 180 |
| gcgagctcgc tcacattgac cctcacatac tcccagacac cgggcctcgg gcggatggca | 240 |
| agggcaaccc atggggagat aacaatcccc tcctgcatga taaaaaacaa ttacaagtta | 300 |
| agttagagca agcggtagag taaagatgga tctctgtgat gcaatgaaat ctgaatctga | 360 |
| ttcaaacctg tgcactcctc aggacatcct caaaagcacc gtccttcagc ttctcacgat | 420 |
| cagcctcaga gattgcgttg ttgtactcag caatgatctg gtgggcctga agcattccct | 480 |
| ttccgaggtt aaccagcctg cgcaaataac agtgtcaaca aaaatatcag gccagatcta | 540 |
| tcaactcagc ctataaatat ctcaataaga taattttagc acttgagcat ttgcgcataa | 600 |
| taagaaaatt tgctattagc cacttaaaaa gaccatatat gatctgtttg cattgagatg | 660 |
| aattaaaaat ttcattgtag atatgaaatg attagttttg accatttaat tggacttaat | 720 |
| gaaatatgcg cgataatcag atctacgcgc tcgcgccaat agatctagta agatgtaggt | 780 |
| ttttttatttt ttttgtgaaa ctttgctacc acaacaagca tctgtaccag tgcagaattc | 840 |
| attacttgta ttcagtttgt aaaccgtata tataatataa ataacatgca catgcagtca | 900 |
| gatctagcac taccagtcca cagtaatcca aaactacatt tgtatatttc atcattattc | 960 |
| agtagtacta ggtttgtaca aaatcttggc tgcagaaggc cgcacttaaa tattcattct | 1020 |
| aatcagaaac ttaaaaaaaa agtgactaca aaatgattgc atccaattca gtaaatatga | 1080 |
| gccattcctg gccagatcta acaatctcaa caacaaagat cctatatgaa catctccttc | 1140 |
| taaaagaaaa tacagtaaca tctgaaggca gtagactaga aaccaacaaa atctaatgct | 1200 |
| gggaaatcac taaatcagca cgaacctggt gaagacggcg acgagctcat tggggtgggc | 1260 |
| ggagagggag tcgccgatgc gctccctgac gctgtggagg cggctcagga cgcggtcgcc | 1320 |
| ggcagcttcc cccattgctc tcctcttcct cttggctcct caagcctgcg tgcacaacca | 1380 |
| accaccatca tcagatacat ccagacccag tcaacacaat cactccagga aaaaaaaag | 1440 |
| tcaagccata accccaacc aaaaaccacg cctttgacaa acactggaag aaaaagaaaa | 1500 |
| tcgcagcttt ttcacaagca atctagaaga aagaaaaag aaaagactac atagcagcta | 1560 |
| taattgactg agaagcatac aggaatcaaa caatggagaa ggggagggag gaagaacaat | 1620 |
| gatgctccag gctgaggacc gaggaactgg gtgaagcggg gtaggcgcgt atttatgcag | 1680 |
| atctgaggag agaaaccacc aaaacaatcc gatggtttca acgaaaaaga tcgtcgcttc | 1740 |
| ttgctgcacc agctcacccca tagccgttga gatcgaagct aagctagcag cagcaaagct | 1800 |
| ggaacgaaga gtgacgcatt caagctcctc tcctctcctc tcctctcctc cggagcacga | 1860 |
| ggccagcatg ggatggattg gggtttcttg ttggccatgg caaaggagga ggtcattaac | 1920 |

```
gttgacacgg cgtaatttaa ttaaatctta tcttaaaata tgatttaagt ggtagtaaca    1980
aggaagatta atactatgaa                                                2000

<210> SEQ ID NO 43
<211> LENGTH: 2000
<212> TYPE: DNA
<213> ORGANISM: Oryza sativa

<400> SEQUENCE: 43
gctgtttaag aaaaacagaa gtaaaattca gtcactgtta ttttgcttca gttataatct      60
gcaaatcgtc gttctggtac ttactgtcca tcaacaagct gttccttgaa tgccaagtac     120
tcagaaacac tcagctcttc cactgccaac tcacttacat tcacccgaat gtagtcccag     180
acaccaggcc ttggcctgat ggccagtgca acccagggcg gcagcacaat ggcttcctac     240
atacagtcaa ggaagtaagt tagaaagact ggtatttgac tttgagttga ctatcataac     300
catcctggct cattgccaaa tttacctgag cagcccggag aatgtcttca aagggagcat     360
atttctcttt gtcagcttcg atcaaggcat cgaactccgc aagcagctgg tgacgctgga     420
gcattccctt tccctggtta acatacctgc atagagtgat atttaagaaa tagaaccaat     480
gcttagatct cacatccttt ctgcggctga actatgttaa tggcactacc acataaacct     540 gattttact  tcttattttt aagaccacat gatctgtact taatctagct atgaacaaac     600
aatatttcaa catcatctaa gattcatgac tcaagacaaa aatgttagag ctcatcacag     660
attattatag ataccatcat taaaactaaa gagatgcata accttgtcag ctaagaattt     720
gtaacatact aacatgttat cgtttcacat ctgggttgac taagaactaa ccaactgtat     780
ggataaaatc attgaaaact caaacaatt  agtagcaggt tccaagaaga cacaagatat     840
tatattgaga tcttcaccta gaagagtg   caatcaactc attgggatga gacgagaagg     900
tggcaccgag gcgttcgcgg agactgtgga ggcgagctag cttggcagcc atgactcaat     960
ttcaggaact gcaaagaaag gttacactta gcaacacgta ccaaaaccac tcacttgcac    1020
aagaataatt agtcaacagc catcactaag cattgcaaga ctatctctga acaggaaagc    1080
catgctaaat caaacactaat aacatcacac aaaagcattg gaagatcaaa acataactaa   1140
aaacagctgt ttcatctaca caactgaaag catctatggt ttacgaagca gagtgcgagt    1200
actgattcaa aataaatcaa cctgaaccaa tatactctga caatgttttc aaagggataa    1260
aagaaccagc tttatcaaat ggatttgttg ggttttagta agtatcattg agataccgat    1320
ggcatatctc aaactttgca aaattataat ggcatggttc caaattaccc tttagtatta    1380
gcaccagtta gatcctaatt cctaaatccg ataggacaga gcgaaagatc cctggagata    1440
tgaagatttg gctacagatt aagcagagcc aacatgaagt tccgaatatt atgaatccgc    1500
aagcggggag atcaaagaga agaatacgga aggtcgcgac tccatgaaag aatccaacca    1560
aaaacccaaa gatttttctc agttcaaaaa aaaaaaaccc ttcattttg gttcgccatc    1620 caccgacagg caccaagaca ttcctcagga agcaaaaaag attaagcaga acaagtgata    1680
agcaagacac agtatcaacg gactacgagt cgagaaaatc actgaggcgc gattcttact    1740
gcaccaagta aaaaaaaatt tgggggcaaa agaactctg  caatgggcg  gagcaacgtg    1800 gcagcaaaac taaggtcga  ggatttgagg ttttttgccg gttttcctcg aaaccccgaa    1860
tccgctcata gtaaacccac taaactgcag cagaaacccc cctcttggtt cagatttacc    1920
gaaagcagta aacccaagaa catgtcagca aaaactcctg caagattcag ctgacgaccc    1980
accaaagaat cgcaagaaat                                                2000
```

<210> SEQ ID NO 44
<211> LENGTH: 2000
<212> TYPE: DNA
<213> ORGANISM: Oryza sativa

<400> SEQUENCE: 44

```
tggcggacgc gccacgcaca aacacaaacc tgcacacccc tgtgtcagag gaggagaggc      60
caagaaagga aatcgagtgg aggaagtgag gagcggcgga gacgtaggag gaggagggg     120
agatggaaat ggaaagccgc gcgagagagg aggcgcgtgc tggatgggag gaggaggagg    180
aggtggtggg tttgtgtttg gagagacgag cgagagaggc gaagcattta agggaggaa     240
gaggggggaga gagagagaga gagagagaga gagagagaga gagagagaaa ggaggaatat   300
aataaagggt ggtgcacctg ccaactgcta tgctcaccaa cactttgtac acacccagtt    360
acacccccct gcctttatta tttccagtgc agtaataact tcaacaatta ttgaaatgaa    420
aatggaatta atggagttag tatcggatta gcgacacgct tgccgagctt ctagacggtg    480
cgattatttc agcgggaacg actttctgta ggtgaattta atagaggagt gtttttaaatc   540
cactcgacgt tgtaatagct ggtttaattc gtttgtactg tcgagtagtt atccaaaatc    600
aattttggat atttaaaaga aaaaaaaaca gatccgaagt attggaccta ctggcaaata    660
ggaattttgc tatatatagg tgtgcgttca tttataatgg agtagcatgg agttttatta    720
atccagtaaa tgttttcatt gatttaatta atataacgaa tttcgcttga ggccatattt    780
gttaaacgct tttatctcta tcatcattca tcctaccagt aaagagcacc ggagatcgca    840
cttcatttaa atatatgtcc atgttggata aaccatagtt tattatagtg ttctttata    900
tgttttgtgg ggaatttaga ttgtttaata tggcatacat atccatccat cattattata    960
ttctaacaca actggataag tgttctaaac tattgtagaa taactttgta gtatgatcga   1020
tcttgtggaa taaaaaaagt ctgacaataa cctttcataa aggaatatga ataccccgtaa   1080
tcaacgcatc aaatcattca cggtgtacgc ctagcgaatt cgttggcgag tgctcgtgcg   1140
gccgtgggct cgctgtgatg catgcatggc tctctggcta cgtcgagata gcgattagta   1200
gcaaaattaa gcaagccact tattaattaa tctttggaga tatcatatga ttaaggcatt   1260
aattcgtacg tactcgtcgt cagcgttttc tgcaaagtcc actacagttt tttctttctt   1320
tgctgaaaat gctgatgtgt tggagatgga gtgacgtgca caacctgccg ccacgtggat   1380
ggttgctgga gcctacgtgt catcttaatt tgaacaaaaa aaaagagga ataatacatc     1440
aatacatttt cgaatttcag ttctgccatt gaccagtaat acacatgtcg gcctcacatt   1500
ttaccctgat cttagtaacg ggtggtcgcc tggtcggtca ctgaaaaaag ttcaggaaat   1560
tatagtcaaa ctgaaacgaa catattcact ccttaaaaaa actaaatctt tttatatatt   1620
tgtgatattg taaaatagct acgggataat gatatagata tatatagtga taagggatag   1680
atggatcgag atatggagtt gtgctttctt taatttccac tacttgggct accatattat    1740
ggtagttggt atgaaaagat acacagcagt atagtgatgt gatcaatgac atgtatatct    1800
cacatgctcc catgttggag tcaaattttg ctagactaaa atccaattcc aagcagtccc    1860
tagccaagaa caaacaaaat tcagtgaggt cactgctgca ccaaggactg catgcatgca    1920
ggagaagggc atttctctct ttttcttttg gagactcgat tcaattcggt cggtcggtcg   1980
caatggtcag cttaattaaa                                               2000
```

<210> SEQ ID NO 45

<211> LENGTH: 2000
<212> TYPE: DNA
<213> ORGANISM: Oryza sativa

<400> SEQUENCE: 45

| | |
|---|---|
| tgtgaaaggt ggcggcacca gcttagccgc agcttctctc gtcgtctccc tgaaacgaga | 60 |
| gggaggaagt tggtagcgtg atatatttag gcatgtcatc tcttgtataa gaagtcttat | 120 |
| ctgtgctaat tcacacggtt ctctaatctc tctccattct gttttttgtaa attggttcag | 180 |
| tagatagcgt agggttatgc ttatatatac tccgtgaagt atatatttaa aaattagtca | 240 |
| cacgtaaagt actatacatg ttttatcgtc taataacaat aaaaacacta atcataaaat | 300 |
| tttttttaaat aatacgaatg gttaaacgtt gaatatgaac cgtgcaaaac tatatttatt | 360 |
| ttgtaacaga gaaatatttt cacattaatt agattgttgt tttatggaag gttggagagc | 420 |
| tgcgccgccg ttgcgcagac ctaggaggct gcttataagt tataatcaat caattcacgg | 480 |
| atgccggctg ggacgcggcc catcgtccgg gaagacgaca actcaacgca aaaagccgat | 540 |
| atgcctccaa attgccattg ccacctctac ggctgtttat actgctccaa atcaaaagcg | 600 |
| tccatggaag aatctagtat ttcccgcaaa gacgatgatg atatgcagga ttggatatat | 660 |
| aggggggttgt tgcatgattg ctagaactcc cgtttccgaa gttgttcgtc cattttttaaa | 720 |
| gctgccaaat aggaatttat tttgttttca agtgtaatag agttctgtcc agatgagtga | 780 |
| attataattt ggttcacatt ttatttgcta agtttcagtt tgaacattct caaataactt | 840 |
| ttttcttcac ttttttaaccg agtaacttag ttattttttc cgtttggacc acccaacaat | 900 |
| ttgttgctaa gtcatctca cccgtcaaat aattccttttg aatccaaatt caattatatc | 960 |
| ccaaaaataa aaaacttctg aattccacat caattcaaac cccaaccatt ttaatttctc | 1020 |
| tccatatttt ccatttctct attttttacct ttctcttttt tccatctatt tattttttttc | 1080 |
| cttttctatt tctttctttc tccttccttt ctctgtttcc ttcttcttct cctcggctag | 1140 |
| gcccgagcca gcccgtgccg cctcgcgcca acctgtgcc gccttacgcc gcgcttgcgt | 1200 |
| gcgctcgcgc ccacctcgtg cccaaccccgc gcacgccaca cgcacacacg aggacgatcg | 1260 |
| acggacgaat gcaatcatat ccccttcctt actcagctag aaggctcaag aaccgcaact | 1320 |
| tgatctctt ccaccctctc aaatccgccc caacccctgc tgactcaatc gccattaccg | 1380 |
| gaggaaaaat ccccgaaacc ctattaccgg cgccactaac agagctccaa aattcgtcgc | 1440 |
| ataattcgaa aatattctga aattgaaggt aaaaatggaa tctacatgcg aagtactccc | 1500 |
| tttcccctcc aatccgtcac tggaacgccg ccggcgccgc ctcccgctgc cactgccctg | 1560 |
| tttggccgcc gacagccgca cggcgcgccg ctgctccagg ccgccctagc ttcaaccacc | 1620 |
| gccacctttg gctccgcctc cctcctctta tgctcaccaa gcccgcctcc ctcgccggag | 1680 |
| atcgccggaa ccaccgccgc catggccgcc accgcctcct gcttctggcc gccgccgcca | 1740 |
| gcctcgccac cggcgccat gccaccgccg accacggaaa cggagtccct acaccttggg | 1800 |
| gaccacaaaa ccgcggcat ccctcccaaa accggcctcc tccaccgccg gcgttcgtgg | 1860 |
| gattccggcc agttctgtgc agagcgagag aagaagagga aaaatagatt ttcctattga | 1920 |
| aagataaatc agaaaattcc ttttttctttt cctatcaagt tgaccatccg tttgacctca | 1980 |
| aaatcaaaat ctgagaccta | 2000 |

<210> SEQ ID NO 46
<211> LENGTH: 786
<212> TYPE: DNA
<213> ORGANISM: Zea mays

<400> SEQUENCE: 46

```
gacatggagg tggaaggcct gacgtagata gagaagatgc tcttagcttt cattgtcttt      60
cttttgtagt catctgattt acctctctcg tttatacaac tggttttta aacactcctt      120
aacttttcaa attgtctctt tctttaccct agactagata attttaatgg tgattttgct     180
aatgtggcgc catgttagat agaggtaaaa tgaactagtt aaaagctcag agtgataaat     240
caggctctca aaaattcata aactgttttt taaatatcca aatattttta catggaaaat     300
aataaattt agtttagtat taaaaaattc agttgaatat agttttgtct tcaaaaatta     360
tgaaactgat cttaattatt tttccttaaa accgtgctct atctttgatg tctagtttga     420
gacgattata taattttttt tgtgcttaac tacgacgagc tgaagtacgt agaaatacta     480
gtggagtcgt gccgcgtgtg cctgtagcca ctcgtacgct acagcccaag cgctagagcc     540
caagaggccg gaggtggaag gcgtcgcggc actatagcca ctcgccgcaa gagcccaaga    600
gaccggagct ggaaggatga gggtctgggt gttcacgaat tgcctggagg caggaggctc    660
gtcgtccgga gccacaggcg tggagacgtc cgggataagg tgagcagccg ctgcgatagg    720
ggcgcgtgtg aaccccgtcg cgccccacgg atggtataag aataaaggca ttccgcgtgc    780
aggatt                                                                 786
```

<210> SEQ ID NO 47
<211> LENGTH: 1160
<212> TYPE: DNA
<213> ORGANISM: Zea mays

<400> SEQUENCE: 47

```
atgtgctggt gccccataag gtaggcacct aggtctgtgt ttgaagcatc gacagatttg     60
taaacatgtt cctatgaacc tatttctgat tgataatttg tcaaaactca tcatttgtct    120
tcatccttgc ctgcttgcgt tcacgtgaca aagtacgtgt atgtcttcgg cctttgctgt    180
gtatgtttcg cattgcttag atgtggtgaa agaacatcag aagatgcatt gatggcgtgc    240
ttaaaccagt gatgtgctcc aggtgttcct gcagtctgca gagatattta ctcttgtagt    300
cttgttgaca gcacagttgt atgtgatttc ttggatgtaa tgtaaaccaa atgaaagata    360
ggaacagttc gtcctcttcc gtatacgaag gtcactgtat catttgtcgt ggcacaagat    420
gatctgcagg caggactgca acatggtttc ttggactgtc ctgaatgccc gttcttgttc    480
tttagttgag ccagagcagc agcctggtgt cggtgcctga gacctgacga agcacacggc    540
aaacaaacaa gtcgcagcag ctagcagggg cgttgccatc gccacaagcc cccaagagac    600
ccgccgagga aaagaaaaaa aaactacggc cgccgttgcc aagccgagcg tgcgaaccga    660
tccacggatg ggagatcaga gatcacccac cgcaggcggg cggcagtggc tggcgaggtg    720
cgtccacaga acctgctgca ggtccctgtc cgtcccggcg accccttttc taggcgagca    780
actccccatg gcagagctgc acgcagcagg gcccgtcgtt ggttgcagct ttaacccttt    840
ttgtttttaac catacaatgc agagtcgcag aggtgaaaca ggacggaaat tacagaaaag    900
atggtggtgt gccagcagcc ccagcatgaa gaagatcagg acaaaagaaa agcttgtgat    960
tggtgacagc aacaggattg gattggagcc aagctaggca gtgagaggca ggcagcaaga   1020
cgcgtcagcc actgaaatcc agagggcaac ctcggcctca caactcatat cccttgtgc    1080
tgttgcgcgc cgtggttagc caggtgtgct gcaggcctcc tccttgttta tatatgggag   1140
atgctctcac cctctaaggt                                                 1160
```

<210> SEQ ID NO 48
<211> LENGTH: 1532
<212> TYPE: DNA
<213> ORGANISM: Oryza sativa

<400> SEQUENCE: 48

| | | | | | |
|---|---|---|---|---|---|
| tagtcctcta | atatatgaaa | ttttgatata | ggtaaagaag | ggtattgcaa | ggataagaat | 60 |
| gtaaaaagaa | ataagagtaa | tccttaccga | taatagtatt | ccttctctac | cgttaaaagt | 120 |
| taaacctgtg | cgtgtagcat | tttaatccag | gatctatcga | atccgtccct | cgttggcgtg | 180 |
| ggcgacgaac | acgtgcagaa | gaagctttcc | ccagaaagca | cctcaccgcc | tcgccgtctg | 240 |
| gcagactggc | acgcggggcc | ctaccctcgc | tgcgcctggg | cccgtccgcc | ttctgcacac | 300 |
| tgtcacgccc | ccacccgctc | gccgcctcgc | gcctctctct | ccgcctccgc | cgcggccgcc | 360 |
| cgacgtgata | gcgacacgta | ggactcgcca | aacacaaaaa | atccatcgcg | atttttggaa | 420 |
| ttttgttaca | aaccaaatcc | cgcattagag | atttaatttg | atttaattta | attacgtagg | 480 |
| agtaccagat | aaggagatcg | agttaaaaaa | gctaacggcg | cggcgtggtt | atctccgaat | 540 |
| cggctgtggc | tccccgcgtc | ggcgtcggcg | cggcggcggc | gcgccggccg | aaccctggcc | 600 |
| gtcggatcgg | gcgtcgtcct | gggcccacg | cgccacgggc | ggctgtcgtt | tgctcctcgg | 660 |
| agcggggtgg | gcccaccatg | gccaccacca | caggtcgcgg | tcgcggctga | cctggcggtg | 720 |
| gtcccgtgct | cgcggtgttt | ttttttttttc | actctctttc | tctcggtgga | cagtagcggg | 780 |
| ggccgcggcc | cgcgggggca | gagattgcaa | aaacagcgga | aacggaagat | tgcaaaattg | 840 |
| caactgcttt | cctgttttta | attcgggatc | aaaaagattc | tttcgtcggg | gtccccgtgc | 900 |
| cattgttgta | ttgcgcgtag | gtccttgctt | gtaaagata | atctccttaa | tttttctttt | 960 |
| gtactactag | tgtatatgca | gtaagaatat | accatgagta | aaatgaacca | caaaactaat | 1020 |
| tacgatatac | cattctcatg | tagacgttct | cttttctttt | gctagtcata | cgtgcatata | 1080 |
| taaccaaaca | aaaaaatgtt | tgaagtactc | ctatccaatt | tattactcca | gtagacaaca | 1140 |
| aaagaaaatg | tttgaagtaa | taactgatcc | atggtacagt | agggttgtcg | tcaatcttgt | 1200 |
| gtttctttca | ttccattgta | cttacaatcg | tactccagct | agcacagcac | aatgggctta | 1260 |
| agctttggac | cccaaattct | gatcttgtcg | ggacccgta | cgaaaatact | cccgtagaga | 1320 |
| tgcagatacc | gtcacaacct | acaaccaacg | aatgttaaga | aaacaagg | aaaaaaaaag | 1380 |
| aggcgaattc | ggaggagaaa | aaacggtggc | taaaatatag | tgcgggtgtg | gggacgcgac | 1440 |
| gcgagcgacg | aaagaggaga | gaggatgggt | tggcctgccc | cccctcccc | tgtctataaa | 1500 |
| tgcagaggcg | ccgagtgccc | tagtcgccgc | tc | | | 1532 |

<210> SEQ ID NO 49
<211> LENGTH: 841
<212> TYPE: DNA
<213> ORGANISM: Oryza sativa

<400> SEQUENCE: 49

| | | | | | |
|---|---|---|---|---|---|
| tcgaggtcat | tcatatgctt | gagaagagag | tcggatagt | ccaaaataaa | acaaaggtaa | 60 |
| gattacctgg | tcaaaagtga | aaacatcagt | taaaagtgg | tataaagtaa | aatatcggta | 120 |
| ataaaaggtg | gcccaaagtg | aaatttactc | ttttctacta | ttataaaaat | tgaggatgtt | 180 |
| tttgtcggta | ctttgatacg | tcatttttgt | atgaattggt | ttttaagttt | attcgctttt | 240 |
| ggaaatgcat | atctgtattt | gagtcggggtt | ttaagttcgt | ttgcttttgt | aaatacagag | 300 |
| ggatttgtat | aagaaatatc | tttagaaaaa | cccatatgct | aatttgacat | aatttttgag | 360 |

```
aaaaatatat attcaggcga attctcacaa tgaacaataa taagattaaa atagctttcc      420
cccgttgcag cgcatgggta ttttttctag taaaaataaa agataaactt agactcaaaa      480
catttacaaa aacaacccct aaagttccta aagcccaaag tgctatccac gatccatagc      540
aagcccagcc caacccaacc caacccaacc caccccagtc cagccaactg gacaatagtc      600
tccacacccc cccactatca ccgtgagttg tccgcacgca ccgcacgtct cgcagccaaa      660 aaaaaaaga aagaaaaaa agaaaagaa aaacagcag gtgggtccgg gtcgtggggg      720
ccggaaacgc gaggaggatc gcgagccagc gacgaggccg ccctccctc cgcttccaaa      780 gaaacgcccc ccatcgccac tatatacata cccccccctc tcctcccatc cccccaaccc      840
t                                                                     841
```

<210> SEQ ID NO 50
<211> LENGTH: 1392
<212> TYPE: DNA
<213> ORGANISM: Oryza sativa
<400> SEQUENCE: 50

```
ctcgaggtca ttcatatgct tgagaagaga gtcgggatag tccaaaataa acaaaggta       60 agattacctg gtcaaaagtg aaaacatcag ttaaaaggtg gtataagtaa aatatcggta      120
ataaaaggtg gccaaagtg aaatttactc ttttctacta ttataaaaat tgaggatgtt      180
ttgtcggtac tttgatacgt cattttttgta tgaattggtt tttaagttta ttcgcgattt    240
tggaaatgca tatctgtatt tgagtcgggt tttaagttcg tttgcttttg taaatacaga     300
gggatttgta taagaaatat cttaaaaaaa acccatatgc taatttgaca taattttttga   360 gaaaatatata tattcaggcg aattctcaca atgaacaata ataagattaa aatagcttgc   420
ccccgttgca gcgatgggta ttttttctag taaaataaaa gataaactta gactcaaaac    480
atttacaaaa acaacccta aagtcctaaa gcccaaagtg ctatgcacga tccatagcaa     540
gcccagccca acccaaccca acccaaccca ccccagtgca gccaactggc aaatagtctc    600
cacaccccgg cactatcacc gtgagttgtc cgcaccaccg cacgtctcgc agccaaaaaa    660 aaaaaagaa agaaaaaaaa gaaaagaaa aacagcagg tgggtccggg tcgtggggggc     720 cggaaaagcg aggaggatcg cgagcagcga cgaggccggc cctccctccg cttccaaaga    780
aacgcccccc atcgccacta tatacatac cccccctctc ctcccatccc ccaaccccta    840
ccaccaccac caccaccacc tcctccccccc tcgctgccgg acgacgagct cctccccct    900 ccccctccgc cgccgccggt aaccacccg cgtccctctc ctctttcttt tccgttttt     960 tttttccgtc tcgtctcgat ctttggcctt ggtagtttgg gggcgagagg cggcttcgtc    1020
gcccagatcg gtgcgcggga ggggcgggat ctcgcggctg gtctcggcg tgcggccgga    1080 tcctcgcggg gaatggggct ctcggatgta gatctgatcc gccgttgttg ggggagatga   1140
tggggcgttt aaaatttcgc catgctaaac aagatcagga agaggggaaa agggcactat    1200
ggtttatatt tttatatatt tctgctgctg ctcgtcaggc ttagatgtgc tagatcttc     1260 tttcttcttt ttgtgggtag aatttgaatc cctcagcatt gttcatcggt agttttttctt  1320 ttcatgattt gtgacaaatg cagcctcgtg cggagctttt tgtaggtag aagatggctg     1380 acgccgagga ta                                                         1392
```

<210> SEQ ID NO 51
<211> LENGTH: 743
<212> TYPE: DNA

<213> ORGANISM: Oryza sativa

<400> SEQUENCE: 51

```
gaattcccgg acctccatgc ctacatcaac taatttgatt ccttgagttt acgtttagtg      60
atatgtctat ttttagagct tgttggggct tcggcctcag ctctagccag ccaaacatgt     120
tctaccaagt accctatgtt ggcatgatat agtgatgcat tataacaata aatgagcgag     180
ggattgctgg ctgaaaaagc tatactagct gcatttggtt atagttaacc gaactattaa     240
ttgcgtgtac aacaaaataa aaaaaatgca tgttgcacat tctttcatta acattatgtt     300
ttggtagtgt gaattagaaa tttgattgac agtagatcga caaacatagt ttcaatatgc     360
ttaagttagt tatgacttta acatatcagt ctccttgata ttttcgtttt agattcgtct     420
ctctactagt gtgtatgtcc accttccata gcagtgaagg gttccattcc atccctggta     480
aaaaaaaatc aaccactact atttatttcc taaaaagcaa aatgataaaa tatcattttt     540
ttaataaaaa taaaaaaatt ttggggtaca taattgatgt tgccccttgg gattaacctt     600
aaaaaagggc gaattttcta ggtttggcc aagttttgca atgcaccaaa ttattcccct     660
tgggccggcc gccaccccaa aaaaaacccc aacccccaac tttccattga aggccgggcc     720
cccttaaatc ctcatccccc caa                                             743
```

<210> SEQ ID NO 52
<211> LENGTH: 144
<212> TYPE: DNA
<213> ORGANISM: Oryza sativa

<400> SEQUENCE: 52

```
taaaaaaggg cgaattttct agggtttggc caagttttgc aatgcaccaa attattcccc      60
tgggccggc cgccacccca aaaaaaaccc caacccccaa ctttccattg aaggccgggc     120
ccccttaaat cctcatcccc ccaa                                             144
```

<210> SEQ ID NO 53
<211> LENGTH: 612
<212> TYPE: DNA
<213> ORGANISM: Cauliflower mosaic virus

<400> SEQUENCE: 53

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg aaaaagaag acgttccaac cacgtcttca     240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg     540
gatgacgcac aatcccacta tccttcgcaa gaccttcct ctatataagg aagttcattt     600
catttggaga gg                                                         612
```

<210> SEQ ID NO 54
<211> LENGTH: 837
<212> TYPE: DNA
<213> ORGANISM: Coix lacryma-jobi

<400> SEQUENCE: 54

```
agcagactcg cattatcgat ggagctctac caaactggcc ctaggcatta acctaccatg    60
gatcacatcg taaaaaaaaa accctaccat ggatcctatc tgttttcttt ttgccctgaa   120
agagtgaagt catcatcata tttaccatgg cgcgcgtagg agcgcttcgt cgaagaccca   180
taggggggcg gtactcgcac cgtggttgtt tcctgttatg taatatcgga tgggggagca   240
gtcggctagg ttggtcccat cggtactggt cgtcccctag tgcgctagat gcgcgatgtt   300
tgtcctcaaa aactcttttc ttcttaataa caatcatacg caaattttt gcgtattcga    360
gaaaaaaga agattctatc tgttttttt ttgaaatggc tccaatttat aggaggagcc     420
cgtttaacgg cgtcgacaaa tctaacggac accaaccagc gaatgagcga acccaccagc   480
gccaagctag ccaagcgaag cagacggccg agacgctgac accttgcct ggcgcggca     540
tctccgtcgc tggctcgctg gctctggccc cttcgcgaga gttccggtcc acctccacct   600
gtgtcggttt ccaactccgt tccgccttcg cgtgggactt gttccgttca tccgttggcg   660
gcatccggaa attgcgtggc gtagagcacg gggccctcct ctcacacggc acggaaccgt   720
cacgagctca cggcaccggc agcacggcgg ggattccttc cccaccaccg ctccttccct   780
ttcccttcct cgcccgccat cataaatagc caccctccc agcttccttc gccacat       837
```

<210> SEQ ID NO 55
<211> LENGTH: 947
<212> TYPE: DNA
<213> ORGANISM: Oryza sativa

<400> SEQUENCE: 55

```
aatccgaaaa gtttctgcac cgttttcacg tcctaactaa caatataggg aacgtgtgct    60
aaatataaaa tgagacctta tatgtagc gctgataact agaactatgt aagaaaaact     120
catccaccta ctttagtggc aatcgggcta aataaaaaag agtcgctaca ctagtttcgt   180
tttccttagt aattaagtgg gaaatgaaa tcattattgc ttagaatata cgttcacatc    240
tctgtcatga agttaaatta ttcgaggtag ccataattgt catcaaactc ttcttgaata   300
aaaaaatctt tctagctgaa ctcaatgggt aaagagagat atttttttt aaaaaaaaat    360
agaatgaaga tattctgaac gtatcggcaa agatttaaac atataattat ataattttat   420
agtttgtgca ttcgttatat cgcacgtcat taaggacatg tcttactcca tctcaatttt   480
tatttagtaa ttaaagacaa ttgacttatt tttattattt atctttttc gattagatgc    540
aaggtactta cgcacacact ttgtgctcat gtgcatgtgt gagtgcacct cctcaataca   600
cgttcaacta gcgacacatc tccaatatca ctcgcctatt taatacattt aggtagcaat   660
atctgaattc aagcactcca ccatcaccag accacttta ataatatcta aaatacaaaa    720
aataatttta cagaatagca tgaaaagtat gaaacgaact attaggtttt tcacataca    780
aaaaaaaaaa gaattttgct cgtgcgcgag cgccaatctc ccatattggg cacacaggca   840
acaacagagt ggctgcccac agaacaaccc acaaaaaacg atgatctaac ggaggacagc   900
aagtccgcaa caaccttta acagcaggct ttgcggccag gagagag                   947
```

<210> SEQ ID NO 56
<211> LENGTH: 721
<212> TYPE: DNA
<213> ORGANISM: Mirabilis mosaic caulimovirus

<400> SEQUENCE: 56

```
tggagattca gaaaaatctc catcaacaaa taatccaagt aaggattaat ggattgatca      60
acatccttac cgctatgggt aagattgatg aaaagtcaaa aacaaaaatc aattatgcac     120
accagcatgt gttgatcacc agctattgtg ggacaccaat ttcgtccaca gacatcaaca     180
tcttatcgtc cttttgaagat aagataataa tgttgaagat aagagtggga gccaccacta    240
aaacattgct ttgtcaaaag ctaaaaaaga tgatgcccga cagccacttg tgtgaagcat     300
gtgaagccgg tccctccact aagaaaatta gtgaagcatc ttccagtggt ccctccactc     360
acagctcaat cagtgagcaa caggacgaag gaaatgacgt aagccatgac gtctaatccc     420
acaagaattt ccttatataa ggaacacaaa tcagaaggaa gagatcaatc gaaatcaaaa     480
tcggaatcga aatcaaaatc ggaatcgaaa tctctcatct ctctctacct tctctctaaa     540
aaacacttag atgtgtgagt aatcacccac ttggggttgt aatatgtagt agtaaataag     600
ggaaccttag ggtataccat tgttgtaata ttatttttcag tatcaataaa ataatctttc    660
agtttatctt atattcattt gtgtgacacc gtattcccat aaaaccgatc ctaatctctc     720
c                                                                     721

<210> SEQ ID NO 57
<211> LENGTH: 352
<212> TYPE: DNA
<213> ORGANISM: Peanut chlorotic streak caulimovirus

<400> SEQUENCE: 57
acagagggat ttctctgaag atcatgtttg ccagctatgc gaacaatcat cgggagatct      60
tgagccaatc aaagaggagt gatgtagacc taaagcaata atggagccat gacgtaaggg     120
cttacgccat tacgaaataa ttaaaggctg atgtgacctg tcggtctctc agaaccttta     180 cttttttatat ttggcgtgta ttttttaaatt tccacggcaa tgacgatgtg acctgtgcat    240
ccgctttgcc tataaataag ttttagtttg tattgatcga cacgatcgag aagacacggc     300
catttggacg atcatttgag agtctaaaag aacgagtctt gtaatatgtt tt             352

<210> SEQ ID NO 58
<211> LENGTH: 7139
<212> TYPE: DNA
<213> ORGANISM: Zea mays

<400> SEQUENCE: 58
gctctgccac tctgctgagg tgggggggaga ggagctcccc ctccctcctc tcccctcctc     60
gccatgtcta gcagcgaccc ggaggagatc agggcgcgcg tcgtcgttct cggttcgccc    120
catgccgacg gcggcgacga gtgggcccgg cccgagctcg aggccttcca tctgccgtct    180
cccgcccacc agcctcctgg cttcctagcc gggcaaccgg aagcagcaga gcaacccacg    240
ctccctgctc ctgctggccg cagcagcagc agcagcaaca cgcctactac atctgccggt    300
ggcggcgctg ctcctcctcc tccttcttcg cctccccctc cgccggcttc tctggagacc    360
gagcagccgc ccaatgccag gccagcctcc gccggcgcca atgacagcaa gaagcccacc    420
ccgcccgccg ccctgcgcga cctcttccgc ttcgccgacg gcctcgactg cgcgctcatg    480
ctcatcggca ccctcggcgc gctcgtccac gggtgctcgc tccccgtctt cctccgcttc    540
ttcgccgacc tcgtcgactc cttcggctcc cacgccgacg accggacac catggtccgc      600 ctcgtcgtca agtacgcctt ctacttcctc gtcgtcggag cggcaatctg ggcatcctcg     660
tgggcaggta cgctatccct cctcctcctg ccgcccccag ttgtgtgcgt cgcgaattgg    720
cggtcaattt ggattggatg acaaatcacg tcggtcagcc aatcgccgtg gctacaaacg    780
```

```
agatgttcaa atcgttcgcc ccgctcgcaa gagatctctt gctggatgtg gaccggcgag    840
cggcagtcga cgcggatgcg gattcggtac ctggacgcgg cgctgcggca ggacgtgtcc    900
ttcttcgaca ccgacgtgcg ggcctcggac gtgatctacg ccatcaacgc ggacgccgtg    960
gtggtgcagg acgccatcag ccagaaactg gcaacctca tccactacat ggccaccttc   1020
gtggccggct tcgtcgtggg gttcacggcc gcgtggcagc tggcgctggt cacgctggcc   1080
gtggtgccgc tcatcgccgt catcggcggg ctgagcgccg ccgcgctcgc caagctctcg   1140
tcccgcagcc aggacgcgct ctcgggcgcc agcggcatcg cggagcaggc gctcgcgcag   1200
atacggatcg tgcaggcgtt cgttggcgag gagcgcgaga tgcgggccta ctcggcggcg   1260
ctggccgtgg cgcagaggat cggctaccgc agcggcttcg ccaaggggct cggcctcggc   1320
ggcacctact tcaccgtctt ctgctgctac gggctcctgc tctggtacgg cggccacctc   1380
gtgcgcgccc agcacaccaa cggcgggctc gccatcgcca ccatgttctc cgtcatgatc   1440
ggcggactgt aaggcccacc acaccacgca ctctctcctt ctgctgtcct cggccgcccc   1500
cgtcgtcatt gctgctgacg gtatctgtgg atcgcgtgca ggcctcggca gtcggcgccg   1560
agcatggccg cgttcgccaa ggcgcgtgtg cggctgccaa agatcttccg catcatcgac   1620
cacaggccgg gcatctcctc gcgcgacggc gcggagccag agtcggtgac ggggcgggtg   1680
gagatgcggg gcgtggactt cgcgtacccg tcgcggccgg acgtccccat cctgcgcggc   1740
ttctcgctga gcgtgcccgc cgggaagacc atcgcgctgg tgggcagctc cggctccggg   1800
aagagcacgg tggtgtcgct catcgagaga ttctacgacc ccagcgcagg tatacctagt   1860
actgttacta cttttagcgc attaatctga ggatgtccag ttcgcttgct tgccaatcgc   1920
cattgccatc gcaacaacaa tacttcgcca actgccattg ctgggtagat tagtacagta   1980
gcagttagaa gaagcctcca ctgtacattg cattgccaaa caaaagtgaa ttgtgcagta   2040
actctgtacc accacattga catggaaatg aagtgaatgc ttggagcatg cagagctggc   2100
cggcctcatg ggctgctgct acctgctagc tagccaacca gaaccagcca tcctctttct   2160
tgcttttctt tttactttct ttggtcgtgg ctgtttgtgg tcatacatac attcacgcag   2220
agcagaagag ctagctaagc taggtgggtg tgcctgcaac gcgggacaaa gaaaactatt   2280
tgttgcctgg caagatgcta ctgttgccta gcacatgcct gccattgacc gactgctcag   2340
tgagaagtgg ttcagttgtg ctgttgacag tatagataga tatatatagt agccctgtag   2400
attttttttt cagacaaaaa aagaagaaga acgagatgaa gtctgcaatt cggttttggc   2460
agggcaaatc ctgctggacg ggcacgacct caggtcgctg gagctgcggt ggctgcggcg   2520
gcagatcggg ctggtgagcc aggagccggc gctgttcgcg acgagcatca gggagaacct   2580
gctgctgggg cggacagcc agagcgcgac gctggcggag atggaggagg cggccagggt   2640
ggccaacgcc cactccttca tcatcaaact ccccgacggc tacgacacgc aggtccgtcc   2700
cgtatagcta gctcactagc tgcactgcca cttctctcgc ttgctccccc accgttgctg   2760
cctgttgctc tccaatccac ttgtcggtgt ctggaccaca cgtgctgctt gcctagctgc   2820
tccacatctg ctttccctgt ccaaccttat gcaactcact ctaatactat atcaaataca   2880
tttctagagt ttaaagctta tcttagaata aatgcatctt tagctacgag acaacctaac   2940
ttcagttgtt gttgttgttt ttttactttt ctctcttctc acaaatacta tgattacgtc   3000
tttacagcga tctttttat tccaaaccta aaaatgcatg cactcactct aaaagcgcaa   3060
agggagcatc ttttttttccc ccatcatctg cacgcagcct tttcttttcc tcatgtcacg   3120
```

```
aagggactga aggtgtgtat gcagcgtcaa gtcatccatc cgttccactc cactcactca   3180
tgcgtcgcgc actctgcgct cgtgcctgcc cggggctaaa gctttagtag ctagcctcag   3240
atcagatact gttcgtgttt gttaggccgc ggcagctgca catgagctca tgacagccgg   3300
cagcaccacc accaacgcca tggaagaggg gtcggggtcc atcacataga cataatgcct   3360
gttgtagact aggacgggag ggcaattgtt aggcgcctgt tgccatcgca tttgctgctg   3420
tgggttgcca acaagtaaca tgccaggatg ctttgctatc acgcacagga caggagaggt   3480
ccttttctc gacacaagct ctacagcctc tactaaacta gcacttgctg atgagtgcag   3540
aggatgaatg gacgatgaac atctagagtg agagagaaaa aaatgttaat aataataaaa   3600
agtagtagca ggattaagaa tcaacctggg gtacgtagga agaggtacaa tccctaggaa   3660
tctagagtat gagaagtatg ggaggagttg ggggagtgaa acggaacaaa ttccgagttg   3720
gtattttgtc gggaatgtca agttgatttt tgatcctagt gcaagcaaga attatcaatc   3780
actcagactc agcctgtctg tgtctgtcca ccccagctct tgctactcta cttactactg   3840
tgctactagt gggtagggta ggtatcttac ataaactgtt attataaact gtcatctgag   3900
aaagagagcc agtcaaaccc atgctgctgc ttattttaat cactgtcaaa tggcaggcag   3960
gcaggcagtc tggttagtta ataacatctg ggaagggttt aatcaaacca aatcaaatca   4020
gacgaaatct agaggccaca tgggatgggg ccatatgtac tgtactagca taactagcgg   4080
ctagatttta ttagaacacg gactcacact cccataacta taactgactt gatcatgatt   4140
ccttgccaag caatgctcgc atgcccatgc atgcatcatc cctggtcaaa ctcaaacact   4200
ctccaccgtc agggaataag acttattatt ttattaacaa ttcaattttt atttattaat   4260
tacgtctgga cgaggagtac tggtttattt gatgagagac atggcagtcc aagtcaaact   4320
cgtttgtctg accatggcgg tgatggccgg tgcaggttgg ggagcgcggc ctgcagctct   4380
ccggtgggca gaagcagcgc atcgccatcg cccgcgccat gctcaagaac cccgccatcc   4440
tgctgctgga cgaggccacc agcgcgctgg actccgagtc tgagaagctc gtgcaggagg   4500
cgctggaccg cttcatgatg gggcgcacca cccttggtga tcgcgcaaca ggctgtccac   4560
catccgcaaa ggccgacgtg gtggccgtgc tgcaggcgg cgccgtctcc gagatgagcg   4620
cgcacgacga gctgatggcc aagggcgaga acggcaccta cgccaagctc atccgcatgc   4680
aggagcaggc gcacgaggcg gcgctcgtca acgcccgccg cagcagcgcc aggccctcca   4740
gcgcccgcaa ctccgtcagc tcgcccatca tgacgcgcaa ctcctcctac ggccgctccc   4800
cctactcccg ccgcctctcc gacttctcca cctccgactt caccctctcc atccacgacc   4860
cgcaccacca ccaccggacc atggcggaca agcagctggc gttccgcgcc ggcgccagct   4920
ccttcctgcg cctcgccagg atgaactcgc ccgagtgggc ctacgcgctc gccggctcca   4980
tcggctccat ggtctgcggc tccttcagcg ccatcttcgc ctacatcctc agcgccgtgc   5040
tcagcgtcta ctacgcgccg gaccgcggt acatgaagcg cgagatcgca aaatactgtt   5100
acctgctcat cggcatgtcc tccgcggcgc tgctgttcaa cacggtgcag cacgtgttct   5160
gggacacggt gggcgagaac ttgaccaagc gggtgcgcga agatgttc gccgccgtgt   5220
tccgcaacga gatcgcctgg ttcgacgcgg acgagaacgc cagcgcgcgc gtgaccgcca   5280
ggctagcgct ggacgcccag aacgtgcgct ccgccatcgg ggaccgcatc tccgtcatcg   5340
tccagaactc ggcgctgatg ctggtggcct gcaccgcggg gttcgtcctc cagtggcgcc   5400
tcgcgctcgt gctcctcgcc gtgttccgc tcgtcgtggg cgccaccgtg ctgcagaaga   5460
tgttcatgaa gggcttctcg ggggacctgg aggccgcgca cgccagggcc acgcagatcg   5520
```

```
cgggcgaggc cgtggccaac ctgcgcaccg tggccgcgtt caacgcggag cgcaagatca    5580
cggggctgtt cgaggccaac ctgcgcggcc cgctccggcg ctgcttctgg aaggggcaga    5640
tcgccggcag cggctacggc gtggcgcagt tcctgctgta cgcgtcctac gcgctggggc    5700
tgtggtacgc ggcgtggctg gtgaagcacg gcgtgtccga cttctcgcgc accatccgcg    5760
tgttcatggt gctgatggtg tccgcgaacg cgccgccga  gacgctgacg ctggcgccgg    5820
acttcatcaa aggcgggcgc gcgatgcggt cggtgttcga caatcgac   cgcaagacgg    5880 aggtggagcc ccacgacgtg gacgcggcgc cggtgccgga cggcccaggg gcgaaggtgg    5940
aacttaagca cgtggacttt ttgtacccgt cgcggccgga catccaagtg ttccgcgacc    6000
tgagcctccg tgcgcgcgcc ggaaaaacgt tggcgctggt ggggccgagc gggtccggca    6060
agagctcggt cctggctctg gtgcagcggt tctacaagcc cacgtccggg cgcgtgctct    6120
tggacggcaa ggacgtgcgc aagtacaacc tgcgggcgct gcgcgcgtg  gtggcggtgg    6180 taccgcagga gccgttcctg ttcgcggcga gcatccacga gaacatcgcg tacgggcgcg    6240
agggcgcgac ggaggcggag gtggtggagg cggcggcgca ggcgaacgcg caccggttca    6300
tcgcggcgct gccggagggg taccggacgc aggtgggcga gcgcggggtg cagctgtcgg    6360 ggggcagcg  gcagcggatc gcgatcgcgc gcgcgctggt gaagcaggcg gccatcgtgc    6420
tgctggacga ggcgaccagc gcgctggacg ccgagtcgga gcggtgcgtg caggaggcgc    6480
tggagcgcgc ggggtccggg cgcaccacca tcgtggtggc gaccggctg  gccacggtgc    6540 gcggcgcgca caccatcgcg gtcatcgacg acggcaaggt ggcggagcag gggtcgcact    6600
cgcacctgct caagcaccat cccgacgggt gctacgcgcg gatgctgcag cttgcagcgg    6660
ctgacgggcg cggcggccgg gcccgggccg tcgtcctcgt gcaacggggc cgcgtaggac    6720
ggaatggatg gatggatggg tttggttcct cgagagattg atgggtgagg aagctgaagc    6780
tccggatcaa atggtggtac tccatgatcg caacaatgag gggaaaaaag gaaggagaa    6840 aatacggtgg ttcatatgat tgtacaattt gacgatctgt ttgagtcggg gttttaggat    6900
gatgtaaacc ttcactcgcc ttttttttac tcttgtttct catccgcatc agtatcatct    6960
atctacatac agtgtcagag atgggaactg atcccgcatc atcatctacc tcccaaggca    7020
ccccagattg tattaatgta cttagttagc ctgttttata tatacttata agtaccaaat    7080
agcagaattt tactccttat ctgcagtagc acgaagaaa aaaaaaaaaa gctaaacct    7139
```

<210> SEQ ID NO 59
<211> LENGTH: 143
<212> TYPE: DNA
<213> ORGANISM: Zea mays

<400> SEQUENCE: 59

```
ttgcctagca catgcctgcc attgaccgac tgctcagtga gaagtggttc agttgtgctg     60
ttgacagtat atatagatat atatagtagc cctgtagatt ttttttttcag acaaaaaaag   120 aagaagaacg agatgaagtc tgc                                            143
```

<210> SEQ ID NO 60
<211> LENGTH: 143
<212> TYPE: DNA
<213> ORGANISM: Zea mays

<400> SEQUENCE: 60

```
ctagcacatg cctgccattg accgactgct cagtgagaag tggttcagtt gtgctgttga     60
```

| | |
|---|---|
| cagtatagat atatatatat agtagccctg tagattttt tttcagacaa aaaaagaaga | 120 |
| agaacgagat gaagtctgca att | 143 |

<210> SEQ ID NO 61
<211> LENGTH: 143
<212> TYPE: DNA
<213> ORGANISM: Zea mays

<400> SEQUENCE: 61

| | |
|---|---|
| acatgcctgc cattgaccga ctgctcagtg agaagtggtt cagttgtgct gttgacagta | 60 |
| tagatagata tgtatagtag ccctgtagat tttttttca gacaaaaaaa gaagaagaac | 120 |
| gagatgaagt ctgcaattcg gtt | 143 |

<210> SEQ ID NO 62
<211> LENGTH: 142
<212> TYPE: DNA
<213> ORGANISM: Zea mays

<400> SEQUENCE: 62

| | |
|---|---|
| catgcctgcc attgaccgac tgctcagtga gaagtggttc agttgtgctg ttgacagtat | 60 |
| agatagatat agtagccctg tagattttt tttcagacaa aaaagaaga agaacgagat | 120 |
| gaagtctgca attcggtttt gg | 142 |

<210> SEQ ID NO 63
<211> LENGTH: 140
<212> TYPE: DNA
<213> ORGANISM: Zea mays

<400> SEQUENCE: 63

| | |
|---|---|
| gctgttgaca gtatagatag atatatatag tagccctgta gatttttttt tcagacaaaa | 60 |
| aaagaagaac gagatgaagt ctgcaattcg gttttggcag ggcaaatcct gctggacggg | 120 |
| cacgacctca ggtcgctgga | 140 |

<210> SEQ ID NO 64
<211> LENGTH: 141
<212> TYPE: DNA
<213> ORGANISM: Zea mays

<400> SEQUENCE: 64

| | |
|---|---|
| tgacagtata gatagatata tatagtagcc ctgtagattt tttttcaga caaaaaaga | 60 |
| agaagaacgg gatgaagtct gcaattcggt tttggcaggg caaatcctgc tggacgggca | 120 |
| cgacctcagg tcgctggagc t | 141 |

<210> SEQ ID NO 65
<211> LENGTH: 141
<212> TYPE: DNA
<213> ORGANISM: Zea mays

<400> SEQUENCE: 65

| | |
|---|---|
| tgacagtata gatagatata tatagtagcc ctgtagattt tttttcaga caaaaaaga | 60 |
| agaagaacgg gatgaagtct gcaattcggt tttggcaggg caaatcctgc tggacgggca | 120 |
| cgacctcagg tcgctggagc t | 141 |

<210> SEQ ID NO 66
<211> LENGTH: 144
<212> TYPE: DNA
<213> ORGANISM: Zea mays

<400> SEQUENCE: 66

```
aggcggccag ggtggccaac gcccactcct tcatcatcaa actccccgac ggctacgaca      60
cgcaggtccg tgtccgtccc gtatagctag ctcactagct gcactgccac ttctctcgct     120
tgctccccca ccgttgctgc ctgt                                            144
```

<210> SEQ ID NO 67
<211> LENGTH: 136
<212> TYPE: DNA
<213> ORGANISM: Zea mays

<400> SEQUENCE: 67

```
caacgcccac tccttcatca tcaaactccc cgacggctac gacacgcagg tccgtcccgt      60
atagcggtag ctcactagct gcactgccac ttctctcgct tgctccccca ccgttgctgc     120
ctgttgctct ccaatc                                                     136
```

<210> SEQ ID NO 68
<211> LENGTH: 136
<212> TYPE: DNA
<213> ORGANISM: Zea mays

<400> SEQUENCE: 68

```
gcccactcct tcatcatcaa actccccgac ggctacgaca cgcaggtccg tcccgtatag      60
ctatagctca ctagctgcac tgccacttct ctcgcttgct cccccaccgt tgctgcctgt     120
tgctctccaa tccact                                                     136
```

<210> SEQ ID NO 69
<211> LENGTH: 133
<212> TYPE: DNA
<213> ORGANISM: Zea mays

<400> SEQUENCE: 69

```
ctccttcatc atcaaactcc ccgacggcta cgacacgcag gtccgtcccg tatagctagc      60
taactagctg cactgccact tctctcgctt gctcccccac cgttgctgcc tgttgctctc     120
caatccactt gtc                                                        133
```

<210> SEQ ID NO 70
<211> LENGTH: 141
<212> TYPE: DNA
<213> ORGANISM: Zea mays

<400> SEQUENCE: 70

```
cacacgcaca cacacagatc gcctgacaag ccagccattg cttcagatca agaaactgc       60
gtaataattt ctttctttct ttctttcttt ctttccagag cacaagggag gggggttata     120
atggctagta cctgactgac t                                               141
```

<210> SEQ ID NO 71
<211> LENGTH: 143
<212> TYPE: DNA
<213> ORGANISM: Zea mays

<400> SEQUENCE: 71

```
agccagccat tgcttcagat caaagaaact gcgtaataat tcctttcttt ctttctttct      60
ttctttccag atcacaaggg agggggggtta taatggctag tacctgactg actgtacgag    120
ccgagattaa cggcagtcac ctc                                             143
```

```
<210> SEQ ID NO 72
<211> LENGTH: 143
<212> TYPE: DNA
<213> ORGANISM: Zea mays

<400> SEQUENCE: 72
atcgccctgc tggccatttg gcaccaccta gtcgtacatg tgttcagtca tttccgtcca      60
ttactactac ggccgtgctc acccgtgccg acgcgccgtg catggtcccc gtcccggctg     120
gaacgcgtcc tcggaagaga gag                                             143

<210> SEQ ID NO 73
<211> LENGTH: 143
<212> TYPE: DNA
<213> ORGANISM: Zea mays

<400> SEQUENCE: 73
ccattactac tacgaccgtg ctcacccgtg ccgacgcgcc gtgcatggtc cccgtcccgg      60
ctggaacgcg tgctcggaag agagagatag agcacagcag acaggagaca agggatggaa     120
ggatggcgtt cgcccggtac agg                                             143

<210> SEQ ID NO 74
<211> LENGTH: 143
<212> TYPE: DNA
<213> ORGANISM: Zea mays

<400> SEQUENCE: 74
cattactact acgaccgtgc tcacccgtgc cgacgcgccg tgcatggtcc ccgtcccggc      60
tggaacgcgt catcggaaga gagagataga gcacagcaga cagggagaca gggatggaag     120
gatggcgttc gcccggtaca ggt                                             143

<210> SEQ ID NO 75
<211> LENGTH: 143
<212> TYPE: DNA
<213> ORGANISM: Zea mays

<400> SEQUENCE: 75
attactacta cgaccgtgct cacccgtgcc gacgcgccgt gcatggtccc cgtcccggct      60
ggaacgcgtc cccggaagag agagatagag cacagcagac agggagacag ggatggaagg     120
atggcgttcg cccggtacag gtt                                             143

<210> SEQ ID NO 76
<211> LENGTH: 143
<212> TYPE: DNA
<213> ORGANISM: Zea mays

<400> SEQUENCE: 76
ttactactac gaccgtgctc acccgtgccg acgcgccgtg catggtcccc gtcccggctg      60
gaacgcgtcc tgggaagaga gagatagagc acagcagaca gggagacagg gatggaagga    120
tggcgttcgc ccggtacagg ttg                                             143

<210> SEQ ID NO 77
<211> LENGTH: 143
<212> TYPE: DNA
<213> ORGANISM: Zea mays

<400> SEQUENCE: 77
tactactacg accgtgctca cccgtgccga cgcgccgtgc atggtccccg tcccggctgg      60
```

```
aacgcgtcct ccgaagagag agatagagca cagcagacag ggagacaggg atggaaggat    120
ggcgttcgcc cggtacaggt tgc                                          143

<210> SEQ ID NO 78
<211> LENGTH: 143
<212> TYPE: DNA
<213> ORGANISM: Zea mays

<400> SEQUENCE: 78
ctactacgac cgtgctcacc cgtgccgacg cgccgtgcat ggtccccgtc ccggctggaa    60
cgcgtcctcg gtagagagag atagagcaca gcagacaggg agacaggat ggaaggatgg    120 cgttcgcccg gtacaggttg cta                                          143

<210> SEQ ID NO 79
<211> LENGTH: 143
<212> TYPE: DNA
<213> ORGANISM: Zea mays

<400> SEQUENCE: 79
tactacgacc gtgctcaccc gtgccgacgc gccgtgcatg gtccccgtcc cggctggaac    60
gcgtcctcgg acgagagaga tagagcacag cagacaggga gacagggatg gaaggatggc    120
gttcgcccgg tacaggttgc tag                                          143

<210> SEQ ID NO 80
<211> LENGTH: 146
<212> TYPE: DNA
<213> ORGANISM: Zea mays

<400> SEQUENCE: 80
actacgaccg tgctcacccg tgccgacgcg ccgtgcatgg tccccgtccc ggctggaacg    60
cgtcctcgga actcggagag agatagagca cagcagacag ggagacaggg atggaaggat    120
ggcgttcgcc cggtacaggt tgctag                                       146

<210> SEQ ID NO 81
<211> LENGTH: 143
<212> TYPE: DNA
<213> ORGANISM: Zea mays

<400> SEQUENCE: 81
caggaggcgc tggaccgctt catgatcggg cgcaccaccc tggtgatcgc gcacaggctg    60
tccaccatcc gcaaggccga cgtggtggcc gtgctgcagg gcggcgccgt ctccgagatg    120
ggcgcgcacg acgagctgat ggc                                          143

<210> SEQ ID NO 82
<211> LENGTH: 143
<212> TYPE: DNA
<213> ORGANISM: Zea mays

<400> SEQUENCE: 82
tccatcggct ccatggtctg cggctccttc agcgccatct tcgcctacat cctcagcgcc    60
gtgctcagcg tctactacgc gccggacccg cggtacatga agcgcgagat cgcaaaatac    120
tgctacctgc tcatcggcat gtc                                          143

<210> SEQ ID NO 83
<211> LENGTH: 143
<212> TYPE: DNA
```

<213> ORGANISM: Zea mays

<400> SEQUENCE: 83

```
gcctacatcc tcagcgccgt gctcagcgtc tactacgcgc cggacccgcg gtacatgaag    60
cgcgagatcg caaaatactg ctacctgctc atcggcatgt cctccgcggc gctgctgttc   120
aacacggtgc agcacgtgtt ctg                                           143
```

<210> SEQ ID NO 84
<211> LENGTH: 143
<212> TYPE: DNA
<213> ORGANISM: Zea mays

<400> SEQUENCE: 84

```
ctggttcgac gcggacgaga acgccagcgc gcgcgtggcc gccaggctag cgctggacgc    60
ccagaacgtg cgctccgcca tcggggaccg catctccgtc atcgtccaga actcggcgct   120
gatgctggtg gcctgcaccg cgg                                           143
```

<210> SEQ ID NO 85
<211> LENGTH: 143
<212> TYPE: DNA
<213> ORGANISM: Zea mays

<400> SEQUENCE: 85

```
cagaacgtgc gctccgccat cggggaccgc atctccgtca tcgtccagaa ctcggcgctg    60
atgctggtgg cctgcaccgc ggggttcgtc ctccagtggc gcctcgcgct cgtgctcctc   120
gccgtgttcc cgctcgtcgt ggg                                           143
```

<210> SEQ ID NO 86
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 86

```
ttgcctagca catgcctgcc attgaccgac tgctcagtga gaagtggttc agttgtgctg    60
ttgacagtat anatagatat atatagtagc cctgtagatt tttttttcag acaaaaaaag   120
aagaagaacg agatgaagtc tgc                                           143
```

<210> SEQ ID NO 87
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 87

```
ctagcacatg cctgccattg accgactgct cagtgagaag tggttcagtt gtgctgttga    60
cagtatagat anatatatat agtagccctg tagattttttt tttcagacaa aaaagaaga   120
agaacgagat gaagtctgca att                                           143
```

<210> SEQ ID NO 88
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 88
acatgcctgc cattgaccga ctgctcagtg agaagtggtt cagttgtgct gttgacagta      60
tagatagata tntatagtag ccctgtagat ttttttttca gacaaaaaaa gaagaagaac    120
gagatgaagt ctgcaattcg gtt                                            143

<210> SEQ ID NO 89
<211> LENGTH: 146
<212> TYPE: DNA
<213> ORGANISM: Zea mays
<220> FEATURE:
<221> NAME/KEY: modified_base
<222> LOCATION: (72)..(75)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 89
catgcctgcc attgaccgac tgctcagtga gaagtggttc agttgtgctg ttgacagtat      60
agatagatat annnngtagc cctgtagatt ttttttcag acaaaaaaag aagaagaacg     120
agatgaagtc tgcaattcgg ttttgg                                         146

<210> SEQ ID NO 90
<211> LENGTH: 143
<212> TYPE: DNA
<213> ORGANISM: Zea mays
<220> FEATURE:
<221> NAME/KEY: modified_base
<222> LOCATION: (70)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 90
gctgttgaca gtatagatag atatatatag tagccctgta gatttttttt tcagacaaaa      60
aaagaagaan nncgagatga agtctgcaat tcggttttgg cagggcaaat cctgctggac    120
gggcacgacc tcaggtcgct gga                                            143

<210> SEQ ID NO 91
<211> LENGTH: 141
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 91

```
tgacagtata gatagatata tatagtagcc ctgtagattt tttttttcaga caaaaaaaga      60 agaagaacgn gatgaagtct gcaattcggt tttggcaggg caaatcctgc tggacgggca     120
cgacctcagg tcgctggagc t                                                141
```

<210> SEQ ID NO 92
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 92

```
tttttttttc agacaaaaaa agaagaagaa cgagatgaag tctgcaattc ggttttggca      60
gggcaaatcc tnctggacgg gcacgacctc aggtcgctgg agctgcggtg gctgcggcgg     120
cagatcgggc tggtgagcca gga                                              143
```

<210> SEQ ID NO 93
<211> LENGTH: 144
<212> TYPE: DNA
<213> ORGANISM: Zea mays
<220> FEATURE:
<221> NAME/KEY: modified_base
<222> LOCATION: (72)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 93

```
aggcggccag ggtggccaac gcccactcct tcatcatcaa actccccgac ggctacgaca      60
cgcaggtccg tnnnnnnccc gtatagctag ctcactagct gcactgccac ttctctcgct     120
tgctccccca ccgttgctgc ctgt                                             144
```

<210> SEQ ID NO 94
<211> LENGTH: 136
<212> TYPE: DNA
<213> ORGANISM: Zea mays
<220> FEATURE:
<221> NAME/KEY: modified_base
<222> LOCATION: (66)..(67)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 94

```
caacgcccac tccttcatca tcaaactccc cgacggctac gacacgcagg tccgtcccgt      60
atagcnntag ctcactagct gcactgccac ttctctcgct tgctccccca ccgttgctgc     120
ctgttgctct ccaatc                                                      136
```

<210> SEQ ID NO 95
<211> LENGTH: 136
<212> TYPE: DNA
<213> ORGANISM: Zea mays
<220> FEATURE:
<221> NAME/KEY: modified_base
<222> LOCATION: (64)..(65)
<223> OTHER INFORMATION: a, c, t, g, or absent
<220> FEATURE:

```
<223> OTHER INFORMATION: See specification as filed for detailed
      description of substitutions and preferred embodiments

<400> SEQUENCE: 95
gcccactcct tcatcatcaa actccccgac ggctacgaca cgcaggtccg tcccgtatag    60
ctanngctca ctagctgcac tgccacttct ctcgcttgct cccccaccgt tgctgcctgt   120
tgctctccaa tccact                                                  136

<210> SEQ ID NO 96
<211> LENGTH: 133
<212> TYPE: DNA
<213> ORGANISM: Zea mays
<220> FEATURE:
<221> NAME/KEY: modified_base
<222> LOCATION: (62)..(62)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 96
ctccttcatc atcaaactcc ccgacggcta cgacacgcag gtccgtcccg tatagctagc    60
tnactagctg cactgccact tctctcgctt gctcccccac cgttgctgcc tgttgctctc   120
caatccactt gtc                                                     133

<210> SEQ ID NO 97
<211> LENGTH: 141
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 97
cacacgcaca cacacagatc gcctgacaag ccagccattg cttcagatca aagaaactgc    60
gtaataattn ctttctttct ttctttcttt ctttccagag cacaagggag gggggttata   120
atggctagta cctgactgac t                                            141

<210> SEQ ID NO 98
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 98
agccagccat tgcttcagat caaagaaact gcgtaataat tcctttcttt ctttctttct    60
ttctttccag ancacaaggg aggggggtta taatggctag tacctgactg actgtacgag   120
ccgagattaa cggcagtcac ctc                                          143

<210> SEQ ID NO 99
<211> LENGTH: 143
<212> TYPE: DNA
<213> ORGANISM: Zea mays
```

-continued

```
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 99
atcgccctgc tggccatttg gcaccaccta gtcgtacatg tgttcagtca tttccgtcca      60
ttactactac gnccgtgctc acccgtgccg acgcgccgtg catggtcccc gtcccggctg     120
gaacgcgtcc tcggaagaga gag                                             143

<210> SEQ ID NO 100
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 100
ccattactac tacgaccgtg ctcacccgtg ccgacgcgcc gtgcatggtc cccgtcccgg      60
ctggaacgcg tnctcggaag agagagatag agcacagcag acagggagac agggatggaa    120
ggatggcgtt cgcccggtac agg                                             143

<210> SEQ ID NO 101
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 101
cattactact acgaccgtgc tcacccgtgc cgacgcgccg tgcatggtcc ccgtcccggc      60
tggaacgcgt cntcggaaga gagagataga gcacagcaga cagggagaca gggatggaag    120
gatggcgttc gcccggtaca ggt                                             143

<210> SEQ ID NO 102
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 102
attactacta cgaccgtgct cacccgtgcc gacgcgccgt gcatggtccc cgtcccggct      60
ggaacgcgtc cncggaagag agagatagag cacagcagac agggagacag ggatggaagg    120
atggcgttcg cccggtacag gtt                                             143
```

<210> SEQ ID NO 103
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 103
ttactactac gaccgtgctc acccgtgccg acgcgccgtg catggtcccc gtcccggctg      60
gaacgcgtcc tnggaagaga gagatagagc acagcagaca gggagacagg gatggaagga     120
tggcgttcgc ccggtacagg ttg                                             143

<210> SEQ ID NO 104
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 104
ttactactac gaccgtgctc acccgtgccg acgcgccgtg catggtcccc gtcccggctg      60
gaacgcgtcc tnggaagaga gagatagagc acagcagaca gggagacagg gatggaagga     120
tggcgttcgc ccggtacagg ttg                                             143

<210> SEQ ID NO 105
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 105
ctactacgac cgtgctcacc cgtgccgacg cgccgtgcat ggtccccgtc ccggctggaa      60
cgcgtcctcg gnagagagag atagagcaca gcagacaggg agacagggat ggaaggatgg     120
cgttcgcccg gtacaggttg cta                                             143

<210> SEQ ID NO 106
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 106
tactacgacc gtgctcaccc gtgccgacgc gccgtgcatg gtccccgtcc cggctggaac      60
gcgtcctcgg angagagaga tagagcacag cagacaggga gacagggatg gaaggatggc    120
gttcgcccgg tacaggttgc tag                                            143

<210> SEQ ID NO 107
<211> LENGTH: 146
<212> TYPE: DNA
<213> ORGANISM: Zea mays
<220> FEATURE:
<221> NAME/KEY: modified_base
<222> LOCATION: (72)..(75)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 107
actacgaccg tgctcacccg tgccgacgcg ccgtgcatgg tccccgtccc ggctggaacg     60
cgtcctcgga annnngagag agatagagca cagcagacag ggagacaggg atggaaggat   120
ggcgttcgcc cggtacaggt tgctag                                        146

<210> SEQ ID NO 108
<211> LENGTH: 143
<212> TYPE: DNA
<213> ORGANISM: Zea mays
<220> FEATURE:
<221> NAME/KEY: modified_base
<222> LOCATION: (72)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 108
ttgcctagca catgcctgcc attgaccgac tgctcagtga gaagtggttc agttgtgctg     60
ttgacagtat annnnnntat atatagtagc cctgtagatt tttttttcag acaaaaaaag   120
aagaagaacg agatgaagtc tgc                                           143

<210> SEQ ID NO 109
<211> LENGTH: 148
<212> TYPE: DNA
<213> ORGANISM: Zea mays
<220> FEATURE:
<221> NAME/KEY: modified_base
<222> LOCATION: (76)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 109
catgcctgcc attgaccgac tgctcagtga gaagtggttc agttgtgctg ttgacagtat     60
agatagatat atatanngta gccctgtaga tttttttttc agacaaaaaa agaagaagaa   120
cgagatgaag tctgcaattc ggttttgg                                      148

<210> SEQ ID NO 110
<211> LENGTH: 142
<212> TYPE: DNA
<213> ORGANISM: Zea mays
<220> FEATURE:
<221> NAME/KEY: modified_base
<222> LOCATION: (66)..(69)
<223> OTHER INFORMATION: a, c, t, g, or absent
<220> FEATURE:
<223> OTHER INFORMATION: See specification as filed for detailed description of substitutions and preferred embodiments

<400> SEQUENCE: 110
caacgcccac tccttcatca tcaaactccc cgacggctac gacacgcagg tccgtcccgt      60
atagcnnnnt agctcactag ctgcactgcc acttctctcg cttgctcccc caccgttgct     120
gcctgttgct ctccaatcca ct                                              142

<210> SEQ ID NO 111
<211> LENGTH: 146
<212> TYPE: DNA
<213> ORGANISM: Zea mays
<220> FEATURE:
<221> NAME/KEY: modified_base
<222> LOCATION: (71)..(76)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 111
tttctagagt ttaaagctta tcttagaata aatgcatctt tagctacgag acaacctaac      60
ttcagttgtt nnnnnngttt tttttacttt ctctcttctc acaaatacta tgattacgtc     120
tttacagcga tcttttttat tccaaa                                          146

<210> SEQ ID NO 112
<211> LENGTH: 146
<212> TYPE: DNA
<213> ORGANISM: Zea mays
<220> FEATURE:
<221> NAME/KEY: modified_base
<222> LOCATION: (77)..(77)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 112
tttctagagt ttaaagctta tcttagaata aatgcatctt tagctacgag acaacctaac      60
ttcagttgtt gttgttnttt tttttacttt ctctcttctc acaaatacta tgattacgtc     120
tttacagcga tcttttttat tccaaa                                          146

<210> SEQ ID NO 113
<211> LENGTH: 105
<212> TYPE: DNA
<213> ORGANISM: Zea mays
<220> FEATURE:
<221> NAME/KEY: modified_base
<222> LOCATION: (60)..(61)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 113
attccaaacc taaaaatgca tgcactcact ctaaaagcgc aaagggagca tctttttttn      60 nccccccatca tctgcacgca gccttttctt ttcctcatgt cacga                    105

<210> SEQ ID NO 114
<211> LENGTH: 181
<212> TYPE: DNA
<213> ORGANISM: Zea mays
<220> FEATURE:
<221> NAME/KEY: modified_base
<222> LOCATION: (63)..(111)

<223> OTHER INFORMATION: a, c, t, g, or absent
<220> FEATURE:
<223> OTHER INFORMATION: See specification as filed for detailed
      description of substitutions and preferred embodiments

<400> SEQUENCE: 114
tcggtgctgg ctctggtgca gcggttctac gagcccacgt ccgggcgcgt gctcctggac      60
ggnnnnnnnn nnnnnnnnnn nnnnnnnnnn nnnnnnnnnn nnnnnnnnnn ncaaggacgt     120
gcgcaagtac aacctgcggg cgctgcggcg cgtggtggcg gtggtaccgc aggagccgtt     180
c                                                                    181

<210> SEQ ID NO 115
<211> LENGTH: 185
<212> TYPE: DNA
<213> ORGANISM: Zea mays
<220> FEATURE:
<221> NAME/KEY: modified_base
<222> LOCATION: (51)..(135)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 115
agaacacgga ctcacactcc cataactata actgacttga tcatgattcc nnnnnnnnnn      60
nnnnnnnnnn nnnnnnnnnn nnnnnnnnnn nnnnnnnnnn nnnnnnnnnn nnnnnnnnnn    120
nnnnnnnnnn nnnnnatttt attaacaatt caatttttat ttattaatta cgtctggacg    180
aggag                                                                185

<210> SEQ ID NO 116
<211> LENGTH: 140
<212> TYPE: DNA
<213> ORGANISM: Zea mays
<220> FEATURE:
<221> NAME/KEY: modified_base
<222> LOCATION: (52)..(69)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 116
ccaccgtcag ggaataagac ttattatttt attaacaatt caatttttat tnnnnnnnnn      60
nnnnnnnnnt attaattacg tctggacgag gagtactggt ttatttgatg agagacatgg    120
cagtccaagt caaactcgtt                                                140

<210> SEQ ID NO 117
<211> LENGTH: 711
<212> TYPE: DNA
<213> ORGANISM: Zea mays
<220> FEATURE:
<221> NAME/KEY: modified_base
<222> LOCATION: (66)..(644)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 117
actgaaggtg tgtatgcagc gtcaagtcat ccatccgttc cactccactc actcatgcgt      60
cgcgcnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180

```
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnactctg cgctcgtgcc    660
tgcccggggc taaagcttta gtagctagcc tcagatcaga tactgttcgt g              711

<210> SEQ ID NO 118
<211> LENGTH: 114
<212> TYPE: DNA
<213> ORGANISM: Zea mays
<220> FEATURE:
<221> NAME/KEY: modified_base
<222> LOCATION: (68)..(80)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 118
gcactcagga ctcgcagcga gagaattttt ttaatcaagc ctaaaattca ctttcggaca    60
aatcgaannn nnnnnnnnnn ctactcataa atattaacca tgagacccttt tcgc         114

<210> SEQ ID NO 119
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 119
ttagcgcatt aatctgagga tgtccagttc gcttgcttgc caatcgccat tgccatcgca    60
acaacaatac ntcgccaact gccattgctg ggtagactag tacagtagca gttagaagaa   120
gcctccactg tacattgcat t                                              141

<210> SEQ ID NO 120
<211> LENGTH: 141
<212> TYPE: DNA
<213> ORGANISM: Zea mays
<220> FEATURE:
<221> NAME/KEY: modified_base
<222> LOCATION: (73)..(73)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 120
ttagcgcatt aatctgagga tgtccagttc gcttgcttgc caatcgccat tgccatcgca    60
acaacaatac ttngccaact gccattgctg ggtagactag tacagtagca gttagaagaa   120
gcctccactg tacattgcat t                                              141
```

<210> SEQ ID NO 121
<211> LENGTH: 144
<212> TYPE: DNA
<213> ORGANISM: Zea mays
<220> FEATURE:
<221> NAME/KEY: modified_base
<222> LOCATION: (72)..(73)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 121
ccatcctctt tcttgctttt cttttactt tctttggtcg tggctgtttg tggtcataca      60
tacattcacg cnnagagcag aagagctagc taagctaggt gggtgtgcct gcaacgcggg    120
acaaagaaaa ctatttgttg cctg                                           144

<210> SEQ ID NO 122
<211> LENGTH: 138
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 122
tgtgtctgtc cacccagct cttgctactc tacttactac tgtgctacta gtggtagggt      60
aggtatcttn cataaactgt tattataaac tgtcatctga gaaagagagc cagtcaaacc    120
catgctgctg cttatttt                                                  138

<210> SEQ ID NO 123
<211> LENGTH: 142
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 123
tcttacataa actgttatta taaactgtca tctgagaaag agagccagtc aaacccatgc      60
tgctgcttan ttttaatcac tgtcaaatgg caggcaggca ggcagtctgg ttagttaata    120
acatctggga agggtttaat ca                                             142

<210> SEQ ID NO 124
<211> LENGTH: 141
<212> TYPE: DNA
<213> ORGANISM: Zea mays
<220> FEATURE:
<221> NAME/KEY: modified_base
<222> LOCATION: (70)..(70)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 124

```
ggcaggcagg caggcagtct ggttagttaa taacatctgg gaagggttta atcaaaccaa      60
atcaaatcan acgaaatcta gaggccacat gggatggggc catatgtact gtactagcat     120
aactagcggc tagattttat t                                               141
```

<210> SEQ ID NO 125
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 125

```
caaaccaaat caaatcagac gaaatctaga ggccacatgg gatggggcca tatgtactgt      60
actagcataa ntagcggcta gattttatta gaacacggac tcacactccc ataactataa    120
ctgacttgat catgattcct t                                               141
```

<210> SEQ ID NO 126
<211> LENGTH: 143
<212> TYPE: DNA
<213> ORGANISM: Zea mays
<220> FEATURE:
<221> NAME/KEY: modified_base
<222> LOCATION: (72)..(72)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 126

```
tactgtacta gcataactag cggctagatt ttattagaac acggactcac actcccataa      60
ctataactga cnttgatcat gattccttgc caagcaatgc tcgcatgccc atgcatgcat    120
catccctggt caaactcaaa cac                                             143
```

<210> SEQ ID NO 127
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 127

```
catcatccct ggtcaaactc aaacactctc caccgtcagg gaataagact tattatttta      60
ttaacaattc nattttatt tattaattac gtctggacga ggagtactgg tttatttgat    120
gagagacatg gcagtccaag t                                               141
```

<210> SEQ ID NO 128
<211> LENGTH: 141
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:

<223> OTHER INFORMATION: See specification as filed for detailed
      description of substitutions and preferred embodiments

<400> SEQUENCE: 128
aacactctcc accgtcaggg aataagactt attattttat taacaattca attttattt      60 attaattacg nctggacgag gagtactggt ttatttgatg agagacatgg cagtccaagt    120
caaactcgtt tgtctgacca t                                              141

<210> SEQ ID NO 129
<211> LENGTH: 139
<212> TYPE: DNA
<213> ORGANISM: Zea mays
<220> FEATURE:
<221> NAME/KEY: modified_base
<222> LOCATION: (71)..(71)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 129
gggaataaga cttattattt tattaacaat tcaattttta tttattaatt acgtctggac     60
gaggagtact ngtttatttg atgagagaca tggcagtcca agtcaaactc gtttgtctga   120
ccatggcggt gatggccgg                                                 139

<210> SEQ ID NO 130
<211> LENGTH: 134
<212> TYPE: DNA
<213> ORGANISM: Zea mays
<220> FEATURE:
<221> NAME/KEY: modified_base
<222> LOCATION: (68)..(68)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 130
tttatttgat gagagacatg gcagtccaag tcaaactcgt tgtctgacc atggcggtga     60 tggccggntg caggttgggg agcgcggcct gcagctctcc ggtgggcaga agcagcgcat    120
cgccatcgcc cgcg                                                      134

<210> SEQ ID NO 131
<211> LENGTH: 141
<212> TYPE: DNA
<213> ORGANISM: Zea mays
<220> FEATURE:
<221> NAME/KEY: modified_base
<222> LOCATION: (65)..(74)
<223> OTHER INFORMATION: a, c, t, g, or absent
<220> FEATURE:
<223> OTHER INFORMATION: See specification as filed for detailed
      description of substitutions and preferred embodiments

<400> SEQUENCE: 131
gtcgtacatg tgttcagtca tttccgtcca ttactactac gaccgtgctc acccgtgccg     60
acgcnnnnnn nnnngccgtg catggtcccc gtcccggctg gaacgcgtcc tcggaagaga    120
gagatagagc acagcagaca g                                              141